United States Patent
Esposito et al.

(10) Patent No.: US 12,054,475 B2
(45) Date of Patent: Aug. 6, 2024

(54) SUBSTITUTED HETEROCYCLES AS ALDEHYDE DEHYDROGENASE INHIBITORS

(71) Applicants: KayoThera Inc., Seattle, WA (US); The Trustees of Princeton University, Princeton, NJ (US)

(72) Inventors: Mark Esposito, Cazenovia, NY (US); John Proudfoot, Newtown, CT (US); Yibin Kang, Princeton, NJ (US); John Piwinski, Lebanon, NJ (US)

(73) Assignees: KayoThera Inc., Seattle, WA (US); The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 18/488,924

(22) Filed: Oct. 17, 2023

(65) Prior Publication Data
US 2024/0132469 A1 Apr. 25, 2024

Related U.S. Application Data

(63) Continuation of application No. PCT/US2022/026059, filed on Apr. 22, 2022.

(60) Provisional application No. 63/178,309, filed on Apr. 22, 2021.

(51) Int. Cl.
| | |
|---|---|
| A61K 31/4709 | (2006.01) |
| A61K 31/473 | (2006.01) |
| A61K 31/4738 | (2006.01) |
| A61P 35/00 | (2006.01) |
| C07D 215/227 | (2006.01) |
| C07D 215/50 | (2006.01) |
| C07D 401/12 | (2006.01) |
| C07D 413/12 | (2006.01) |
| C07D 417/12 | (2006.01) |
| C07D 471/04 | (2006.01) |
| C07D 471/14 | (2006.01) |
| C07D 491/048 | (2006.01) |
| C07D 498/04 | (2006.01) |
| C07D 513/04 | (2006.01) |

(52) U.S. Cl.
CPC ............ C07D 401/12 (2013.01); A61P 35/00 (2018.01); C07D 215/50 (2013.01); C07D 413/12 (2013.01); C07D 417/12 (2013.01); C07D 471/04 (2013.01); C07D 491/048 (2013.01); C07D 498/04 (2013.01); C07D 513/04 (2013.01)

(58) Field of Classification Search
CPC .............. A61K 31/4709; A61K 31/473; A61K 31/4738; C07D 215/227; C07D 471/14

USPC .............................. 514/290, 312; 546/79, 153
See application file for complete search history.

(56) References Cited

U.S. PATENT DOCUMENTS

| | | |
|---|---|---|
| 4,593,035 A | 6/1986 | Tominaga et al. |
| 4,954,498 A | 9/1990 | Mertens et al. |
| 10,752,640 B2 | 8/2020 | Seitzberg et al. |
| 2005/0239825 A1 | 10/2005 | Heise et al. |
| 2011/0112067 A1 | 5/2011 | Hartmann et al. |
| 2017/0057982 A1 | 3/2017 | Yang et al. |
| 2017/0182009 A1 | 6/2017 | Piomelli et al. |
| 2021/0155602 A1 | 5/2021 | Esposito et al. |
| 2023/0128402 A1 | 4/2023 | Esposito et al. |

FOREIGN PATENT DOCUMENTS

| | | |
|---|---|---|
| JP | S61145162 A | 7/1986 |
| JP | S63192773 A | 8/1988 |
| JP | H01319453 A | 12/1989 |
| JP | 2006349902 A | 12/2006 |
| WO | WO-2004099146 A1 | 11/2004 |
| WO | WO-2005046589 A2 | 5/2005 |
| WO | WO-2013027168 A1 | 2/2013 |
| WO | WO-2015127137 A1 | 8/2015 |
| WO | WO-2016016316 A1 | 2/2016 |
| WO | WO-2020028461 A1 | 2/2020 |
| WO | WO-2021151062 A1 | 7/2021 |
| WO | WO-2022123039 A1 | 6/2022 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — COOLEY LLP

(57) ABSTRACT

Provided herein are novel heterocyclic compounds, for example, compounds of Formula (IV-C). Also provided herein are pharmaceutical compositions comprising the compounds and methods of using the same, for example, in inhibiting aldehyde dehydrogenases, retinoid pathway activation, and/or for treating various cancers, cancer metastasis, type 2 diabetes, pulmonary arterial hypertension (PAH) or neointimal hyperplasia (NIH) or as a male contraceptive.

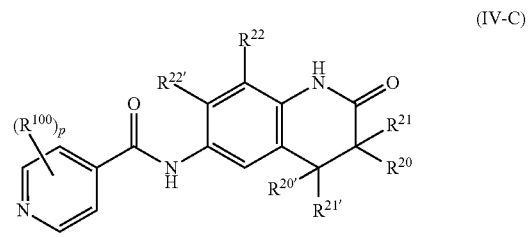

(IV-C)

30 Claims, 24 Drawing Sheets

(56) References Cited

FOREIGN PATENT DOCUMENTS

WO    WO-2022226383 A1    10/2022

OTHER PUBLICATIONS

Dörwald, F. Zaragoza. Side Reactions in Organic Synthesis: A Guide to Successful Synthesis Design, Weinheim: WILEY-VCH Verlag Gmbh & Co. KGaA, 2005, Preface.*
Buchman, C.D., et al., "Discovery of a series of aromatic lactones as ALDH1/2-directed inhibitors", Chem Biol Interact, 2015, 234, 38-44.
Chefetz, I., "A Pan-ALDH1A Inhibitor Induces Necroptosis in Ovarian Cancer Stem-Like Cells", Cell Rep. 2019, 26, 3061-3075.
Database Caplus [Online] STN; Jan. 1, 1976 (Jan. 1, 1976), Nakagawa Kazuyuki: "Carbostyril derivatives", Database accession No. 1977:468181; rn:63430-44-4, 2 pages.
Database Registry Chemical Abstracts Service, Columbus, Ohio, US, Database accession No. 1152985-39-1, entered Jun. 7, 2009, Supplier: UkrOrgSynthesis, 1 page.
Database Registry Chemical Abstracts Service, Columbus, Ohio, US, Database accession No. 1153283-51-2, entered Jun. 7, 2009, Supplier: UkrOrgSynthesis, 1 page.
Database Registry Chemical Abstracts Service, Columbus, Ohio, US, Database accession No. 1153283-98-7, Supplier: UkrOrgSynthesis, entered Jun. 7, 2009, 1 page.
Database Registry Chemical Abstracts Service, Columbus, Ohio, US, Database accession No. 1153284-52-6, entered Jun. 7, 2009, Supplier: UkrOrgSynthesis, 1 page.
Database Registry Chemical Abstracts Service, Columbus, Ohio, US, Database accession No. 1153285-10-9, entered Jun. 7, 2009, Supplier: UkrOrgSynthesis, 1 page.
Database Registry Chemical Abstracts Service, Columbus, Ohio, US, Database accession No. 1153285-30-3 rn: 1153285-30-3, entered Jun. 7, 2009, Supplier: UkrOrgSynthesis, 1 page.
Database Registry Chemical Abstracts Service, Columbus, Ohio, US, Database accession No. 1154533-39-7, entered Jun. 9, 2009, Supplier: UkrOrgSynthesis, 1 page.
Database Registry Chemical Abstracts Service, Columbus, Ohio, US, Database accession No. 1154533-72-8 rn: 1154533-72-8, entered Jun. 9, 2009, Supplier: UkrOrgSynthesis, 1 page.
Database Registry Chemical Abstracts Service, Columbus, Ohio, US, Database accession No. 1303823-01-9 rn: 1303823-01-9, entered Jun. 1, 2011, Supplier: Ryan Scientific, Inc., 1 page.
Database Registry Chemical Abstracts Service, Columbus, Ohio, US, Database accession No. 1304933-67-2 rn: 1304933-67-2, entered Jun. 3, 2011, Supplier: Ryan Scientific, Inc., 1 page.
Database Registry Chemical Abstracts Service, Columbus, Ohio, US, Database accession No. 1306404-60-3 rn: 1306404-60-3, entered Jun. 6, 2011, Supplier: Ryan Scientific, Inc., 1 page.
Database Registry Chemical Abstracts Service, Columbus, Ohio, US, Database accession No. 1308446-19-6 rn: 1308446-19-6, entered Jun. 10, 2011, Supplier: Ryan Scientific, Inc., 1 page.
Database Registry Chemical Abstracts Service, Columbus, Ohio, US, Database accession No. 1468571-74-5 rn: 1468571-74-5, entered Nov. 3, 2013, Supplier: Aurora Fine Chemicals, 1 page.
Database Registry Chemical Abstracts Service, Columbus, Ohio, US, Database accession No. 1798740-10-9 rn: 1798740-10-9, entered Jul. 10, 2015, Supplier: Aurora Fine Chemicals, 1 page.
Database Registry Chemical Abstracts Service, Columbus, Ohio, US; Database accession No. 1874534-18-5 rn: 1874534-18-5, entered Feb. 26, 2016, Supplier: Ukrorgsyntez Ltd., 1 page.
Database Registry Chemical Abstracts Service, Columbus, Ohio, US; Database accession No. 1875411-98-5 rn: 1875411-98-5, entered Feb. 28, 2016, Supplier: Ukrorgsyntez Ltd., 1 page.
Database Registry Chemical Abstracts Service, Columbus, Ohio, US, Database accession No. 2094147-63-2, entered May 2, 2017, Supplier: Enamine LLC, 1 page.
Database Registry Chemical Abstracts Service, Columbus, Ohio, US, Database accession No. 2094666-41-6 rn: 2094666-41-6, entered May 2, 2017, Supplier: Enamine LLC, 1 page.
Database Registry Chemical Abstracts Service, Columbus, Ohio, US, Database accession No. 2195663-27-3 rn: 2195663-27-3, entered Mar. 21, 2018, Supplier: Aurora Fine Chemicals, 1 page.
Database Registry Chemical Abstracts Service, Columbus, Ohio, US, Database accession No. 2217474-28-5, entered Apr. 22, 2018, Supplier: Aurora Fine Chemicals, 1 page.
Database Registrychemical Abstracts Service, Columbus, Ohio, US, Database accession No. 1292643-91-4 rn: 1292643-91-4, entered May 10, 2011, Supplier: Ryan Scientific, Inc., 1 page.
Henry et al., "One-pot ortho-amination of aryl C—H bonds using consecutive iron and copper catalysis," Org. Biomol. Chem., 2019, 17: 4629-4639.
Huddle, B.C., "Structure-Based Optimization of a Novel Class of Aldehyde Dehydrogenase 1A (ALDH1A) Subfamily-Selective Inhibitors as Potential Adjuncts to Ovarian Cancer Chemotherapy," J. Med. Chem., 2018, 61, 8754-8773.
International Preliminary Report on Patentability for International Application No. PCT/US2022/026059 dated Nov. 2, 2023, 7 pages.
International Search Report and Written Opinion for International Application No. PCT/US2022/026059 dated Sep. 9, 2022, 14 Pages.
International Search Report and Written Opinion for PCT Application No. PCT/US2019/044278 dated Nov. 27, 2019, 14 pages.
International Search Report and Written Opinion issued in PCT/US2021/014883, dated Jun. 3, 2021, 9 pages.
Jimenez, R., "Inhibitors of aldehyde dehydrogenases of the 1A subfamily as putative anticancer agents: Kinetic characterization and effect on human cancer cells," Chem. Biol. Interact. 2019, 306, 123-130.
Joshi, P., et al., "Identification of Potent and Selective CYP1 A 1 Inhibitors via Combined Ligand and Structure-Based Virtual Screening and Their in Vitro Validation in Sacchrosomes and Live Human Cells", J Chem Inf Model. Jun. 26, 2017; 57(6): 1309-1320. Epub May 22, 2017.
Khanna, M. et al., "Discovery of a Novel Class of Covalent Inhibitors for Aldehyde Dehydrogenases", J. Biol. Chem., Dec. 16, 2011, 286(50): 43486-43494.
Kimble-Hill, A.C., "Development of selective inhibitors for aldehyde dehydrogenases based on substituted indole-2,3-diones", J. Med. Chem., 2014, 57, 714-722.
Koppaka, V. et al., "Aldehyde dehydrogenase inhibitors: a comprehensive review of the pharmacology, mechanism of action, substrate specificity, and clinical application", Pharmacol. Rev., 2012, 64, 520-539.
Lack, N., et al., "Targeting the binding function 3 (BF3) site of the human androgen receptor through virtual screening", J Med Chem. Dec. 22, 2011; 54(24): 8563-73. Epub Nov. 18, 2011.
Li, D. et al., "Abstract 17192: ALDH1A3 Induces NFY to Coordinate Transcription of Cell Cycle and Metabolic Genes Necessary for Smooth Muscle Proliferation in Pulmonary Hypertension", Circulation, 2018, 138(Supp. 1) (abstract), 1 page.
Liang, D. et al., "Discovery of coumarin-based selective aldehyde dehydrogenase 1A1 inhibitors with glucose metabolism improving activity", Eur. J. Med. Chem, 2020, 187, 111923.
Mertens—Database Caplus [Online] STN; Jan. 1, 1988 (Jan. 1, 1988), Der Saal Alfred, et al., "Preparation of heterocyclobenzimidazoles as cardiovascular agents", Database accession No. 1988:590420; rn: 117242-02-1.
Morgan, C.A. et al., "Characterization of two distinct structural classes of selective aldehyde dehydrogenase 1A1 inhibitors", J. Med. Chem. 2015, 58, 1964-1975.
Nakagawa Nhajime N H, "Black and white heat-developable photographic material", Database Caplus (STN) [Online] Jan. 1, 2006, Database accession No. 2006:1351625—rn: 917242-17-2, 1 page.
Office Action for Japanese Application No. JP20210505202 dated Aug. 17, 2023, 5 pages, with English translation.
Pubchem 165301313, modified Feb. 4, 2023, created Oct. 10, 2022, 7 pages.
Pubchem, SID 322785251, available and deposit Jan. 24, 2017, 7 pages.

(56) References Cited

OTHER PUBLICATIONS

Pubchem, SID 403637055, available and deposit Jan. 24, 2020, 5 pages.
Registry (STN) [online] [date-of-search Jun. 14, 2023] CAS Registration No. 1788963-83-6, entered Jun. 26, 2015, Supplier: Aurora Fine Chemicals, 3 pages.
Vasiliou, V., et al., "Aldehyde dehydrogenases: From eye crystallins to metabolic disease and cancer stem cells", Chem Biol Interact. Feb. 25, 2013; 202(13): 2-10. Epub Nov. 16, 2012.
Xie, X. et al. "ALDH1A3 Regulations of Matricellular Proteins Promote Vascular Smooth Muscle Cell Proliferation", iScience, 2019, 19: 872-882.
Yang, S.M., "Discovery of Orally Bioavailable, Quinoline-Based Aldehyde Dehydrogenase 1A1 (ALDH1A1) Inhibitors with Potent Cellular Activity", J. Med. Chem, 2018, 61, 4883-4903.
Yasgar, A. et al., "A High-Content Assay Enables the Automated Screening and Identification of Small Molecules and Specific ALDH1A1-Inhibitory Activity", PLoS one, 2017, 12, e0170937, 1-19.
Yoshizawa Toyokichi NC: "Preparation of heterocyclyl-substituted benzoquinone derivatives as drugs", Database STN [Online] Jan. 1, 1990 (Jan. 1, 1990), Database accession No. 113:5936; compound with rn: 127430-92-6, 2 pages.
STN International Registry 2217474-28-5/RN; Oct. 11, 2023, 34 pages.
Extended European Search report for Application No. 21744411.6, dated Feb. 8, 2024, 9 pages.
Invitation to Pay Additional Fees for International Application No. PCT/US2023/077659, dated Jan. 17, 2024, 2 pages.
PubChem SID 164995132, Source: Life Chemicals, available date Nov. 14, 2013, 5 pages.
PubChem SID 228844606, Source: SureChEMBL, available date Feb. 12, 2015, 5 pages.
PubChem SID 355035722, Source: Fisher Drug Discovery Resource Center, available date Mar. 12, 2018, 5 pages.
UniProtKB Accession No. P47895, "AL1A3_HUMAN", integrated into UniProtKB/Swiss-Prot., Feb. 1, 1996. Available at: https://www.uniprot.org/uniprotkb/P47895/entry, retrieved on Feb. 13, 2024. 10 printed pages.
Wilen et al., "Strategies in optical resolutions," Tetrahedron, vol. 33, Issue 21, 1977, pp. 2725-2736.
Wilen, S. H., "Tables of Resolving Agents and Optical Resolutions", p. 268, E. L. Eliel, Ed., Univ. of Notre Dame Press, Notre Dame, IN, (1972), 31 printed pages.
International Search Report and Written Opinion for International Application No. PCT/US2023/077659, mailed Mar. 1, 2024, 13 pages.
Pubchem, SID 464908864, Modify Date: Jun. 23, 2022 [retrieved on Mar. 4, 2024], Retrieved from the Internet URL: https://pubchem.ncbi.nlm.nih.gov/substance/464908864, 5 pages.

\* cited by examiner

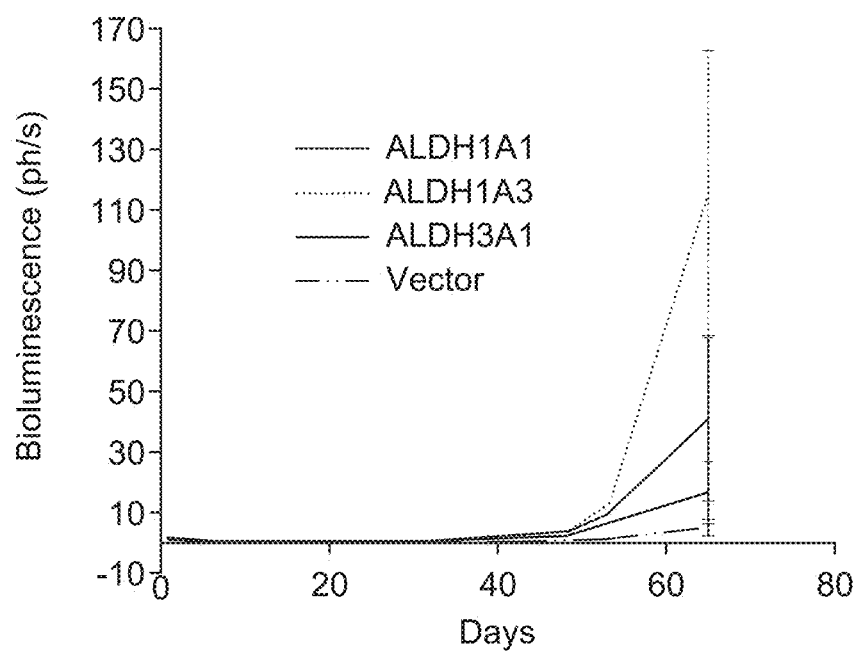
FIG. 3A
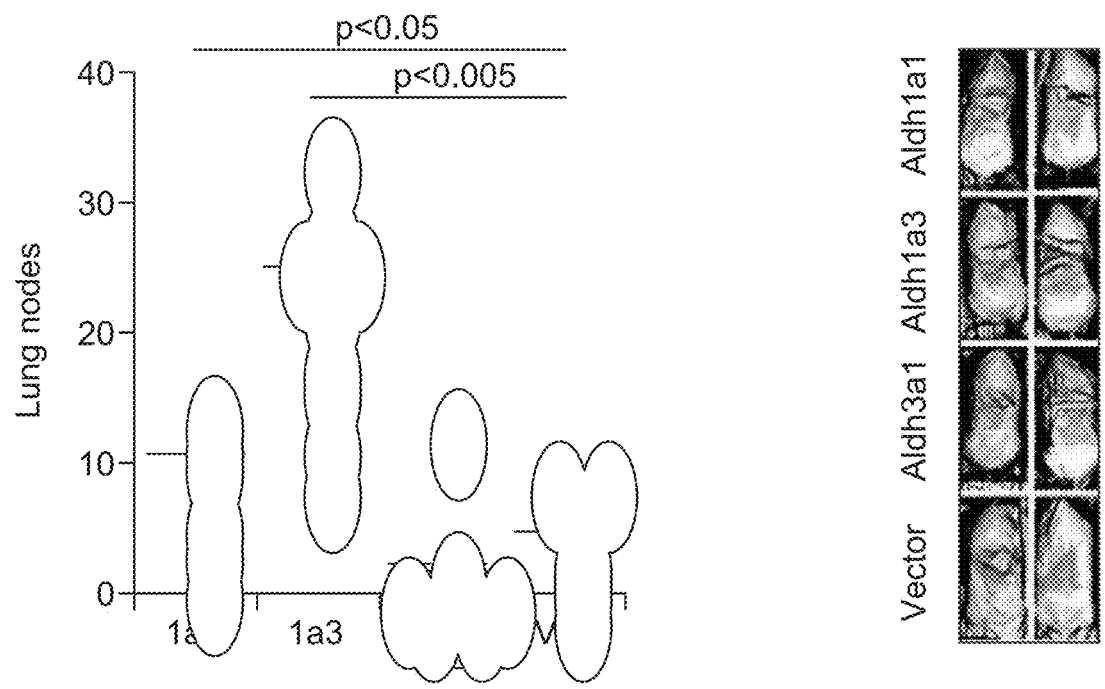
FIG. 3B
FIG. 3C

| Compound | CYP1A2 %Inhibition | CYP2C9 %Inhibition | CYP2C19 %Inhibition | CYP2D6 %Inhibition | CYP3A4 %Inhibition |
|---|---|---|---|---|---|
| MBE1 | 8.6 | 13.9 | 15.8 | 61.3 | 42.0 |
| Compound 140 | 70.6 | 49.9 | 54.3 | 6.3 | 27.7 |
| Compound 151 | 5.6 | 0.0 | 7.0 | 21.6 | 25.8 |

FIG. 16

SUBSTITUTED HETEROCYCLES AS ALDEHYDE DEHYDROGENASE INHIBITORS

CROSS-REFERENCES TO RELATED APPLICATIONS

This application is a continuation of International Patent Application No. PCT/US2022/026059, filed Apr. 22, 2022, which claims priority to and the benefit of U.S. Provisional Application No. 63/178,309, filed on Apr. 22, 2021, the contents of which are hereby incorporated by reference in their entireties.

BACKGROUND OF THE INVENTION

Aldehyde dehydrogenases (ALDHs) belong to a superfamily of NAD(P+)-dependent enzymes that play a role in the metabolism of aldehydes by irreversibly catalyzing the oxidation of both endogenously and exogenously produced aldehydes to their respective carboxylic acids. ALDHs have a broad spectrum of biological activities, including biosynthesis of retinoic acid (RA), oxidation of lipid peroxides, and alcohol metabolism, among others.

The ALDH family of enzymes contains 19 members with diverse functions. Enzymes within this family irreversibly catalyze the oxidation of an aldehyde into the corresponding carboxylic acid while reducing NAD+/NADP+ to NADH/NADPH. These enzymes are found in several cellular compartments, however, most are localized to the cytosol or the mitochondria.

The ALDH enzymes can be classified into 3 main groups: 1) Broad specificity ALDH1 family containing ALDH1a1, 1a2, 1a3, 1b1 and ALDH2 known to oxidize retinal, acetaldehyde, GABA, medium chain lipid aldehydes, cyclophosphamide metabolites and potentially other aldehyde species; 2) Long chain fatty aldehyde-specific ALDH3A1-3B2; 3) Structurally diverse enzymes ALDH4A1, 5A1, 6A1, 7A1, 8A1, 9A1, 18A1, 1L1, and 1L2 catalyze the oxidation of discrete metabolites or semialdehydes (glutamate, succinate, methylmalonate, 10-formyl-THF etc).

BRIEF SUMMARY OF THE INVENTION

Some ALDH enzymes participate in global metabolism via expression in the liver where they function to detoxify acetylaldehyde formed from alcohol dehydrogenases, biosynthesize vitamin A from retinal stereoisomers, or detoxify other reactive aldehydes. In contrast, most ALDH enzymes are expressed in a cell- or disease-specific manner and modulate cellular biochemistry, often with unknown mechanisms of action.

Of particular interest to human health and disease is the ALDH1a subfamily; ALDH1a3 is distinctly upregulated across solid tumor subpopulations, failing pancreatic β cells, and proliferative smooth muscle cells in endothelial diseases. ALDH1a3 is further used to identify tumorigenic and chemoresistant cancer cells. Despite >100 publications studying ALDH1a3 in cancer, a cohesive understanding of its function has remained absent. Our discoveries have resolved this paradox by showing that tumor-expressed ALDH1a3 conditions the tumor microenvironment through the generation of paracrine retinoic acid that suppresses anti-tumor immunity.

A less studied but equally important ALDH1a enzyme is ALDH1a2, which has been implicated as the main myeloid-expressed ALDH1a isoform. Similar to ALDH1a3, ALDH1a2 catalyzes retinaldehyde oxidation, and this activity controls normal immune tolerance through the induction of Regulatory T cells and M2 macrophages. However, few studies have been performed on the role of ALDH1a2 in controlling immune tolerance of cancer or other pathologies.

While insights into the complementary roles of ALDH1a2 and ALDH1a3 in conditioning an immune suppressive niche are novel, retinoid signaling via the RAR nuclear receptors is arguably the most studied nutrient pathway in inflammatory diseases and cancer. Early trials established retinoic acid as a tremendously effective intervention in acute promyelocytic leukemia (APL) through targeting a fusion oncogene unique to APL. However, numerous follow-on clinical trials testing retinoid agonism in solid tumors unexpectedly revealed a pro-tumorigenic role of retinoid signaling across solid tumor types, resulting in numerous early terminations due to excess mortality and increased cancer incidence. Therapeutic retinoid agonism is also associated with hyperlipidemia, osteoarthritis, and various other pathologies caused by immune suppression.

Despite these unexpected clinical findings that retinoid activation drives the progression of solid cancers and is associated with other disease states, antagonists of the retinoid pathway have not progressed into clinical trials.

The present disclosure is based, in part, on the discovery that aldehyde dehydrogenase (Aldh, ALDH), and particularly ALDH isoform 1a3 (ALDH1a3) and/or ALDH isoform 1a2 (ALDH1a2), is implicated in various diseases or disorders such as proliferative diseases or disorders, immune suppression, diseases or disorders associated with retinoid pathway activation, metabolic diseases or disorders, endothelial cell or smooth muscle cell diseases or disorders, cancer and metastasis, etc. The present disclosure further shows that inhibition of the ALDH enzymes such as ALDH1a3 and/or ALDH1a2 can be useful in treating or preventing various cancers, cancer metastasis, and other ALDH1a2 and/or ALDH1a3-mediated diseases and disorders, metabolic diseases, such as such as type 2 diabetes, pulmonary arterial hypertension (PAH) and neointimal hyperplasia (NIH). See also, PCT/US2019/044278, which has an international filing date of Jul. 31, 2019, the content of which is incorporated by reference in its entirety. The present disclosure is further based, in part, on the discovery that various compounds described herein can potently and/or selectively inhibit one or more ALDH enzymes such as ALDH1a3 and/or ALDH1a2, can inhibit the retinoid pathway activation, and can treat various diseases such as cancer and Type 2 Diabetes.

Accordingly, in various embodiments, the present disclosure provides novel compounds and pharmaceutical compositions, which are useful in inhibiting aldehyde dehydrogenase (Aldh, ALDH), and particularly ALDH isoform 1a3 (ALDH1a3) and/or ALDH isoform 1a2 (ALDH1a2), or inhibiting retinoid pathway. In some embodiments, the present disclosure also provides methods of using the novel compounds and pharmaceutical compositions herein for treating various diseases or disorders, such as various cancers, cancer metastasis, metabolic diseases such as type 2 diabetes, pulmonary arterial hypertension (PAH) and neointimal hyperplasia (NIH), or in male contraception.

Some embodiments of the present disclosure are directed to a compound of Formula I, I-P, II, II-P, or III, or a pharmaceutically acceptable salt thereof:

Formula I

Formula II

Formula I-P

Formula II-P

Formula III

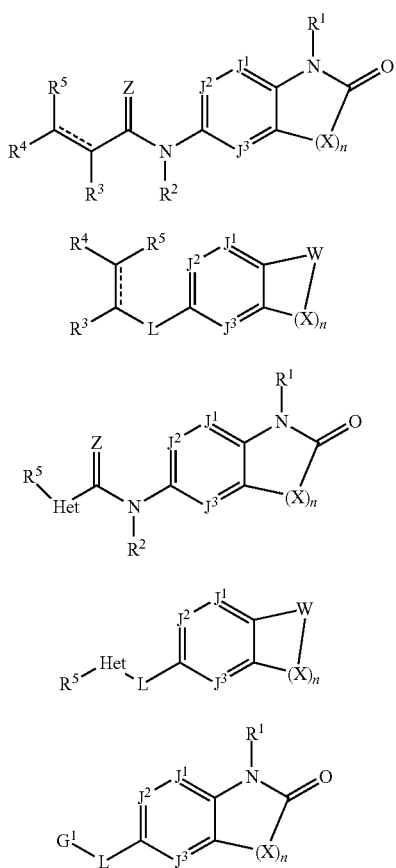

wherein the variables are defined herein. In some embodiments, the compound of Formula I can be characterized as having a subformula of Formula I as defined herein, such as Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C. In some embodiments, the compound of Formula II can be characterized as having a subformula of Formula II as defined herein, such as Formula II-1, II-2, II-3, or II-4. In some embodiments, the compound of Formula III can be characterized as having a subformula of Formula III as defined herein, such as Formula III-1, III-2. In some embodiments, the present disclosure also provides specific compounds, Compound Nos. 139-202 or 139-165, or a pharmaceutically acceptable salt thereof.

In embodiments, the present disclosure provides a compound of Formula (IV)

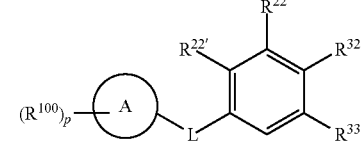

(IV)

or a pharmaceutically acceptable salt thereof,
wherein ring A, L, $R^{22}$, $R^{22'}$, $R^{32}$, $R^{33}$, p and $R^{100}$ are defined herein.

In embodiments, the present disclosure provides a compound of Formula (IV-A)

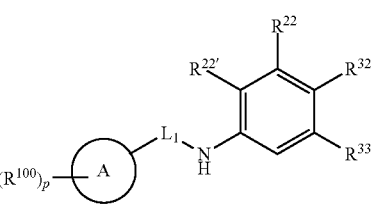

(IV-A)

wherein ring A, $L_1$, $R^{22}$, $R^{22'}$, $R^{32}$, $R^{33}$, p and $R^{100}$ are defined herein.

In embodiments, the present disclosure provides a compound of Formula (IV-B)

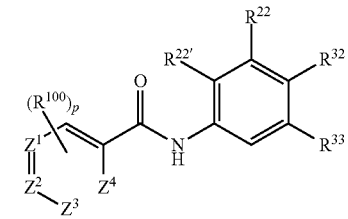

(IV-B)

wherein $Z^1$, $Z^2$, $Z^3$, $Z^4$, $R^{22}$, $R^{22'}$, $R^{32}$, $R^{33}$, p and $R^{100}$ are defined herein.

In embodiments, the present disclosure provides a compound of Formula (IV-C)

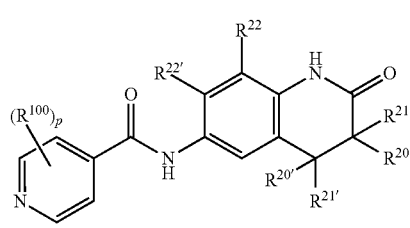

(IV-C)

wherein, $R^{20}$, $R^{21}$, $R^{20'}$, $R^{21'}$, $R^{22}$, $R^{22'}$, p and $R^{100}$ are defined herein.

In embodiments, the present disclosure provides a compound of Formula (IV-D)

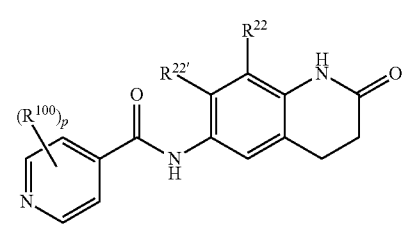

(IV-D)

wherein, $R^{22}$, $R^{22'}$, p and $R^{100}$ are defined herein.

Certain embodiments of the present disclosure are directed to a pharmaceutical composition comprising one or more of the compounds of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) and optionally a pharmaceutically acceptable excipient. The pharmaceutical composition described herein can be formulated for different routes of administration, such as oral administration, parenteral administration, or inhalation etc.

Some embodiments of the present disclosure are directed to a method of inhibiting an aldehyde dehydrogenase, in particular, ALDH1a3 and/or ALDH1a2, in a subject in need thereof.

Some embodiments of the present disclosure are directed to a method of inhibiting the retinoid pathway in a subject in need thereof. In some embodiments, the present disclosure provides a method of inhibiting $T_{reg}$ cell and/or M2 macrophage formation in a subject in need thereof. In some embodiments, the present disclosure provides a method of treating a disease or disorder associated with the retinoid pathway activation in a subject in need thereof, e.g., as described herein.

In some embodiments, the present disclosure provides a method of treating or preventing a disease or disorder associated with aldehyde dehydrogenase, preferably, a disease or disorder associated with aldehyde dehydrogenase isoform 1a3 (ALDH1a3) and/or ALDH1a2 in a subject in need thereof. In some embodiments, the disease or disorder is a proliferative disease such as cancer (e.g., as described herein) associated with aldehyde dehydrogenase isoform 1a3 (ALDH1a3) and/or ALDH1a2. In some embodiments, the disease or disorder is a metabolic disease such as type 2 diabetes or hyperlipidemias associated with aldehyde dehydrogenase isoform 1a3 (ALDH1a3) and/or ALDH1a2. In some embodiments, the disease or disorder is an endothelial cell or smooth muscle cell disease or disorder, such as pulmonary arterial hypertension or neointimal hyperplasia, associated with aldehyde dehydrogenase isoform 1a3 (ALDH1a3) and/or ALDH1a2. In some embodiments, the disease or disorder is an immunologically-driven disease or disorder, such as acute graft-vs-host disease or osteoarthritis pain, associated with aldehyde dehydrogenase isoform 1a3 (ALDH1a3) and/or ALDH1a2.

In some embodiments, the present disclosure provides a method of treating cancer in a subject in need thereof. In some embodiments, the cancer is associated with ALDH1a3 and/or ALDH1a2 activities, such as having cancer cells with higher expression level compared to a control, and/or having cancer cells with ALDH1a3 and/or ALDH1a2 activities, e.g., positive in Aldefluor™ assay, which can be reduced with an ALDH1a3 and/or ALDH1a2 inhibitor or genetic knockout or knockdown. In some embodiments, the cancer is a solid cancer. In some embodiments, the cancer is metastatic cancer or chemoresistant cancer. In some embodiments, the cancer can be a breast cancer, colorectal cancer, kidney cancer, ovarian cancer, gastric cancer, thyroid cancer, urothelial cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, hematologic cancer, leukemia, lymphoma, and/or sarcoma. In some embodiments, the cancer can also be gastrointestinal stromal tumor, peripheral nerve sheath tumor, myeloma, and/or endometrial cancer. In some embodiments, the cancer is unresponsive to one or more immunotherapy, e.g., an anti-PD-1, anti-CTLA4, anti-LAG-3, anti-TIGIT or anti-PD-L1 antibody. In some embodiments, the subject has developed resistance to one or more immunotherapy, e.g., an anti-PD-1 or anti-PD-L1 antibody. In some embodiments, the method further comprises administering to the subject one or more immunotherapy (e.g., as described herein).

In some embodiments, the present disclosure provides a method of treating or preventing metastasis of a cancer in a subject in need thereof. In some embodiments, the cancer has established metastasis. In some embodiments, the cancer has not metastasized prior to treatment with the methods herein, and the method delays or prevents metastasis of the cancer. In some embodiments, the cancer is associated with ALDH1a3 and/or ALDH1a2 activities.

In some embodiments, the present disclosure provides a method of treating a metabolic disease, such as type 2 diabetes in a subject in need thereof. In embodiments, the present disclosure provides a method of treating or hyperlipidemia in a subject in need thereof. In some embodiments, the present disclosure further provides a method of treating an endothelial cell or smooth muscle cell disease or disorder, such as pulmonary arterial hypertension or neointimal hyperplasia, in a subject in need thereof. In some embodiments, the present disclosure provides a method of inducing male contraception in a subject in need thereof.

The method described herein typically comprises administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. The administering is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, compounds of the present disclosure can be administered as the only active ingredient(s). In some embodiments, compounds of the present disclosure can be used in combination with an additional therapy, such as conventional surgery or radiotherapy, immunotherapy, cell therapy, therapeutic antibodies, or chemotherapy.

It is to be understood that both the foregoing summary and the following detailed description are exemplary and explanatory only, and are not restrictive of the invention herein.

BRIEF DESCRIPTION OF THE DRAWINGS

FIG. 3A is a line graph of bioluminescence (ph/s) versus time (days), and shows the development of lung metastasis in mice injected with SUM159-M1b cells transduced with vectors encoding three ALDH enzymes, ALDH1a1, ALDH1a3 and ALDH3a1 compared to empty vector (vector).

FIG. 3B is a plot of lung nodes counted ex vivo at the endpoint of the experiment described in FIG. 3A. Student's t-test, two-tailed, assuming unequal variance.

FIG. 3C shows sample images of bioluminescence at Day1 (left) and endpoint (right) from the experiment described in FIG. 3A and FIG. 3B.

FIG. 16 shows CYP inhibiting properties of Compounds MBE1, 140, 151 tested at 10 uM using human CYP enzymes and standard operating protocols.

DETAILED DESCRIPTION OF THE INVENTION

As explained in more detail in the Examples section, Aldh1a3 was found to be an essential driver of tumor metastasis and resistance to chemotherapy. Data herein demonstrated that genetic ablation of Aldh1a3 in the triple negative breast cancer models Sum159-M1a and MDA-MB-468 sensitizes orthotopic tumors to paclitaxel treatment. Aldh1a3 was found to be a critical determinant of metastasis initiation and growth both as a single genetic element and when combined with chemotherapy. Genetic experiments demonstrate that Aldh1a3 is necessary for lung and bone metastasis in triple negative breast cancer metastasis. Further, clinical analysis of multiple cancer types supports Aldh1a3 as the differentiated Aldh isoform predicting worse outcome across multiple solid tumor indications. For example, high Aldh1a3 expression predicts worse overall survival in the more metastatic and aggressive estrogen receptor negative (ER-) breast cancer patients, and this prognosis is further worsened if those patients had received neoadjuvant chemotherapy (Table 1).

Also shown herein, genetic knockout of ALDH1a3 or inhibition of ALDH1a3 with representative ALDH1a3 inhibitors can slow primary tumor growth, sensitize tumors to chemotherapy, slow metastasis, and enhance survival time. In studies in mouse xenograft models, ALDH1a3 inhibitors (MBE1 or MBE1.5; shown below and disclosed in PCT/US2021/014883) in conjunction with a chemotherapy agent (paclitaxel), have been shown to be effective in treating established metastatic diseases and can cause regression of primary tumors, slow various metastasis, and extend survival time. Reseach has also shown that diseases such as type 2 diabetes, pulmonary arterial hypertension (PAH) or neointimal hyperplasia (NIH) are also caused by ALDH1a3 expression and/or activities.

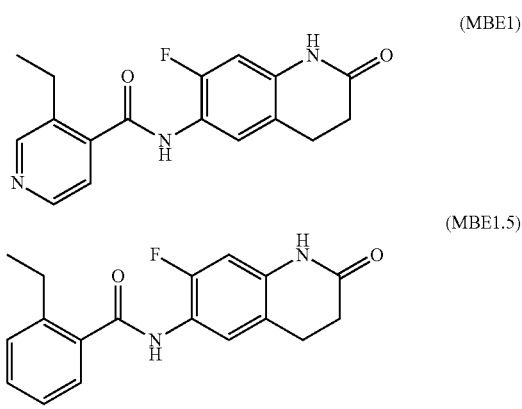

Figure 7:
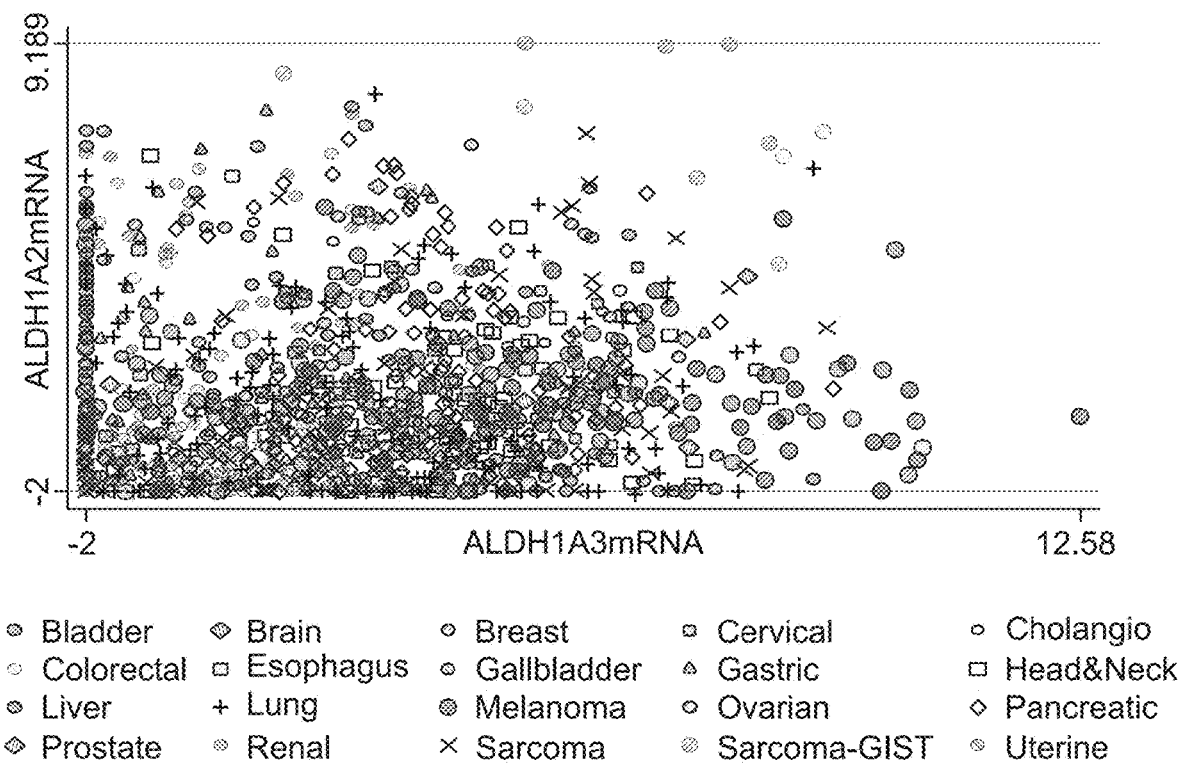
FIG. 7. Expression of ALDH1a2 and ALDH1a3 mRNA in patient-derived xenograft models from multiple human cancers shows expression of ALDH1a2 and ALDH1a3 enzymes across multiple tumor types.

Also shown in detail in the Examples section herein, the present disclosure shows that among the tested isoforms, only ALDH1a2 and ALDH1a3 induce retinoid pathway activation and ALDH1a2 and ALDH1a3 drive retinoid pathway activation in solid tumors in vivo. Further, as shown in FIG. 7, expression of ALDH1a2 and ALDH1a3 mRNA in patient-derived xenograft models from multiple human cancers shows expression of ALDH1a2 and ALDH1a3 enzymes across multiple tumor types. Exemplary ALDH1a2 and/or ALDH1a3 inhibitors were also shown herein as effective in inhibiting tumor growth in vivo either as a single agent or in a synergistic combination treatment with an immune checkpoint inhibitor (anti-PD-1 antibody).

As also detailed herein, compounds described herein are orally available and exhibit sufficient pharmacokinetic exposure to effectively inhibit Aldh1a3 and/or Aldh1a2 in mouse models.

In addition, Aldh1a3 was found to be an important driver of Type 2 Diabetes progression. Data herein demonstrate that ALDH1a3 is involved in the metabolism of medium chain fatty acids known to cause pathogenesis of Type 2 Diabetes and various endothelial disorders such as PAH and NIH. Data herein also demonstrated that pharmacologic inhibition of Aldh1a3 in the leptin-deficient db/db mouse strain effectively treats Type 2 Diabetes by restoring insulin secretion and subsequent blood glucose control.

Also shown herein, pancreatic islet cells isolated from obese diabetic C57/BL6 wild-type mice express active Aldh1a3 that is inhibited by compound MBE1.5 while pancreatic cells from non-obese, non-diabetic C57/BL6 mice do not express Aldh1a3. Accordingly, in various embodiments, the present disclosure provides novel compounds and compositions, which are useful for inhibiting ALDH such as ALDH1a3 and/or Aldh1a2, and methods of using the same, for example, for inhibiting retinoid pathway activation, treating various diseases or disorders associated with ALDH1a3 and/or Aldh1a2, treating various diseases or disorders associated with retinoid pathway activation, treating various cancers, cancer metastasis, metabolic diseases such as type 2 diabetes, pulmonary arterial hypertension (PAH) or neointimal hyperplasia (NIH) or as male contraceptive.

Compounds

Provided herein are a range of compounds that can be useful for inhibiting ALDH, in particular, ALDH1a3 and/or Aldh1a2.

Formula I

In some embodiments, the present disclosure provides a compound of Formula I, or a pharmaceutically acceptable salt thereof:

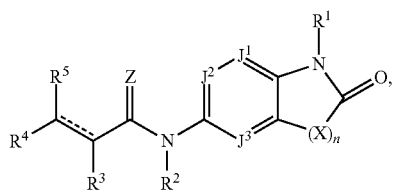

Formula I wherein:
- X at each occurrence is independently selected from O, $NR^{10}$, and $CR^{20}R^{21}$ provided that at most one X is selected from O and $NR^{10}$;
- n is 1, 2, 3, or 4;
- $J^1$, $J^2$, and $J^3$ are each independently selected from $CR^{22}$ or N, preferably, at least one of $J^1$, $J^2$, and $J^3$ is not N;
- $R^1$ and $R^2$ are each independently hydrogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), or a nitrogen protecting group;
- $R^3$ and $R^4$ are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring);
- Z is O, and $R^5$ is hydrogen, $-NR^{11}R^{12}$, $-CR^{23}R^{24}R^{25}$, or $-OR^{30}$;
- or Z is O, and $R^3$, $R^4$ and $R^5$ are joined to form an optionally substituted bicyclic or polycyclic ring system, wherein the ring system is an aryl, heteroaryl, carbocyclic, or heterocyclic ring system;
- or $R^5$ and Z are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring); and
- "$\rightleftharpoons$" in Formula I indicates the bond is an aromatic bond, a double bond or a single bond as valance permits, and when a single bond, the two carbons forming the bond can be optionally further substituted as valance permits;

wherein:
- $R^{10}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring;
- $R^{20}$ and $R^{21}$ at each occurrence are each independently hydrogen, halogen, $-OR^{31}$, $-NR^{13}R^{14}$ an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or
- $R^{10}$ and one of $R^{20}$ and $R^{21}$ are joined to form a bond, an optionally substituted 4-8 membered heterocyclic ring or an optionally substituted 5 or 6 membered heteroaryl ring, wherein the other of $R^{20}$ and $R^{21}$ is defined above;
- $R^{20}$ and $R^{21}$ together with the carbon they are both attached to form —C(O)—, an optionally substituted $C_{3-8}$ carbocyclic ring, or an optionally substituted 3-8 membered heterocyclic ring; or
- one of $R^{20}$ and $R^{21}$ in one $CR^{20}R^{21}$ is joined with one of $R^{20}$ and $R^{21}$ in a different $CR^{20}R^{21}$ to form a bond, an optionally substituted $C_{3-8}$ carbocyclic ring, an optionally substituted 3-8 membered heterocyclic ring, wherein the others of $R^{20}$ and $R^{21}$ are defined above;
- $R^{22}$ at each occurrence is independently hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), —CN, —S(O)-alkyl (e.g., —S(O)—$C_{1-6}$ alkyl), —S(O)$_2$-alkyl (e.g., —S(O)$_2$—$C_{1-6}$ alkyl), or —$OR^{31}$; or two adjacent $R^{22}$ are joined to form an optionally substituted ring structure, such as an optionally substituted $C_{3-8}$ carbocyclic ring, optionally substituted 4-8 membered heterocyclic ring, optionally substituted phenyl, or optionally substituted 5 or 6 membered heteroaryl ring;
- one of $R^{11}$ and $R^{12}$ is hydrogen or a nitrogen protecting group, and the other of $R^{11}$ and $R^{12}$ is hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl;
- one of $R^{23}$, $R^{24}$, and $R^{25}$ is hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, an optionally substituted 5-10 membered heteroaryl, —$OR^{31}$, or —$NR^{13}R^{14}$, and the other two of $R^{23}$, $R^{24}$, and $R^{25}$ are independently selected from hydrogen, fluorine, or methyl, preferably, —$CR^{23}R^{24}R^{25}$ is not —$CH_3$;
- $R^{30}$ is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring; and wherein:
- each of $R^{13}$ and $R^{14}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{13}$ and $R^{14}$ are joined to form a 3-8 membered optionally substituted heterocyclic or a 5-10 membered optionally substituted heteroaryl; and $R^{31}$ at each occurrence is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl.

Typically, Z in Formula I is O and the compound can be characterized as having Formula I-O:

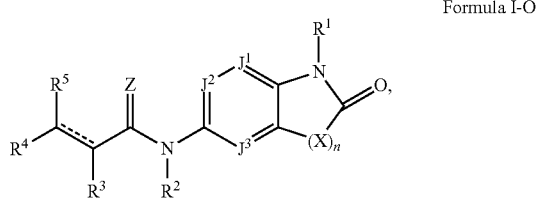

Formula I-O wherein $R^1$, $R^2$, $R^3$, $R^4$, $R^5$, $J^1$, $J^2$, $J^3$, X, and n are defined herein.

Typically, $R^3$ and $R^4$ in Formula I (e.g., Formula I-O) are joined to form an optionally substituted phenyl, an optionally substituted 5 or 6-membered heteroaryl, e.g., having one or two ring nitrogen atoms, an optionally substituted $C_{4-7}$ cycloalkyl group (preferably cyclopentyl or cyclohexyl), or an optionally substituted 4 to 7-membered (preferably 6-membered) heterocyclic ring having one or two ring heteroatoms. To be clear, when it is said that $R^3$ and $R^4$ in Formula I are joined to form a ring system described herein, it should be understood that $R^3$ and $R^4$, together with the two intervening carbon atoms, are joined to form the ring system.

In some embodiments, $R^3$ and $R^4$ in Formula I (e.g., Formula I-O) can be joined to form an optionally substituted phenyl ring, i.e., the moiety of

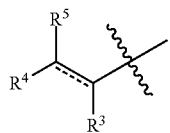

in Formula I is

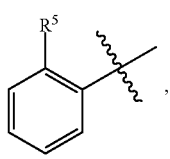

wherein $R^5$ is defined herein, and wherein the phenyl can be further optionally substituted at any available position, for example, with one or two substituents independently selected from F; Cl; hydroxyl; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkyl optionally substituted with 1-3 substituents independently selected from fluorine and methyl, preferably, cyclopropyl or cyclobutyl; and —CN. In some embodiments, $R^5$ is —O—$R^{30}$ or —$CR^{23}R^{24}R^{25}$ as defined herein. For example, in some embodiments, $R^5$ is ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$—cyclobutyl, —$CH_2$—O—$CH_3$, —$CH_2$—O—$C_2H_5$, —$CH_2$—O-n-propyl, —$CH_2$—O-isopropyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl. In some embodiments, $R^5$ is hydrogen.

In some embodiments, $R^3$ and $R^4$ in Formula I (e.g., Formula I-O) can be joined to form an optionally substituted 5 or 6-membered heteroaryl, such as those described herein. For example, in some embodiments, $R^3$ and $R^4$ in Formula I (e.g., Formula I-O) can be joined to form an optionally substituted pyrazole, imidazole, oxazole, thiazole, isoxazole, isothiazole, pyridyl, pyrimidinyl, pyridazinyl, or pyrazinyl. For example, in some embodiments, the moiety of

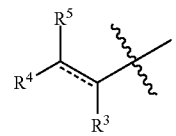

in Formula I (e.g., Formula I-O) can be selected from the following:

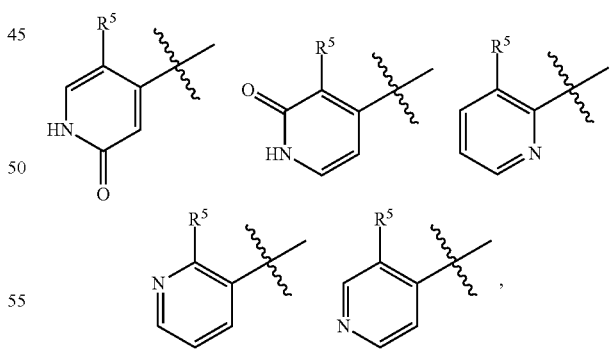

wherein $R^5$ is defined herein, and wherein the pyridyl or pyridone can be further optionally substituted at any available position, including the ring nitrogen in the case of pyridone, for example, with one or two substituents (preferably one) independently selected from F; Cl; OH; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkyl optionally substituted with 1-3 substituents independently selected from fluorine and methyl, preferably, cyclopropyl or cyclobutyl; and —CN. In some embodiments, the moiety of

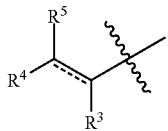

in Formula I can be

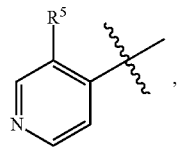

wherein $R^5$ is defined herein, and wherein the pyridyl can be further optionally substituted at any available position, for example, with one or two substituents (preferably one) independently selected from F; Cl; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkyl optionally substituted with 1-3 substituents independently selected from fluorine and methyl, preferably, cyclopropyl or cyclobutyl; and —CN. In some embodiments, $R^5$ is —O—$R^{30}$ or —$CR^{23}R^{24}R^{25}$ as defined herein. For example, in some embodiments, $R^5$ is ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$-cyclobutyl, —$CH_2$—O—$CH_3$, —$CH_2$—O—$C_2H_5$, —$CH_2$—O-n-propyl, —$CH_2$—O-isopropyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl. In some embodiments, $R^5$ can also be hydrogen.

In some embodiments, $R^3$ and $R^4$ in Formula I (e.g., Formula I-0) can be joined to form an optionally substituted 5 or 6-membered saturated ring system optionally containing one or two (preferably one) ring heteroatoms selected from O or N, such as cylopentyl, cyclohexyl, tetrahydropyranyl, piperidinyl, etc. Typically, when substituted, the 5 or 6-membered saturated ring system can be further optionally substituted by one or two substituents independently selected from F and $C_{1-4}$ alkyl optionally substituted with 1-3 fluorines. In some embodiments, the moiety of

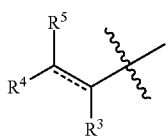

in Formula I can be

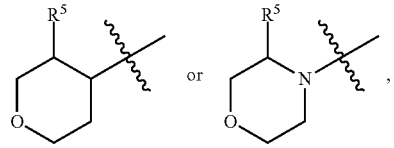

wherein $R^5$ is defined herein, and wherein the tetrahydropyranyl or morpholinyl can be further optionally substituted at any available position, for example, with one or two substituents independently selected from F and $C_{1-4}$ alkyl optionally substituted with 1-3 fluorines. In some embodiments, $R^5$ is —O—$R^{30}$ or —$CR^{23}R^{24}R^{25}$ as defined herein. For example, in some embodiments, $R^5$ is ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$-cyclobutyl, —$CH_2$—O—$CH_3$, —$CH_2$—O—$C_2H_5$, —$CH_2$—O-n-propyl, —$CH_2$—O-isopropyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl.

In some embodiments, $R^5$ in Formula I (e.g., Formula I-0) can be hydrogen. However, typically, $R^5$ in Formula I (e.g., Formula I-0) is —$NR^{11}R^{12}$, —$CR^{23}R^{24}R^{25}$, or —$OR^{30}$, more typically, —$CR^{23}R^{24}R^{25}$ or —$OR^{30}$, wherein $R^{11}$, $R^{12}$, $R^{23}$, $R^{24}$, $R^{25}$, and $R^{30}$ are defined herein. For example, in any of the embodiments described herein, unless specified or obviously contradictory from context, $R^5$ in Formula I (e.g., Formula I-0) can be —$CR^{23}R^{24}R^{25}$, wherein
$R^{23}$ is hydrogen or fluorine;
$R^{24}$ is hydrogen or fluorine; and
$R^{25}$ is hydrogen, halogen, an optionally substituted $C_{1-4}$ alkyl, an optionally substituted $C_{3-6}$ carbocyclic ring, an optionally substituted 3-6 membered heterocyclic ring, an optionally substituted phenyl, or an optionally substituted 5 or 6 membered heteroaryl.

In some embodiments, $R^{25}$ can be fluorine. In some embodiments, $R^{25}$ can be a $C_{1-4}$ alkyl optionally substituted with one or more (e.g., 1, 2, or 3) substituents independently selected from fluorine, hydroxyl, fluoro-substituted $C_{1-4}$ alkyl (e.g., $CF_3$), $C_{1-4}$ alkoxy, fluoro-substituted $C_{1-4}$ alkoxy (e.g., —$OCF_3$), $NH_2$, —NH($C_{1-4}$ alkyl), —N($C_{1-4}$ alkyl) ($C_{1-4}$ alkyl), $C_{3-6}$ cycloalkyl, and 3-6 membered heterocyclic ring. As used herein, the two "$C_{1-4}$ alkyl" in —N($C_{1-4}$ alkyl)($C_{1-4}$ alkyl) can be the same or different. In some embodiments, $R^{25}$ can be a $C_{3-6}$ cycloalkyl, such as cyclopropyl or cyclobutyl, which is optionally substituted with one or more (e.g., 1, 2, or 3) substituents independently selected from fluorine, $C_{1-4}$ alkyl, fluoro-substituted $C_{1-4}$ alkyl (e.g., $CF_3$), $C_{1-4}$ alkoxy, fluoro-substituted $C_{1-4}$ alkoxy (e.g., —$OCF_3$), $NH_2$, —NH($C_{1-4}$ alkyl), and —N($C_{1-4}$ alkyl) ($C_{1-4}$ alkyl). In some embodiments, $R^{25}$ can also be an optionally substituted 3-6 membered heterocyclic ring, such as an oxetanyl ring. In some embodiments, $R^{25}$ can be an optionally substituted phenyl. In some embodiments, $R^{25}$ can be an optionally substituted 5 or 6 membered heteroaryl, e.g., those described herein.

In some embodiments, $R^5$ in Formula I (e.g., Formula I-0) can be —$CR^{23}R^{24}R^{25}$, wherein
$R^{23}$ is hydrogen or fluorine;
$R^{24}$ is hydrogen or fluorine;
$R^{25}$ is hydrogen; fluorine; $C_{1-4}$ alkyl optionally substituted with 1-3 fluorines and/or a $C_{3-6}$ cycloalkyl; a $C_{1-4}$ alkoxy optionally substituted with 1-3 fluorines and/or a $C_{3-6}$ cycloalkyl; a $C_{3-6}$ cycloalkoxy optionally substituted with 1-3 substituents independently selected from fluorine and methyl; a $C_{3-6}$ cycloalkyl optionally substituted with 1-3 substituents independently selected from fluorine and methyl; or a 3-6 membered heterocyclic ring optionally substituted with 1-3 substituents independently selected from fluorine and methyl; and preferably, at least one of $R^{23}$, $R^{24}$, and $R^{25}$ is not hydrogen. More preferably, $R^{25}$ is fluorine; $C_{1-4}$ alkyl optionally substituted with 1-3 fluorines and/or a $C_{3-6}$ cycloalkyl; or a $C_{3-6}$ cycloalkyl (e.g., cyclopropyl or cyclobutyl) optionally substituted with 1-3 substituents independently selected from fluorine and methyl. To be clear, when a $C_{1-4}$ alkyl is said to be optionally substituted with 1-3 fluorines and/or a $C_{3-6}$ cycloalkyl, it should be understood as encompassing unsubstituted $C_{1-4}$ alkyl, a $C_{1-4}$ alkyl substituted with 1-3 fluorines (e.g., $CF_3$), a $C_{1-4}$ alkyl substituted with a $C_{3-6}$ cycloalkyl (e.g., —$CH_2$-cyclopropyl), and a $C_{1-4}$ alkyl substituted with 1-3 fluorines and a $C_{3-6}$ cycloalkyl (e.g., —$CF_2$—$CH_2$-cyclopropyl). Other similar expressions should be interpreted similarly.

In some embodiments, $R^5$ in Formula I (e.g., Formula I-0) can be —$CH_2R^{25}$, wherein $R^{25}$ is defined herein, for example, $R^{25}$ can be hydrogen; fluorine; $C_{1-4}$ alkyl optionally substituted with 1-3 fluorines and/or a $C_{3-6}$ cycloalkyl; a $C_{1-4}$ alkoxy optionally substituted with 1-3 fluorines and/or a $C_{3-6}$ cycloalkyl; a $C_{3-6}$ cycloalkoxy optionally substituted with 1-3 substituents independently selected from fluorine and methyl; a $C_{3-6}$ cycloalkyl optionally substituted with 1-3 substituents independently selected from fluorine and methyl; or a 3-6 membered heterocyclic ring optionally substituted with 1-3 substituents independently selected from fluorine and methyl, preferably, $R^{25}$ is not hydrogen. In any of the embodiments described herein, unless specified or obviously contradictory from context, $R^5$ in Formula I (e.g., Formula I-0) can be —$CH_2R^{25}$, wherein $R^{25}$ is $C_{1-4}$ alkyl optionally substituted with 1-3 fluorines and/or a $C_{3-6}$ cycloalkyl, preferably, methyl, ethyl, n-propyl, isopropyl, or —$CF_3$; or a $C_{3-6}$ cycloalkyl optionally substituted with 1-3 substituents independently selected from fluorine and methyl, preferably, cyclopropyl or cyclobutyl. In any of the embodiments described herein, unless specified or obviously contradictory from context, $R^5$ in Formula I (e.g., Formula I-0) can be —$CH_2R^{25}$, wherein $R^{25}$ can be methyl, ethyl, n-propyl, isopropyl, difluoromethyl, trifluoromethyl, —$CH_2$—$CF_3$, —$CH_2$-cyclopropyl, cyclopropyl or cyclobutyl.

In any of the embodiments described herein, unless specified or obviously contradictory from context, $R^5$ in Formula I (e.g., Formula I-0) can be ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$-cyclobutyl, —$CH_2$—O—$CH_3$, —$CH_2$—O—$C_2H_5$, —$CH_2$—O-n-propyl, —$CH_2$—O-isopropyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl.

In some embodiments, the compound of Formula I-O can be characterized in that $R^3$, $R^4$ and $R^5$ are joined to form an optionally substituted bicyclic or polycyclic ring system, wherein the ring system is an aryl, heteroaryl, carbocyclic, or heterocyclic ring system. For example, in some embodiments, the moiety of

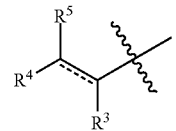

in Formula I can be

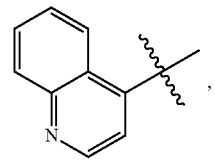 [SMILES: *c1ccnc2ccccc12]

which is optionally substituted.

In some embodiments, Z in Formula I is joined with $R^5$ to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring). For example, in some embodiments, Z in Formula I is joined with $R^5$ to form an optionally substituted heteroaryl. In some embodiments, the compound of Formula I can have a formula of Formula I-F:

Formula I-F

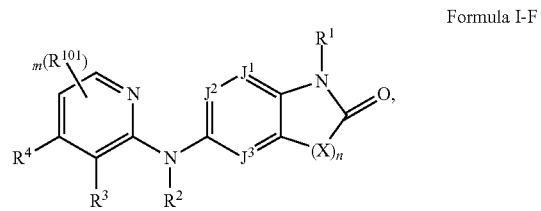

wherein $R^{101}$ at each occurrence is independently selected from halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), —CN, or —$OR^{31}$; and m is 0, 1, 2, or 3, preferably, m is 0 or 1; and wherein $R^1$, $R^2$, $R^3$, $R^4$, $R^{31}$, $J^1$, $J^2$, $J^3$, X, and n are defined herein. In some embodiments, $R^3$ and $R^4$ in Formula I-F are joined to form an optionally substituted phenyl, an optionally substituted 5 or 6-membered heteroaryl, e.g., having one or two ring nitrogen atoms, an optionally substituted $C_{4-7}$ cycloalkyl group (e.g., cyclopentyl or cyclohexyl), or an optionally substituted 4 to 7-membered (e.g., 6-membered) heterocyclic ring having one or two ring heteroatoms. In some embodiments, $R^3$ and $R^4$ in Formula I-F can be joined to form an optionally substituted phenyl, for example, unsubstituted phenyl, or phenyl substituted with one or two substituents independently selected from F; Cl; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkyl optionally substituted with 1-3 substituents independently selected from fluorine and methyl, preferably, cyclopropyl or cyclobutyl; and —CN. In some embodiments, $R^3$ and $R^4$ in Formula I-F can be joined to form an optionally substituted 5 or 6-membered heteroaryl.

In some specific embodiments, the compound of Formula I can be characterized as having Formula I-1 or I-2:

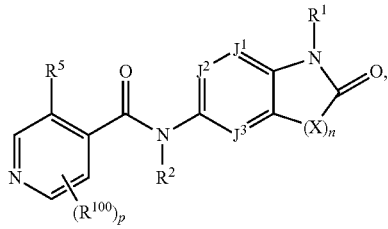

Formula I-1

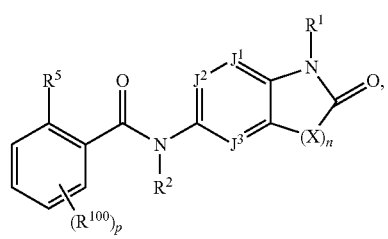

Formula I-2 wherein:
$R^{100}$ at each occurrence is independently selected from halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), —CN, or —OR$^{31}$;
p is 0, 1, 2, or 3, preferably, p is 0 or 1; and
$R^1$, $R^2$, $R^5$, $R^{31}$, $J^1$, $J^2$, $J^3$, X, and n are defined herein. In some embodiments, in Formula I-1 or I-2, $R^{100}$ at each occurrence is independently selected from F; Cl; $C_{1-4}$ alkyl optionally substituted with 1-3 fluorines, preferably, methyl, ethyl, n-propyl, isopropyl, or —CF$_3$; a $C_{1-4}$ alkoxy optionally substituted with 1-3 fluorines, preferably, methoxy, ethoxy, n-propoxy, isopropoxy, or —OCF$_3$; a $C_{3-6}$ cycloalkyl optionally substituted with 1-3 substituents independently selected from fluorine and methyl, preferably, cyclopropyl or cyclobutyl; and —CN.

In some embodiments, in Formula I-1 or I-2, p is 0. In some embodiments, in Formula I-1 or I-2, p is 1. In some embodiments, in Formula I-1 or I-2, p is 1, and $R^{100}$ is F, Cl, methyl, ethyl, n-propyl, isopropyl, —CF$_3$, methoxy, ethoxy, n-propoxy, isopropoxy, —OCF$_3$, cyclopropyl, or —CN. In some embodiments, in Formula I-1 or I-2, p is 1, and $R^{100}$ is OH. In some embodiments, in Formula I-1 or I-2, p is 1, and $R^{100}$ is F, Cl, OH, methyl, or ethyl.

In some specific embodiments, the compound of Formula I can be characterized as having Formula I-1-A or Formula I-2-A:

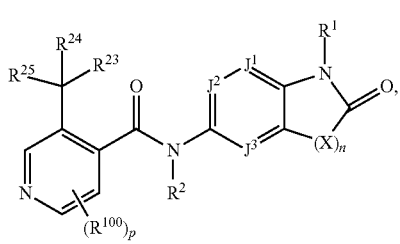

Formula I-1-A

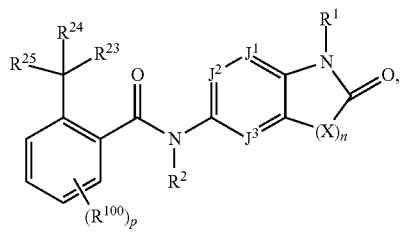

Formula I-2-A wherein $R^1$, $R^2$, $R^{23}$, $R^{24}$, $R^{25}$, $R^{100}$, $J^1$, $J^2$, $J^3$, X, p, and n are defined herein. In some embodiments, in Formula I-1-A or I-2-A:
$R^{23}$ is hydrogen or fluorine;
$R^{24}$ is hydrogen or fluorine;
$R^{25}$ is hydrogen; fluorine; $C_{1-4}$ alkyl optionally substituted with 1-3 fluorines and/or a $C_{3-6}$ cycloalkyl; a $C_{1-4}$ alkoxy optionally substituted with 1-3 fluorines and/or a $C_{3-6}$ cycloalkyl; a $C_{3-6}$ cycloalkoxy optionally substituted with 1-3 substituents independently selected from fluorine and methyl; a $C_{3-6}$ cycloalkyl optionally substituted with 1-3 substituents independently selected from fluorine and methyl; or a 3-6 membered heterocyclic ring optionally substituted with 1-3 substituents independently selected from fluorine and methyl; and
preferably at least one of $R^{23}$, $R^{24}$, and $R^{25}$ is not hydrogen. In some embodiments, $R^{23}$ in Formula I-1-A or I-2-A is hydrogen.

In some embodiments, in Formula I-1-A or I-2-A, $R^{23}$ and $R^{24}$ are both hydrogen. In some embodiments, in Formula I-1-A or I-2-A, $R^{25}$ is a $C_{1-4}$ alkyl optionally substituted with 1-3 fluorines and/or a $C_{3-6}$ cycloalkyl, preferably, methyl, ethyl, n-propyl, isopropyl, or —CF$_3$; or a $C_{3-6}$ cycloalkyl optionally substituted with 1-3 substituents independently selected from fluorine and methyl, preferably, cyclopropyl or cyclobutyl. For example, in some embodiments, in Formula I-1-A or I-2-A, $R^{25}$ is methyl, ethyl, n-propyl, isopropyl, difluoromethyl, trifluoromethyl, —CH$_2$—CF$_3$, —CH$_2$-cyclopropyl, cyclopropyl or cyclobutyl.

In some embodiments, the compound of Formula I-1-A or I-2-A can be characterized as having Formula I-1-A1, Formula I-1-A2, Formula I-1-A3, Formula I-2-A1, Formula I-2-A2; Formula I-2-A3:

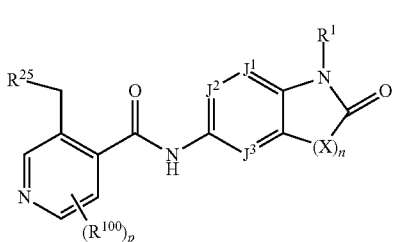

Formula I-1-A1

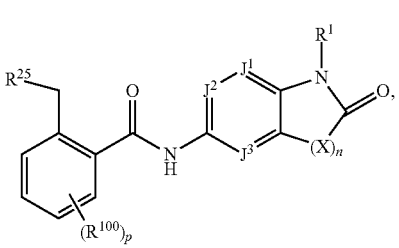

Formula I-2-A1

Formula I-1-A2

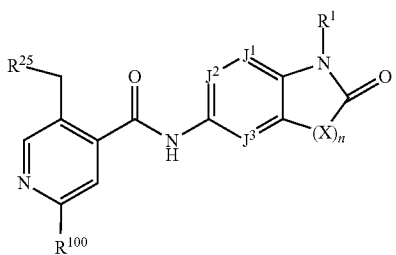

Formula I-2-A2

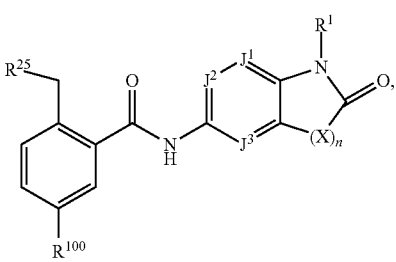

Formula I-1-A3

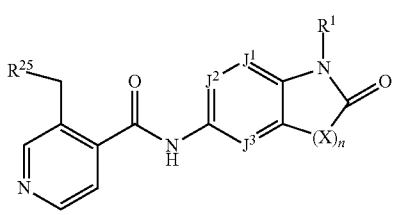

Formula I-2-A3

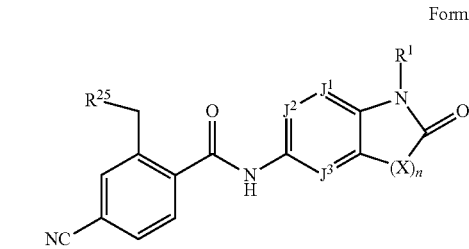

wherein $R^1$, $R^{25}$, $R^{100}$, $J^1$, $J^2$, $J^3$, X, p, and n are defined herein. In some embodiments, in Formula I-1-A1, Formula I-1-A2, Formula I-1-A3, Formula I-2-A1, Formula I-2-A2, or Formula I-2-A3, $R^{25}$ is $C_{1-4}$ alkyl optionally substituted with 1-3 fluorines and/or a $C_{3-6}$ cycloalkyl, preferably, methyl, ethyl, n-propyl, isopropyl, or —$CF_3$; or a $C_{3-6}$ cycloalkyl optionally substituted with 1-3 substituents independently selected from fluorine and methyl, preferably, cyclopropyl or cyclobutyl. In some specific embodiments, $R^{25}$ in Formula I-1-A1, Formula I-1-A2, Formula I-1-A3, Formula I-2-A1, Formula I-2-A2, or Formula I-2-A3 can be methyl, ethyl, n-propyl, isopropyl, difluoromethyl, trifluoromethyl, —$CH_2$—$CF_3$, —$CH_2$-cyclopropyl, cyclopropyl or cyclobutyl.

In some embodiments, in Formula I-1-A1, Formula I-1-A2, Formula I-2-A1, or Formula I-2-A2, $R^{100}$ at each occurrence is independently selected from F; Cl; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkyl optionally substituted with 1-3 substituents independently selected from fluorine and methyl, preferably, cyclopropyl or cyclobutyl; and —CN. In some embodiments, in Formula I-1-A1, Formula I-1-A2, Formula I-2-A1, or Formula I-2-A2, one instance of $R^{100}$ can be hydroxyl. In some embodiments, in Formula I-1-A1 or I-2-A1, p is 1. In some embodiments, in Formula I-1-A1 or I-2-A1, p is 2. In some embodiments, in Formula I-1-A1 or I-2-A1, p is 1, and $R^{100}$ is F, Cl, methyl, ethyl, n-propyl, isopropyl, —$CF_3$, methoxy, ethoxy, n-propoxy, isopropoxy, —$OCF_3$, cyclopropyl, or —CN. In some embodiments, in Formula I-1-A1 or I-2-A1, p is 1, and $R^{100}$ is F, Cl, or methyl. In some embodiments, in Formula I-1-A2 or Formula I-2-A2, $R^{100}$ is F, Cl, methyl, ethyl, n-propyl, isopropyl, —$CF_3$, methoxy, ethoxy, n-propoxy, isopropoxy, —$OCF_3$, cyclopropyl, or —CN. In some embodiments, in Formula I-1-A2 or Formula I-2-A2, $R^{100}$ is F, Cl, or methyl.

In some embodiments, the compound of Formula I-1 or I-2 can be characterized as having Formula I-1-B, I-1-C, I-2-B, or I-2-C:

Formula I-1-B

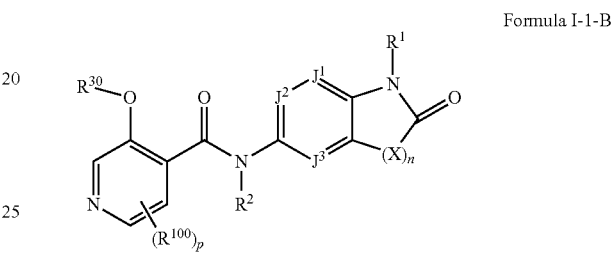

Formula I-2-B


Formula I-1-C

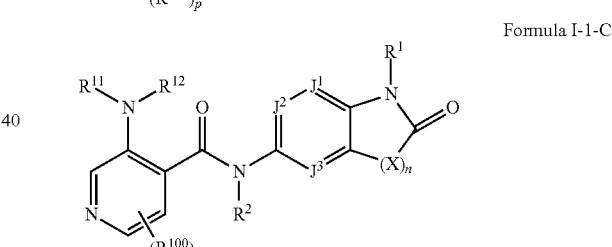

Formula I-2-C

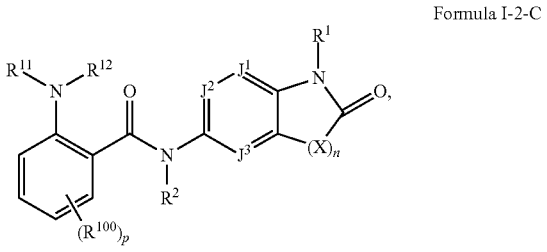

wherein $R^1$, $R^2$, $R^{30}$, $R^{11}$, $R^{12}$, $R^{100}$, $J^1$, $J^2$, $J^3$, X, p, and n are defined herein. In some embodiments, in Formula I-1-B or I-2-B, $R^{30}$ can be hydrogen; $C_{1-4}$ alkyl optionally substituted with 1-3 fluorines and/or a $C_{3-6}$ cycloalkyl, preferably, methyl, ethyl, n-propyl, isopropyl, difluoromethyl, trifluoromethyl, —$CH_2$—$CF_3$, or —$CH_2$-cyclopropyl; a $C_{3-6}$ cycloalkyl optionally substituted with 1-3 substituents independently selected from fluorine and methyl, preferably, cyclopropyl or cyclobutyl; or a 3-6 membered heterocyclic ring optionally substituted with 1-3 substituents independently selected from fluorine and methyl, preferably,

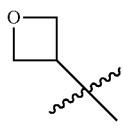

In some embodiments, $R^{30}$ can be methyl, ethyl, n-propyl, isopropyl, difluoromethyl, trifluoromethyl, —CH$_2$—CF$_3$, or —CH$_2$-cyclopropyl. In some embodiments, $R^{30}$ can be cyclopropyl, cyclobutyl; or

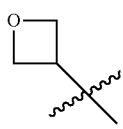

In some embodiments, in Formula I-1-C or I-2-C, one of $R^{11}$ and $R^{12}$ is hydrogen or a nitrogen protecting group, and the other of $R^{11}$ and $R^{12}$ is hydrogen, a nitrogen protecting group, C$_{1-4}$ alkyl optionally substituted with 1-3 fluorines or a C$_{3-6}$ cycloalkyl, preferably, methyl, ethyl, n-propyl, isopropyl, difluoromethyl, trifluoromethyl, —CH$_2$—CF$_3$, or —CH$_2$-cyclopropyl; a C$_{3-6}$ cycloalkyl optionally substituted with 1-3 substituents independently selected from fluorine and methyl, preferably, cyclopropyl or cyclobutyl; or a 3-6 membered heterocyclic ring optionally substituted with 1-3 substituents independently selected from fluorine and methyl, preferably,

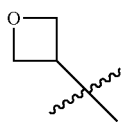

In some embodiments, in Formula I-1-B, I-1-C, I-2-B, or I-2-C, $R^{100}$ at each occurrence is independently selected from F; Cl; C$_{1-4}$ alkyl optionally substituted with 1-3 fluorines, preferably, methyl, ethyl, n-propyl, isopropyl, or —CF$_3$; a C$_{1-4}$ alkoxy optionally substituted with 1-3 fluorines, preferably, methoxy, ethoxy, n-propoxy, isopropoxy, or —OCF$_3$; a C$_{3-6}$ cycloalkyl optionally substituted with 1-3 substituents independently selected from fluorine and methyl, preferably, cyclopropyl or cyclobutyl; and —CN. In some embodiments, in Formula I-1-B, I-1-C, I-2-B, or I-2-C, p is 0. In some embodiments, in Formula I-1-B, I-1-C, I-2-B, or I-2-C, p is 1. In some embodiments, in Formula I-1-B, I-1-C, I-2-B, or I-2-C, p is 1 and $R^{100}$ is F, Cl, methyl, ethyl, n-propyl, isopropyl, —CF$_3$, methoxy, ethoxy, n-propoxy, isopropoxy, —OCF$_3$, cyclopropyl, or —CN.

In some embodiments, the compound of Formula I-1 or I-2 can be characterized as having Formula I-1-B1, Formula I-1-B2, Formula I-2-B1, Formula I-2-B2:

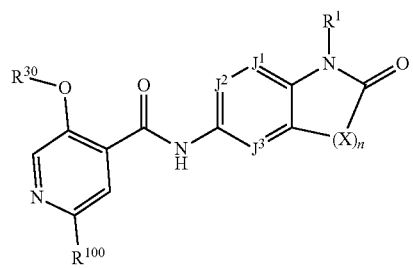

Formula I-1-B1

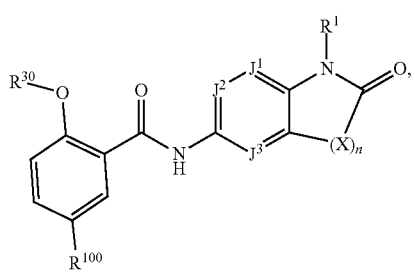

Formula I-2-B1

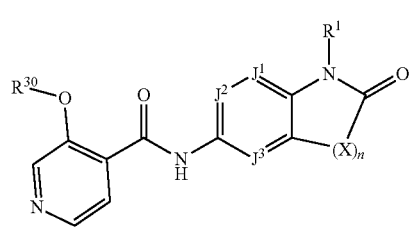

Formula I-1-B2

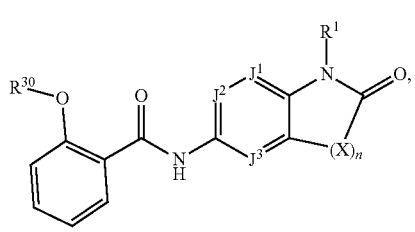

Formula I-2-B2 wherein $R^1$, $R^{30}$, $R^{100}$, $J^1$, $J^2$, $J^3$, X, p, and n are defined herein. In some embodiments, $R^{30}$ can be hydrogen; C$_{1-4}$ alkyl optionally substituted with 1-3 fluorines and/or a C$_{3-6}$ cycloalkyl, preferably, methyl, ethyl, n-propyl, isopropyl, difluoromethyl, trifluoromethyl, —CH$_2$—CF$_3$, or —CH$_2$-cyclopropyl; a C$_{3-6}$ cycloalkyl optionally substituted with 1-3 substituents independently selected from fluorine and methyl, preferably, cyclopropyl or cyclobutyl; or a 3-6 membered heterocyclic ring optionally substituted with 1-3 substituents independently selected from fluorine and methyl, preferably,

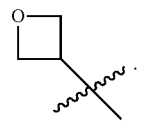

In some embodiments, $R^{30}$ can be hydrogen, methyl, ethyl, n-propyl, isopropyl, difluoromethyl, trifluoromethyl, —CH$_2$—CF$_3$, —CH$_2$-cyclopropyl, cyclopropyl or cyclobutyl. In some embodiments, $R^{100}$ in Formula I-1-B1 or I-2-B1 can be F, Cl, methyl, ethyl, n-propyl, isopropyl, —$CF_3$, methoxy, ethoxy, n-propoxy, isopropoxy, —$OCF_3$, cyclopropyl, or —CN.

In some specific embodiments, the moiety of

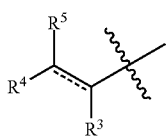

in Formula I (e.g., any of the applicable subformulae) can have a structure according to one of the following:

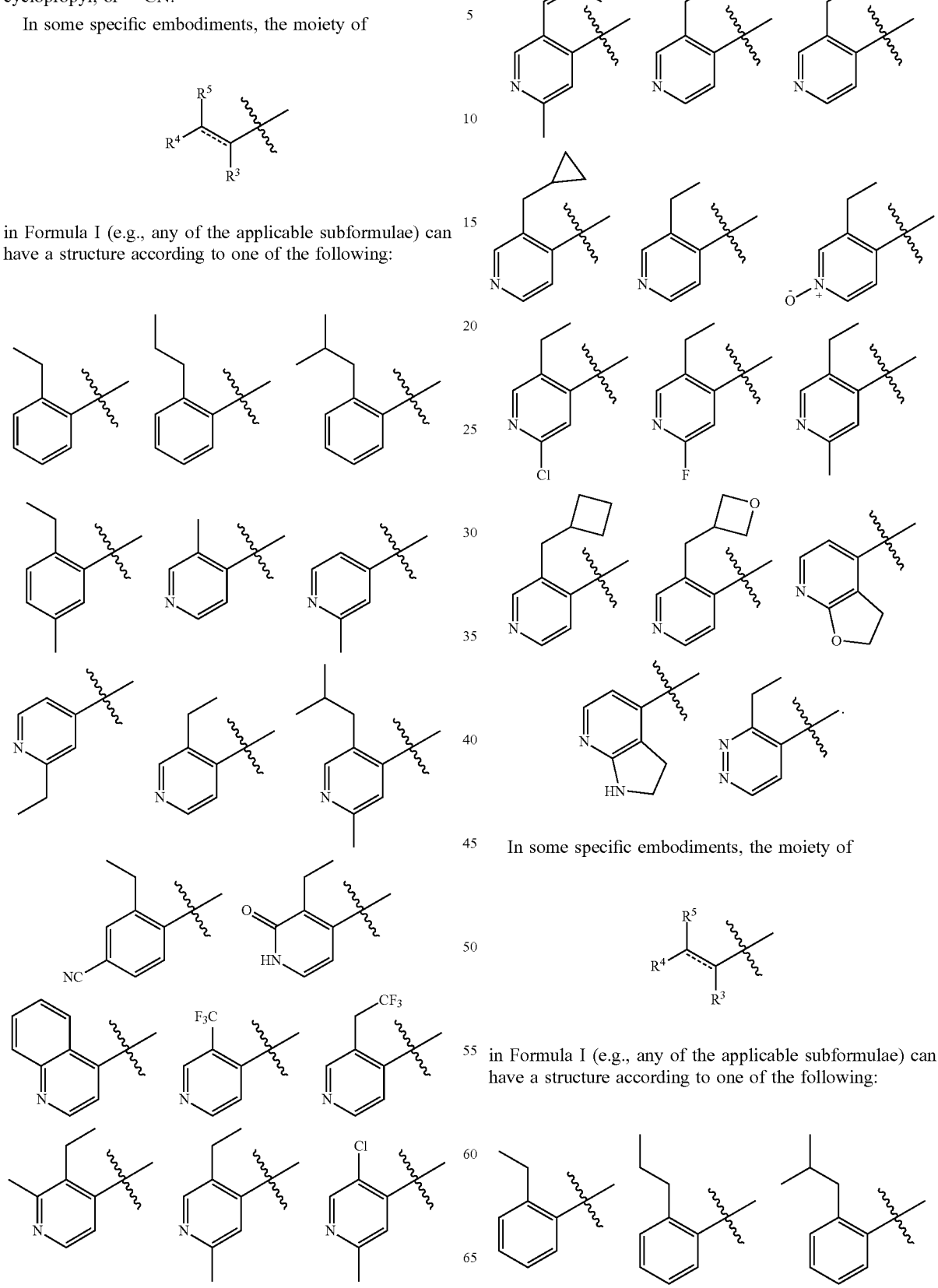

In some specific embodiments, the moiety of in Formula I (e.g., any of the applicable subformulae) can have a structure according to one of the following:

-continued

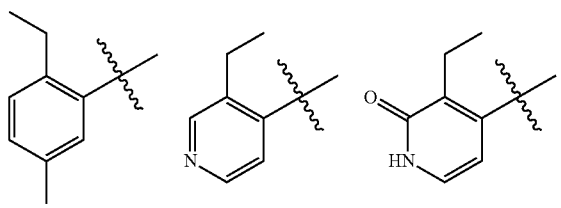
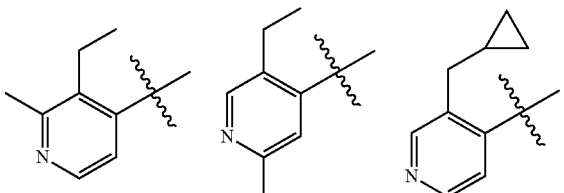
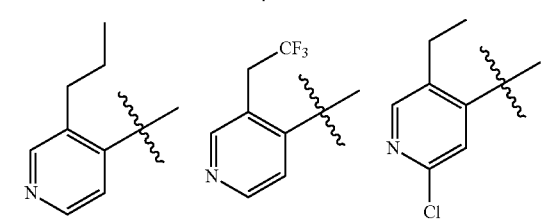
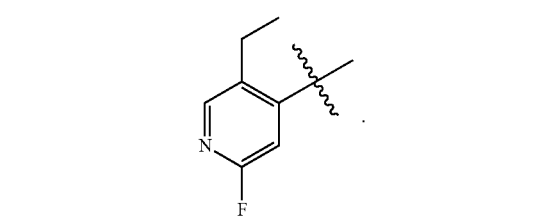
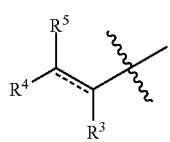

In some specific embodiments, the moiety of 3 in Formula I (e.g., any of the applicable subformulae) can have a structure according to one of the following:

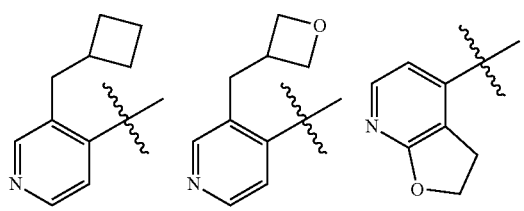
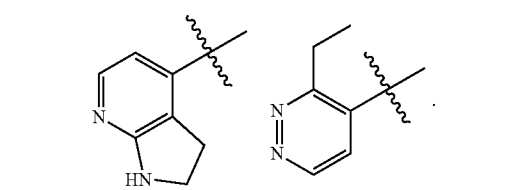

In some embodiments, the moiety of

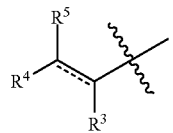

in Formula I (e.g., any of the applicable subformulae) can have a structure of any of the corresponding moieties in Compound Nos. 139-202 or 139-165 as disclosed herein, as applicable. In some embodiments, the moiety of

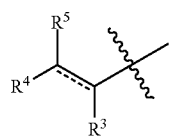

in Formula I (e.g., any of the applicable subformulae) can have a structure of any of the corresponding moieties in the specific compounds disclosed herein, as applicable, that have an activity level of A or B shown in Table 3A of the present disclosure in inhibiting hALDH1a3 and or an $IC_{50}$ shown in Table 3B of less than 250 nM in inhibiting hALDA1a2.

Typically, $R^1$ and $R^2$ in Formula I are both hydrogen. For example, in some embodiments, $R^1$ and $R^2$ in any of the sub-formulae of Formula I, such as Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C, can be both hydrogen.

Typically, $J^1$ in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C) is CH. In some embodiments, $J^1$ in Formula I (including any of the subformulae of Formula I) can also be N.

In some embodiments, $J^1$ in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C) is $CR^{22}$. In some embodiments, $J^1$ in Formula I is $CR^{22}$ and $R^{22}$ is hydrogen, F, Cl, CN, or $C_{1-4}$ alkyl (preferably methyl). As shown in the Examples herein, it was unexpectedly found that substituents at this position can have an impact on selectivities of the compounds for the different ALDH isoforms. For example, data herein shows that representative compounds with $J^1$ being $CR^{22}$ and $R^{22}$ is substituted e.g., substituted with a methyl, have a significantly enhanced activity in inhibiting hALDH1a2 compared to otherwise identical compounds except with $J^1$ being CH.

Typically, $J^2$ in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C) is $CR^{22}$, wherein $R^{22}$ is defined herein. In some embodiments, $R^{22}$ is hydrogen, F, Cl, CN, or methyl. In some embodiments, $J^2$ in Formula I (including any of the subformulae of Formula I) can also be N.

Typically, $J^3$ in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C) is CH. In some embodiments, $J^3$ in Formula I (including any of the subformulae of Formula I) can also be N.

Typically, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C) at least one of $J^1$, $J^2$, and $J^3$ is not N. In some embodiments, none of $J^1$, $J^2$, and $J^3$ is N, for example, $J^1$ can be CH, $J^2$ can be $CR^{22}$, and $J^3$ can be CH, wherein $R^{22}$ is hydrogen, F, Cl, CN, or methyl. In some embodiments, none of $J^1$, $J^2$, and $J^3$ is N, for example, $J^1$ can be $CR^{22}$, $J^2$ can be CH, and $J^3$ can be CH, wherein $R^{22}$ is hydrogen, F, Cl, CN, or $C_{1-4}$ alkyl (preferably methyl). In some embodiments, none of $J^1$, $J^2$, and $J^3$ is N, for example, $J^1$ can be $CR^{22}$, $J^2$ can be $CR^{22}$, and $J^3$ can be CH, wherein $R^{22}$ at each occurrence is independently hydrogen, F, Cl, CN, or $C_{1-4}$ alkyl (preferably methyl).

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), $J^1$ and $J^2$ are both $CR^{22}$, and $J^3$ is $CR^{22}$ or N, wherein the two adjacent $R^{22}$ (i.e., from $J^1$ and $J^2$) are joined to form an optionally substituted ring structure, such as an optionally substituted $C_{3-8}$ carbocyclic ring, optionally substituted 4-8 membered heterocyclic ring, optionally substituted phenyl, or optionally substituted 5 or 6 membered heteroaryl ring, for example, a pyridine ring.

Typically, in Formula I, n is 1, 2, or 3. Preferably, n is 2.

In Formula I, each instance of X can be O, $NR^{10}$, or $CR^{20}R^{21}$, provided that at most one X is selected from O and $NR^{10}$. In some embodiments, at least one instance of X is $CR^{20}R^{21}$, wherein $R^{20}$ and $R^{21}$ are defined herein.

In some embodiments, n is 1 and X is O. In some embodiments, n is 1 and X is $NR^{10}$ wherein $R^{10}$ is defined herein, for example, hydrogen or $C_{1-4}$ alkyl. In some embodiments, n is 1 and X is $CR^{20}R^{21}$, wherein $R^{20}$ and $R^{21}$ are defined herein. In some embodiments, in the $CR^{20}R^{21}$ unit,
$R^{20}$ and $R^{21}$ are both methyl;
one of $R^{20}$ and $R^{21}$ is methyl, and the other of $R^{20}$ and $R^{21}$ is ethyl or methoxy; or
$R^{20}$ and $R^{21}$, together with the carbon they are both attached to, form a $C_{3-6}$ cycloalkyl (preferably cyclopropyl, cyclobutyl, or cyclopentyl), or an oxetanyl ring. In some embodiments, in the $CR^{20}R^{21}$ unit, one of $R^{20}$ and $R^{21}$ is methyl, and the other of $R^{20}$ and $R^{21}$ is hydrogen. In some embodiments, in the $CR^{20}R^{21}$ unit, $R^{20}$ and $R^{21}$ are both hydrogen. In some embodiments, in the $CR^{20}R^{21}$ unit, $R^{20}$ and $R^{21}$ are both fluorine.

In some embodiments, n is 2, one instance of X is O, and one instance of X is $CR^{20}R^{21}$, wherein $R^{20}$ and $R^{21}$ are defined herein. In some embodiments, n is 2, one instance of X is $NR^{10}$, and one instance of X is $CR^{20}R^{21}$, wherein $R^{10}$, $R^{20}$ and $R^{21}$ are defined herein. In some embodiments, n is 2, and both instances of X are $CR^{20}R^{21}$ as defined herein. In some embodiments, $R^{20}$ and $R^{21}$ are independently hydrogen or $C_{1-4}$ alkyl, or $R^{20}$ and $R^{21}$, together with the carbon they are both attached to, form a $C_{3-6}$ cycloalkyl (preferably cyclopropyl, cyclobutyl, or cyclopentyl), or an oxetanyl ring. In some embodiments, $R^{10}$ is hydrogen or $C_{1-4}$ alkyl. In some embodiments, the compound includes at least one $CR^{20}R^{21}$ unit, wherein:
$R^{20}$ and $R^{21}$ are both methyl;
one of $R^{20}$ and $R^{21}$ is methyl, and the other of $R^{20}$ and $R^{21}$ is ethyl or methoxy; or
$R^{20}$ and $R^{21}$, together with the carbon they are both attached to, form a cyclopropyl, cyclobutyl, or an oxetanyl ring. In some embodiments, in the at least one $CR^{20}R^{21}$ unit, one of $R^{20}$ and $R^{21}$ is methyl, and the other of $R^{20}$ and $R^{21}$ is hydrogen. In some embodiments, in the $CR^{20}R^{21}$ unit, $R^{20}$ and $R^{21}$ are both hydrogen.

In some embodiments, n is 3, one instance of X is O, and two instances of X are independently selected $CR^{20}R^{21}$, wherein $R^{20}$ and $R^{21}$ are defined herein. In some embodiments, n is 3, one instance of X is $NR^{10}$, and and two instances of X are independently selected $CR^{20}R^{21}$ wherein $R^{10}$, $R^{20}$ and $R^{21}$ are defined herein. In some embodiments, n is 3, and all instances of X are $CR^{20}R^{21}$ as defined herein. In some embodiments, $R^{20}$ and $R^{21}$ are independently hydrogen or $C_{1-4}$ alkyl, or $R^{20}$ and $R^{21}$, together with the carbon they are both attached to, form a $C_{3-6}$ cycloalkyl (preferably cyclopropyl, cyclobutyl, or cyclopentyl), or an oxetanyl ring. In some embodiments, $R^{10}$ is hydrogen or $C_{1-4}$ alkyl. In some embodiments, the compound includes at least one $CR^{20}R^{21}$ unit, wherein:
$R^{20}$ and $R^{21}$ are both methyl;
one of $R^{20}$ and $R^{21}$ is methyl, and the other of $R^{20}$ and $R^{21}$ is ethyl or methoxy; or
$R^{20}$ and $R^{21}$, together with the carbon they are both attached to, form a cyclopropyl, cyclobutyl, or an oxetanyl ring. In some embodiments, in at least one $CR^{20}R^{21}$ unit, one of $R^{20}$ and $R^{21}$ is methyl, and the other of $R^{20}$ and $R^{21}$ is hydrogen. In some embodiments, in at least one $CR^{20}R^{21}$ unit, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

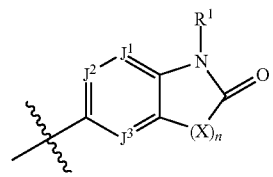

can be selected from the following:

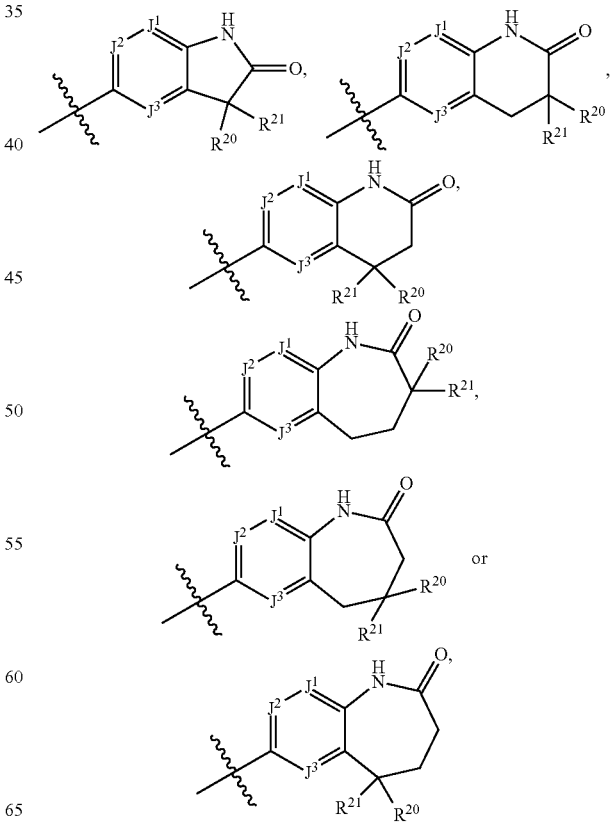

wherein $J^1$, $J^2$, $J^3$, $R^{20}$ and $R^{21}$ are defined herein. In some embodiments, $J^1$ is CH. In some embodiments, $J^2$ is N or $CR^{22}$, wherein $R^{22}$ is defined herein, for example, hydrogen, F, Cl, CN, or methyl. In some embodiments, $J^3$ is CH. In some embodiments, $J^1$ can be $CR^{22}$, $J^2$ can be CH, and $J^3$ can be CH, wherein $R^{22}$ is hydrogen, F, Cl, CN, or $C_{1-4}$ alkyl (preferably methyl). In some embodiments, $J^1$ can be $CR^{22}$, $J^2$ can be $CR^{22}$, and $J^3$ can be CH, wherein $R^{22}$ at each occurrence is independently hydrogen, F, Cl, CN, or $C_{1-4}$ alkyl (preferably methyl). In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;
one of $R^{20}$ and $R^{21}$ is methyl, and the other of $R^{20}$ and $R^{21}$ is ethyl or methoxy; or
$R^{20}$ and $R^{21}$, together with the carbon they are both attached to, form a cyclopropyl, cyclobutyl, or an oxetanyl ring. In some embodiments, in the $CR^{20}R^{21}$ unit, one of $R^{20}$ and $R^{21}$ is methyl, and the other of $R^{20}$ and $R^{21}$ is hydrogen. In some embodiments, in the $CR^{20}R^{21}$ unit, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

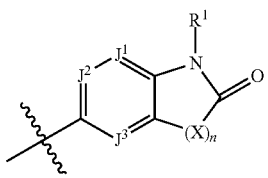

can be selected from the following:

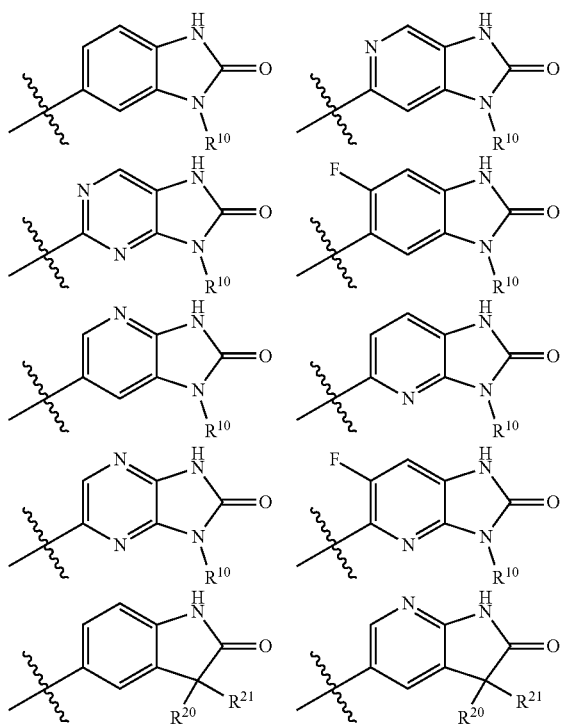

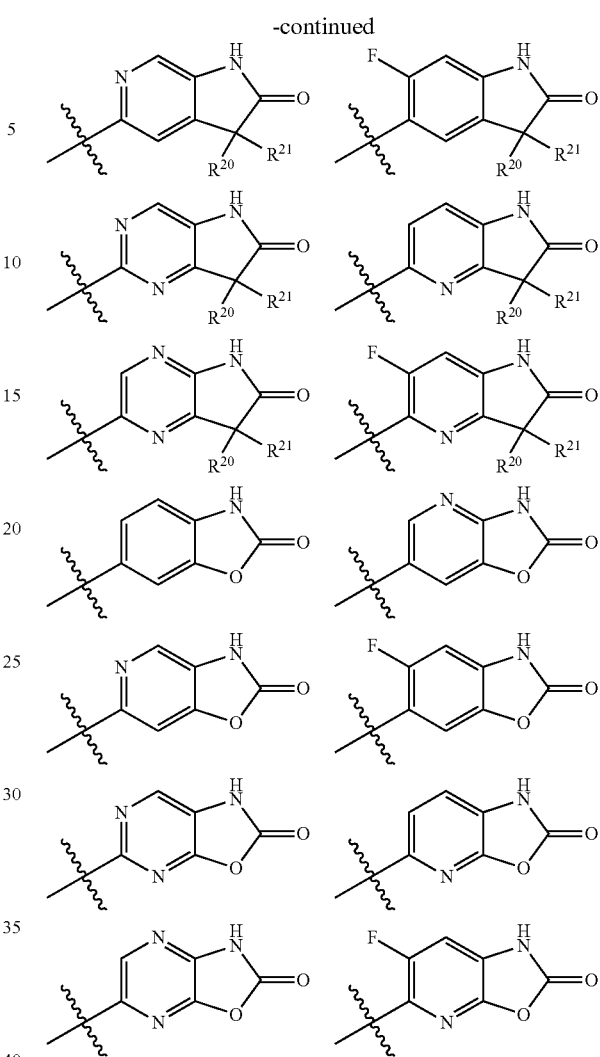

wherein:

$R^{10}$ is independently hydrogen or $C_{1-4}$ alkyl (e.g., methyl, ethyl, etc.);

$R^{20}$ and $R^{21}$ are independently hydrogen or $C_{1-4}$ alkyl (e.g., methyl, ethyl, etc.), or $R^{20}$ and $R^{21}$ together with the carbon they are both attached to, form a cyclopropyl, cyclobutyl, cyclopentyl, or an oxetanyl ring. In some embodiments, one of $R^{20}$ and $R^{21}$ is methyl, and the other of $R^{20}$ and $R^{21}$ is hydrogen. In some embodiments, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

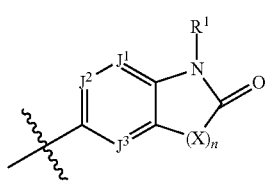

can be selected from the following:

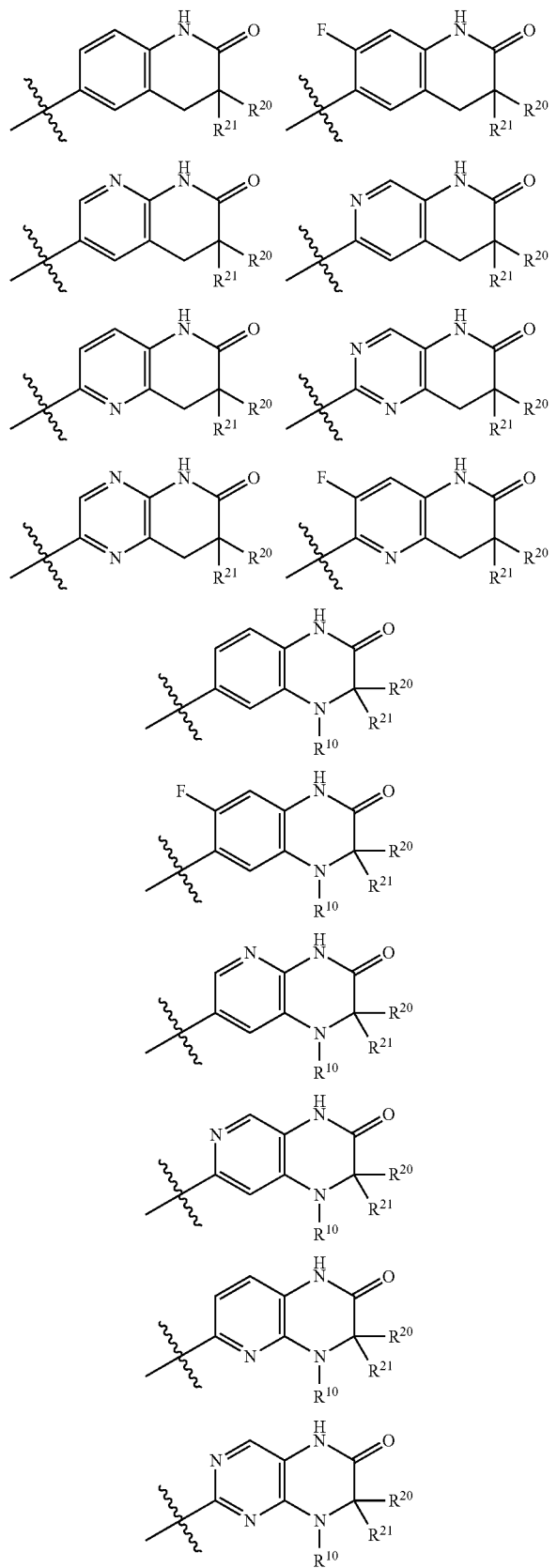
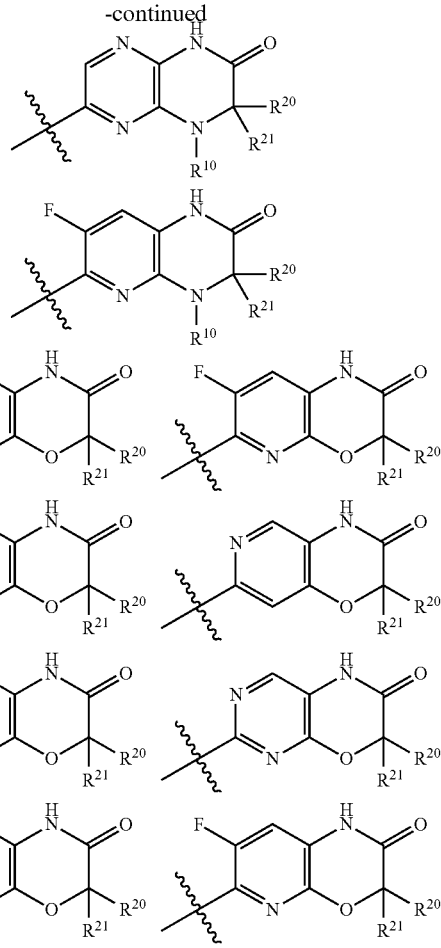

wherein $R^{10}$, $R^{20}$, and $R^{21}$ are defined herein. In some embodiments, $R^{10}$ is independently hydrogen or $C_{1-4}$ alkyl (e.g., methyl, ethyl, etc.). In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;
one of $R^{20}$ and $R^{21}$ is methyl, and the other of $R^{20}$ and $R^{21}$ is ethyl or methoxy; or
$R^{20}$ and $R^{21}$, together with the carbon they are both attached to, form a cyclopropyl, cyclobutyl, or an oxetanyl ring. In some embodiments, one of $R^{20}$ and $R^{21}$ is methyl, and the other of $R^{20}$ and $R^{21}$ is hydrogen. In some embodiments, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

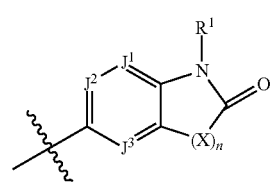

can be selected from the following:

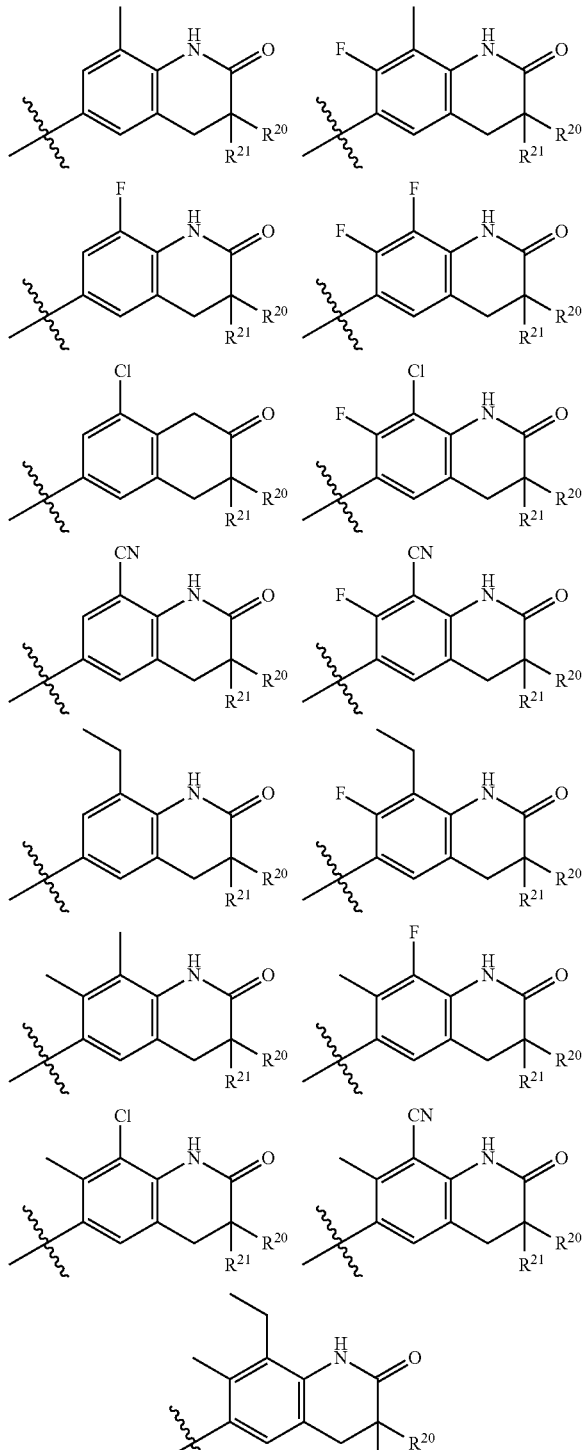

wherein $R^{20}$ and $R^{21}$ are defined herein. In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;

one of $R^{20}$ and $R^{21}$ is methyl, and the other of $R^{20}$ and $R^{21}$ is ethyl or methoxy; or $R^{20}$ and $R^{21}$, together with the carbon they are both attached to, form a cyclopropyl, cyclobutyl, or an oxetanyl ring. In some embodiments, one of $R^{20}$ and $R^{21}$ is methyl, and the other of $R^{20}$ and $R^{21}$ is hydrogen. In some embodiments, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

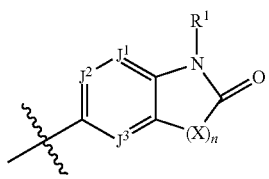

can be selected from the following:

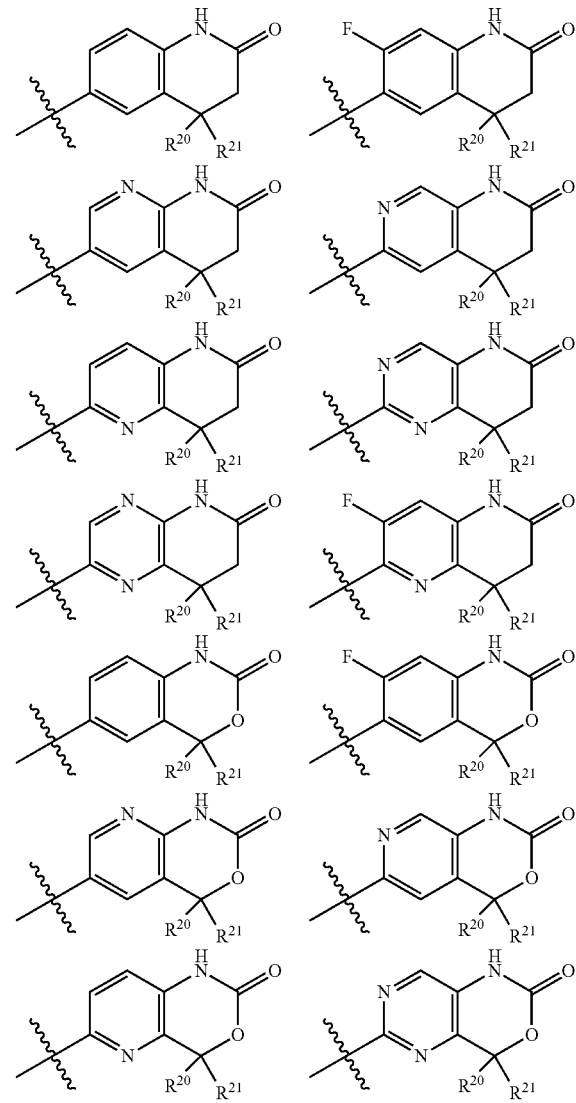

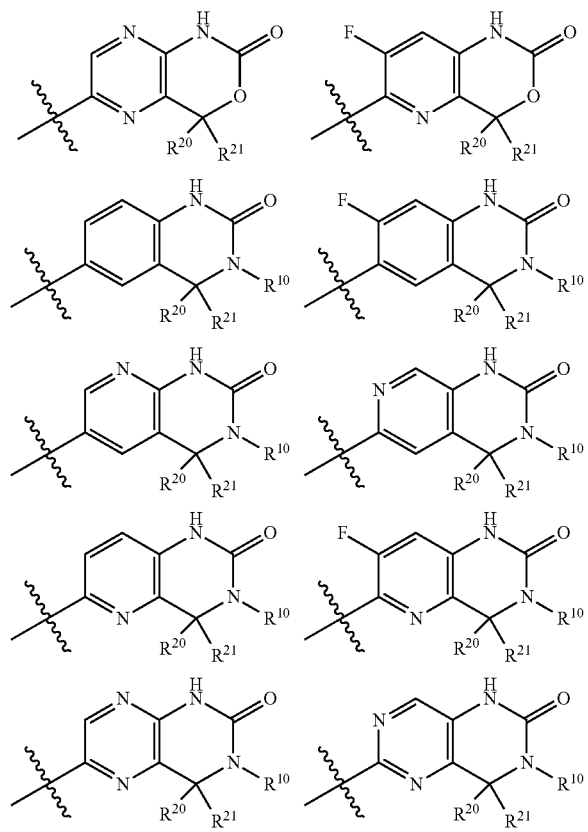

wherein $R^{10}$, $R^{20}$, and $R^{21}$ are defined herein. In some embodiments, $R^{10}$ is independently hydrogen or $C_{1-4}$ alkyl (e.g., methyl, ethyl, etc.). In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;

one of $R^{20}$ and $R^{21}$ is methyl, and the other of $R^{20}$ and $R^{21}$ is ethyl or methoxy; or $R^{20}$ and $R^{21}$, together with the carbon they are both attached to, form a cyclopropyl, cyclobutyl, or an oxetanyl ring. In some embodiments, one of $R^{20}$ and $R^{21}$ is methyl, and the other of $R^{20}$ and $R^{21}$ is hydrogen. In some embodiments, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

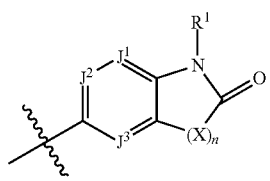

can be selected from the following:

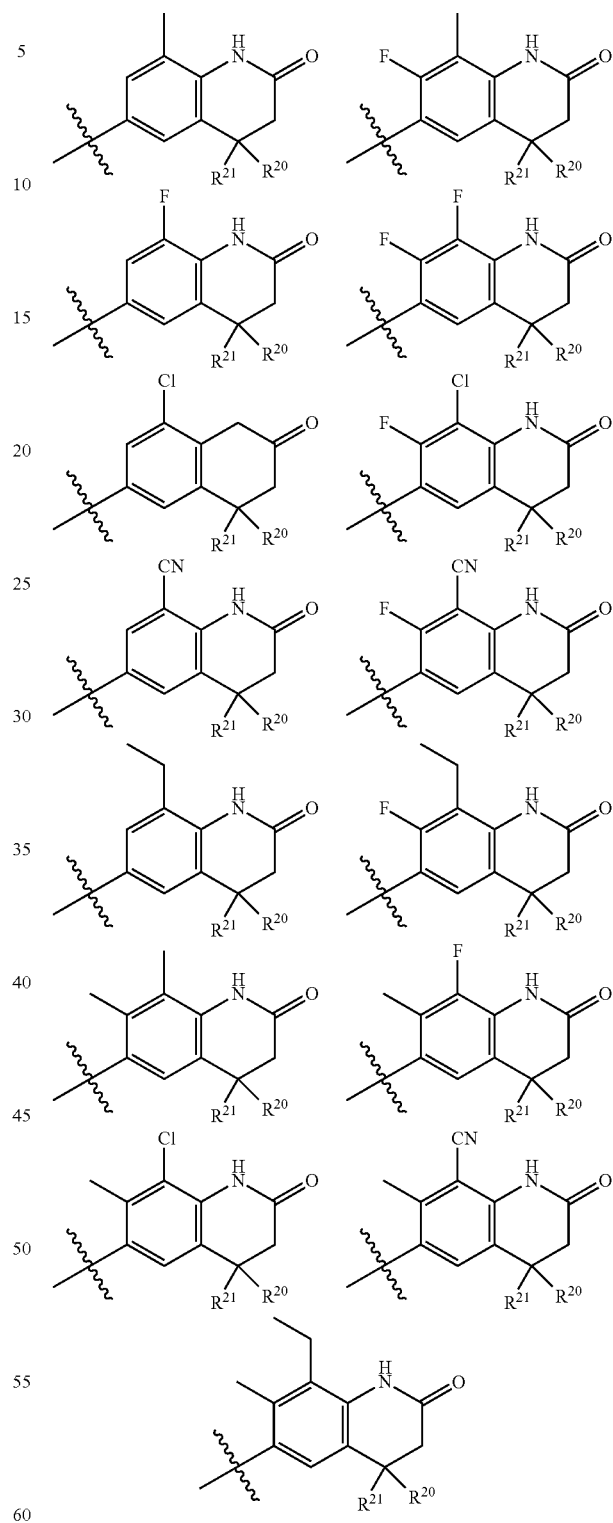

wherein $R^{20}$ and $R^{21}$ are defined herein. In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;

one of $R^{20}$ and $R^{21}$ is methyl, and the other of $R^{20}$ and $R^{21}$ is ethyl or methoxy; or $R^{20}$ and $R^{21}$, together with the carbon they are both attached to, form a cyclopropyl, cyclobutyl, or an oxetanyl ring. In some embodiments, one of $R^{20}$ and $R^{21}$ is methyl, and the other of $R^{20}$ and $R^{21}$ is hydrogen. In some embodiments, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

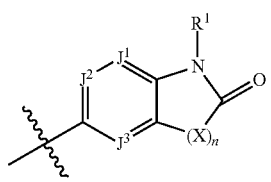

can be selected from the following:

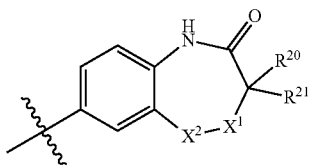

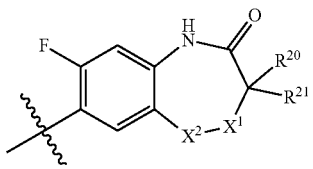

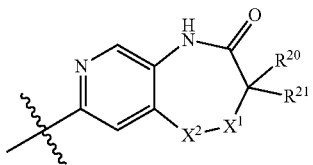

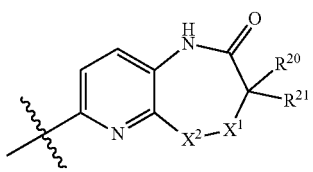

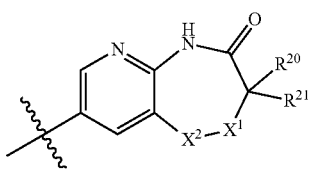

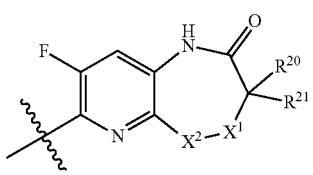

-continued

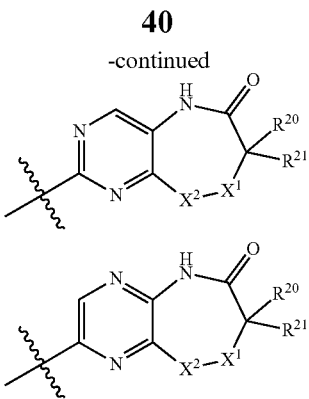

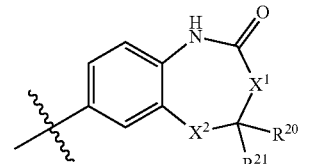

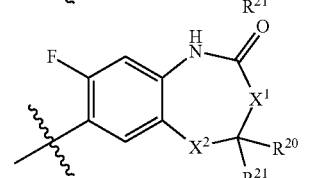

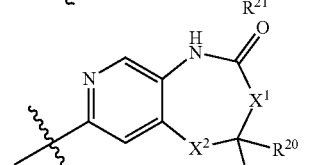

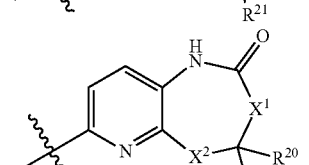

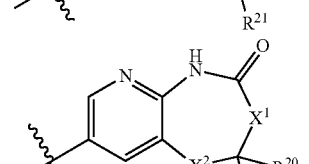

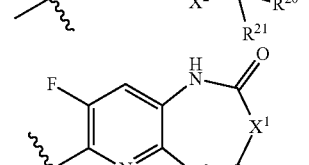

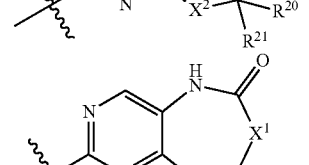

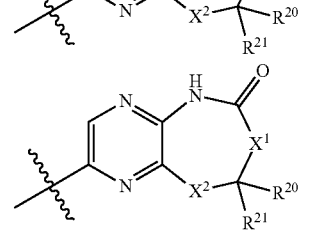

-continued

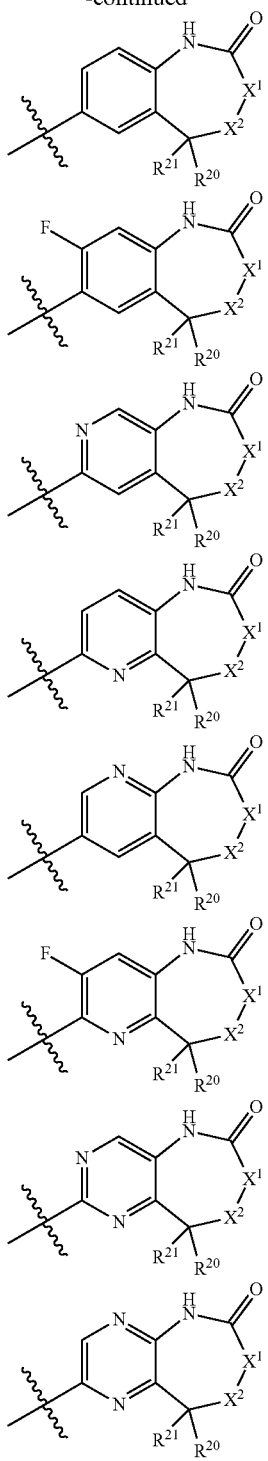

wherein $X^1$ and $X^2$ are independently O, $NR^{10}$, or $CH_2$, provided that at least one of $X^1$ and $X^2$ is $CH_2$; and $R^{10}$, $R^{20}$, and $R^{21}$ are defined herein. In some embodiments, both $X^1$ and $X^2$ are $CH_2$. In some embodiments, one of $X^1$ and $X^2$ is $NR^{10}$. In some embodiments, $R^{10}$ is independently hydrogen or $C_{1-4}$ alkyl (e.g., methyl, ethyl, etc.). In some embodiments, $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring. In some embodiments, in the $CR^{20}R^{21}$ unit:

$R^{20}$ and $R^{21}$ are both methyl;

one of $R^{20}$ and $R^{21}$ is methyl, and the other of $R^{20}$ and $R^{21}$ is ethyl or methoxy; or $R^{20}$ and $R^{21}$, together with the carbon they are both attached to, form a cyclopropyl, cyclobutyl, or an oxetanyl ring. In some embodiments, in the $CR^{20}R^{21}$ unit, one of $R^{20}$ and $R^{21}$ is methyl, and the other of $R^{20}$ and $R^{21}$ is hydrogen. In some embodiments, in the $CR^{20}R^{21}$ unit, $R^{20}$ and $R^{21}$ are both hydrogen.

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

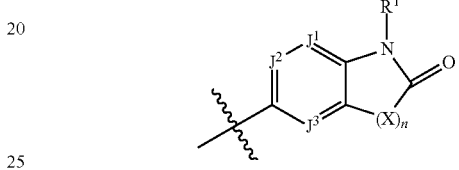

can be selected from the following:

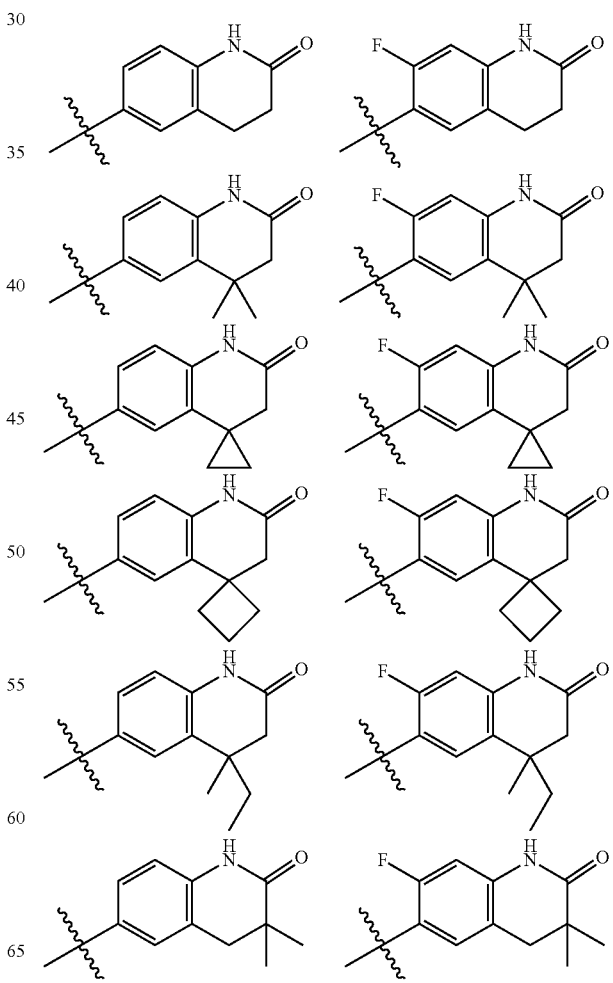

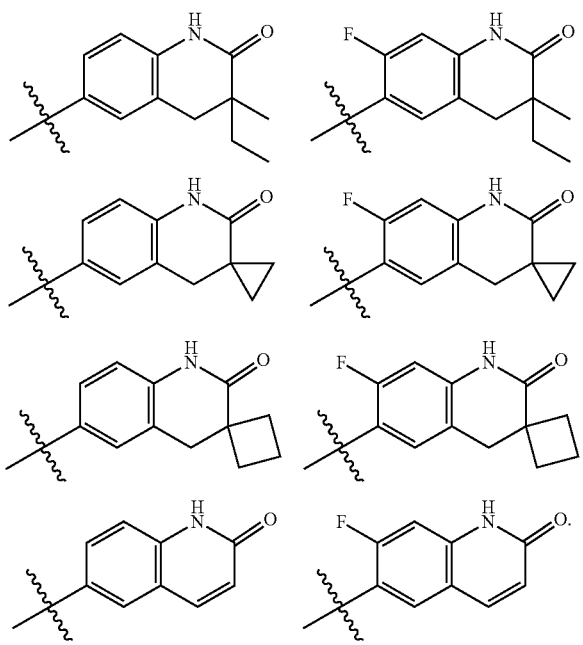
In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the
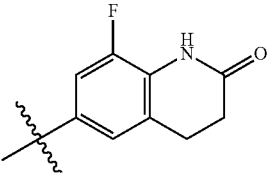
can be selected from the following:
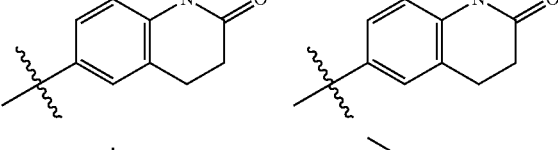
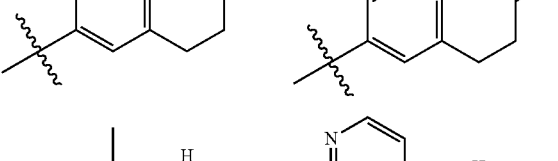
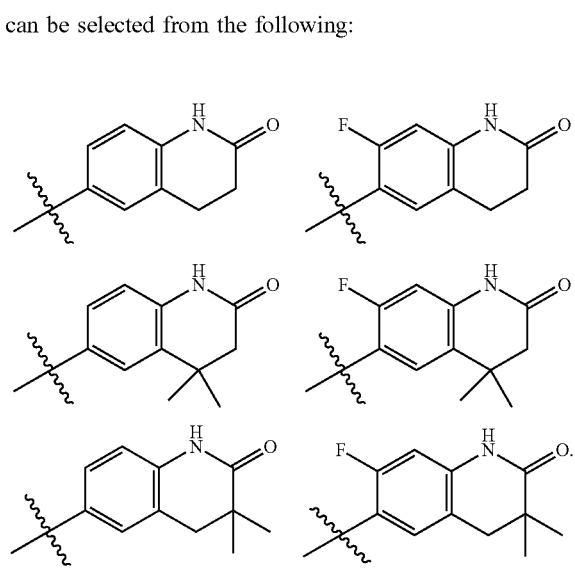
In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the
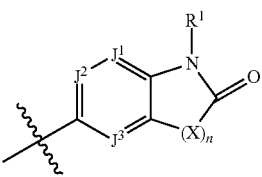
can be selected from the following:
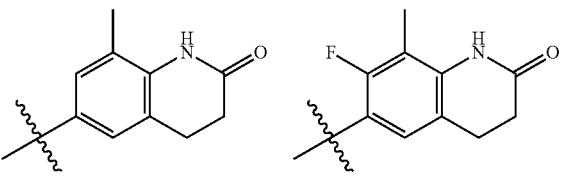
In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the
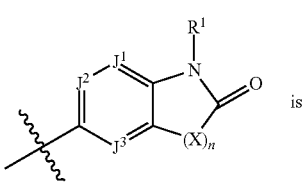 is

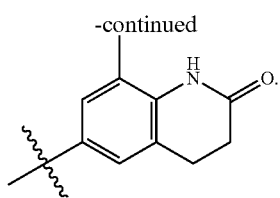

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

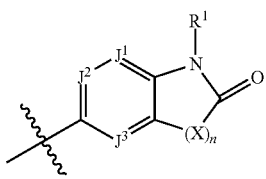

can be selected from the following:

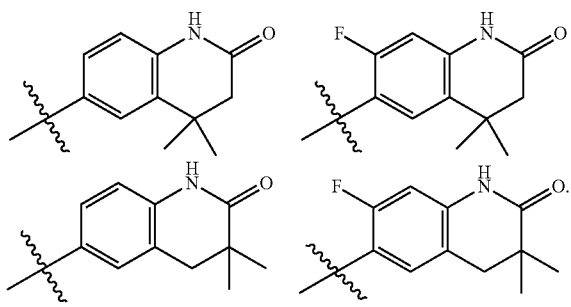

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

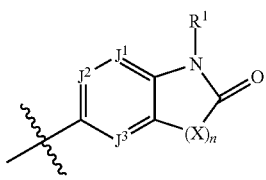

can be selected from the following:

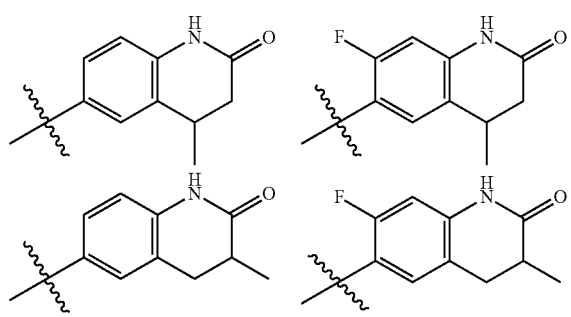

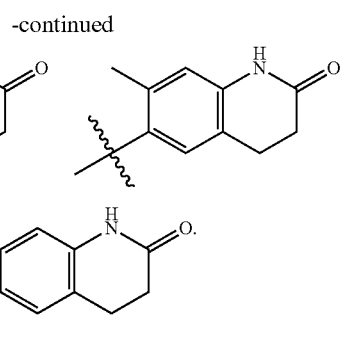

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

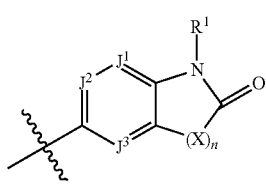

can be selected from the following:

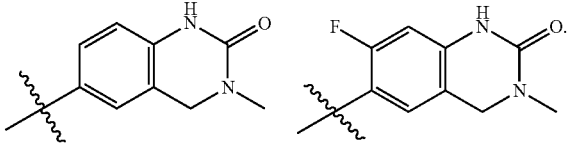 [SMILES: *c1ccc2c(c1)CN(C)C(=O)N2 ; *c1cc2c(cc1F)NC(=O)N(C)C2]

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

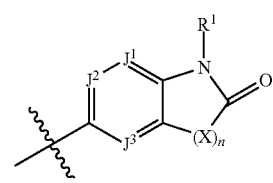

can be selected from the following:

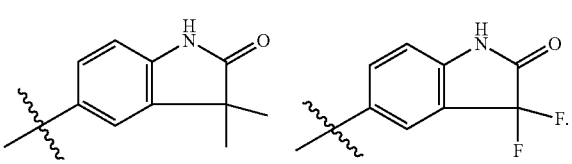 [SMILES: *c1ccc2c(c1)C(C)(C)C(=O)N2 ; *c1ccc2c(c1)C(F)(F)C(=O)N2]

In some embodiments, in Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), the

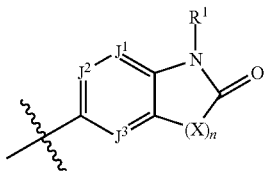 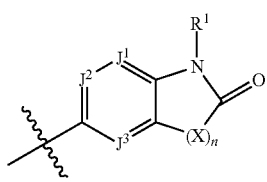

can be any of the corresponding moieties shown in Compound Nos. 139-202, or 139-165 disclosed herein, as applicable.

In some embodiments, the present disclosure also provides a compound of Formula I-P, or a pharmaceutically acceptable salt thereof:

Formula I-P

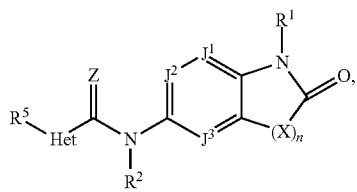

wherein Het represents an optionally substituted heterocyclic or heteroaryl ring structure, preferably, 5 or 6 membered heterocyclic ring or 5 or 6 membered heteroaryl ring, wherein $R^1$, $R^2$, $R^5$, $J^1$, $J^2$, $J^3$, X, and n can be any of those defined herein for Formula I (including its subformulae). Preferably, when Z is O, Het is a 5 or 6 membered heteroaryl, and in Formula I-P, $R^5$ is attached to the Het at an ortho position of —C(=Z)—. It will also be understood that in Formula I-P, $R^5$ can be attached to a ring nitrogen as valance permits.

In some embodiments, in Formula I-P, Z is O, $R^2$ is hydrogen or methyl,

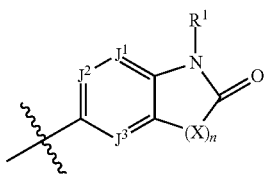

and $R^5$ can be any of those described for Formula I (including its subformulae), and Het is an optionally substituted 5 or 6 membered heteroaryl described herein, for example, Het is a 5 or 6 membered heteroaryl, preferably, a pyrazole, imidazole, oxazole, thiazole, isoxazole, isothiazole, pyridyl, pyrimidinyl, pyridazinyl, or pyrazinyl, which is optionally substituted with one or two (preferably one) substituents independently selected from F; Cl; $C_{1-4}$ alkyl optionally substituted with 1-3 fluorines, preferably, methyl, ethyl, n-propyl, isopropyl, or —CF$_3$; a $C_{1-4}$ alkoxy optionally substituted with 1-3 fluorines, preferably, methoxy, ethoxy, n-propoxy, isopropoxy, or —OCF$_3$; a $C_{3-6}$ cycloalkoy optionally substituted with 1-3 substituents independently selected from fluorine and methyl; a $C_{3-6}$ cycloalkyl optionally substituted with 1-3 substituents independently selected from fluorine and methyl, preferably, cyclopropyl or cyclobutyl; and —CN. In some embodiments in Formula I-P can be selected from the following:

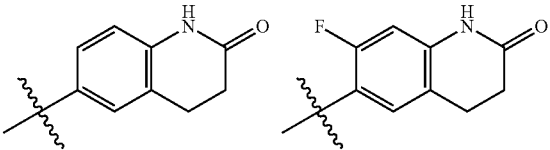
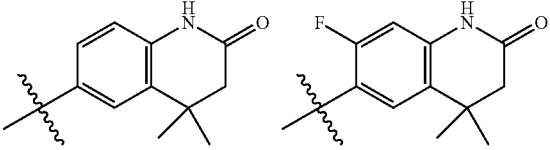
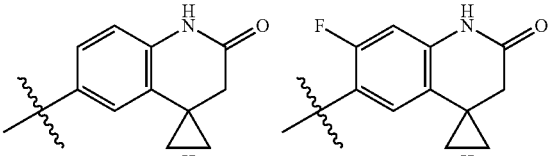
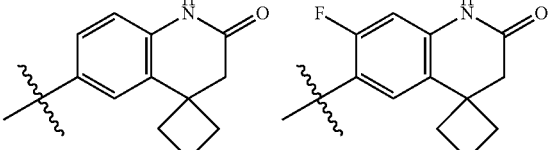
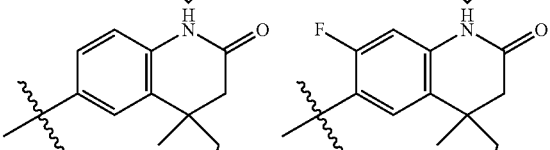
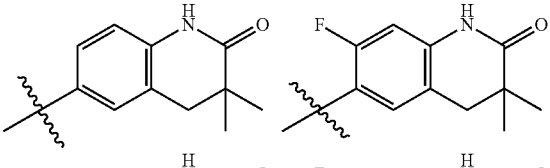
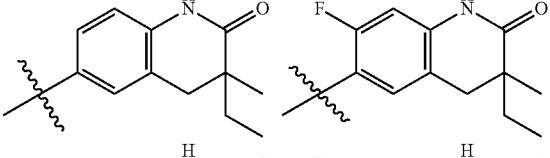
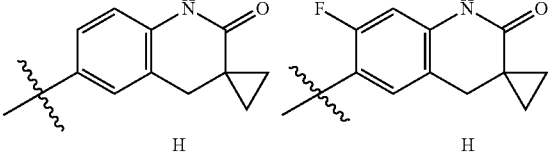
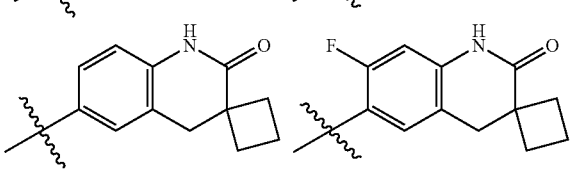

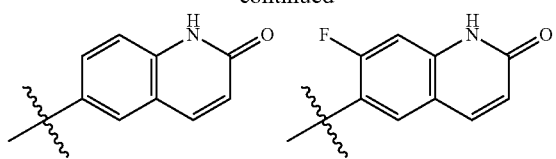
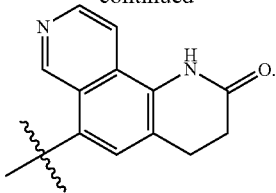
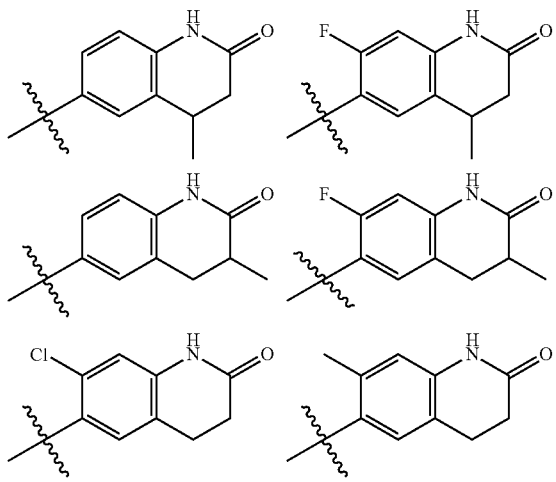
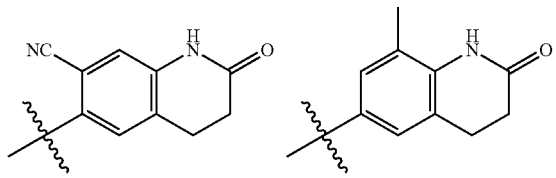
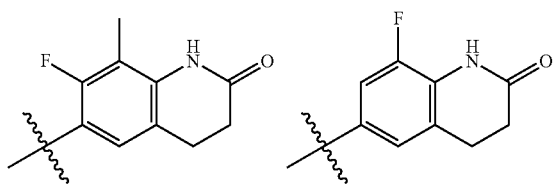
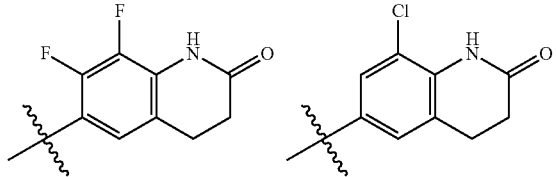
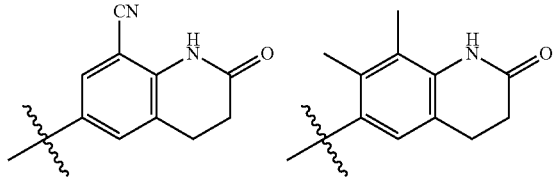
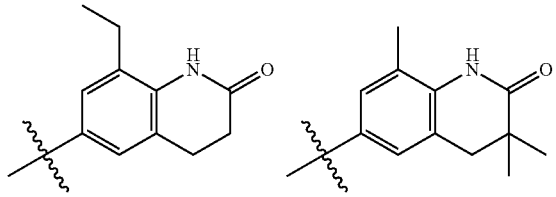

In some embodiments, $R^5$ in Formula I-P is —O—$R^{30}$ or —$CR^{23}R^{24}R^{25}$ as defined herein. In some embodiments, $R^5$ in Formula I-P is ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$-cyclobutyl, —$CH_2$—O—$CH_3$, —$CH_2$—O—$C_2H_5$, —$CH_2$—O-n-propyl, —$CH_2$—O-iso-propyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl.

Formula II

Some embodiments of the present disclosure are directed to compounds of Formula II, or a pharmaceutically acceptable salt thereof:

Formula II

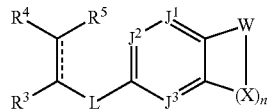

wherein:
W is —N($R^1$)—C(O)—, —N($R^1$)—S(O)—, or —N($R^1$)—S(O)$_2$—;
L is —($CR^{A1}R^{B1}$)$_{t1}$-$Q^1$-$Q^2$-$Q^3$-($CR^{A2}R^{B2}$)$_{t2}$—, wherein:
$Q^1$ and $Q^3$ are independently null, O or $NR^2$;
$Q^2$ is null, —C(O)—, —C(=Z)—, —S(O)—, or —S(O)$_2$—;
t1 is 0, 1, 2, or 3;
t2 is 0, 1, 2, or 3; and
$R^{A1}$, $R^{B1}$, $R^{A2}$, and $R^{B2}$ at each occurrence are independently hydrogen, $C_{1-4}$ alkyl (e.g., methyl), or fluorine, or
two adjacent $CR^{A1}R^{B1}$ or two adjacent $CR^{A2}R^{B2}$ can form —C($R^{A1}$)=C($R^{B1}$)—, —C($R^{A2}$)=C($R^{B2}$)—, or

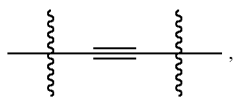

wherein $R^{A1}$, $R^{B1}$, $R^{A2}$, and $R^{B2}$ at each occurrence are independently hydrogen, $C_{1-4}$ alkyl (e.g., methyl), or fluorine;
X at each occurrence is independently selected from O, $NR^{10}$, and $CR^{20}R^{21}$, provided that at most one X is selected from O and $NR^{10}$;
n is 1, 2, 3, or 4;
$J^1$, $J^2$, and $J^3$ are each independently selected from $CR^{22}$ or N, preferably, at least one of $J^1$, $J^2$, and $J^3$ is not N;
$R^1$ and $R^2$ at each occurrence are each independently hydrogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), or a nitrogen protecting group;

$R^3$ and $R^4$ are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring);

$R^5$ is hydrogen, $-NR^{11}R^{12}$, $-CR^{23}R^{24}R^{25}$, or $-OR^{30}$;

$R^3$, $R^4$ and $R^5$ are joined to form an optionally substituted bicyclic or polycyclic ring system, wherein the ring system is an aryl, heteroaryl, carbocyclic, or heterocyclic ring system; or when $Q^2$ is $-C(=Z)-$, $R^5$ and Z are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring);

"$=$" in Formula II indicates the bond is an aromatic bond, a double bond or a single bond as valance permits, and when a single bond, the two carbons forming the bond can be optionally further substituted as valance permits;

wherein:

$R^{10}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring;

$R^{20}$ and $R^{21}$ at each occurrence are each independently hydrogen, halogen, $-OR^{31}$, $-NR^{13}R^{14}$, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{10}$ and one of $R^{20}$ and $R^{21}$ are joined to form a bond, an optionally substituted 4-8 membered heterocyclic ring or an optionally substituted 5 or 6 membered heteroaryl ring, wherein the other of $R^{20}$ and $R^{21}$ is defined above;

$R^{20}$ and $R^{21}$ together with the carbon they are both attached to form $-C(O)-$, an optionally substituted $C_{3-8}$ carbocyclic ring, or an optionally substituted 3-8 membered heterocyclic ring; or one of $R^{20}$ and $R^{21}$ in one $CR^{20}R^{21}$ is joined with one of $R^{20}$ and $R^{21}$ in a different $CR^{20}R^{21}$ to form a bond, an optionally substituted $C_{3-8}$ carbocyclic ring, an optionally substituted 3-8 membered heterocyclic ring, wherein the others of $R^{20}$ and $R^{21}$ are defined above;

$R^{22}$ at each occurrence is independently hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), $-CN$, $-S(O)$-alkyl, $-S(O)_2$-alkyl, or $-OR^{31}$; or two adjacent $R^{22}$ are joined to form an optionally substituted ring structure, such as an optionally substituted $C_{3-8}$ carbocyclic ring, optionally substituted 4-8 membered heterocyclic ring, optionally substituted phenyl, or optionally substituted 5 or 6 membered heteroaryl ring;

one of $R^{11}$ and $R^{12}$ is hydrogen or a nitrogen protecting group, and the other of $R^{11}$ and $R^{12}$ is hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl;

one of $R^{23}$, $R^{24}$, and $R^{25}$ is hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, an optionally substituted 5-10 membered heteroaryl, $-OR^{31}$, or $-NR^{13}R^{14}$, and the other two of $R^{23}$, $R^{24}$, and $R^{25}$ are independently selected from hydrogen, fluorine, or methyl, preferably, $-CR^{23}R^{24}R^{25}$ is not $-CH_3$;

$R^{30}$ is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring; and wherein:

each of $R^{13}$ and $R^{14}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{13}$ and $R^{14}$ are joined to form a 3-8 membered optionally substituted heterocyclic or a 5-10 membered optionally substituted heteroaryl; and $R^{31}$ at each occurrence is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl.

Typically, in Formula II, the variables $R^3$, $R^4$, $R^5$, $J^1$, $J^2$, $J^3$, X, and n can be any of those described hereinabove in connection with Formula I and its subformulae. For example, in some embodiments, $R^3$ and $R^4$ in Formula II are joined to form an optionally substituted phenyl, an optionally substituted 5 or 6-membered heteroaryl, e.g., having one or two ring nitrogen atoms, an optionally substituted $C_{4-7}$ cycloalkyl group (preferably cyclopentyl or cyclohexyl), or an optionally substituted 4 to 7-membered (preferably 6-membered) heterocyclic ring having one or two ring heteroatoms. In some embodiments, the moiety of

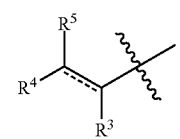

in Formula II is

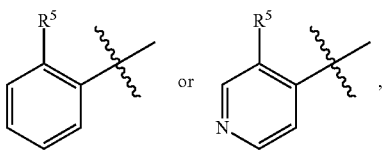

wherein R⁵ is defined herein, and wherein the phenyl or pyridyl can be further optionally substituted at any available position, for example, with one or two substituents independently selected from F; Cl; $C_{1-4}$ alkyl optionally substituted with 1-3 fluorines, preferably, methyl, ethyl, n-propyl, isopropyl, or —CF₃; a $C_{1-4}$ alkoxy optionally substituted with 1-3 fluorines, preferably, methoxy, ethoxy, n-propoxy, isopropoxy, or —OCF₃; a $C_{3-6}$ cycloalkyl optionally substituted with 1-3 substituents independently selected from fluorine and methyl, preferably, cyclopropyl or cyclobutyl; and —CN. In some embodiments, R⁵ is —O—R³⁰ or —CR²³R²⁴R²⁵ as defined herein. In some embodiments, R⁵ is ethyl, n-propyl, isopropyl, n-butyl, isobutyl, sec-butyl, —CH₂—CHF₂, —CH₂—CF₃, —CF₃, —CH₂-cyclopropyl, —CH₂-cyclobutyl, —CH₂—O—CH₃, —CH₂—O—C₂H₅, —CH₂—O-n-propyl, —CH₂—O-isopropyl, —C₂H₄-cyclopropyl, —C₂H₄-cyclobutyl, methoxy, ethoxy, n-propoxy, isopropoxy, n-butoxy, isobutoxy, sec-butoxy, —O—CH₂—CF₃, —O—CF₃, —O—CH₂-cyclopropyl, —O—CH₂-cyclobutyl, —O—C₂H₄-cyclopropyl, or —O—C₂H₄-cyclobutyl. In some embodiments, n is 2. In some embodiments, J¹ is CH. In some embodiments, J² is N or CR²², wherein R²² is defined herein. In some embodiments, R²² is hydrogen, F, Cl, CN, or methyl. In some embodiments, J³ is CH. In some embodiments, J¹ can be CR²², J² can be CH, and J³ can be CH, wherein R²² is hydrogen, F, Cl, CN, or $C_{1-4}$ alkyl (preferably methyl). In some embodiments, J¹ can be CR²², J² can be CR²², and J³ can be CH, wherein R²² at each occurrence is independently hydrogen, F, Cl, CN, or $C_{1-4}$ alkyl (preferably methyl). In some embodiments, each instance of X in Formula II is independently selected CR²⁰R²¹, and R²⁰ and R²¹ are independently hydrogen or $C_{1-4}$ alkyl (e.g., methyl, ethyl, etc.), or R²⁰ and R²¹, together with the carbon they are both attached to, form a cyclopropyl, cyclobutyl, cyclopentyl, or an oxetanyl ring. In some embodiments, in the CR²⁰R²¹ unit:

R²⁰ and R²¹ are both methyl;

one of R²⁰ and R²¹ is methyl, and the other of R²⁰ and R²¹ is ethyl or methoxy; or R²⁰ and R²¹, together with the carbon they are both attached to, form a cyclopropyl, cyclobutyl, or an oxetanyl ring. In some embodiments, in the CR²⁰R²¹ unit, one of R²⁰ and R²¹ is methyl, and the other of R²⁰ and R²¹ is hydrogen. In some embodiments, in the CR²⁰R²¹ unit, R²⁰ and R²¹ are both hydrogen.

W in Formula II is typically —N(R¹)—C(O)— or —N(R¹)—S(O)₂—, wherein either the nitrogen atom or the C(O)— or S(O)₂— can be directly attached to an X, in other words, the expression is bi-directional. Typically, R¹ is hydrogen or a $C_{1-4}$ alkyl. For example, in some embodiments, the compound of Formula II can have a Formula II-1, II-2, II-3, or II-4:

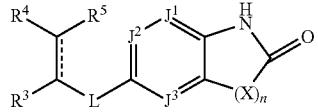

Formula II-1

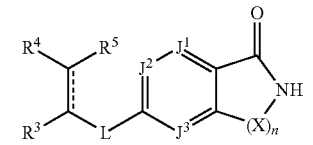

Formula II-2

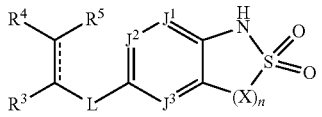

Formula II-3

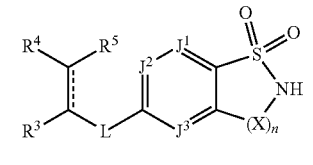

Formula II-4 wherein R³, R⁴, R⁵, L, J¹, J², J³, X, and n are defined herein.

L in Formula II (e.g., Formula II-1, II-2, II-3, or II-4) is typically —(CR^{A1}R^{B1})_{t1}-Q¹-Q²-Q³-(CR^{A2}R^{B2})_{t2}—, wherein:

(1) Q² is —C(O)—, one of Q¹ and Q³ is null, the other of Q¹ and Q³ is NR² as defined herein, t1 is 0 or 1, and t2 is 0 or 1, preferably, both t1 and t2 are 0, R² is hydrogen or methyl;

(2) Q¹, Q² and Q³ are null, t1 is 0, t2 is 2, and two adjacent CR^{A2}R^{B2} form —C(R^{A2})=C(R^{B2})— as defined herein, preferably, R^{A2} and R^{B2} are both hydrogen; or (3) Q² is null, and one of Q¹ and Q³ is null, the other of Q¹ and Q³ is NR² as defined herein, t1 is 0 or 1, and t2 is 0 or 1, preferably, R² is hydrogen or methyl, and t1 and t2 are not both 0.

It should also be noted that the bivalent linker L, —(CR^{A1}R^{B1})_{t1}-Q¹-Q²-Q³-(CR^{A2}R^{B2})_{t2}—, in Formula II can link the remaining structures in either direction. For example, the

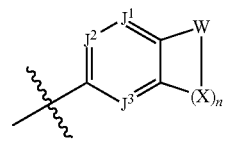

unit can be directly attached to the —(CR^{A1}R^{B1})_{t1} end of the linker or the (CR^{A2}2R^{B2})_{t2}— end of the linker. In some embodiments, a NR² is directly linked to the

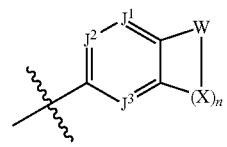

unit.

In some embodiments, the

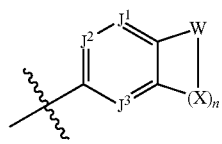

unit in Formula II (e.g., Formula II-1, II-2, II-3, or II-4) can be selected from any of those described as suitable

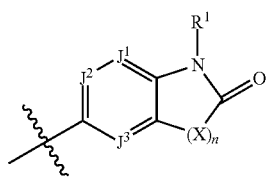

in connection with Formula I herein, for example,

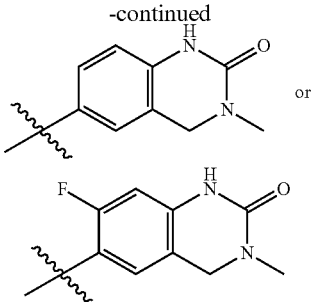

or selected from:

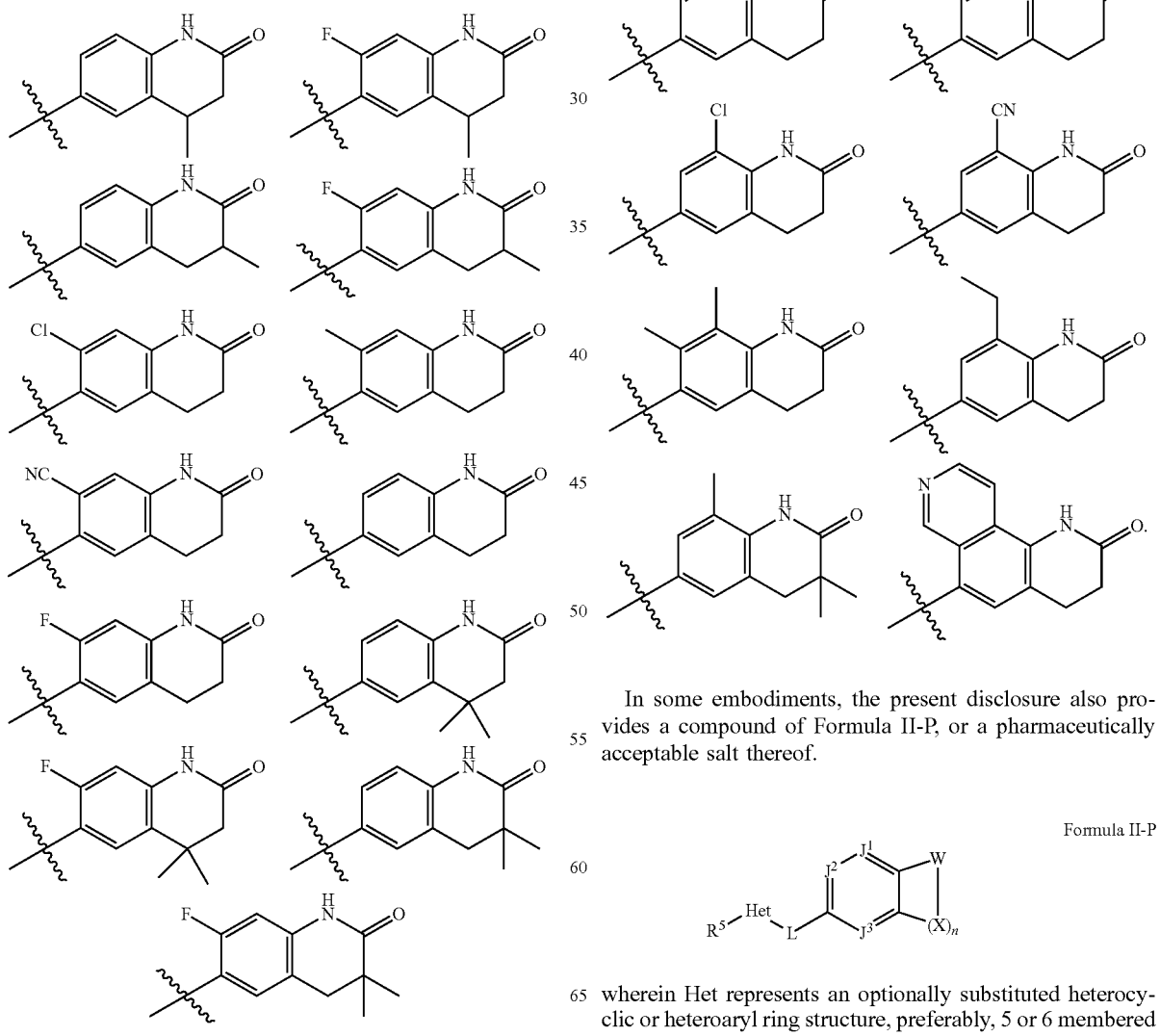

In some embodiments, the present disclosure also provides a compound of Formula II-P, or a pharmaceutically acceptable salt thereof.

Formula II-P

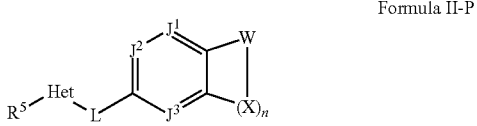

wherein Het represents an optionally substituted heterocyclic or heteroaryl ring structure, preferably, 5 or 6 membered heterocyclic ring or 5 or 6 membered heteroaryl ring, wherein $R^5$, $J^1$, $J^2$, $J^3$, L, W, X, and n can be any of those defined herein for Formula II (including its subformulae). Preferably, Het is a 5 or 6 membered heteroaryl, and in Formula II-P, $R^5$ is attached to the Het at an ortho position of the linker L. It will also be understood that in Formula II-P, $R^5$ can be attached to a ring nitrogen as valance permits.

In some embodiments, in Formula II-P, Het is an optionally substituted 5 or 6 membered heteroaryl described herein, for example, Het is a 5 or 6 membered heteroaryl, preferably, a pyrazole, imidazole, oxazole, thiazole, isoxazole, isothiazole, pyridyl, pyrimidinyl, pyridazinyl, or pyrazinyl, which is optionally substituted with one or two (preferably one) substituents independently selected from F; Cl; $C_{1-4}$ alkyl optionally substituted with 1-3 fluorines, preferably, methyl, ethyl, n-propyl, isopropyl, or —$CF_3$; a $C_{1-4}$ alkoxy optionally substituted with 1-3 fluorines, preferably, methoxy, ethoxy, n-propoxy, isopropoxy, or —$OCF_3$; a $C_{3-6}$ cycloalkoy optionally substituted with 1-3 substituents independently selected from fluorine and methyl; a $C_{3-6}$ cycloalkyl optionally substituted with 1-3 substituents independently selected from fluorine and methyl, preferably, cyclopropyl or cyclobutyl; and —CN. In some embodiments, $R^5$ is —O—$R^{30}$ or —$CR^{23}R^{24}R^{25}$ as defined herein. In some embodiments, $R^5$ is ethyl, n-propyl, isopropyl, n-butyl, isobutyl, sec-butyl, —$CH_2$—$CHF_2$, —$CH_2$—$CF_3$, —$CF_3$, —$CH_2$-cyclopropyl, —$CH_2$-cyclobutyl, —$CH_2$—O—$CH_3$, —$CH_2$—O—$C_2H_5$, —$CH_2$—O-n-propyl, —$CH_2$—O-isopropyl, —$C_2H_4$-cyclopropyl, —$C_2H_4$-cyclobutyl, methoxy, ethoxy, n-propoxy, isopropoxy, n-butoxy, isobutoxy, sec-butoxy, —O—$CH_2$—$CF_3$, —O—$CF_3$, —O—$CH_2$-cyclopropyl, —O—$CH_2$-cyclobutyl, —O—$C_2H_4$-cyclopropyl, or —O—$C_2H_4$-cyclobutyl. In some embodiments, the

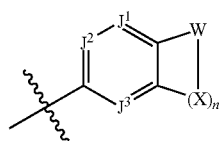

unit in Formula II-P can be selected from the following:

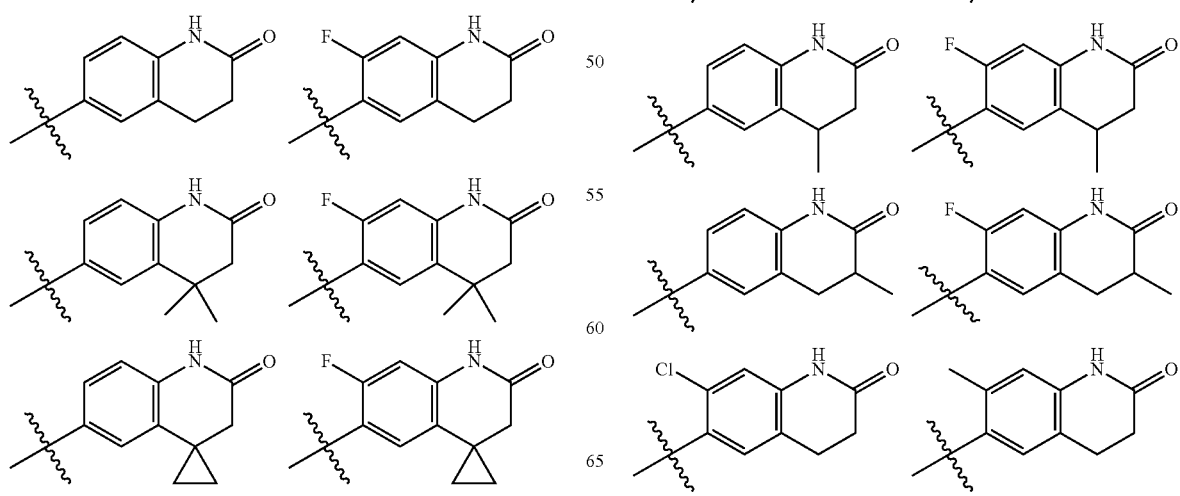

-continued

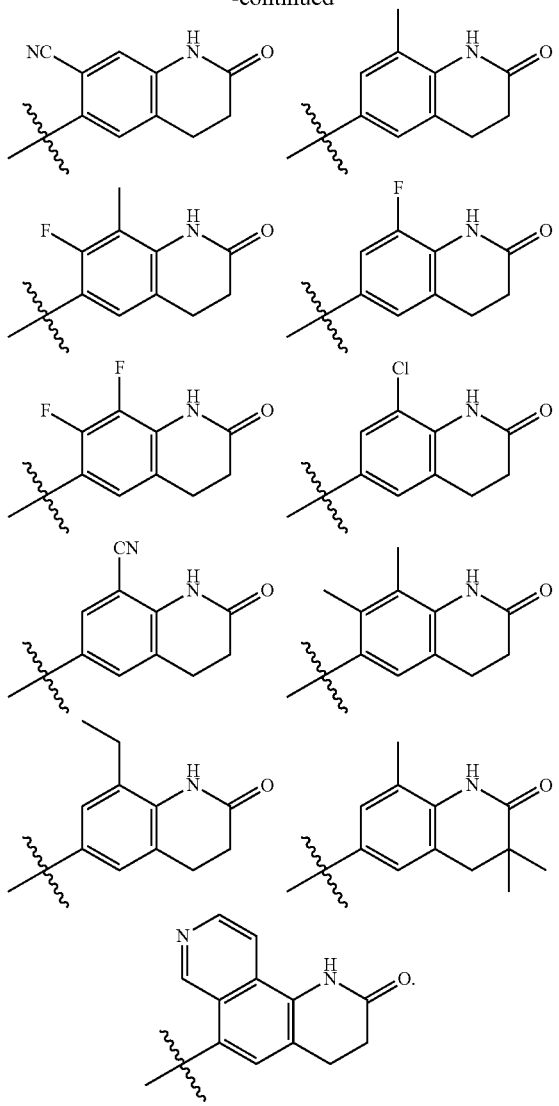

Formula III

In some embodiments, the present disclosure provides a compound of Formula III, or a pharmaceutically acceptable salt thereof:

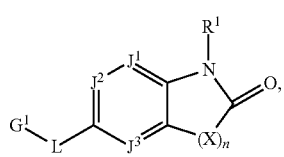

Formula III wherein:
X at each occurrence is independently selected from O, NR$^{10}$, and CR$^{20}$R$^{21}$, provided that at most one X is selected from O and NR$^{10}$;
n is 1, 2, 3, or 4;
J$^1$, J$^2$, and J$^3$ are each independently selected from CR$^{22}$ or N, preferably, at least one of J$^1$, J$^2$, and J$^3$ is not N;
R$^1$ is hydrogen, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), or a nitrogen protecting group;
L is NH, O, or selected from:

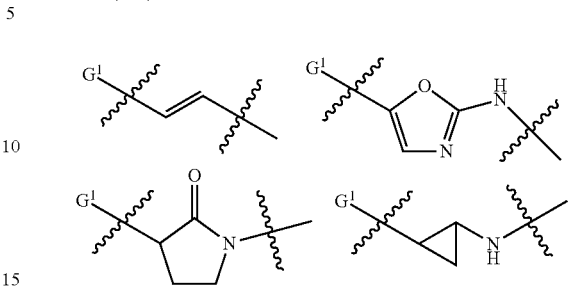

G$^1$ is an optionally substituted phenyl, optionally substituted heteroaryl (e.g., 5- or 6-membered heteroaryl, or 8-10 membered bicyclic heteroaryl), or an optionally substituted heterocyclyl, wherein:
R$^{10}$ at each occurrence is independently hydrogen, a nitrogen protecting group, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), an optionally substituted C$_{3-8}$ carbocyclic ring, or an optionally substituted 3-8 membered heterocyclic ring;
R$^{20}$ and R$^{21}$ at each occurrence are each independently hydrogen, halogen, —OR$^{31}$, —NR$^{13}$R$^{14}$, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), an optionally substituted C$_{3-8}$ carbocyclic ring, an optionally substituted 3-8 membered heterocyclic ring, an optionally substituted phenyl, or an optionally substituted 5-10 membered heteroaryl; or
R$^{10}$ and one of R$^{20}$ and R$^{21}$ are joined to form a bond, an optionally substituted 4-8 membered heterocyclic ring or an optionally substituted 5 or 6 membered heteroaryl ring, wherein the other of R$^{20}$ and R$^{21}$ is defined above;
R$^{20}$ and R$^{21}$ together with the carbon they are both attached to form —C(O)—, an optionally substituted C$_{3-8}$ carbocyclic ring, or an optionally substituted 3-8 membered heterocyclic ring; or one of R$^{20}$ and R$^{21}$ in one CR$^{20}$R$^{21}$ is joined with one of R$^{20}$ and R$^{21}$ in a different CR$^{20}$R$^{21}$ to form a bond, an optionally substituted C$_{3-8}$ carbocyclic ring, an optionally substituted 3-8 membered heterocyclic ring, wherein the others of R$^{20}$ and R$^{21}$ are defined above;
R$^{22}$ at each occurrence is independently hydrogen, halogen, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), —CN, —S(O)-alkyl (e.g., —S(O)—C$_{1-6}$ alkyl), —S(O)$_2$-alkyl (e.g., —S(O)$_2$—C$_{1-6}$ alkyl), or —OR$^{31}$; or two adjacent R$^{22}$ are joined to form an optionally substituted ring structure, such as an optionally substituted C$_{3-8}$ carbocyclic ring, optionally substituted 4-8 membered heterocyclic ring, optionally substituted phenyl, or optionally substituted 5 or 6 membered heteroaryl ring;
wherein:
each of R$^{13}$ and R$^{14}$ at each occurrence is independently hydrogen, a nitrogen protecting group, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{13}$ and $R^{14}$ are joined to form a 3-8 membered optionally substituted heterocyclic or a 5-10 membered optionally substituted heteroaryl; and $R^{31}$ at each occurrence is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl.

In some embodiments, the compound of Formula III can have a Formula III-1 or III-2:

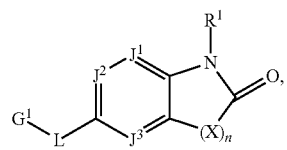

Formula III-1

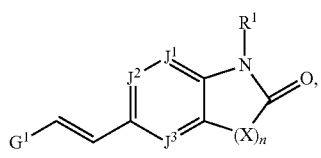

Formula III-2 wherein $R^1$, $G^1$, $J^1$, $J^2$, $J^3$, X, and n are defined herein.

In some embodiments,

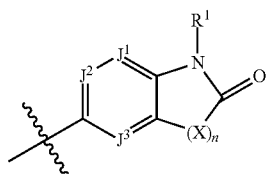

in Formula III (e.g., III-1 or III-2) can be any of those described for Formula I (including its subformulae). For example, in some embodiments,

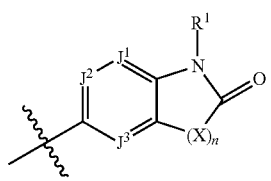

in Formula III (e.g., III-1 or III-2) can be selected from the following:

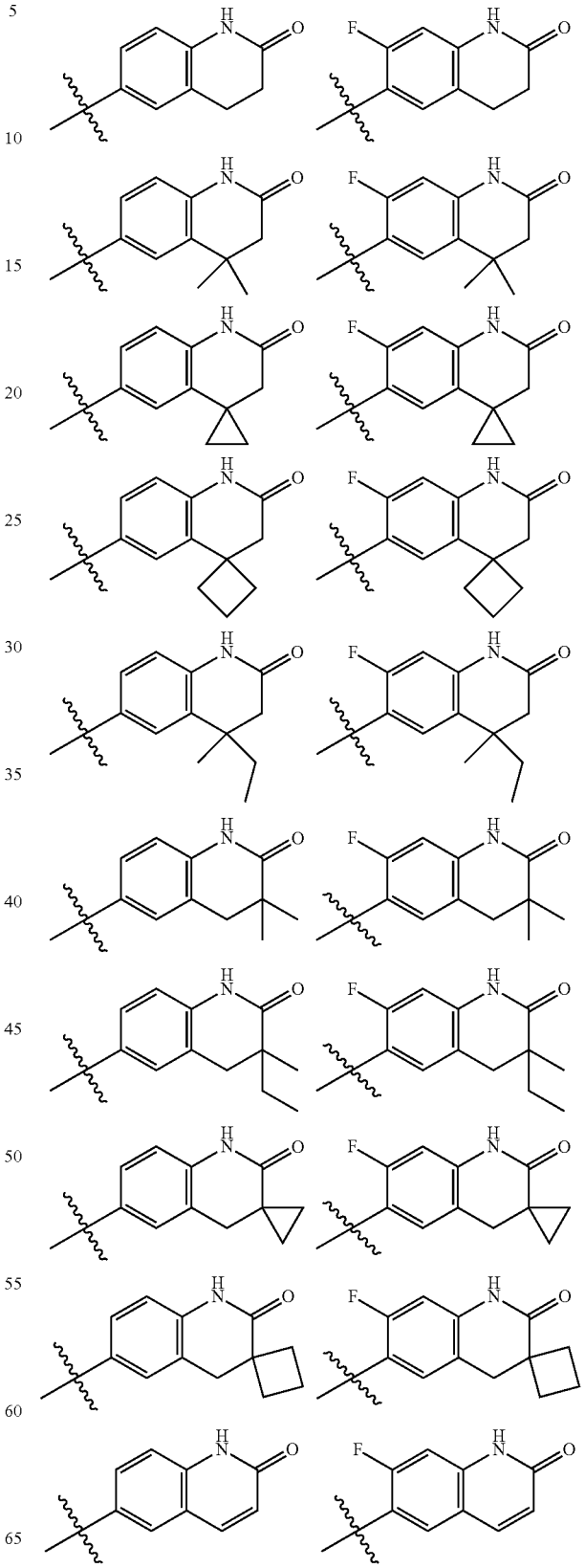

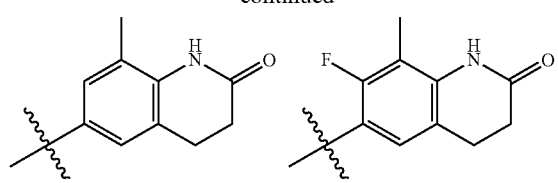
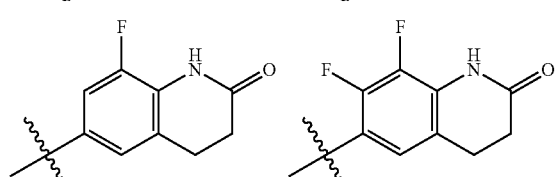
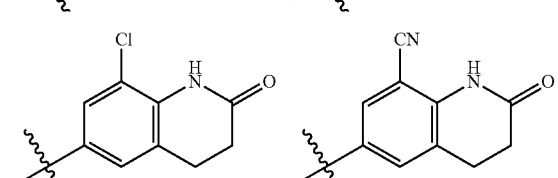
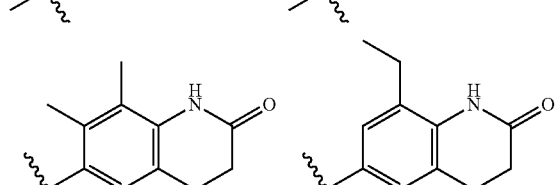
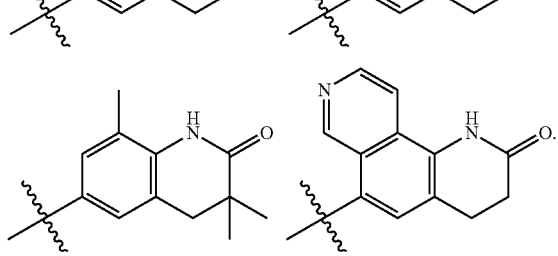
In some embodiments
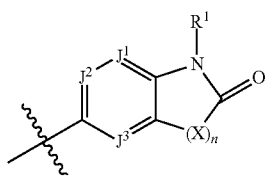
in Formula III (e.g., III-1 or III-2) can be selected from the following:
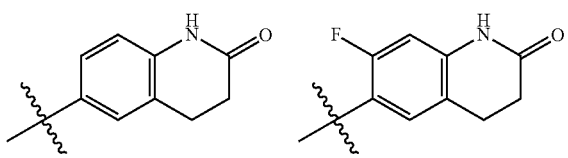
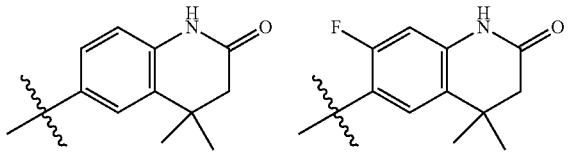
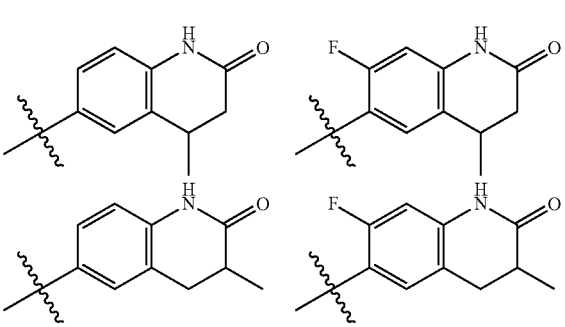
In some embodiments,
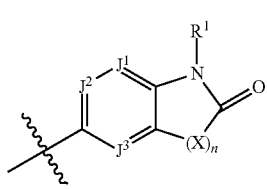
in Formula III (e.g., III-1 or III-2) can be selected from the following:
In some embodiments, in Formula III (e.g., III-1 or III-2) can be

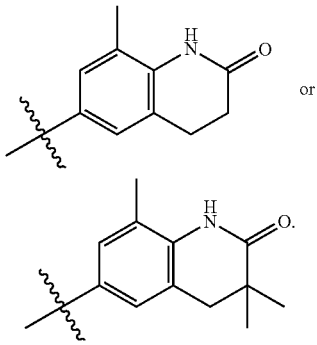

In some embodiments, in Formula III (e.g., Formula III-1 or III-2), the

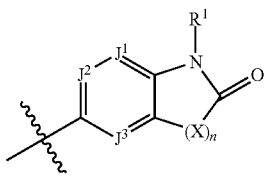

can be any of the corresponding moieties shown in Compound Nos. 139-202, or 139-165 disclosed herein, as applicable.

$G^1$ in Formula III is typically an optionally substituted phenyl or optionally substituted heteroaryl, which includes any of those described herein.

In some embodiments, the compound of Formula III is characterized as having a formula of III-1, wherein $G^1$ is an optionally substituted 5- or 6-membered heteroaryl or an optionally substituted 8-10 membered bicyclic heteroaryl. In some embodiments, the compound of Formula III is characterized as having a formula of III-1, wherein $G^1$ is selected from the following:

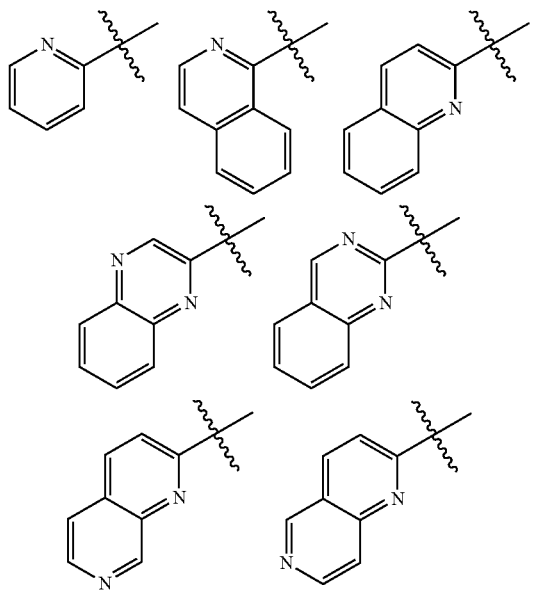

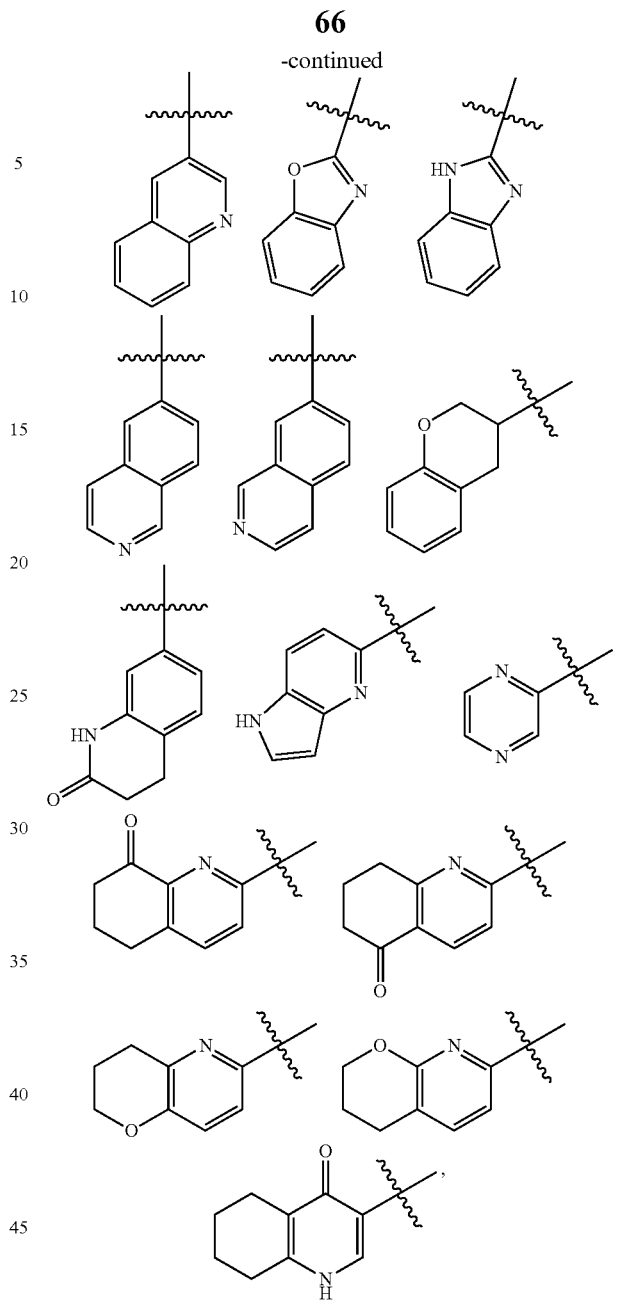

wherein each of the groups is optionally further substituted, for example, with one or two substituents each independently halogen (e.g., Cl), $C_{1-4}$ alkyl, CN, hydroxyl, COOH, C(O)—O—($C_{1-4}$ alkyl), etc. In some embodiments, the compound of Formula III is characterized as having a formula of III-1, wherein $G^1$ is

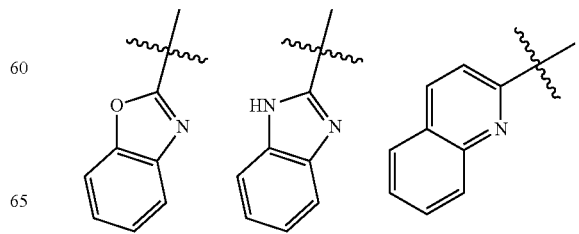

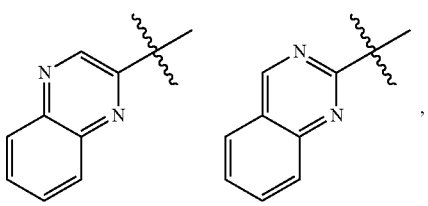

wherein the bicyclic heteroaryl is unsubstituted or further substituted with one or two (preferably one) substituents. When substituted, the substituents can be preferably independently selected from Cl, methyl, and hydroxyl. Representative heteroaryls suitable as $G^1$ for Formula III-1 are shown in the exemplified compounds herein.

In some embodiments, the compound of Formula III is characterized as having a formula of III-2, wherein $G^1$ can be any of those described herein as suitable as the moiety of

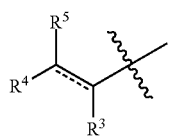

in Formula I (e.g., any of the applicable subformulae). For example, in some embodiments, the compound of Formula III is characterized as having a formula of III-2, wherein $G^1$ can be selected from any of the following:

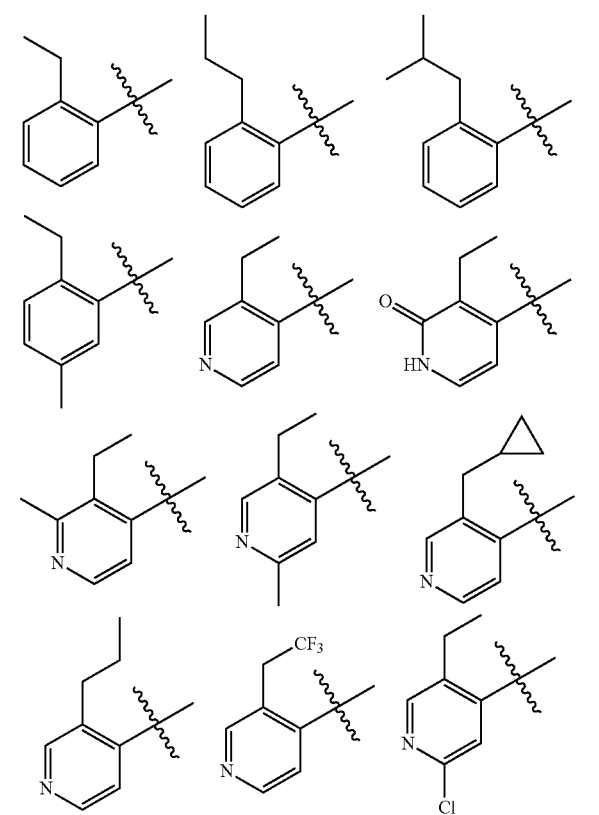

In some embodiments, the compound of Formula III is characterized as having a formula of III-2, wherein $G^1$ can be selected from any of the following:

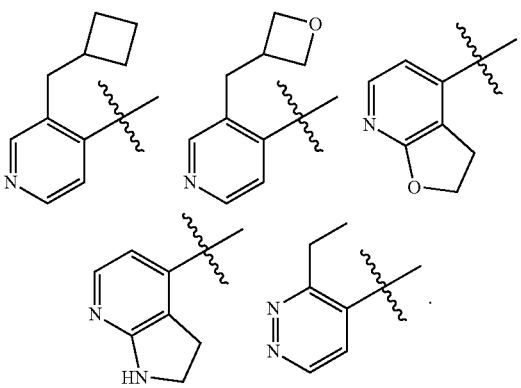

Formula (IV)

In embodiments, the present disclosure provides a compound of Formula (IV)

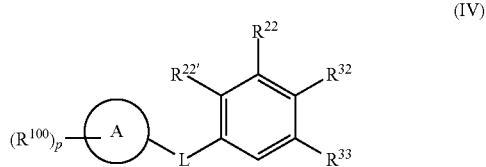

or a pharmaceutically acceptable salt thereof,
wherein:
ring A is a heterocycle or heteroaryl;
L is —NH—, —C(O)—NH—, —S(O)NH—, —S(O)$_2$NH—, —S(O)—, or —S(O)$_2$—; $R^{22}$ is halo, —CN, —C$_{1-6}$ alkyl, —C$_{1-6}$ alkyl-CN, —C$_{1-6}$ haloalkyl, or carbocyclyl;
$R^{22'}$ is H, halo, —C$_{1-6}$ alkyl, or —C$_{1-6}$ haloalkyl; or
$R^{22}$ and $R^{22'}$ are joined to form a heteroaryl, carbocyclyl, or heterocyclyl, each of which may be substituted with one or more halo;
$R^{32}$ and $R^{33}$ are joined to form a heterocyclyl and substituted with oxo; and wherein the heterocycle may be further optionally substituted with one or more $R^{101}$;
p is 0, 1 or 2;
each $R^{100}$ is independently halo, —C$_{1-6}$ alkyl, —C$_{1-6}$ alkylene-carbocyclyl, —C$_{1-6}$ alkylene-heterocyclyl, or —C$_{1-6}$ haloalkyl; and
each $R^{101}$ is independently hydrogen, halo, or —C$_{1-6}$ alkyl.

In embodiments, of the compounds of Formula (IV), L is —NH—, —C(O)—NH—, —S(O)NH—, —S(O)$_2$NH—, —S(O)—, or —S(O)$_2$—. In embodiments, L is —NH—. In embodiments, L is —C(O)—NH—. In embodiments, L is —S(O)NH—. In embodiments, L is —S(O)$_2$NH—. In embodiments, L is —S(O)—. In embodiments, L is —S(O)$_2$—.

In embodiments, the compound of Formula (IV) is a compound of Formula (IV-A)

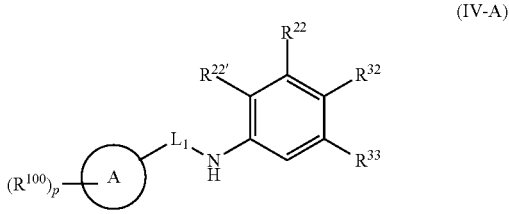

(IV-A)

or a pharmaceutically acceptable salt thereof, wherein:
L$_1$ is absent, —C(O)—, —S(O)—, or —S(O)$_2$—;
Ring A is a heterocycle or heteroaryl;
R$^{22}$ is halo, —CN, —C$_{1-6}$ alkyl, —C$_{1-6}$ alkyl-CN, —C$_{1-6}$ haloalkyl, or carbocyclyl;
R$^{22'}$ is H, halo, —C$_{1-6}$ alkyl, or —C$_{1-6}$ haloalkyl; or
R$^{22}$ and R$^{22'}$ are joined to form a heteroaryl, carbocyclyl, or heterocyclyl, each of which may be substituted with one or more halo;
R$^{32}$ and R$^{33}$ are joined to form a heterocyclyl substituted with oxo; and wherein the heterocyclyl may be further optionally substituted with one or more R$^{101}$;
p is 0, 1 or 2;
each R$^{100}$ is independently halo, —C$_{1-6}$ alkyl, —C$_{1-6}$ alkylene-carbocyclyl, —C$_{1-6}$ alkylene-heterocyclyl, or —C$_{1-6}$ haloalkyl; and
each R$^{101}$ is independently hydrogen, halo, or —C$_{1-6}$ alkyl.

In embodiments of the compounds of Formula (IV-A), L$_1$ is absent, —C(O)—, —S(O)—, or —S(O)$_2$—.

In embodiments of the compounds of Formula (IV-A), L$_1$ is —C(O)—, —S(O)—, or —S(O)$_2$—.

In embodiments of the compounds of Formula (IV-A), L$_1$ is absent.

In embodiments of the compounds of Formula (IV-A), L$_1$ is —C(O)—.

In embodiments of the compounds of Formula (IV-A), L$_1$ is —S(O)—.

In embodiments of the compounds of Formula (IV-A), L$_1$ is —S(O)$_2$—.

In embodiments, of the compounds of Formula (IV) or Formula (IV-A), Ring A is a heteroaryl.

In embodiments, of the compounds of Formula (IV) or Formula (IV-A), Ring A is a heterocycle.

In embodiments of the compounds of Formula (IV) or Formula (IV-A), ring ring A is a 5 or 6-membered heteroaryl, a 5,6-bicyclic heteroaryl, a 5,6-bicyclic heterocyclyl, a 6,6-bicyclic heterocyclyl, a 6,6-bicyclic heteroaryl, or a 3-8 membered heterocyclyl.

In embodiments of the compounds of Formula (IV) or Formula (IV-A), ring A is a 5 or 6-membered heteroaryl, a 5,6-bicyclic heteroaryl, a 6,6-bicyclic heteroaryl, or a 3-8 membered heterocyclyl.

In embodiments of the compounds of Formula (IV) or Formula (IV-A), ring A is a 5 or 6-membered heteroaryl. In embodiments, ring A is a 5-membered heteroaryl. In embodiments, ring A is a 6-membered heteroaryl.

In embodiments of the compounds of Formula (IV) or Formula (IV-A), ring A is a 5,6-bicyclic heteroaryl.

In embodiments of the compounds of Formula (IV) or Formula (IV-A), ring A is a 6,6-bicyclic heteroaryl, or a 3-8 membered heterocyclyl.

In embodiments of the compounds of Formula (IV) or Formula (IV-A), ring A is pyridyl, pyrimidinyl, pyridazinyl, quinazolinyl, quinoxalinyl, or morpholinyl.

In embodiments, of the compounds of Formula (IV) or Formula (IV-A), ring A is pyridyl. In embodiments, ring A is pyrimidinyl. In embodiments, ring A is pyridazinyl. In embodiments, ring A is quinazolinyl. In embodiments, ring A is quinoxalinyl. In embodiments, ring A is morpholinyl.

In embodiments, of the compounds of Formula (IV) or Formula (IV-A), ring A-(R$^{100}$)$_p$ is:

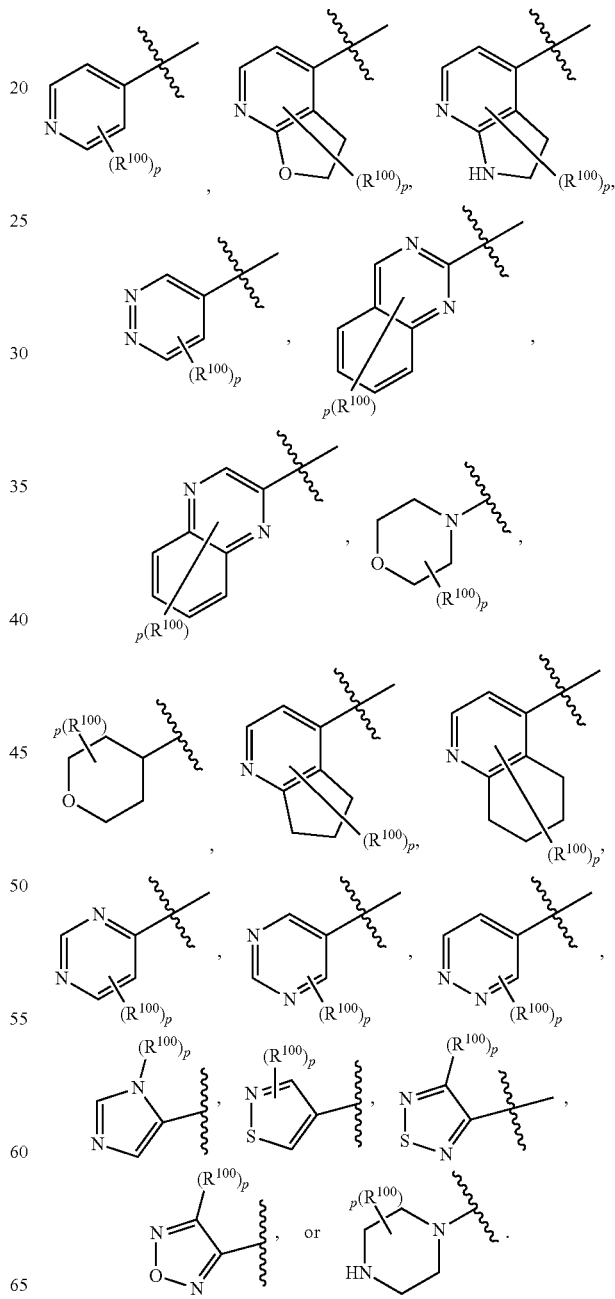

In embodiments, of the compounds of Formula (IV) or Formula (IV-A), ring A-(R$^{100}$)$_p$ is

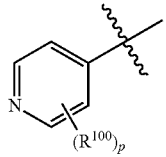

In embodiments, ring A-(R$^{100}$)$_p$ is:

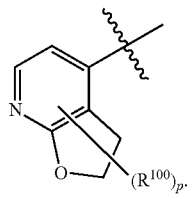

In embodiments, ring A-(R$^{100}$)$_p$ is:

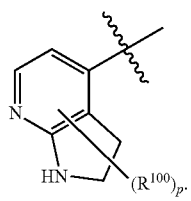

In embodiments, ring A-(R$^{100}$)$_p$ is:

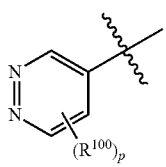

In embodiments, ring A-(R$^{100}$)$_p$ is:

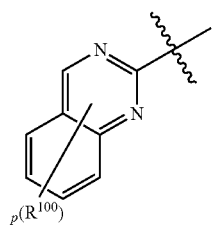

In embodiments, ring A-(R$^{100}$)$_p$ is:

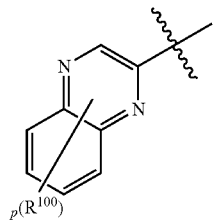

In embodiments, ring A-(R$^{100}$)$_p$ is:

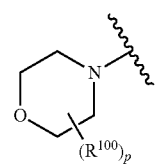

In embodiments, ring A-(R$^{100}$)$_p$ is:

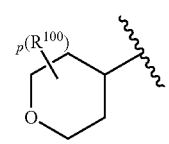

In embodiments, ring A-(R$^{100}$)$_p$ is:

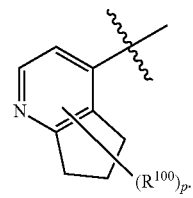

In embodiments, ring A-(R$^{100}$)$_p$ is:

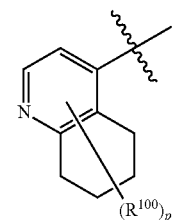

In embodiments, ring A-(R$^{100}$)$_p$ is:

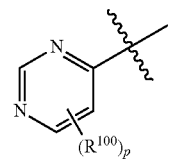

In embodiments, ring A-(R$^{100}$)$_p$ is:

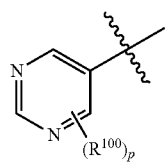

In embodiments, ring A-(R$^{100}$)$_p$ is:

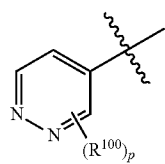

In embodiments, ring A-(R$^{100}$)$_p$ is:

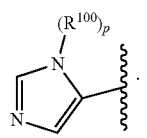

In embodiments, ring A-(R$^{100}$)$_p$ is:

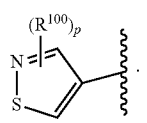

In embodiments, ring A-(R$^{100}$)$_p$ is:

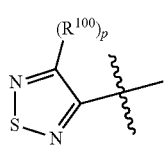

In embodiments, ring A-(R$^{100}$)$_p$ is:

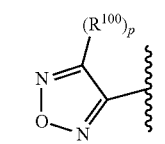

In embodiments, ring A-(R$^{100}$)$_p$ is:

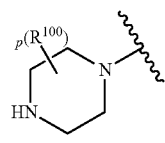

In embodiments, of the compounds of Formula (IV) or Formula (IV-A), ring A-(R$^{100}$)$_p$ is:

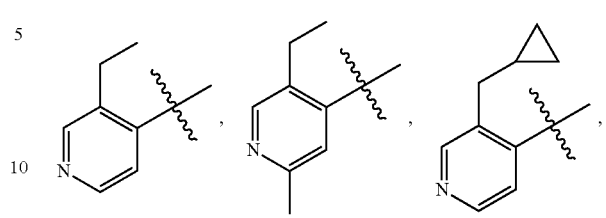

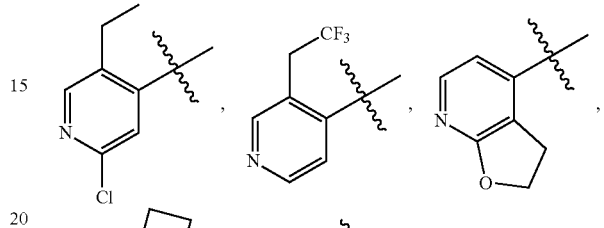

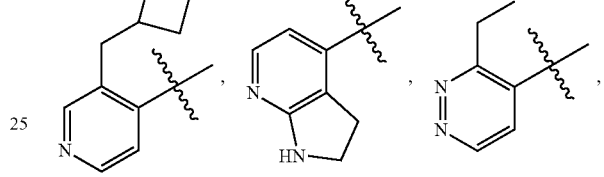

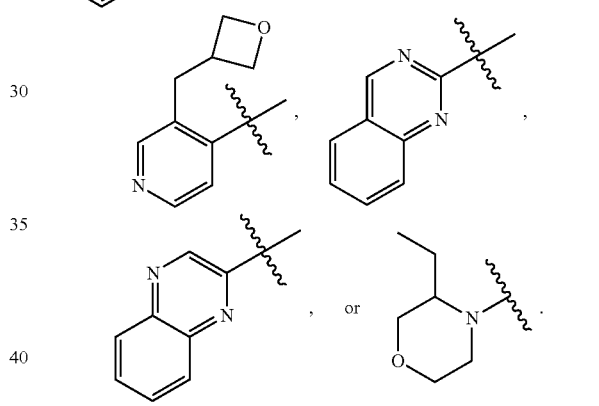

In embodiments, of the compounds of Formula (IV) or Formula (IV-A), ring A-(R$^{100}$)$_p$ is:

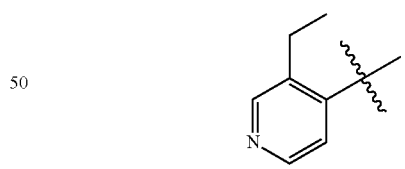

In embodiments, ring A-(R$^{100}$)$_p$ is:

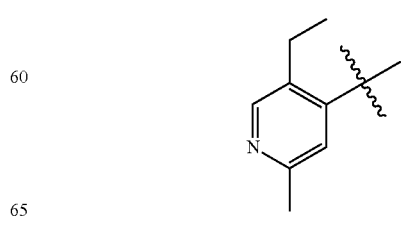

In embodiments, ring A-(R$^{100}$)$_p$ is:
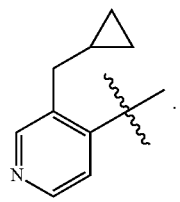
In embodiments, ring A-(R$^{100}$)$_p$ is:
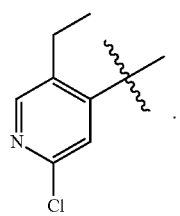
In embodiments, ring A-(R$^{100}$)$_p$ is:
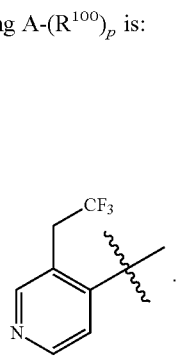
In embodiments, ring A-(R$^{100}$)$_p$ is:
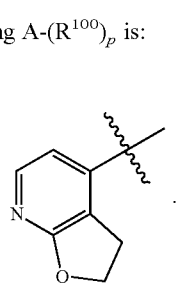
In embodiments, ring A-(R$^{100}$)$_p$ is:
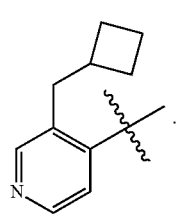
In embodiments, ring A-(R$^{100}$)$_p$ is:
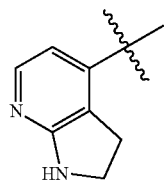
In embodiments, ring A-(R$^{100}$)$_p$ is:
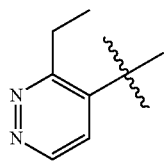
In embodiments, ring A-(R$^{100}$)$_p$ is:
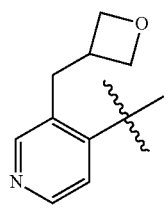
In embodiments, ring A-(R$^{100}$)$_p$ is:
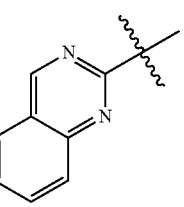
In embodiments, ring A-(R$^{100}$)$_p$ is:
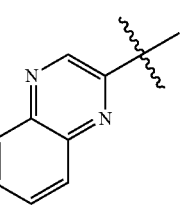
In embodiments, ring A-(R$^{100}$)$_p$ is:
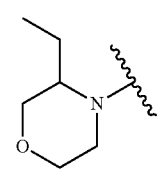

In embodiments, of the compounds of Formula (IV) or Formula (IV-A), ring A-$(R^{100})_p$ is.

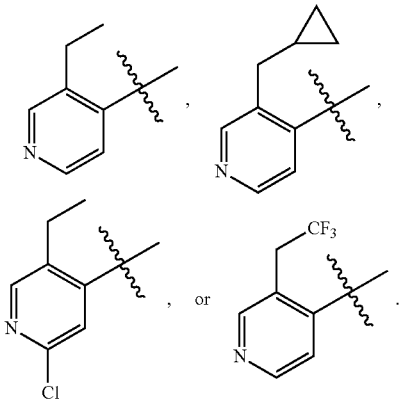

In embodiments, the compound of Formula (IV) is a compound of Formula (IV-B)

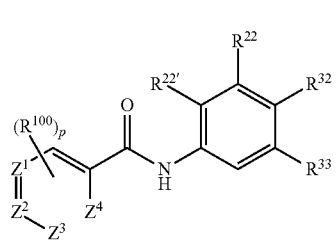

or a pharmaceutically acceptable salt thereof,
wherein:
each of $Z^1$, $Z^2$, $Z^3$, and $Z^4$ are independently CH or N, and at least one of $Z^1$, $Z^2$, $Z^3$, and $Z^4$ are N;
$R^{22}$ is halo, —CN, —$C_{1-6}$ alkyl, —$C_{1-6}$ alkyl-CN, —$C_{1-6}$ haloalkyl, or carbocyclyl;
$R^{22'}$ is H, halo, —$C_{1-6}$ alkyl, or —$C_{1-6}$ haloalkyl; or
$R^{22}$ and $R^{22'}$ are joined to form a heteroaryl, carbocyclyl, or heterocyclyl, each of which may be substituted with one or more halo
$R^{32}$ and $R^{33}$ are joined to form a heterocyclyl substituted with oxo; and wherein the heterocyclyl may be further optionally substituted with one or more $R^{101}$;
p is 0, 1 or 2;
each $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl; and
each $R^{101}$ is independently hydrogen, halo, or $C_{1-6}$ alkyl.

In embodiments of the compounds of Formula (IV-B), 1 or 2 of $Z^1$, $Z^2$, $Z^3$, and $Z^4$ is —N and the rest are —CH.

In embodiments of the compounds of Formula (IV-B), $Z^2$ is N and $Z^1$, $Z^3$, and $Z^4$ are CH;
$Z^1$ and $Z^2$ are N and $Z^3$, and $Z^4$ are CH;
$Z^2$ and $Z^4$ are N and $Z^1$ and $Z^3$ are CH;
$Z^1$ and $Z^3$ are N and $Z^2$, and $Z^4$ are CH; or
$Z^2$ and $Z^3$ are N and $Z^1$, and $Z^4$ are CH.

In embodiments of the compounds of Formula (IV-B), $Z^2$ is N and $Z^1$, $Z^3$, and $Z^4$ are CH; or
$Z^1$ and $Z^2$ are N and $Z^3$, and $Z^4$ are CH.

In embodiments of the compounds of Formula (IV-B), $Z^2$ is N and $Z^1$, $Z^3$, and $Z^4$ are CH.

In embodiments of the compounds of Formula (IV-B), $Z^1$ and $Z^2$ are N and $Z^3$, and $Z^4$ are CH;

In embodiments of the compounds of Formula (IV-B), $Z^2$ and $Z^4$ are N and $Z^1$ and $Z^3$ are CH;

In embodiments of the compounds of Formula (IV-B), $Z^1$ and $Z^3$ are N and $Z^2$, and $Z^4$ are CH.

In embodiments of the compounds of Formula (IV-B), $Z^2$ and $Z^3$ are N and $Z^1$, and $Z^4$ are CH.

In embodiments, of the compounds of Formula (IV), Formula (IV-A), or Formula (IV-B), $R^{32}$ and $R^{33}$ are joined to form a heterocycle containing at least one N atom in the ring and substituted with oxo.

In embodiments, of the compounds of Formula (IV), Formula (IV-A), or Formula (IV-B), $R^{32}$ and $R^{33}$ are joined to form a 6-7 membered heterocycle containing at least one N atom in the ring and substituted with oxo.

In embodiments, of the compounds of Formula (IV), Formula (IV-A), or Formula (IV-B), $R^{32}$ and $R^{33}$ are joined to form a 6-membered heterocycle containing one N atom in the ring and substituted with oxo.

In embodiments, the present disclosure provides a compound of Formula (IV-C):

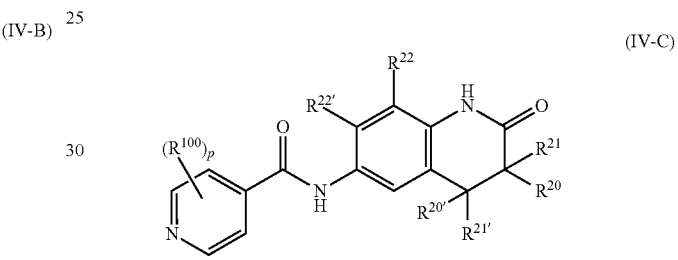

or a pharmaceutically acceptable salt thereof,
wherein:
$R^{20}$, $R^{21}$, $R^{20'}$, $R^{21'}$, are each independently hydrogen, halo, or —$C_{1-4}$ alkyl; or one of $R^{20}$ and $R^{21}$ is joined with one of $R^{20'}$ and $R^{21'}$ to form a $C_{3-8}$ carbocyclic ring, or a 3-8 membered heterocyclic ring;
$R^{22}$ is halo, —CN, —$C_{1-6}$alkyl, —$C_{1-6}$ alkyl-CN, —$C_{1-6}$ haloalkyl, or carbocyclyl;
$R^{22'}$ is H, halo, —$C_{1-6}$ alkyl, —$C_{1-6}$ haloalkyl;
or $R^{22}$ and $R^{22'}$ are taken together to form heteroaryl, carbocyclyl, or heterocyclyl, each of which may be substituted with one or more halo;
p is 0, 1 or 2; and
each $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl; or
when p is 2, two adjacent $R^{100}$ may be joined to form a carbocyclyl or heterocyclyl, each of which may be substituted with one or more halo.

In embodiments of the compounds of Formula (IV-C), $R^{20}$ and $R^{21}$ are independently —H, $C_{1-4}$ alkyl, or halo; and $R^{20'}$ and $R^{21'}$ are hydrogen; or $R^{20}$ is joined with $R^{20'}$ to form a cyclopropyl ring, or a 5-6 membered heterocyclic ring; and $R^{21}$ and $R^{21'}$ are —H.

In embodiments of the compounds of Formula (IV-C), $R^{20}$ and $R^{21}$ are independently —H, methyl, or fluoro; and $R^{20'}$ and $R^{21'}$ are hydrogen.

In embodiments of the compounds of Formula (IV-C), $R^{20}$ and $R^{21}$ are hydrogen, In embodiments of the compounds of Formula (IV-C), $R^{20}$ and $R^{21}$ are methyl.

In embodiments of the compounds of Formula (IV-C), $R^{20}$ and $R^{21}$ are fluoro.

In embodiments of the compounds of Formula (IV-C), $R^{20'}$ and $R^{21'}$ are hydrogen.

In embodiments of the compounds of Formula (IV-C), $R^{20}$ is joined with $R^{20'}$ to form a cyclopropyl ring, or a 5-6 membered heterocyclyl containing one or two heteroatoms independently selected from N and O; and $R^{21}$ and $R^{21'}$ are —H.

In embodiments, of the compounds of Formula (IV-C), $R^{20}$ is joined with $R^{20'}$ to form a cyclopropyl ring and $R^{21}$ and $R^{21'}$ are —H.

In embodiments of the compounds of Formula (IV-C), $R^{20}$ is joined with $R^{20'}$ to form a 5-6 membered heterocyclyl containing one or two heteroatoms independently selected from N and O; and $R^{21}$ and $R^{21'}$ are —H.

In embodiments, $R^{20}$ is joined with $R^{20'}$ to form a pyrrolidinyl ring and $R^{21}$ and $R^{21'}$ are —H.

In embodiments, $R^{20}$ is joined with $R^{20'}$ to form a morpholinyl ring and $R^{21}$ and $R^{21'}$ are —H.

In embodiments, the present disclosure provides a compound is of Formula (IV-D)

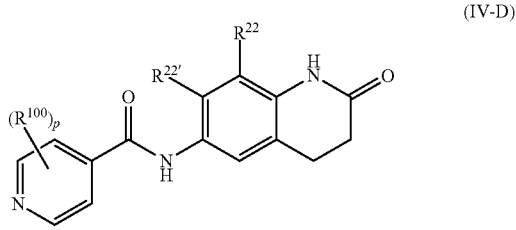

(IV-D)

or a pharmaceutically acceptable salt thereof,
wherein:
$R^{22}$ is halo, —CN, —$C_{1-6}$ alkyl, —$C_{1-6}$ alkyl-CN, —$C_{1-6}$ haloalkyl, or carbocyclyl;
$R^{22'}$ is —H, halo, —$C_{1-6}$ alkyl, —$C_{1-6}$ haloalkyl;
or $R^{22}$ and $R^{22'}$ are taken together to form a heteroaryl, carbocyclyl, or heterocyclyl, each of which may be substituted with one or more halo;
p is 0, 1 or 2;
each $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl;
or, when p is 2, two $R^{100}$ may be joined to form a carbocyclyl or heterocyclyl, each of which may be substituted with one or more halo.

In embodiments of the compounds of Formula (IV), (IV-A), (IV-B), (IV-C), or (IV-D), $R^{22}$ is halo, —CN, —$C_{1-6}$ alkyl, —$C_{1-6}$ alkyl-CN, —$C_{1-6}$ haloalkyl, or carbocyclyl.

In embodiments of the compounds of Formula (IV), (IV-A), (IV-B), (IV-C), or (IV-D), $R^{22}$ is halo, —CN, —$C_{1-6}$ alkyl, or $C_{1-6}$ haloalkyl.

In embodiments of the compounds of Formula (IV), (IV-A), (IV-B), (IV-C), or (IV-D), $R^{22}$ is halo, —CN, or —$C_{1-6}$ alkyl.

In embodiments of the compounds of Formula (IV), (IV-A), (IV-B), (IV-C), or (IV-D), $R^{22}$ is halo, —$C_{1-6}$ alkyl, or —$C_{1-6}$ haloalkyl.

In embodiments of the compounds of Formula (IV), (IV-A), (IV-B), (IV-C), or (IV-D), $R^{22}$ is halo, —$C_{1-4}$ alkyl, or —$C_{1-4}$ haloalkyl.

In embodiments of the compounds of Formula (IV), (IV-A), (IV-B), (IV-C), or (IV-D), $R^{22}$ is halo or —$C_{1-4}$ alkyl.

In embodiments of the compounds of Formula (IV), (IV-A), (IV-B), (IV-C), or (IV-D), $R^{22}$ is halo.

In embodiments of the compounds of Formula (IV), (IV-A), (IV-B), (IV-C), or (IV-D), $R^{22}$ —Cl or —F. In embodiments, $R^{22}$ —Cl. In embodiments, $R^{22}$ —F, In embodiments of the compounds of Formula (IV), (IV-A), (IV-B), (IV-C), or (IV-D), $R^{22}$ is —CN.

In embodiments of the compounds of Formula (IV), (IV-A), (IV-B), (IV-C), or (IV-D), $R^{22}$ is —$C_{1-6}$ alkyl. In embodiments, $R^{22}$ is —$C_{1-4}$ alkyl.

In embodiments of the compounds of Formula (IV), (IV-A), (IV-B), (IV-C), or (IV-D), $R^{22}$ is —$CH_3$ or —$CH_2CH_3$. In embodiments, $R^{22}$ is —$CH_3$. In embodiments, $R^{22}$ is —$CH_2CH_3$.

In embodiments of the compounds of Formula (IV), (IV-A), (IV-B), (IV-C), or (IV-D), $R^{22}$ is —$C_{1-6}$ alkyl-CN.

In embodiments of the compounds of Formula (IV), (IV-A), (IV-B), (IV-C), or (IV-D), $R^{22}$ is —$CH_2CN$.

In embodiments of the compounds of Formula (IV), (IV-A), (IV-B), (IV-C), or (IV-D), $R^{22}$ is —$C_{1-6}$ haloalkyl. In embodiments of the compounds of Formula (IV), (IV-A), (IV-B), (IV-C), or (IV-D), $R^{22}$ is —$C_{1-4}$ haloalkyl.

In embodiments of the compounds of Formula (IV), (IV-A), (IV-B), (IV-C), or (IV-D), $R^{22}$ is —$CF_3$. In embodiments, $R^{22}$ is —$CH_2CF_3$.

In embodiments of the compounds of Formula (IV), (IV-A), (IV-B), (IV-C), or (IV-D), $R^{22}$ is carbocyclyl.

In embodiments of the compounds of Formula (IV), (IV-A), (IV-B), (IV-C), or (IV-D), $R^{22}$ is cyclopropyl.

In embodiments of the compounds of Formula (IV), (IV-A), (IV-B), (IV-C), or (IV-D), $R^{22}$ —Cl, —F, —CN, —$CH_3$, —$CH_2CH_3$, —$CH_2CN$, —$CF_3$, —$CH_2CF_3$, or cyclopropyl.

In embodiments of the compounds of Formula (IV), (IV-A), (IV-B), (IV-C), or (IV-D), $R^{22}$ is —Cl, —F, —CN, —$CH_3$, or —$CH_2CH_3$.

In embodiments of the compounds of Formula (IV), (IV-A), (IV-B), (IV-C), or (IV-D), $R^{22}$ is —Cl, —F, —$CH_3$, or —$CH_2CH_3$.

In embodiments of the compounds of Formula (IV), (IV-A), (IV-B), (IV-C), or (IV-D), $R^{22}$ is —Cl, —F, or —$CH_3$.

In embodiments of the compounds of Formula (IV), (IV-A), (IV-B), (IV-C), or (IV-D), $R^{22}$ and $R^{22'}$ are taken together to form:
(i) a 5-6 membered heteroaryl containing 1 or 2 heteroatoms independently selected from N, O, and S;
(ii) a 5-membered carbocyclyl optionally substituted with one or more fluoro; or
(iii) a 6-membered heterocyclyl containing 1 or 2 heteroatoms independently selected from N and O.

In embodiments of the compounds of Formula (IV), (IV-A), (IV-B), (IV-C), or (IV-D), $R^{22}$ and $R^{22'}$ are taken together to form a 5-6 membered heteroaryl containing 1 or 2 heteroatoms independently selected from N, O, and S.

In embodiments of the compounds of Formula (IV), (IV-A), (IV-B), (IV-C), or (IV-D), $R^{22}$ and $R^{22'}$ are taken together to form a 5-membered carbocyclyl optionally substituted with one or more fluoro.

In embodiments of the compounds of Formula (IV), (IV-A), (IV-B), (IV-C), or (IV-D), $R^{22}$ and $R^{22'}$ are taken together to form a 6-membered heterocyclyl containing 1 or 2 heteroatoms independently selected from N and O.

In embodiments of the compounds of Formula (IV), (IV-A), (IV-B), (IV-C), or (IV-D), $R^{22}$ and $R^{22'}$ are taken together to form a 6-membered heteroaryl containing 1 nitrogen atom.

In embodiments of the compounds of Formula (IV), (IV-A), (IV-B), (IV-C), or (IV-D), $R^{22'}$ is —H, halo, —$C_{1-6}$ alkyl, or —$C_{1-6}$ haloalkyl.

In embodiments of the compounds of Formula (IV), (IV-A), (IV-B), (IV-C), or (IV-D), $R^{22'}$ is —H or halo, or —$C_{1-6}$ alkyl.

In embodiments of the compounds of Formula (IV), (IV-A), (IV-B), (IV-C), or (IV-D), $R^{22'}$ is —H or halo.

In embodiments of the compounds of Formula (IV), (IV-A), (IV-B), (IV-C), or (IV-D), $R^{22'}$ is —H.

In embodiments of the compounds of Formula (IV), (IV-A), (IV-B), (IV-C), or (IV-D), $R^{22'}$ is halo. In embodiments, $R^{22'}$ is —F.

In embodiments of the compounds of Formula (IV), (IV-A), (IV-B), (IV-C), or (IV-D), $R^{22'}$ is —$C_{1-6}$ alkyl. In embodiments, $R^{22'}$ is —$CH_3$.

In embodiments of the compounds of Formula (IV), (IV-A), (IV-B), (IV-C), or (IV-D), $R^{22'}$ is —$C_{1-6}$ haloalkyl. In embodiments, $R^{22'}$ is -$CF_3$.

In embodiments of the compounds of Formula (IV), (IV-A), (IV-B), (IV-C), or (IV-D), $R^{22}$ is —H, —F, —$CH_3$, or —$CF_3$.

In embodiments of the compounds of Formula (IV), (IV-A), (IV-B), (IV-C), or (IV-D), $R^{22'}$ is —H, —F, or —$CH_3$, In embodiments of the compounds of Formula (IV), (IV-A), (IV-B), (IV-C), or (IV-D), $R^{22'}$ is —H or —F.

In embodiments of the compounds of Formula (IV), (IV-A), (IV-B), (IV-C), or (IV-D), $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl.

In embodiments of the compounds of Formula (IV), (IV-A), (IV-B), (IV-C), or (IV-D), each $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl; or when p is 2, two adjacent $R^{100}$ may be joined to form a carbocyclyl or heterocyclyl, each of which may be substituted with one or more halo.

In embodiments of the compounds of Formula (IV), (IV-A), (IV-B), (IV-C), or (IV-D), $R^{100}$ is independently halo, —$C_{1-6}$ alkyl, —$C_{1-6}$ alkylene-carbocyclyl, or —$C_{1-6}$ haloalkyl.

In embodiments of the compounds of Formula (IV), (IV-A), (IV-B), (IV-C), or (IV-D), $R^{100}$ is independently —$CH_2CH_3$, —$CH_3$, —$CH_2$-cyclopropyl, —Cl, —$CH_2$—$CF_3$, —$CH_2$— cyclobutyl, —$CH_2$-oxetanyl, —$CF_2CH_3$, or two adjacent $R^{100}$ may be joined to form a $C_{5-6}$ carbocyclyl, or a 5-membered heterocyclyl containing a N or O heteroatom; and wherein the carbocyclyl is optionally substituted with one or more fluoro.

In embodiments of the compounds of Formula (IV), (IV-A), (IV-B), (IV-C), or (IV-D), $R^{100}$ is —$C_{1-6}$ alkyl. In embodiments, $R^{100}$ is —$C_{1-4}$ alkyl. In embodiments, $R^{100}$ is —$C_{1-3}$ alkyl. In embodiments, $R^{100}$ is —$CH_3$. In embodiments, $R^{100}$ is —$CH_2CH_3$.

In embodiments of the compounds of Formula (IV), (IV-A), (IV-B), (IV-C), or (IV-D), $R^{100}$ is halo. In embodiments, $R^{100}$ is —Cl.

In embodiments of the compounds of Formula (IV), (IV-A), (IV-B), (IV-C), or (IV-D), $R^{100}$ is-$C_{1-6}$ haloalkyl. In embodiments, $R^{100}$ is —$C_{1-4}$ haloalkyl. In embodiments, $R^{100}$ is —$CH_2$—$CF_3$. In embodiments, $R^{100}$ is —$CF_2CH_3$.

In embodiments of the compounds of Formula (IV), (IV-A), (IV-B), (IV-C), or (IV-D), $R^{100}$ is-$C_{1-6}$ alkylene-carbocyclyl. In embodiments, $R^{100}$ is —$CH_2$-cyclopropyl. In embodiments, $R^{100}$ is —$CH_2$-cyclobutyl.

In embodiments of the compounds of Formula (IV), (IV-A), (IV-B), (IV-C), or (IV-D), $R^{100}$ is —$C_{1-6}$ alkylene-heterocyclyl. In embodiments, $R^{100}$ is —$CH_2$-oxetanyl.

In embodiments of the compounds of Formula (IV), (IV-A), (IV-B), (IV-C), or (IV-D), $R^{100}$ is independently for each occurrence —$CH_2CH_3$, —$CH_3$, —$CH_2$-cyclopropyl, —Cl, —$CH_2$—$CF_3$, —$CH_2$-cyclobutyl, or —$CH_2$-oxetanyl.

In embodiments of the compounds of Formula (IV), (IV-A), (IV-B), (IV-C), or (IV-D), $R^{100}$ is independently for each occurrence —$CH_2CH_3$, —$CH_3$, —$CH_2$-cyclopropyl, —Cl, or —$CH_2$—$CF_3$.

In embodiments of the compounds of Formula (IV), (IV-A), (IV-B), (IV-C), or (IV-D), p is 0, 1 or 2.

In embodiments of the compounds of Formula (IV), (IV-A), (IV-B), (IV-C), or (IV-D), p is 1 or 2.

In embodiments of the compounds of Formula (IV), (IV-A), (IV-B), (IV-C), or (IV-D), p is 0.

In embodiments of the compounds of Formula (IV), (IV-A), (IV-B), (IV-C), or (IV-D), p is 1.

In embodiments of the compounds of Formula (IV), (IV-A), (IV-B), (IV-C), or (IV-D), p is 2.

In embodiments of the compounds of Formula (IV), (IV-A), (IV-B), (IV-C), or (IV-D), p is 1 and $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl.

In embodiments of the compounds of Formula (IV), (IV-A), (IV-B), (IV-C), or (IV-D), p is 1 and $R^{100}$ is independently halo, —$C_{2-6}$ alkyl, —$C_{1-6}$ alkylene-carbocyclyl, —$C_{1-6}$ alkylene-heterocyclyl, or —$C_{1-6}$ haloalkyl.

In embodiments of the compounds of Formula (IV), (IV-A), (IV-B), (IV-C), or (IV-D), p is 1 and $R^{100}$ is independently halo, —$C_{2-6}$ alkyl, —$C_{1-6}$ alkylene-carbocyclyl, —$C_{1-6}$ alkylene-heterocyclyl, or —$C_{2-6}$ haloalkyl.

In embodiments of the compounds of Formula (IV), (IV-A), (IV-B), (IV-C), or (IV-D), p is 1 and $R^{100}$ is —$C_{1-6}$ alkyl, —$C_{1-6}$ alkylene-carbocyclyl, or —$C_{1-6}$ haloalkyl.

In embodiments of the compounds of Formula (IV), (IV-A), (IV-B), (IV-C), or (IV-D), p is 1 and $R^{100}$ is —$C_{2-6}$ alkyl, —$C_{1-6}$ alkylene-carbocyclyl, or —$C_{1-6}$ haloalkyl.

In embodiments of the compounds of Formula (IV), (IV-A), (IV-B), (IV-C), or (IV-D), p is 1 and $R^{100}$ is —$C_{2-6}$ alkyl, —$C_{1-6}$ alkylene-carbocyclyl, or —$C_{2-6}$ haloalkyl.

In embodiments of the compounds of Formula (IV), (IV-A), (IV-B), (IV-C), or (IV-D), p is 1 and $R^{100}$ is —$CH_2CH_3$, —$CH_2$-cyclopropyl, or —$CH_2$—$CF_3$.

In embodiments of the compounds of Formula (IV-C), or (IV-D), p is 1 and $R^{100}$ is substituted at the meta-position of the pyridine.

In embodiments of the compounds of Formula (IV-C), or (IV-D), p is 1 and $R^{100}$ is substituted at the ortho-position of the pyridine.

In embodiments of the compounds of Formula (IV), (IV-A), (IV-B), (IV-C), or (IV-D), p is 2 and $R^{100}$ is independently halo, —$C_{1-6}$ alkyl, —$C_{1-6}$ alkylene-carbocyclyl, —$C_{1-6}$ alkylene-heterocyclyl, or —$C_{1-6}$ haloalkyl.

In embodiments of the compounds of Formula (IV), (IV-A), (IV-B), (IV-C), or (IV-D), p is 2 and $R^{100}$ is independently halo, —$C_{2-6}$ alkyl, —$C_{1-6}$ alkylene-carbocyclyl, —$C_{1-6}$ alkylene-heterocyclyl, or —$C_{1-6}$ haloalkyl.

In embodiments of the compounds of Formula (IV), (IV-A), (IV-B), (IV-C), or (IV-D), p is 2 and $R^{100}$ is independently halo, —$C_{2-6}$ alkyl, —$C_{1-6}$ alkylene-carbocyclyl, —$C_{1-6}$ alkylene-heterocyclyl, or —$C_{2-6}$ haloalkyl.

In embodiments of the compounds of Formula (IV), (IV-A), (IV-B), (IV-C), or (IV-D), p is 2 and $R^{100}$ is independently halo and —$C_{1-6}$ alkyl.

In embodiments of the compounds of Formula (IV), (IV-A), (IV-B), (IV-C), or (IV-D), p is 2 and $R^{100}$ is independently halo and —$C_{2-6}$ alkyl.

In embodiments of the compounds of Formula (IV), (IV-A), (IV-B), (IV-C), or (IV-D), p is 2 and $R^{100}$ is —$CH_2CH_3$ and —Cl.

In embodiments of the compounds of Formula (IV), (IV-A), (IV-B), (IV-C), or (IV-D), p is 2 and two $R^{100}$ may be joined to form a $C_{5-6}$ carbocyclyl, or a 5-membered heterocyclyl containing a N or O heteroatom; and wherein the carbocyclyl is optionally substituted with one or more fluoro.

In embodiments of the compounds of Formula (IV), (IV-A), (IV-B), (IV-C), or (IV-D), p is 2 and two $R^{100}$ are joined to form a C5-6 carbocyclyl and wherein the carbocyclyl is optionally substituted with one or more fluoro. In embodiments, the C5-6 carbocyclyl is substituted with 2 fluoro.

In embodiments of the compounds of Formula (IV), (IV-A), (IV-B), (IV-C), or (IV-D), p is 2 and two $R^{100}$ are joined to form a 5-membered heterocyclyl containing a N atom.

In embodiments of the compounds of Formula (IV), (IV-A), (IV-B), (IV-C), or (IV-D), p is 2 and two $R^{100}$ are joined to form a 5-membered heterocyclyl containing a O atom.

In embodiments of the compounds of Formula (IV-C), or (IV-D), p is 2 and $R^{100}$ is substituted at the meta-position and the ortho-position of the pyridine.

Formula V

In embodiments, provided herein is a compound of Formula (V)

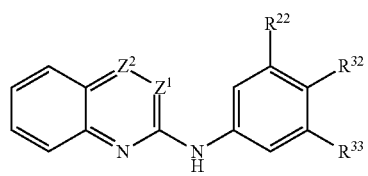

(V)

or a pharmaceutically acceptable salt thereof,
wherein:
$Z^1$ and $Z^2$ are independently CH or N;
$R^{22}$ is —H, or —$C_{1-6}$ alkyl; and
$R^{32}$ and $R^{33}$ are joined to form a heterocycle containing at least one N atom in the ring and substituted with oxo; and wherein the heterocycle may be further optionally substituted with one or more $R^{101}$; and
$R^{101}$ is independently hydrogen, halo, or $C_{1-6}$ alkyl.

In embodiments, the compound of Formula (V) is a compound of Formula (V-A)

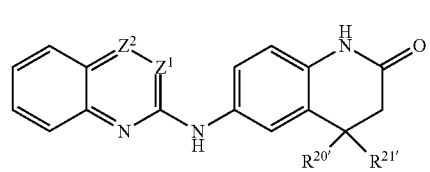

(V-A)

or a pharmaceutically acceptable salt thereof,
wherein:
$R^{20'}$ is halo or $C_{1-6}$ alkyl; and
$R^{21'}$ is halo or $C_{1-6}$ alkyl.

In embodiments of the compounds of Formula (V) or (V-A), $Z^1$ is —CH— and $Z^2$ is —N—.

In embodiments of the compounds of Formula (V) or (V-A), $Z^1$ is —N— and $Z^2$ is —CH—.

In embodiments of the compounds of Formula (V), $R^{32}$ and $R^{33}$ are joined to form a heterocycle one N atom in the ring and substituted with oxo.

In embodiments of the compounds of Formula (V), $R^{22}$ is —H, or —$C_{1-6}$ alkyl. In embodiments, $R^{22}$ is H or —$CH_3$.

In embodiments of the compounds of Formula (V-A), $R^{20'}$ is halo. In embodiments of the compounds of Formula (V-A), $R^{20'}$ is —F.

In embodiments of the compounds of Formula (V-A), $R^{21'}$ is —$C_{1-6}$ alkyl. In embodiments, $R^{21'}$ is —$CH_3$.

In embodiments, the present disclosure provides a compound of Formula (V-B):

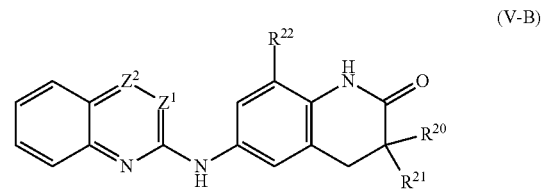

(V-B)

or a pharmaceutically acceptable salt thereof,
wherein:
$Z^1$ and $Z^2$ are independently —CH— or —N—;
$R^{22}$ is H or —$C_{1-6}$ alkyl
$R^{20}$ is halo or —$C_{1-6}$ alkyl
$R^{21}$ is halo or —$C_{1-6}$ alkyl In embodiments of the compounds of Formula (V-B), $Z^1$ is —CH— and $Z^2$ is —N—.

In embodiments of the compounds of Formula (V-B), $Z^1$ is —N— and $Z^2$ is —CH—.

In embodiments of the compounds of Formula (V-B), $R^{22}$ is —$CH_3$.

In embodiments of the compounds of Formula (V-B), $R^{20}$ is halo. In embodiments $R^{20}$ is —F.

In embodiments of the compounds of Formula (V-B), $R^{21}$ is halo. In embodiments $R^{21}$ is —F.

In embodiments of the compounds of Formula (V-B), $R^{20}$ is —$C_{1-6}$ alkyl. In embodiments, $R^{20}$ is —$CH_3$.

In embodiments of the compounds of Formula (V-B), $R^{21}$ is —$C_{1-6}$ alkyl. In embodiments, $R^{21}$ is —$CH_3$.

In some embodiments, the present disclosure also provides a compound selected from compound Nos. 139-202 or a pharmaceutically acceptable salt thereof:

In some embodiments, the present disclosure also provides a compound selected from compound Nos. 139-165 or a pharmaceutically acceptable salt thereof:

TABLE 1-A

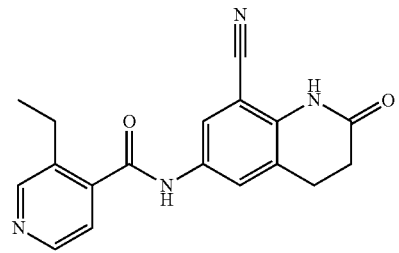

139

TABLE 1-A-continued
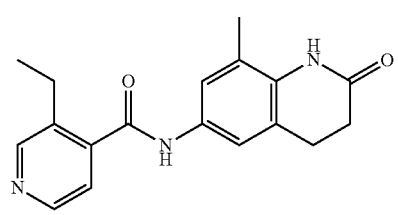
140
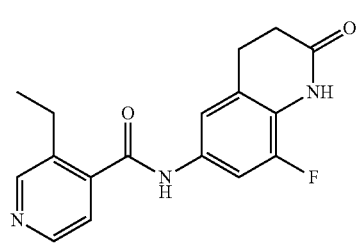
141
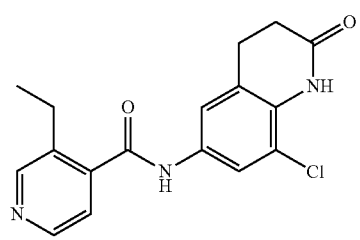
142
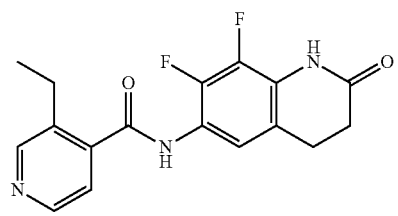
143
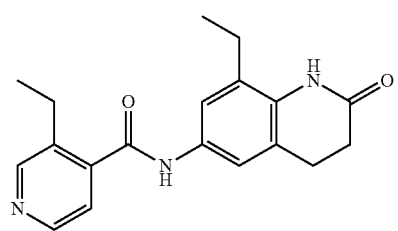
144
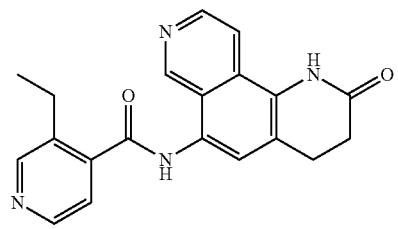
145
TABLE 1-A-continued
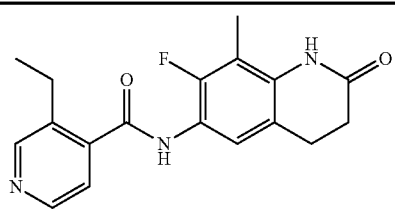
146
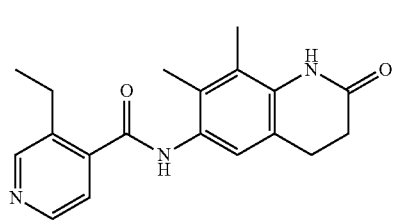
147
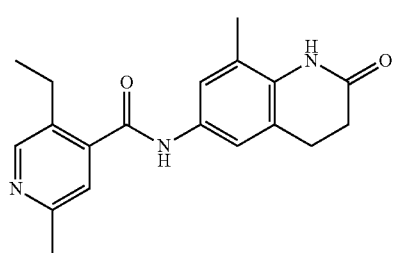 [SMILES: CCc1cnncc1C(=O)Nc1cc(C)c2c(c1)CCC(=O)N2]
148
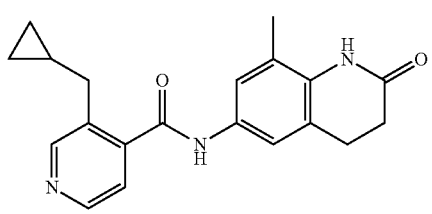
149
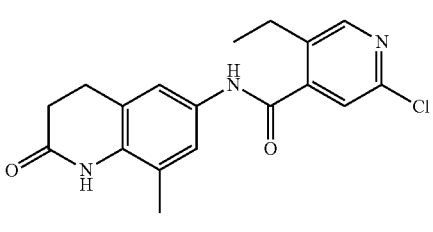
150
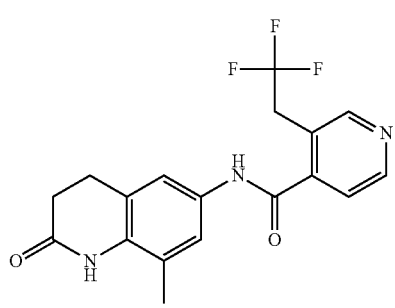
151

TABLE 1-A-continued
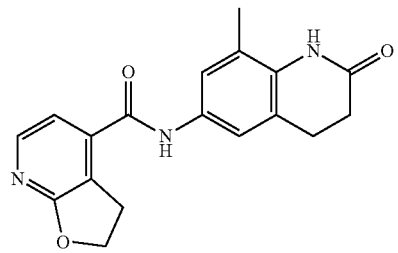
152
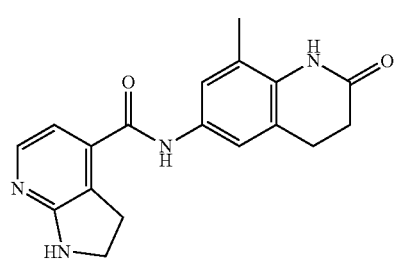
153
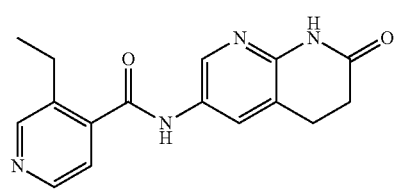
154
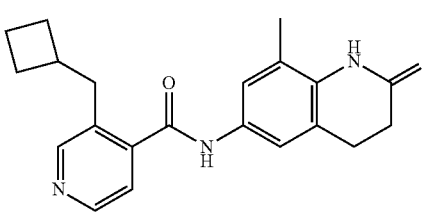
155
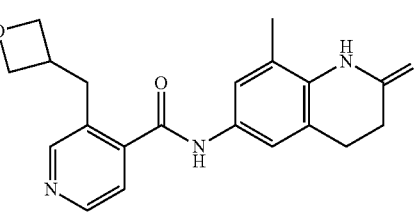
156
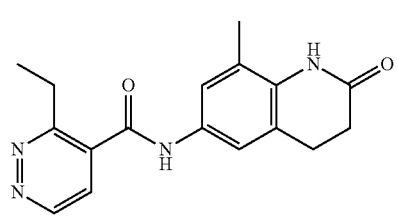
157
TABLE 1-A-continued
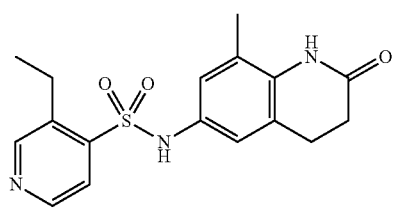
158
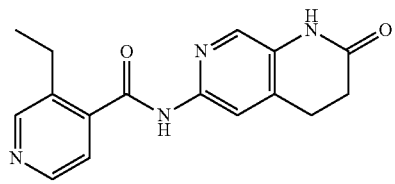
159
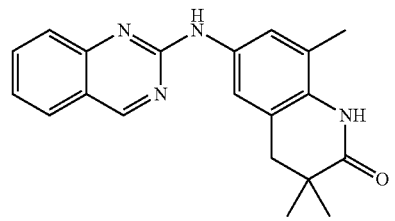
160
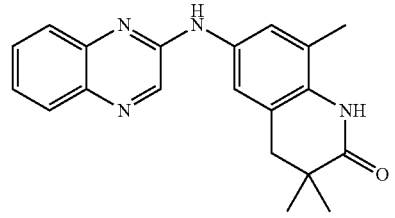
161
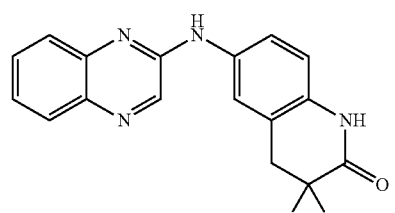
162
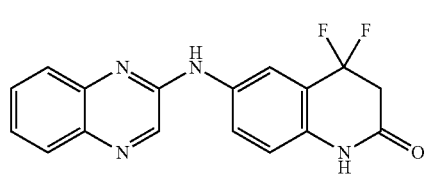
163

TABLE 1-A-continued
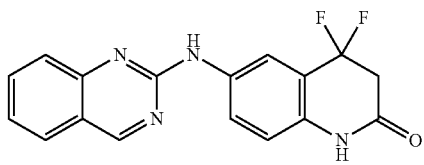
164
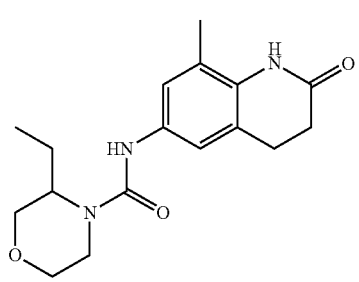
165
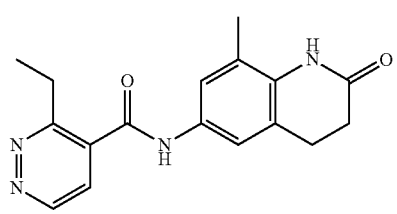
166
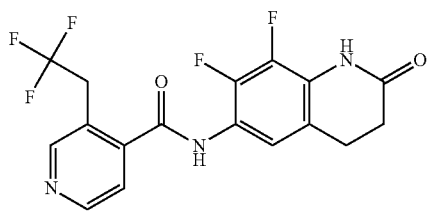
167
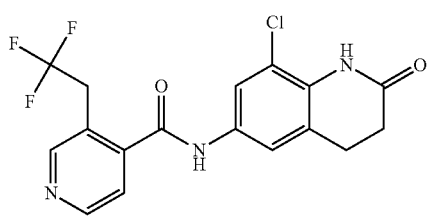
168
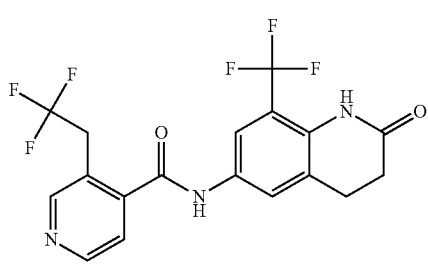
169
TABLE 1-A-continued
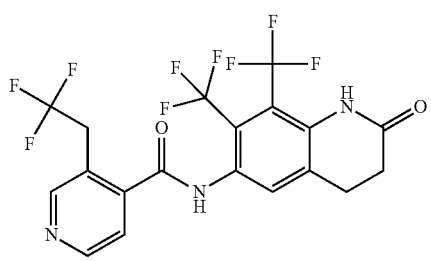
170
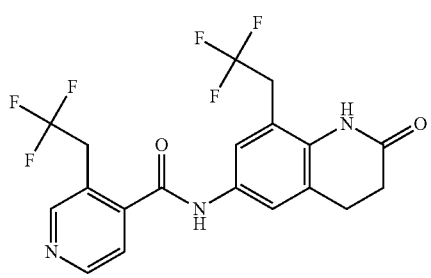
171
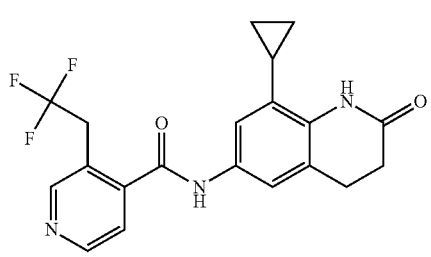
172
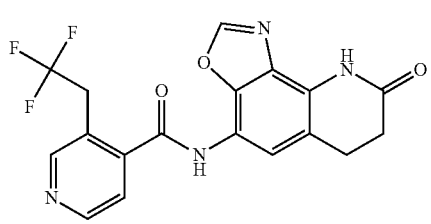
173
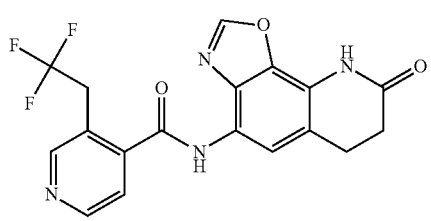
174

TABLE 1-A-continued
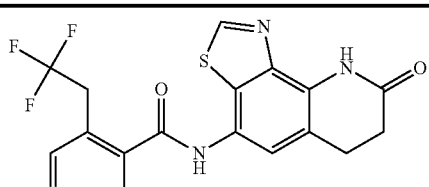
175
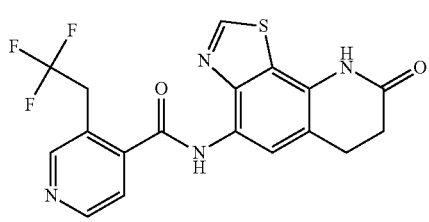
176
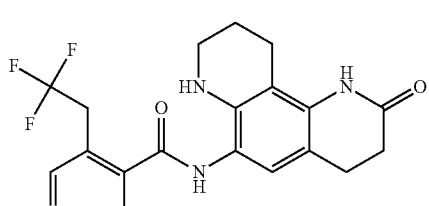
177
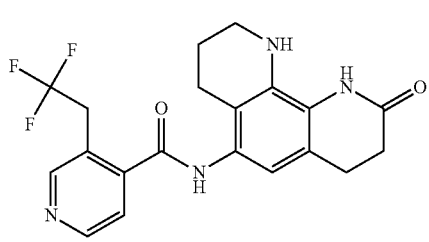
178
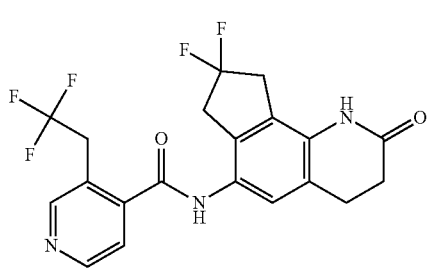
179
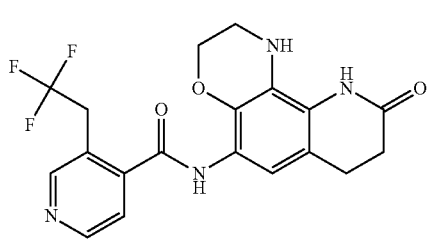
180
TABLE 1-A-continued
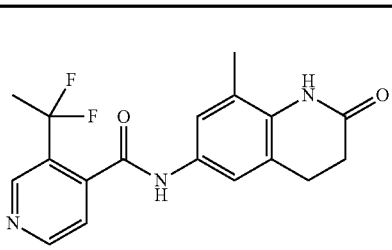
182
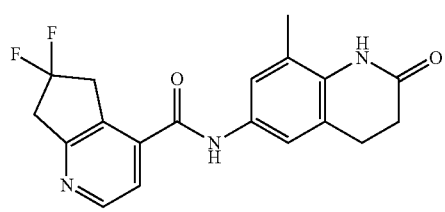
183
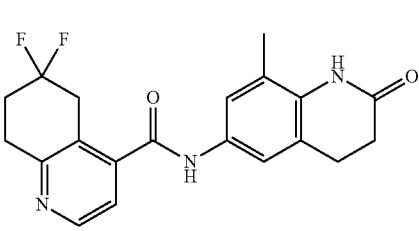
184
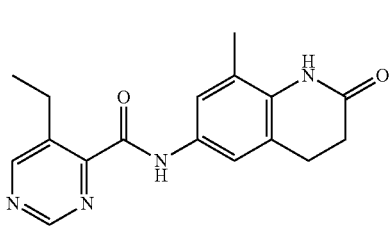
185
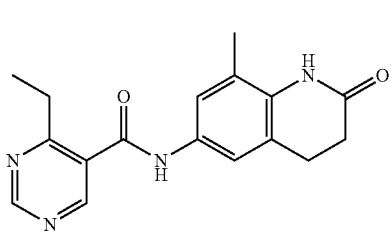
186
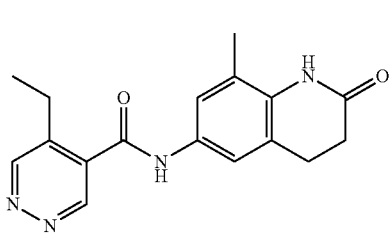
187

TABLE 1-A-continued
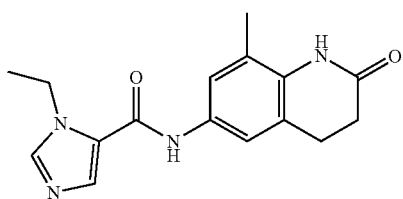
188
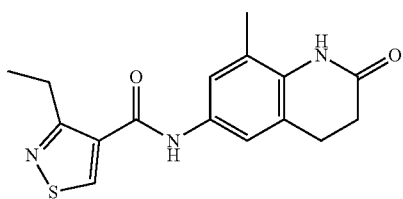
189
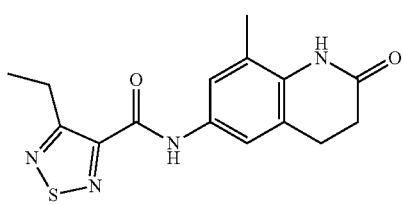
190
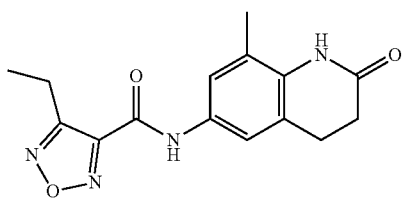
191
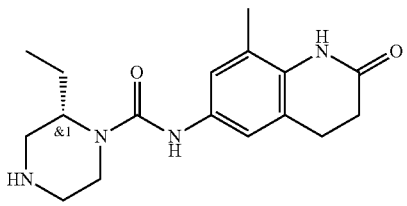
192
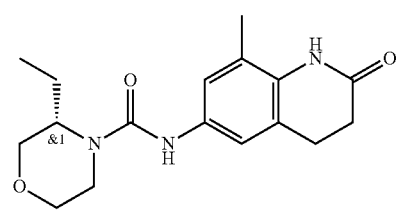
193
TABLE 1-A-continued
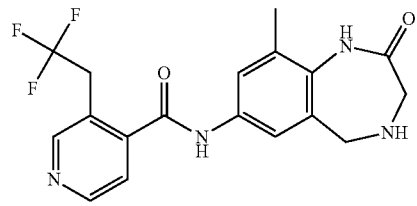
194
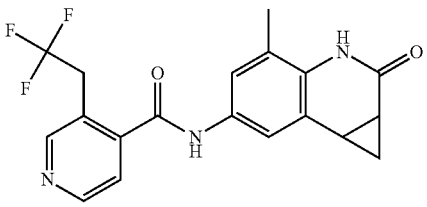
195
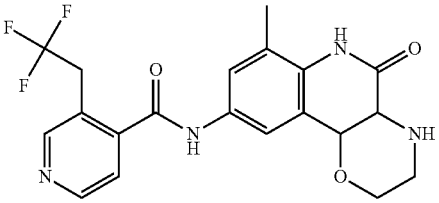
196
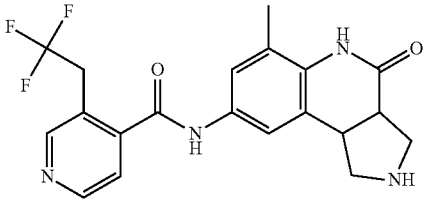
197
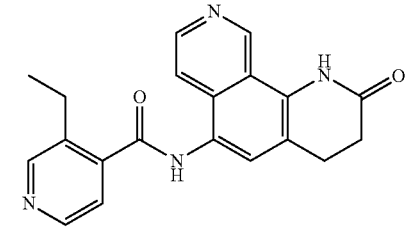
198
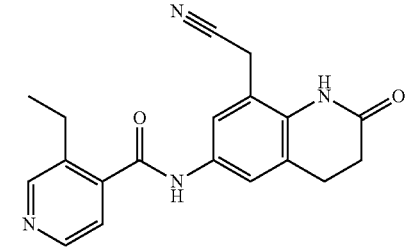
199

TABLE 1-A-continued

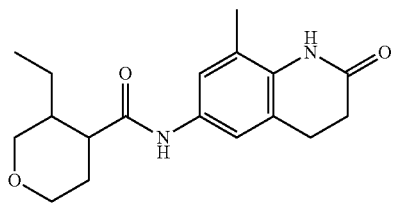

200

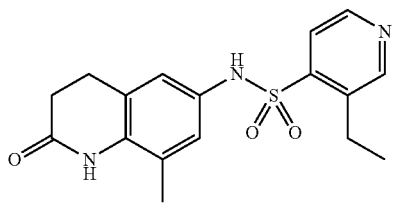

201

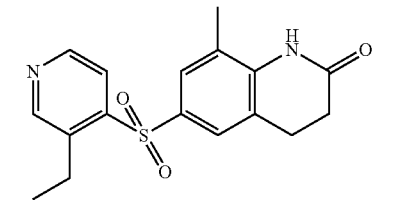

202

In some embodiments, to the extent applicable, the genus of compounds described herein also excludes any specifically known single compound(s) prior to this disclosure. In some embodiments, to the extent applicable, any sub-genus of compounds prior to this disclosure that are entirely within a genus of compounds described herein can also be excluded from such genus herein.

Method of Synthesis Compounds of the present disclosure can be readily synthesized by those skilled in the art in view of the present disclosure. Exemplified synthesis are also shown in the Examples section.

The synthesis of compounds of Formula I-1 as shown in Scheme 1 is a representative method for the preparation of compounds herein.

Scheme 1:

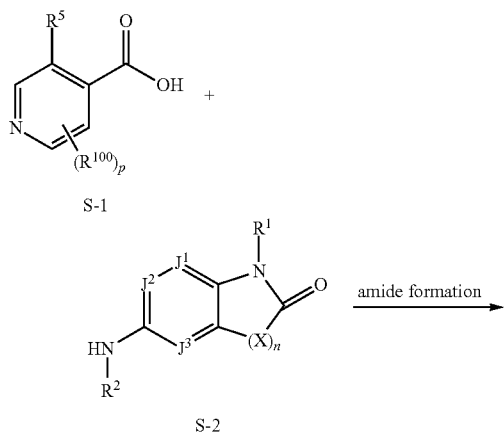

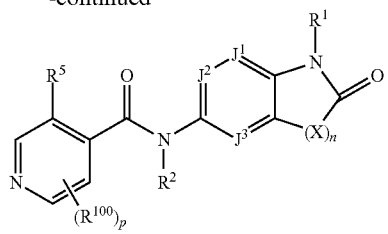

Formula I-1

As shown in Scheme 1, compounds of Formula I-1 can be typically prepared by an amide coupling reaction between suitable coupling partners, S-1 and S-2. Amide coupling reaction conditions are generally known by those skilled in the art and also exemplified in the Examples section herein. Typically, the acid S-1 can be converted into an activated form, such as acyl chloride, anhydride, active esters, etc., which can then react with the amine S-2 to form the compound of Formula I-1. For example, the Examples section describe a representative EDCI (1-Ethyl-3-(3-dimethylaminopropyl)carbodiimide) mediated amide coupling reaction. The acid S-1 and amine S-2 can be readily available or be prepared by those skilled in the art in view of the present disclosure. The variables of $R^1$, $R^2$, $R^5$, $R^{100}$, $J^1$, $J^2$, $J^3$, X, p, and n are defined herein in connection with Formula I-1. Typically, $R^2$ in S-2 is hydrogen. Other compounds of Formula I, I-P, II, or II-P with an amide linkage can be prepared similarly.

Compounds of Formula I, I-P, II, II-P or III that are not connected with an amide linkage can be typically prepared by other cross coupling reactions known to those skilled in the art, such as various palladium catalyzed cross-coupling reactions including Hartwig-Buchwald amination, Heck reaction, Suzuki reaction, etc. Exemplified procedures are described in the Examples section herein.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4$^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7$^{th}$ Edition), and Larock's Comprehensive Organic Transformations (Wiley-VCH, 1999), and any of available updates as of this filing.

Pharmaceutical Compositions Certain embodiments are directed to a pharmaceutical composition comprising one or more compounds of the present disclosure.

The pharmaceutical composition can optionally contain a pharmaceutically acceptable excipient. In some embodiments, the pharmaceutical composition comprises a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202, or 139-165, or a pharmaceutically acceptable salt thereof, e.g., in a therapeutically effective amount. In any of the embodiments described herein, the pharmaceutical composition can comprise a therapeutically effective amount of a compound selected from Compound Nos. 139-202 or 139-165 (e.g., any of the compounds having an activity level of A or B against hALDH1a3 shown in Table 3A of the present disclosure or those having an $IC_{50}$ of less than 250 nM against hALDH1a2 as shown in Table 3B of the present disclosure), or a pharmaceutically acceptable salt thereof. In some embodiments, the pharmaceutical composition can comprise a therapeutically effective amount of any compound of the present disclosure having an efficacy in ALDH1a3 inhibition comparable to Compound 1 or better, e.g., measured by any of the methods described herein. In some embodiments, the pharmaceutical composition can comprise a therapeutically effective amount of any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting hALDH1a3 when measured by the method described herein according to Biological Example 5B. In some embodiments, the pharmaceutical composition can comprise a therapeutically effective amount of any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting hALDH1a2 when measured by the method described herein according to Biological Example 5C. In some embodiments, the pharmaceutical composition can comprise a therapeutically effective amount of any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting both hALDH1a3 and hALDH1a2 when measured by the method described herein according to Biological Example 5B and 5C.

The pharmaceutical composition can also be formulated for delivery via any of the known routes of delivery, which include but are not limited to oral, parenteral, inhalation, etc. For example, in some embodiments, the pharmaceutical composition can be formulated for administering to a subject orally, nasally, transdermally, pulmonary, inhalationally, buccally, sublingually, intraperintoneally, subcutaneously, intramuscularly, intravenously, rectally, intrapleurally, intrathecally or parenterally.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion.

In some embodiments, the pharmaceutical composition is formulated for inhalation. The inhalable formulations can be, for example, formulated as a nasal spray, dry powder, or an aerosol administrable through a metered-dose inhaler.

Compounds of the present disclosure can be used alone, in combination with each other, or in combination with one or more additional therapeutic agents, e.g., metformin, recombinant insulin, liraglutide, semaglutide, empagliflozin, paclitaxel, doxorubicin, 5-fluorouracil, tamoxifen, octreotide, etc. When used in combination with one or more additional therapeutic agents, compounds of the present disclosure or pharmaceutical compositions herein can be administered to the subject either concurrently or sequentially in any order with such additional therapeutic agents. In some embodiments, the pharmaceutical composition can comprise one or more compounds of the present disclosure and the one or more additional therapeutic agents in a single composition. In some embodiments, the pharmaceutical composition comprising one or more compounds of the present disclosure can be included in a kit which also comprises a separate pharmaceutical composition comprising the one or more additional therapeutic agents.

As discussed herein, compounds of the present disclosure can sensitize the cancer for chemotherapy treatment. In some embodiments, compounds of the present disclosure can be used in combination with a chemotherapeutic agent, for example, for treating cancer. Any of the known chemotherapeutic agents can be used in combination with one or more compounds of the present disclosure. Non-limiting useful examples of chemotherapeutic agents include antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775).

In some embodiments, compounds of the present disclosure can also be used for treating type 2 diabetes in combination with one or more additional therapeutic agents useful for treating type 2 diabetes, e.g., metformin, recombinant insulin, liraglutide, semaglutide, empagliflozin etc.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure. In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Method of Treatment

Compounds of the present disclosure have various utilities. For example, compounds of the present disclosure can be used as therapeutic active substances for the treatment and/or prophylaxis of diseases or disorders that are associated with aldehyde dehydrogenase, preferably, a disease or disorder associated with aldehyde dehydrogenase isoform 1a3 (ALDH1a3) and/or 1a2 (ALDH1a2), such as proliferative diseases or disorders, metabolic diseases or disorders, endothelial cell or smooth muscle cell diseases or disorders, metastasis, etc. Accordingly, some embodiments of the present disclosure are also directed to methods of using one or more compounds of the present disclosure for inhibiting ALDH enzymes such as ALDH1a3 and/or ALDH1a2, and methods of treating or preventing various cancers, cancer metastasis, and/or other ALDH1a2 and/or ALDH1a3-mediated diseases and disorders, such as type 2 diabetes, pulmonary arterial hypertension (PAH) and neointimal hyperplasia (NIH) or as a male contraceptive. In some embodiments, the present disclosure also provides a method of using one or more compounds of the present disclosure for antagonizing retinoid pathway. Without wishing to be bound by theories, it is believed that retinoid pathway activation can cause immune tolerance, induction of $T_{reg}$ cells and/or M2 macrophages, and/or effector T cell suppression. Inhibition of ALDH1a2 and/or ALDH1a3 by one or more compounds of the present disclosure can inhibit such retinoid signaling, which can be used to treat diseases or disorders associated with undesired retinoid pathway activation and can restore or activate the subject's immune responses, e.g., against cancer cells. For example, in some embodiments, the compounds of the present disclosure can be used in combination with an immunotherapy (e.g., an immune checkpoint inhibitor) to treat diseases or disorders that are unresponsive to the immunotherapy or to treat a subject who has developed resistance to the immunotherapy.

Aldehyde dehydrogenase isoform 1a3 (ALDH1a3) is an isoform/isozyme of the ALDH1a subfamily that is crucial in the biosynthesis of RA and the regulation of RA signaling, and is cell- and disease-specific. ALDH1a3 was known as ALDH6 prior to 2000, and as Raldh3 from 2000-2007 in developmental studies. In normal conditions, ALDH1a3 is only required during embryonic development and is dispensable to healthy adult mice. In adult physiology, humans with homozygous inactivating mutations in Aldh1a3 have been described with incompletely penetrant anopthalmia and no other described pathologies. In contrast to its minor role in normal physiology, ALDH1a3 has recently been shown to be the major determinant of ALDEFLUOR™ reactivity across most cancer types and in de-differentiated pancreatic islet cells. ALDEFLUOR™ activity has long been used as a marker to differentiate aggressive cancer cells from the bulk tumor despite an overlying ignorance regarding if/how ALDEFLUOR™ activity affects tumor progression.

It has been discovered that ALDEFLUOR™ activity driven by ALDH1a3 is a functional driver of cancer aggressiveness, and is critical for tumor progression, metastasis, and resistance to chemotherapy. Thus, human ALDH1a3 (UniProtKB Accession No.: P47895) is a functional driver of chemoresistant and metastatic phenotypes in cancer, including breast cancer. Accordingly, ALDH1a3 represents a potential therapeutic target in multiple pathologies, and targeting ALDH1a3 may overcome the current barrier in treating Stage 3/4 patients whose tumors are resistant to conventional forms of therapy.

As shown in details in the Examples section herein, the present disclosure shows that among the tested ALDH isoforms, only ALDH1a2 and ALDH1a3 induce retinoid pathway activation and ALDH1a2 and ALDH1a3 drive retinoid pathway activation in solid tumors in vivo. Further, as shown in FIG. 7, expression of ALDH1a2 and ALDH1a3 mRNA in patient-derived xenograft models from multiple human cancers shows expression of ALDH1a2 and ALDH1a3 enzymes across multiple tumor types.

Compounds of the present disclosure can inhibit ALDH1a2 and/or ALDH1a3, can inhibit retinoid signaling, and can be used to treat various diseases or disorders associated with ALDH1a2 and/or ALDH1a3, and diseases or disorders associated with retinoid pathway activation.

In some embodiments, the present disclosure provides a method of inhibiting an aldehyde dehydrogenase, in particular, ALDH1a3, ALDH1a2, or a combination of ALDH1a3 and ALDH1a2, in a subject in need thereof. In some embodiments, the method is for inhibiting ALDH1a3. In some embodiments, the method is for inhibiting ALDH1a2. In some embodiments, the method is for inhibiting both ALDH1a3 and ALDH1a2. In some embodiments, the method comprises administering an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, 11-3, or II-4), Formula II-P, Formula III (e.g., Formula III-1 or III-2), Formula IV (e.g., IV-A, IV-B, IV-C, or IV-D) or any of Compound Nos. 139-202, or a pharmaceutically acceptable salt thereof) or an effective amount of a pharmaceutical composition described herein. In some embodiments, the subject suffers from a disease or disorder associated with aldehyde dehydrogenase, preferably, a disease or disorder associated with aldehyde dehydrogenase isoform 1a3 (ALDH1a3) and/or 1a2 (ALDH1a2), in a subject in need thereof. For example, in some embodiments, the subject suffers from a proliferative disease such as cancer (e.g., as described herein). In some embodiments, the subject suffers from a metabolic disease such as type 2 diabetes. In some embodiments, the subject suffers from an endothelial cell or smooth muscle cell disease or disorder, such as pulmonary arterial hypertension or neointimal hyperplasia.

In some embodiments, the present disclosure also provides a method of treating a disease or disorder associated with aldehyde dehydrogenase, preferably, a disease or disorder associated with aldehyde dehydrogenase isoform 1a3 (ALDH1a3) and/or 1a2 (ALDH1a2), in a subject in need thereof. In some embodiments, the method comprises administering an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), or any of Compound Nos. 139-202 or 139-165, or a pharmaceutically acceptable salt thereof) or an effective amount of a pharmaceutical composition described herein. In some embodiments, the disease or disorder is associated with aldehyde dehydrogenase isoform 1a3 (ALDH1a3) in the subject. In some embodiments, the disease or disorder is associated with aldehyde dehydrogenase isoform 1a2 (ALDH1a2) in the subject. In some embodiments, the disease or disorder is associated with aldehyde dehydrogenase isoform 1a3 (ALDH1a3) and 1a2 (ALDH1a2) in the subject. For example, in some embodiments, the disease or disorder is a proliferative disease such as cancer (e.g., as described herein) associated with aldehyde dehydrogenase isoform 1a3 (ALDH1a3) and/or 1a2 (ALDH1a2). In some embodiments, the disease or disorder is a metabolic disease, such as type 2 diabetes, associated with aldehyde dehydrogenase isoform 1a3 (ALDH1a3) and/or 1a2 (ALDH1a2). In some embodiments, the disease or disorder is an endothelial cell or smooth muscle cell disease or disorder, such as pulmonary arterial hypertension or neointimal hyperplasia, associated with aldehyde dehydrogenase isoform 1a3 (ALDH1a3) and/or 1a2 (ALDH1a2). In embodiments, the disease or disorder is an immunologically-driven disease or disorder, such as acute graft-vs-host disease or osteoarthritis pain, associated with aldehyde dehydrogenase isoform 1a3 (ALDH1a3) and/or ALDH1a2.

In some embodiments, the present disclosure provides a method of treating cancer in a subject in need thereof. In some embodiments, the method comprises administering to the subject a therapeutically effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or a therapeutically effective amount of a pharmaceutical composition described herein.

The methods herein are not particularly limited to any specific cancer type. As shown in the Examples section, many cancer types were shown to have ALDH1a3 activities which can be inhibited by representative compounds of the present disclosure. Also, as shown in FIG. 7, many cancer types were shown to express ALDH1a2 and ALDH1a3 enzymes, the activities of which can be inhibited by representative compounds of the present disclosure. In some embodiments, the cancer is a solid cancer. In some embodiments, the cancer is metastatic cancer or chemoresistant cancer. In some embodiments, the cancer is resistant to one or more immunotherapy, such as an immune checkpoint inhibitor, such as an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.

In some embodiments, the cancer is a breast cancer, colorectal cancer, kidney cancer, ovarian cancer, gastric cancer, thyroid cancer, urothelial cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, hematologic cancer, sarcoma, gastrointestinal stromal tumor, peripheral nerve sheath tumor, myeloma, and/or endometrial cancer.

In some embodiments, the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, and/or sarcoma. In some embodiments, the cancer is breast caner (e.g., (e.g., ER negative breast cancer, triple negative breast cancer, basal-like breast cancers, or HER2-positive breast cancers), clear cell renal cell cancer, gastric cancer, bladder cancer, ovarian cancer, squamous cell lung cancer, colorectal cancer or glioma (e.g., low-grade glioma) cancer. In some embodiments, the cancer can also be gastrointestinal stromal tumor, peripheral nerve sheath tumor, myeloma, leukemia, lymphoma and/or endometrial cancer. In some embodiments, the cancer can also be any of those shown in FIG. 7 herein, such as a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer can also be any of those described as treatable with an ALDH1a3 inhibitor in PCT/US2019/044278, which has an international filing date of Jul. 31, 2019, the content of which is incorporated by reference in its entirety.

In some embodiments, the cancer has established metastasis. In some embodiments, the cancer has not metastasized prior to treatment with the methods herein, and the method comprises administering an effective amount of one or more compounds of the present disclosure to delay or prevent metastasis of the cancer. In any of the embodiments described herein, the cancer is associated with ALDH1a3 and/or ALDH1a2 activities, such as having higher expression level compared to a control, and/or having cancer cells with ALDH1a3 and/or ALDH1a2 activities, e.g., positive in Aldefluor™ assay, which can be reduced with an ALDH1a3 and/or ALDH1a2 inhibitor or genetic knockout or knockdown, as applicable. In some embodiments, the method further comprises administering to the subject an effective amount of a second anti-cancer therapy, such as a chemotherapeutic agent (e.g., described herein, such as paclitaxel), a receptor tyrosine kinase inhibitor, or a therapeutic antibody. In some embodiments, the method further comprises administering to the subject an effective amount of an immunotherapy, such as an immune check point inhibitor.

Suitable immunotherapy for the methods described herein is not particularly limited and can include any of those known in the art, which can include for example, anti-PD-1 antibody (e.g., nivolumab, pembrolizumab, lambrolizumab, pidilizumab, BMS-936559, or AMP-224), anti-PD-L1 antibody (e.g, atezolizumab, durvalumab, avelumab, YW243.55.S70, MEDI-4736, MSB-0010718C, LY3300054, BMS-936559, MPDL3280A, or MDX-1105), IL-2, autologous T cell therapy, bispecific antibody therapy, anti-TGFβ antibody, a JAK/STAT inhibitor, or any combination thereof.

In some embodiments, the present disclosure provides a method of treating metastatic cancer in a subject in need thereof, the method comprising administering to the subject a therapeutically effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or a therapeutically effective amount of a pharmaceutical composition described herein. In some embodiments, the metastatic cancer is a solid cancer. In some embodiments, the metastatic cancer can be a metastatic breast cancer, metastatic colorectal cancer, metastatic kidney cancer, metastatic ovarian cancer, metastatic gastric cancer, metastatic thyroid cancer, metastatic testicular cancer, metastatic cervical cancer, metastatic nasopharyngeal cancer, metastatic esophageal cancer, metastatic bile duct cancer, metastatic lung cancer, metastatic pancreatic cancer, metastatic prostate cancer, metastatic bone cancer, metastatic blood cancer, metastatic brain cancer, metastatic liver cancer, metastatic mesothelioma, metastatic melanoma, and/or metastatic sarcoma. In some embodiments, the cancer is metastatic breast (e.g., ER negative breast cancer, triple negative breast cancer, basal-like breast cancers, or HER2-positive breast cancers), clear cell renal cell, gastric, bladder, ovarian, squamous cell lung, colorectal or glioma (e.g., low-grade glioma) cancer. In some embodiments, the metastatic cancer can also be a metastatic cancer selected from gastrointestinal stromal tumor, peripheral nerve sheath tumor, myeloma, and/or endometrial cancer. In some embodiments, the metastatic cancer can also be a metastatic cancer selected from a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the metastatic cancer is associated with ALDH1a3 and/or ALDH1a2 activities. In some embodiments, the metastatic cancer can be breast cancer with established lung metastasis, colorectal metastasis, and/or bone metastasis. In some embodiments, the method further comprises administering to the subject an effective amount of a second anti-cancer therapy, such as a chemotherapeutic agent (e.g., described herein, such as paclitaxel), a receptor tyrosine kinase inhibitor, or a therapeutic antibody.

In some embodiments, the present disclosure provides a method of treating chemoresistant cancer in a subject in need thereof, the method comprising administering to the subject a therapeutically effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or a therapeutically effective amount of a pharmaceutical composition described herein. "Chemoresistant cancer," as used herein, refers to a cancer that does not respond to treatment with one or more chemotherapeutic agents. "Chemoresistant cancers" include those that are non-responsive to treatment with one or more therapeutic agents at the beginning of treatment, and those that become non-responsive to treatment with one or more therapeutic agents during treatment. Chemoresistant cancers that are particularly suitable for treatment using the methods described herein include, but are not limited to, cancers that are resistant to treatment with paclitaxel and/or doxorubicin. In some embodiments, the chemoresistant cancer is a solid cancer. In some embodiments, the chemoresistant cancer can be a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, and/or sarcoma. In some embodiments, the cancer can also be gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer can be a breast (e.g., triple negative breast), clear cell renal cell, gastric, bladder, ovarian, squamous cell lung, colorectal or glioma (e.g., low-grade glioma) cancer. In some embodiments, the chemoresistant cancer is associated with ALDH1a3 and/or ALDH1a2 activities. In some embodiments, the method further comprises administering to the subject an effective amount of a second anti-cancer therapy, such as a chemotherapeutic agent (e.g., described herein, such as paclitaxel), a receptor tyrosine kinase inhibitor, or a therapeutic antibody.

In some embodiments, the present disclosure provides a method of sensitizing cancer for chemotherapy in a subject in need thereof, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. Typically, the method can cause the cancer more responsive to treatment with chemotherapeutic agent. In some embodiments, the cancer is a solid cancer. In some embodiments, the cancer can be a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, and/or sarcoma. In some embodiments, the cancer can also be gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer is associated with ALDH1a3 and/or ALDH1a2 activities. In some embodiments, the method further comprises administering to the subject an effective amount of a second anti-cancer therapy, such as a chemotherapeutic agent (e.g., described herein, such as paclitaxel), a receptor tyrosine kinase inhibitor, or a therapeutic antibody.

In some embodiments, the present disclosure provides a method of treating or preventing metastasis of a cancer in a subject in need thereof, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. In some embodiments, the cancer is a solid cancer. In some embodiments, the cancer can be a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, and/or sarcoma. In some embodiments, the cancer can also be gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer is associated with ALDH1a3 and/or ALDH1a2 activities. In some embodiments, the cancer has established metastasis. In some embodiments, the cancer has not metastasized prior to treatment with the methods herein, and the method delays or prevents metastasis of the cancer. In some embodiments, the method further comprises administering to the subject an effective amount of a second anti-cancer therapy, such as a chemotherapeutic agent (e.g., described herein, such as paclitaxel), a receptor tyrosine kinase inhibitor, or a therapeutic antibody.

In some embodiments, the cancer is unresponsive to one or more immunotherapy, e.g., an anti-PD-1, anti-CTLA4, anti-LAG-3, anti-TIGIT or anti-PD-L1 antibody. In some embodiments, the subject has developed resistance to one or more immunotherapy, e.g., an anti-PD-1 or anti-PD-L1 antibody. In some embodiments, the method further comprises administering to the subject one or more immunotherapy (e.g., as described herein).

In some embodiments, the present disclosure provides a method of antagonizing the retinoid pathway in a subject in need thereof. In some embodiments, the method comprises administering to the subject an effective amount of an ALDH1a2 inhibitor. In some embodiments, the method comprises administering to the subject an effective amount of an ALDH1a3 inhibitor. In embodiments, the method of antagonizing the retinoid pathway comprises administering to the subject an effective amount of an ALDH1a2 inhibitor and an ALDH1a3 inhibitor, for example, an effective amount of a dual inhibitor of ALDH1a2 and ALDH1a3 or a combination of one or more ALDH1a2 inhibitor and one or more ALDH1a3 inhibitor. In some embodiments, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, 11-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. In some embodiments, the subject suffers from a disease or disorder associated with retinoid pathway activation (e.g., any of those described herein).

In some embodiments, the present disclosure provides a method of inhibiting $T_{reg}$ cell and/or M2 macrophage formation in a subject in need thereof. In some embodiments, the method comprises administering to the subject an effective amount of an ALDH1a2 inhibitor. In some embodiments, the method comprises administering to the subject an effective amount of an ALDH1a3 inhibitor. In some embodiments, the method of inhibiting $T_{reg}$ cell and/or M2 macrophage formation comprises administering to the subject an effective amount of an ALDH1a2 inhibitor and an ALDH1a3 inhibitor, for example, an effective amount of a dual inhibitor of ALDH1a2 and ALDH1a3 or a combination of one or more ALDH1a2 inhibitor and one or more ALDH1a3 inhibitor. In some embodiments, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. In some embodiments, the subject is characterized as having a cancer (e.g., described herein) unresponsive to one or more immunotherapy or the subject has developed resistance to one or more immunotherapy. In some embodiments, the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer is unresponsive to one or more immunotherapy, such as an anti-PD-1 antibody, anti-PDL-1 antibody, anti-CTLA4 antibody, IL-2, autologous T cell therapy, bispecific antibody therapy, anti-TGFβ antibody, a JAK/STAT inhibitor, or any combination thereof. In some embodiments, the subject has developed resistance to one or more immunotherapy, such as an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof. In some embodiments, the method further comprises administering to the subject one or more immunotherapy, such as an immune checkpoint inhibitor. In some embodiments, the method further comprises administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.

In some embodiments, the present disclosure provides a method of treating a disease or disorder associated with the retinoid pathway activation in a subject in need thereof. In some embodiments, the method comprises administering to the subject an effective amount of an ALDH1a2 inhibitor. In some embodiments, the method comprises administering to the subject an effective amount of an ALDH1a3 inhibitor. In some embodiments, the method of treating a disease or disorder associated with the retinoid pathway activation comprises administering to the subject an effective amount of an ALDH1a2 inhibitor and an ALDH1a3 inhibitor, for example, an effective amount of a dual inhibitor of ALDH1a2 and ALDH1a3 or a combination of one or more ALDH1a2 inhibitor and one or more ALDH1a3 inhibitor. In some embodiments, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. In some embodiments, the disease or disorder is associate with immunosuppression or immunotolerance of the subject. In some embodiments, the disease or disorder is associate with induction of $T_{reg}$ cells and/or M2 macrophages, and/or effector T cell suppression in the subject. In some embodiments, the disease or disorder is cancer (e.g., described herein). In some embodiments, the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer. In some embodiments, the cancer is unresponsive to one or more immunotherapy, such as an anti-PD-1 antibody, anti-PDL-1 antibody, anti-CTLA4 antibody, IL-2, autologous T cell therapy, bispecific antibody therapy, anti-TGFβ antibody, a JAK/STAT inhibitor, or any combination thereof. In some embodiments, the subject has developed resistance to one or more immunotherapy, such as an anti-PD-1 antibody, anti-PDL-1 antibody, anti-CTLA4 antibody, IL-2, autologous T cell therapy, bispecific antibody therapy, anti-TGFβ antibody, a JAK/STAT inhibitor, or any combination thereof. In some embodiments, the method further comprises administering to the subject one or more immunotherapy, such as an immune checkpoint inhibitor. In some embodiments, the method further comprises administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.

In some embodiments, the present disclosure provides a method of treating cancer in a subject in need thereof, wherein the cancer is unresponsive to one or more immunotherapy or the subject has developed resistance to one or more immunotherapy, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein. In some embodiments, the cancer is unresponsive to one or more immunotherapy, such as an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof. In some embodiments, the cancer is unresponsive to treatment with anti-PD-1 or anti-PD-L1 antibodies. In some embodiments, the subject has developed resistance to one or more immunotherapy, such as an anti-PD-1 antibody, anti-PDL-1 antibody, anti-CTLA4 antibody, IL-2, autologous T cell therapy, bispecific antibody therapy, anti-TGFβ antibody, a JAK/STAT inhibitor, or any combination thereof. In some embodiments, the subject has developed resistance to anti-PD-1 or anti-PD-L1 antibodies based treatment. In some embodiments, the method further comprises administering to the subject one or more immunotherapy, such as an immune checkpoint inhibitor. In some embodiments, the method further comprises administering to the subject an anti-PD-1 antibody, anti-PDL-1 antibody, anti-CTLA4 antibody, IL-2, autologous T cell therapy, bispecific antibody therapy, anti-TGFβ antibody, a JAK/STAT inhibitor, or any combination thereof. In some embodiments, the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer.

In some embodiments, the present disclosure provides a method of treating cancer in a subject in need thereof, the method comprising administering to the subject an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein, in combination with an immunotherapy, such as an immune checkpoint inhibitor. In some embodiments, the immunotherapy comprises administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof. In some embodiments, the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer. In some embodiments, the cancer can also be a bladder, brain, breast, cervical, cholangio, esophagus, gallbladder, gastric, head and neck, liver, lung, melanoma, ovarian, pancreatic, prostate, renal, sarcoma, sarcoma-GIST, and/or uterine cancer.

In some embodiments, the present disclosure provides a method of treating or preventing a metabolic disease, such as Type 2 Diabetes, in a subject in need thereof, the method comprising administering to the subject a therapeutically effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or a therapeutically effective amount of a pharmaceutical composition described herein. For example, in some embodiments, the method comprises administering to the subject a therapeutically effective amount of a compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting hALDH1a3 when measured by the method described herein according to Biological Example 5B. As discussed herein, metabolic diseases such as type 2 diabetes are associated with a pathology driven by ALDH1a3 activities. In some embodiments, the method further comprises administering to the subject an effective amount of an additional anti-metabolic diseases agents, such as anti-type 2 diabetes agent. Suitable additional anti-metabolic diseases agents include without limitation an incretin mimic, recombinant insulin, a biguanide, SGLT2 inhibitors, a therapeutic antibody, etc. Any of the known Type 2 Diabetes treatments can be used in combination with the compounds of the present disclosure, for example, for treating Type 2 Diabetes (e.g., described herein) or treating or preventing other metabolic syndromes.

In some embodiments, the present disclosure provides a method of treating an endothelial cell or smooth muscle cell disease or disorder, such as pulmonary arterial hypertension or neointimal hyperplasia, in a subject in need thereof, the method comprising administering to the subject a therapeutically effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or a therapeutically effective amount of a pharmaceutical composition described herein. In some embodiments, the endothelial cell or smooth muscle cell disease or disorder is associated with a pathology driven by ALDH1a3 activities. In some embodiments, the endothelial cell or smooth muscle cell disease or disorder is pulmonary arterial hypertension. In some embodiments, the endothelial cell or smooth muscle cell disease or disorder is neointimal hyperplasia.

Also provided herein is a method of inhibiting the proliferation of a cancer cell (e.g., a metastatic cancer cell, a chemoresistant cancer cell). The method comprises administering to the cell (e.g., an effective amount of) one or more compounds of the present disclosure. In a particular embodiment, the cancer cell is a breast cancer cell (e.g., a basal-like breast cancer cell or a HER-2 positive breast cancer cell). The cell can be a cultured cell (e.g., cell line) or a cell in a subject. In a particular embodiment, the cell is present in a human subject (e.g., a human subject with a cancer).

In some embodiments, the present disclosure provides a method of male contraception, the method comprising administering to a subject in need thereof an effective amount of a compound of the present disclosure (e.g., a compound of Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, II-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, or a pharmaceutically acceptable salt thereof) or an effective amount of a pharmaceutical composition described herein.

In any of the embodiments described herein, unless specified or otherwise contradictory from context, the compound of the present disclosure recited in the methods herein can be any of the compounds having an activity level of A or B shown in Table 3A of the present disclosure against hALDH1a3 and/or those having an $IC_{50}$ of less than 1 uM against hALDH1a2 as shown in Table 3B of the present disclosure. In some embodiments, the compound of the present disclosure recited in the methods herein can also be any compound of the present disclosure having an efficacy in ALDH1a3 inhibition comparable to Compound 1 or better, e.g., measured by any of the methods described herein. In some embodiments, the compound of the present disclosure recited in the methods herein can be any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting hALDH1a3 when measured by the method described herein according to Biological Example 5B. In some embodiments, the compound of the present disclosure recited in the methods herein can be any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting hALDH1a2 when measured by the method described herein according to Biological Example 5C. In some embodiments, the compound of the present disclosure recited in the methods herein, e.g., methods for inhibiting retinoid pathway or for treating a diseases or disorder associated with the retinoid pathway, such as various cancer discussed herein, diseases or disorders associated with immune tolerance, or for male contraception, can be any compound of the present disclosure having an IC50 value of less than 250 nM (preferably, less than 100 nM, such as about 1-100 nM, about 10-100 nM, about 10-50 nM, about 20-100 nM, about 20-50 nM, etc.) in inhibiting both hALDH1a3 and hALDH1a2 when measured by the method described herein according to Biological Example 5B and 5C.

The administering in the methods herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the administering is orally.

As discussed herein, compounds of the present disclosure can be used as a monotherapy or in a combination therapy. In some embodiments according to the methods described herein, compounds of the present disclosure can be administered as the only active ingredient(s). In some embodiments according to the methods described herein, compounds of the present disclosure can be used in combination with conventional surgery or radiotherapy, immunotherapy, cell therapy, therapeutic antibodies, or chemotherapy. In some embodiments, compounds of the present disclosure can be used in combination with, either concurrently or sequentially in any order, a chemotherapy (e.g., paclitaxel, doxorubicin, tamoxifen, cisplatin, mitomycin, 5-fluorouracil, sorafenib, octreotide, dacarbazine (DTIC), cis-platinum, cimetidine, cyclophosphamide), radiation therapy (e.g., proton beam therapy), hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene), or biological therapy. In some embodiments according to the methods described herein, compounds of the present disclosure can be used in combination with conventional treatments, SGLT inhibitors, cell therapy, therapeutic antibodies, or incretin analogues.

In some embodiments according to the methods described herein, compounds of the present disclosure can also be co-administered with an additional pharmaceutically active compound, either concurrently or sequentially in any order, to the subject in need thereof. In some embodiments, the additional pharmaceutically active compound can be a chemotherapeutic agent, a therapeutic antibody, etc. Any of the known chemotherapeutics, immunotherapy, cell therapy, or therapeutic antibodies can be used in combination with the compounds of the present disclosure, for example, for treating cancer (e.g., described herein) or treating or preventing metastasis. Some examples of such additional pharmaceutically active compounds, such as chemotherapeutics, are exemplified herein, which in clude for example, DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775). In some embodiments, the additional pharmaceutically active compound can be an incretin mimic, recombinant insulin, a biguanide, a therapeutic antibody, etc. Any of the known Type 2 Diabetes treatments can be used in combination with the compounds of the present disclosure, for example, for treating Type 2 Diabetes (e.g., described herein) or treating or preventing other metabolic syndromes.

Dosing regimen including doses for the methods described herein can vary and be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for in compounds of Formula I, II, I-P, II-P, III, or subformula thereof, as applicable, are independently selected. The described embodiments of the present disclosure can be combined. Such combination is contemplated and within the scope of the present disclosure. For example, it is contemplated that the definition(s) of any one or more of $R^1$, $R^2$, $R^3$, $R^4$, $R^5$, $J^1$, $J^2$, $J^3$, Z, X, and n of Formula I can be combined with the definition of any one or more of the other(s) of $R^1$, $R^2$, $R^3$, $R^4$, $R^5$, $J^1$, $J^2$, $J^3$, Z, X, and n of Formula I, as applicable, and the resulted compounds from the combination are within the scope of the present disclosure. Combinations of other variables for other Formulae should be understood similarly.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of*

Resolving Agents and Optical Resolutions p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" refers to any of the compounds described herein according to Formula I (e.g., Formula I-O, I-F, I-1, I-2, I-1-A, I-2-A, I-1-A1, I-1-A2, I-1-A3, I-2-A1, I-2-A2, I-2-A3, I-1-B, I-2-B, I-1-C, or I-2-C), Formula I-P, Formula II (e.g., Formula II-1, 11-2, II-3, or II-4), Formula II-P, Formula III (e.g., Formula III-1 or III-2), Formula IV (e.g., IV-A, IV-B, IV-C, or IV-D) or any of Compound Nos. 139-202 or 139-165, isotopically labeled compound(s) thereof (such as a deuterated analog wherein one or more of the hydrogen atoms is/are substituted with a deuterium atom with an abundance above its natural abundance), possible stereoisomers thereof (including diastereoisomers, enantiomers, and racemic mixtures), tautomers thereof, conformational isomers thereof, and/or possible pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic saturated hydrocarbon. In some embodiments, the alkyl which can include one to twelve carbon atoms (i.e., $C_{1-12}$ alkyl) or the number of carbon atoms designated. In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. For example, a $C_{1-4}$ alkyl group as used herein refers to a group selected from methyl, ethyl, propyl (n-propyl), isopropyl, butyl (n-butyl), sec-butyl, tert-butyl, and iso-butyl. An optionally substituted $C_{1-4}$ alkyl group refers to the $C_{1-4}$ alkyl group as defined, optionally substituted with one or more permissible substituents as described herein.

"Alkylene" or "alkylene chain" refers to a fully saturated, straight or branched divalent hydrocarbon chain radical. In embodiments the alkylene has from one to twelve carbon atoms. Non-limiting examples of C1-C12 alkylene include methylene, ethylene, propylene, n-butylene, ethenylene, propenylene, n-butenylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenyl" as used by itself or as part of another group refers to a straight- or branched-chain aliphatic hydrocarbon containing one or more, for example, one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to a straight- or branched-chain aliphatic hydrocarbon containing one or more, for example, one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "haloalkyl" as used by itself or as part of another group refers to an alkyl substituted with one or more fluorine, chlorine, bromine and/or iodine atoms. In embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

"Carbocyclyl" or "carbocyclic" as used by itself or as part of another group refers to a radical of a non-aromatic cyclic hydrocarbon group having from 3 to 10 ring carbon atoms ("$C_{3-10}$ carbocyclyl") and zero heteroatoms in the non-aromatic ring system. The carbocyclyl group can be either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

"Heterocyclyl" or "heterocyclic" or "heterocycle" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is on the heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

"Heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, and the like) the point of attachment can be on either ring, i.e., either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable. Two of the optional substituents can join to form an optionally substituted cycloalkyl, heterocyclyl, aryl, or heteroaryl ring. Substitution can occur on any available carbon, oxygen, or nitrogen atom, and can form a spirocycle. Typically, substitution herein does not result in an O—O, O—N, S—S, S—N(except SO$_2$—N bond), heteroatom-halogen, or —C(O)—S bond or three or more consecutive heteroatoms, with the exception of O—SO$_2$—O, O—SO$_2$—N, and N—SO$_2$—N, except that some of such bonds or connections may be allowed if in a stable aromatic system.

In a broad aspect, the permissible substituents herein include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a cycloalkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aryl, or a heteroaryl, each of which can be substituted, if appropriate.

Exemplary substituents include, but not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, O-aryl, O-alkylene-aryl, acyl, C(O)-aryl, halo, NO$_2$, CN, SF$_5$, C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, O—C(O)-alkyl, O—C(O)-aryl, O—C(O)-cycloalkyl, —C(N—CN)—NH$_2$, —C(NH)—NH$_2$, —C(NH)—NH(alkyl), N(Y$_1$)(Y$_2$), -alkylene-N(Y$_1$)(Y$_2$), C(O)N(Y$_1$)(Y$_2$) and S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl.

Some examples of suitable substituents include, but not limited to, (C$_1$-C$_8$)alkyl groups, (C$_2$-C$_8$)alkenyl groups, (C$_2$-C$_8$)alkynyl groups, (C$_3$-C$_{10}$)cycloalkyl groups, halogen (F, Cl, Br or I), halogenated (C$_1$-C$_8$)alkyl groups (for example but not limited to CF$_3$), 0 (C$_1$-C$_8$)alkyl groups, OH, S (C$_1$-C$_8$)alkyl groups, SH, —NH(C$_1$-C$_8$)alkyl groups, N((C$_1$-C$_8$)alkyl)$_2$ groups, NH$_2$, C(O)NH$_2$, C(O)NH(C$_1$-C$_8$)alkyl groups, C(O)N((C$_1$-C$_8$)alkyl)$_2$, —NHC(O)H, NHC(O) (C$_1$-C$_8$)alkyl groups, —NHC(O) (C$_3$-C$_8$)cycloalkyl groups, N((C$_1$-C$_8$)alkyl)C(O)H, N((C$_1$-C$_8$)alkyl)C(O)(C$_1$-C$_8$)alkyl groups, —NHC(O)NH$_2$, NHC(O)NH(C$_1$-C$_8$)alkyl groups, N((C1-C$_8$)alkyl)C(O)NH$_2$ groups, —NHC(O)N((C$_1$-C$_8$)alkyl)$_2$ groups, N((C$_1$-C$_8$)alkyl)C(O)N((C$_1$-C$_8$)alkyl)$_2$ groups, N((C$_1$-C$_8$)alkyl)C(O)NH((C1-C$_8$)alkyl), C(O)H, C(O)(C$_1$-C$_8$)alkyl groups, CN, NO$_2$, S(O)(C$_1$-C$_8$)alkyl groups, S(O)$_2$ (C1-C$_8$)alkyl groups, S(O)$_2$N((C1-C$_8$)alkyl)$_2$ groups, S(O)$_2$ NH(C1-C$_8$)alkyl groups, S(O)$_2$NH(C$_3$-C$_8$)cycloalkyl groups, S(O)$_2$NH$_2$ groups, NHS(O)$_2$(C1-C$_8$)alkyl groups, N((C1-C$_8$)alkyl)S(O)$_2$(C$_1$-C$_8$)alkyl groups, (C$_1$-C$_8$)alkyl-O (C$_1$-C$_8$)alkyl groups, 0 (C1-C$_8$)alkyl-O (C1-C$_8$)alkyl groups, C(O)OH, C(O)O(C$_1$-C$_8$)alkyl groups, NHOH, NHO (C$_1$-C$_8$)alkyl groups, O-halogenated (C$_1$-C$_8$)alkyl groups (for example but not limited to OCF$_3$), S(O)$_2$-halogenated (C$_1$-C$_8$)alkyl groups (for example but not limited to S(O)$_2$ CF$_3$), —S-halogenated (C$_1$-C$_8$)alkyl groups (for example but not limited to SCF$_3$), (C$_1$-C$_6$) heterocycle (for example but not limited to pyrrolidine, tetrahydrofuran, pyran or morpholine), (C$_1$-C$_6$) heteroaryl (for example but not limited to tetrazole, imidazole, furan, pyrazine or pyrazole), -phenyl, —NHC(O)O—(C$_1$-C$_6$)alkyl groups, N((C$_1$-C$_6$)alkyl)C(O)O—(C1-C$_6$)alkyl groups, C(=NH)—(C$_1$-C$_6$)alkyl groups, C(=NOH)—(C$_1$-C$_6$)alkyl groups, or C(=N—O—(C$_1$-C$_6$)alkyl)-(C$_1$-C$_6$)alkyl groups.

Exemplary carbon atom substituents include, but are not limited to, halogen, —CN, —NO$_2$, —N$_3$, hydroxyl, alkoxy, cycloalkoxy, aryloxy, amino, monoalkyl amino, dialkyl amino, amide, sulfonamide, thiol, acyl, carboxylic acid, ester, sulfone, sulfoxide, alkyl, haloalkyl, alkenyl, alkynyl, C$_{3-10}$ carbocyclyl, C$_{6-10}$ aryl, 3-10 membered heterocyclyl, 5-10 membered heteroaryl, etc. For example, exemplary carbon atom substituents can include F, Cl, —CN, —SO$_2$H, —SO$_3$H, —OH, —OC$_{1-6}$ alkyl, —NH$_2$, —N(C$_{1-6}$ alkyl)$_2$, —NH(C$_{1-6}$ alkyl), —SH, —SC$_{1-6}$ alkyl, —C(=O)(C$_{1-6}$ alkyl), —CO$_2$H, —C$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —NHSO$_2$(C$_{1-6}$ alkyl), —SO$_2$N ($C_{1-6}$ alkyl)$_2$, —SO$_2$NH($C_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal substituents can be joined to form=O.

Nitrogen atoms can be substituted or unsubstituted as valency permits, and include primary, secondary, tertiary, and quaternary nitrogen atoms. Exemplary nitrogen atom substituents include, but are not limited to, hydrogen, acyl groups, esters, sulfone, sulfoxide, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two substituent groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl can be further substituted as defined herein. In certain embodiments, the substituent present on a nitrogen atom is a nitrogen protecting group (also referred to as an amino protecting group). Nitrogen protecting groups are well known in the art and include those described in detail in *Protective Groups in Organic Synthesis*, T. W. Greene and P. G. M. Wuts, 3$^{rd}$ edition, John Wiley & Sons, 1999, incorporated by reference herein. Exemplary nitrogen protecting groups include, but not limited to, those forming carbamates, such as Carbobenzyloxy (Cbz) group, p-Methoxybenzyl carbonyl (Moz or MeOZ) group, tert-Butyloxycarbonyl (BOC) group, Troc, 9-Fluorenylmethyloxycarbonyl (Fmoc) group, etc., those forming an amide, such as acetyl, benzoyl, etc., those forming a benzylic amine, such as benzyl, p-methoxybenzyl, 3,4-dimethoxybenzyl, etc., those forming a sulfonamide, such as tosyl, Nosyl, etc., and others such as p-methoxyphenyl.

Exemplary oxygen atom substituents include, but are not limited to, acyl groups, esters, sulfonates, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl can be further substituted as defined herein. In certain embodiments, the oxygen atom substituent present on an oxygen atom is an oxygen protecting group (also referred to as a hydroxyl protecting group). Oxygen protecting groups are well known in the art and include those described in detail in *Protective Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, those forming alkyl ethers or substituted alkyl ethers, such as methyl, allyl, benzyl, substituted benzyls such as 4-methoxybenzyl, methoxylmethyl (MOM), benzyloxymethyl (BOM), 2-methoxyethoxymethyl (MEM), etc., those forming silyl ethers, such as trymethylsilyl (TMS), triethylsilyl (TES), triisopropylsilyl (TIPS), t-butyldimethylsilyl (TBDMS), etc., those forming acetals or ketals, such as tetrahydropyranyl (THP), those forming esters such as formate, acetate, chloroacetate, dichloroacetate, trichloroacetate, trifluoroacetate, methoxyacetate, etc., those forming carbonates or sulfonates such as methanesulfonate (mesylate), benzylsulfonate, and tosylate (Ts), etc.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

In some embodiments, the "optionally substituted" alkyl, alkenyl, alkynyl, carbocyclic, cycloalkyl, alkoxy, cycloalkoxy, or heterocyclic group herein can be unsubstituted or substituted with 1, 2, 3, or 4 substituents independently selected from F, Cl, —OH, protected hydroxyl, oxo (as applicable), NH$_2$, protected amino, NH($C_{1-4}$ alkyl) or a protected derivative thereof, N($C_{1-4}$ alkyl(($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2, or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl (e.g., CF$_3$), $C_{1-4}$ alkoxy and fluoro-substituted $C_{1-4}$ alkoxy. In some embodiments, the "optionally substituted" aryl or heteroaryl group herein can be unsubstituted or substituted with 1, 2, 3, or 4 substituents independently selected from F, Cl, —OH, —CN, NH$_2$, protected amino, NH($C_{1-4}$ alkyl) or a protected derivative thereof, N($C_{1-4}$ alkyl(($C_{1-4}$ alkyl), —S(=O)($C_{1-4}$ alkyl), —SO$_2$($C_{1-4}$ alkyl), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1, 2 or 3 ring heteroatoms independently selected from O, S, and N, 3-7 membered heterocyclyl containing 1 or 2 ring heteroatoms independently selected from O, S, and N, wherein each of the alkyl, alkenyl, alkynyl, alkoxy, cycloalkyl, cycloalkoxy, phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl, $C_{1-4}$ alkoxy and fluoro-substituted $C_{1-4}$ alkoxy.

"Halo" or "halogen" refers to fluorine (fluoro, —F), chlorine (chloro, —Cl), bromine (bromo, —Br), or iodine (iodo, —I).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

EXAMPLES

The various starting materials, intermediates, and compounds of the embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

The abbreviations used in the Examples section should be understood as having their ordinary meanings in the art unless specifically indicated otherwise or obviously contrary from context. The following shows a list of some of the abbreviations used in the Examples section:

AIBN Azobisisobutyronitrile
DCM dichloromethane
DIPEA di-isopropylethylamine
DMF dimethylformamide
DPPP 1,3-bis(diphenylphosphino)propane
EA or EtOAc ethyl acetate
EDCI N-(3-Dimethylaminopropyl)-N'-ethylcarbodiimide
LAH Lithium Aliminium hydride
NMP N-methylpyrrolidinone
PE petroleum ether
Py. pyridine
THE tetrahydrofuran
TLC thin-layer chromatography Example 1. Synthesis of Compound 142

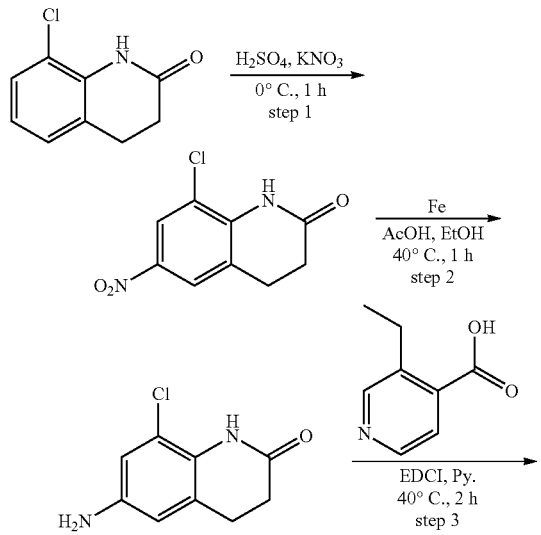

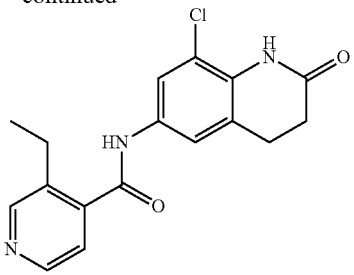

142

Step 1: To the mixture of 8-chloro-3,4-dihydro-1H-quinolin-2-one (0.2 g, 1.10 mmol, 1 eq) in $H_2SO_4$ (2 mL) was added $KNO_3$ (133.60 mg, 1.32 mmol, 1.2 eq) in portions at 0° C. Then the mixture was stirred at 0° C. for 1 hr. The mixture was added to ice (20 mL) slowly. Then the mixture was filtered. The filter cake was washed with water (5 mL). 8-chloro-6-nitro-3,4-dihydro-1H-quinolin-2-one (0.2 g, 882.55 umol, 80.14% yield) was obtained as yellow solid.

Step 2: To the mixture of 8-chloro-6-nitro-3,4-dihydro-1H-quinolin-2-one (0.2 g, 882.55 umol, 1 eq) in AcOH (1 mL) and EtOH (1 mL) was added Fe (246.43 mg, 4.41 mmol, 5 eq). The mixture was stirred at 40° C. for 1 hr. The mixture filtered and concentrated under reduced pressure to give a residue. The residue was purified by prep-TLC ($SiO_2$, Petroleum ether:Ethyl acetate=1:1). Compound 6-amino-8-chloro-3,4-dihydro-1H-quinolin-2-one (55 mg, 279.71 umol, 31.69% yield) was obtained as a white solid.

Step 3: To the mixture of 6-amino-8-chloro-3,4-dihydro-1H-quinolin-2-one (55 mg, 279.71 umol, 1 eq) and 3-ethylpyridine-4-carboxylic acid (50.74 mg, 335.65 umol, 1.2 eq) in Py. (1 mL) was added EDCI (64.34 mg, 335.65 umol, 1.2 eq). The mixture was stirred at 45° C. for 2 hr. The crude production was concentrated under reduced pressure to give a residue. The residue was purified by prep-TLC (SiO2, = Petroleum ether:Ethyl acetate 0:1). Compound N-(8-chloro-2-oxo-3,4-dihydro-1H-quinolin-6-yl)-3-ethyl-pyridine-4-carboxamide (30 mg, 90.06 umol, 32.20% yield, 99% purity) was obtained. $^1$H NMR (400 MHz, MeOD): δ 8.56 (s, 1H), 8.51 (d, J=5.2 Hz, 1H), 7.74 (s, 1H), 7.45-7.47 (m, 2H), 2.99-3.04 (m, 2H), 2.82 (q, J=7.6 Hz, 2H), 2.60-2.64 (m, 2H), 1.27 (t, J=7.6 Hz, 3H). LCMS: (M+H$^+$) 330.0.

Example 2. Synthesis of Compound 143

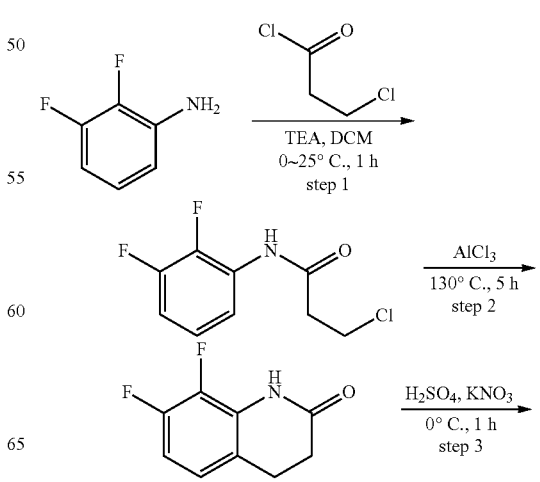

-continued

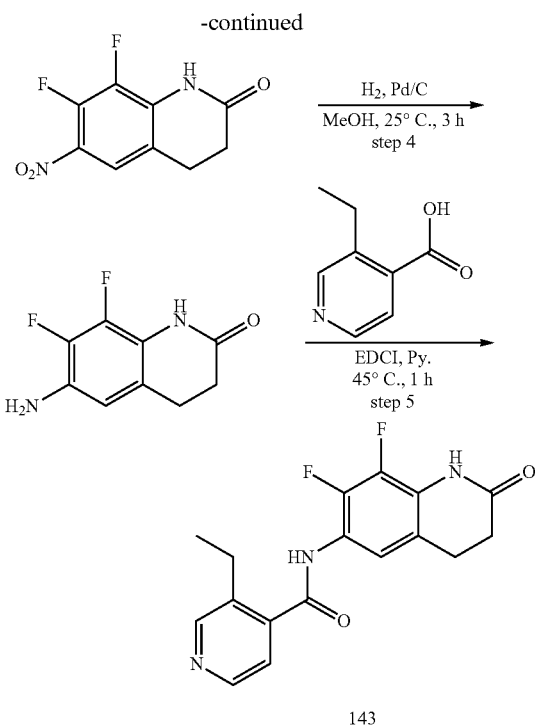

143

Step 1: To the mixture of 2,3-difluoroaniline (5 g, 38.73 mmol, 3.94 mL, 1 eq) and TEA (3.92 g, 38.73 mmol, 5.39 mL, 1 eq) in DCM (80 mL) was added 3-chloropropanoyl chloride (4.67 g, 36.79 mmol, 3.54 mL, 0.95 eq) drop-wise at 0° C. Then the mixture was stirred at 25° C. for 1 hr. To the mixture was added H₂O (50 mL). Then the mixture was extracted with ethyl acetate (50 mL*3). The combined organic phase was washed with brine (50 mL*2), dried with anhydrous Na₂SO₄, filtered and concentrated in vacuum. 3-chloro-N-(2,3-difluorophenyl)propanamide (7 g, 31.87 mmol, 82.30% yield) was obtained as light yellow solid.

Step 2: The mixture of 3-chloro-N-(2,3-difluorophenyl) propanamide (7 g, 31.87 mmol, 1 eq) in AlCl₃ (12.75 g, 95.62 mmol, 5.23 mL, 3 eq) was stirred at 130° C. for 5 hr. The mixture was added to ice-water (100 mL). Then the mixture was extracted with ethyl acetate (50 mL*3). The combined organic phase was washed with brine (30 mL), dried with anhydrous Na₂SO₄, filtered and concentrated in vacuum. The residue was purified by column chromatography (SiO2, Petroleum ether/Ethyl acetate=100/1 to 10/1). Then the crude was purified by prep-HPLC (column: Welch Xtimate C18 100*25 mm*3 um; mobile phase: [water (0.05% HCl)-ACN]; B %: 30%-50%, 8 min). 7,8-difluoro-3,4-dihydro-1H-quinolin-2-one (0.22 g, 12 mmol) was obtained as yellow solid.

Step 3: To the mixture of 7,8-difluoro-3,4-dihydro-1H-quinolin-2-one (0.22 g, 1.20 mmol, 1 eq) in H₂SO₄ (2 mL) was added KNO₃ (145.73 mg, 1.44 mmol, 1.2 eq) in portions at 0° C. The mixture was stirred at 0° C. for 1 hr. The mixture was poured into ice (10 mL) slowly. Then the mixture was filtered. The filter cake was washed with water (10 mL). 7,8-difluoro-6-nitro-3,4-dihydro-1H-quinolin-2-one (0.28 g, crude) was obtained as light yellow solid.

Step 4: To a solution of 7,8-difluoro-6-nitro-3,4-dihydro-1H-quinolin-2-one (0.28 g, 1.23 mmol, 1 eq) in MeOH (10 mL) was added Pd/C (0.05 g, 10%) under N₂. The suspension was degassed under vacuum and purged with H₂ several times. The mixture was stirred under H₂ (15 psi) at 25° C. for 3 hours. The reaction mixture was filtered and the filter was concentrated. 6-amino-7,8-difluoro-3,4-dihydro-1H-quinolin-2-one (160 mg, 807.39 umol, 65.79% yield) was obtained as purple solid.

Step 5: The mixture of 6-amino-7,8-difluoro-3,4-dihydro-1H-quinolin-2-one (80 mg, 403.70 umol, 1 eq) and 3-ethylpyridine-4-carboxylic acid (73.23 mg, 484.44 umol, 1.2 eq), EDCI (92.87 mg, 484.44 umol, 1.2 eq) in Py (1 mL) was stirred at 45° C. for 1 hr. The reaction mixture was concentrated. The residue was purified by prep-TLC (SiO2, Petroleum ether:Ethyl acetate=0:1). N-(7,8-difluoro-2-oxo-3,4-dihydro-1H-quinolin-6-yl)-3-ethyl-pyridine-4-carboxamide (35 mg, 105.64 umol, 26.17% yield, 100% purity) was obtained. LCMS (M+H⁺): 332.0; ¹H NMR (400 MHz, MeOD): δ 8.58 (s, 1H), 8.54 (d, J=5.2 Hz, 1H), 7.52 (d, J=5.2 Hz, 1H), 7.43 (d, J=7.2 Hz, 1H), 3.02-3.06 (m, 2H), 2.90 (q, J=7.6 Hz, 2H), 2.63-2.67 (m, 2H), 1.31 (t, J=7.6 Hz, 3H).

Example 3. Synthesis of Compound 144

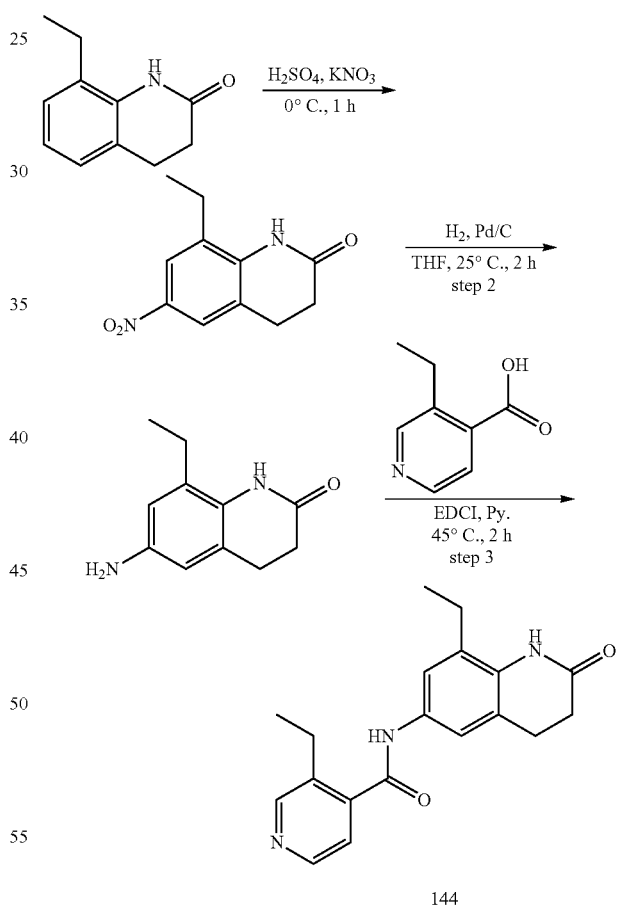

144

Step 1: To the mixture of 8-ethyl-3,4-dihydro-1H-quinolin-2-one (0.18 g, 1.03 mmol, 1 eq) in H₂SO₄ (2 mL) was added KNO₃ (124.63 mg, 1.23 mmol, 1.2 eq) at 0° C. The mixture was stirred at 0° C. for 1 hr. The mixture was poured into ice (20 mL) slowly. The mixture was filtered. The residue was purified by prep-TLC (SiO2, Petroleum ether: Ethyl acetate=1:1). 8-ethyl-6-nitro-3,4-dihydro-1H-quinolin-2-one (88 mg, crude) was obtained as yellow solid.

Step 2: To a solution of 8-ethyl-6-nitro-3,4-dihydro-1H-quinolin-2-one (88 mg, 399.59 umol, 1 eq) in THF (10 mL) was added 10% Pd/C (0.02 g) under N₂. The suspension was degassed under vacuum and purged with H₂ several times. The mixture was stirred under H₂ (15 psi) at 25° C. for 2 hrs. The reaction mixture was filtered and concentrated under reduced pressure to give a residue. The residue was purified by prep-TLC (SiO2, Petroleum ether:Ethyl acetate=0:1). Compound 6-amino-8-ethyl-3,4-dihydro-1H-quinolin-2-one (40 mg, 210.26 umol, 52.62% yield) was obtained as a brown solid.

Step 3: A mixture of 6-amino-8-ethyl-3,4-dihydro-1H-quinolin-2-one (40 mg, 210.26 umol, 1 eq), 3-ethylpyridine-4-carboxylic acid (38.14 mg, 252.31 umol, 1.2 eq), EDCI (48.37 mg, 252.31 umol, 1.2 eq) in Py (1 mL) was degassed and purged with N₂ for 3 times, and then the mixture was stirred at 45° C. for 2 hr under N₂ atmosphere. The reaction was concentrated in vacuum. The residue was purified by prep-TLC (SiO2, Petroleum ether:Ethyl acetate=0:1). Compound 3-ethyl-N-(8-ethyl-2-oxo-3,4-dihydro-1H-quinolin-6-yl)pyridine-4-carboxamide (15 mg, 46.38 umol, 22.06% yield, 100% purity) was obtained. LCMS (M+H⁺): 324.1; ¹H NMR (400 MHz, MeOD): δ 8.55 (s, 1H), 8.50 (d, J=4.8 Hz, 1H), 7.45 (d, J=5.2 Hz, 1H), 7.43 (s, 1H), 7.37 (s, 1H), 2.96-3.00 (m, 2H), 2.85 (q, J=7.6 Hz, 2H), 2.66 (q, J=7.6 Hz, 2H), 2.56-2.60 (m, 2H), 1.27 (t, J=7.6 Hz, 3H), 1.23 (t, J=7.6 Hz, 3H).

Example 4. Synthesis of Compound 146

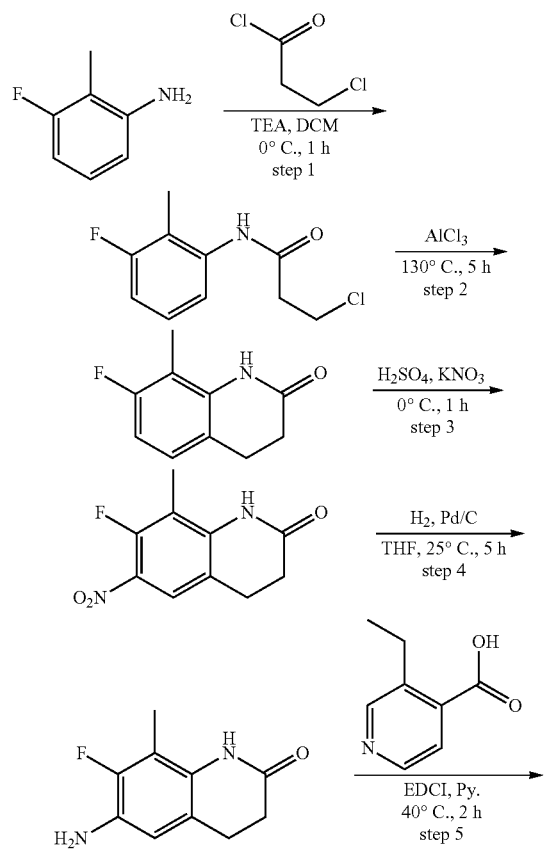

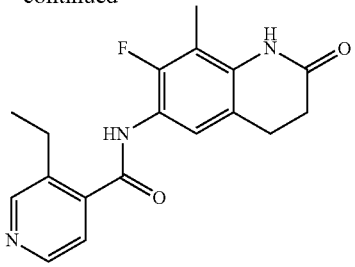

146

Step 1: To the mixture of 3-fluoro-2-methyl-aniline (5 g, 39.95 mmol, 4.55 mL, 1 eq and TEA (4.25 g, 41.95 mmol, 5.84 mL, 1.05 eq in DCM (100 mL) was added 3-chloro-propanoyl chloride (5.07 g, 39.95 mmol, 3.84 mL, 1 eq drop-wise at 0° C. under N₂. The mixture was stirred at 0° C. for 1 hr. The reaction mixture was quenched by addition H₂O 15 mL (5 ml*3) at 0° C., and then extracted with Ethyl acetate 30 mL (10 mL*3). The combined organic layers were concentrated under reduced pressure to give a residue. Compound 3-chloro-N-(3-fluoro-2-methyl-phenyl)propanamide (7 g, crude) was obtained as a white solid.

Step 2: To the mixture of 3-chloro-N-(3-fluoro-2-methyl-phenyl) propanamide (7 g, 32.46 mmol, 1 eq), AlCl3 (12.98 g, 97.38 mmol, 5.32 mL, 3 eq) was degassed and purged with N₂ for 3 times, and then the mixture was stirred at 130° C. for 5 hr under N₂ atmosphere. The reaction mixture was poured into ice water 100 ml. The aqueous phase was extracted with ethyl acetate (50 mL*3). The combined organic phase was washed with brine (30 mL), dried with anhydrous Na₂SO₄, filtered and concentrated in vacuum. The residue was purified by flash silica gel chromatography (ISCO®; 20 g SepaFlash® Silica Flash Column, Eluent of 0~15% Ethyl acetate/Petroleum ethergradient @80 mL/min). 1.2 g crude product was obtained. 0.48 g of the crude product was purified by prep-HPLC (column: Phenomenex Gemini-NX 80*40 mm*3 um; mobile phase: [water(0.04% HCl)-ACN]; B %: 15%-35%, 8 min). Compound 7-fluoro-8-methyl-3,4-dihydro-1H-quinolin-2-one (110 mg, 613.87 umol, 1.89% yield) was obtained as a white solid. 7-fluoro-8-methyl-3,4-dihydro-1H-quinolin-2-one (0.72 g, crude) was obtained as a white solid.

Step 3: The mixture of 7-fluoro-8-methyl-3,4-dihydro-1H-quinolin-2-one (0.11 g, 613.87 umol, 1 eq) in H₂SO₄ (1 mL) was added KNO3 (68.27 mg, 675.26 umol, 1.1 eq) in portions at 0° C. Then the mixture was stirred at 0° C. for 1 hr. The mixture was added to ice (10 mL). Then the mixture was filtered. The filter cake was washed with water (2 mL) and concentrated in vacuum. 7-fluoro-8-methyl-6-nitro-3,4-dihydro-1H-quinolin-2-one (98 mg, 437.13 umol, 71.21% yield) was obtained as yellow solid.

Step 4: To a solution of 7-fluoro-8-methyl-6-nitro-3,4-dihydro-1H-quinolin-2-one (98 mg, 437.13 umol, 1 eq) in THF (5 mL) was added 10% Pd/C (0.02 g) under N₂. The suspension was degassed under vacuum and purged with H₂ several times. The mixture was stirred under H₂ (15 psi) at 25° C. for 5 hr. The reaction mixture was filtered and concentrated under reduced pressure to give a residue. Compound 6-amino-7-fluoro-8-methyl-3,4-dihydro-1H-quinolin-2-one (60 mg, 308.95 umol, 70.68% yield) was obtained as a white solid.

Step 5: To the solution of 6-amino-7-fluoro-8-methyl-3,4-dihydro-1H-quinolin-2-one (50 mg, 257.46 umol, 1 eq)

and 3-ethylpyridine-4-carboxylic acid (57.97 mg, 308.95 umol, 1.2 eq, HCl) in Py (5 mL) was added EDCI (59.23 mg, 308.95 umol, 1.2 eq). The mixture was stirred at 40° C. for 2 hr. The reaction mixture was concentrated under reduced pressure to give a residue. The residue was purified by prep-TLC (SiO2, Petroleum ether:Ethyl acetate=0:1). Compound 3-ethyl-N-(7-fluoro-8-methyl-2-oxo-3,4-dihydro-1H-quinolin-6-yl)pyridine-4-carboxamide (20 mg, 59.81 umol, 23.23% yield, 97.9% purity) was obtained. LCMS (M+H$^+$): 328.1; $^1$H NMR (400 MHz, MeOD): δ 8.56 (s, 1H), 8.51 (d, J=5.2 Hz, 1H), 7.48-7.50 (m, 2H), 2.94-2.98 (m, 2H), 2.87 (q, J=7.6 Hz, 2H), 2.57-2.61 (m, 2H), 2.71 (d, J=1.2 Hz, 3H), 1.30 (t, J=7.6 Hz, 3H).

Example 5. Synthesis of Compound 139

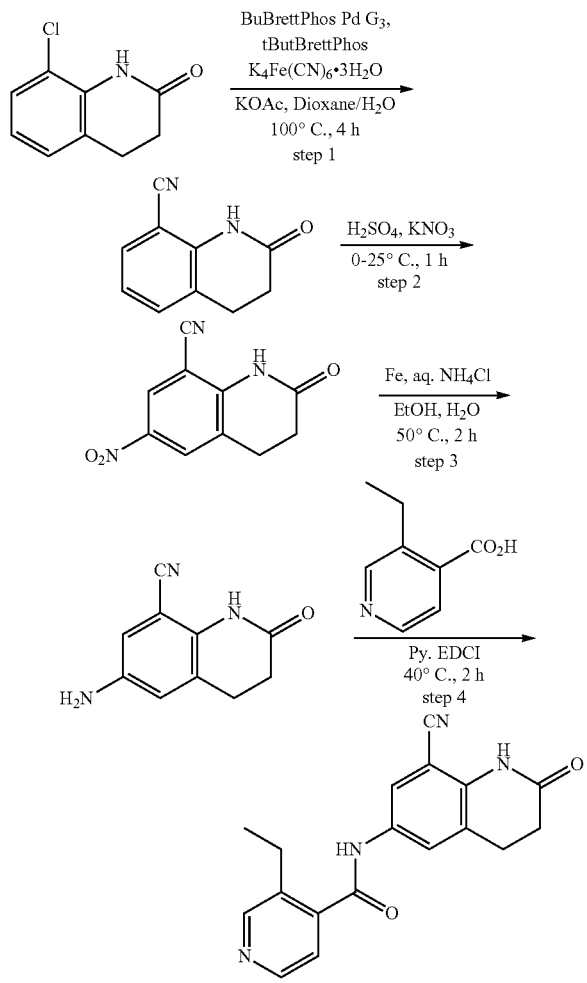

139

Step 1: To the mixture of 8-chloro-3,4-dihydro-1H-quinolin-2-one (0.4 g, 2.20 mmol, 1 eq), Potassium acetate (80.00 mg, 815.14 umol, 0.37 eq), K$_4$Fe(CN)$_6$·3H$_2$O (640.00 mg, 1.94 mmol, 533.33 uL, 8.83e-1 eq) in H$_2$O (0.5 mL), tButBrettPhos (13.3 mg) in dioxane (2 mL) and H$_2$O (1.5 mL) was added tButBrettPhos Pd G3 (188.18 mg, 220.24 umol, 0.1 eq) under N$_2$. The mixture was heated at 100° C. for 4 h under N$_2$. The reaction mixture was filtered and filtrates were concentrated under reduced pressure to give a residue. The residue was purified by prep-TLC (SiO$_2$, Petro ether:EtOAc=1:1). Compound 2-oxo-3,4-dihydro-1H-quinoline-8-carbonitrile (240 mg, 1.39 mmol, 63.29% yield) was obtained as a white solid. LCMS: (M+H)$^+$: 173.1.

Step 2: To a solution of 2-oxo-3,4-dihydro-1H-quinoline-8-carbonitrile (240 mg, 1.39 mmol, 1 eq) in conc·H$_2$SO$_4$ (2 mL) was added KNO$_3$ (155.02 mg, 1.53 mmol, 1.1 eq) at 0° C. The mixture was stirred at 25° C. for 1 hr. The reaction mixture was cooled at 0° C. and the resulting solution was stirred for 15 min at 0° C. Then the mixture was quenched by adding 50 mL of H$_2$O/ice. The suspension was filtered and filter cake was concentrated under reduced pressure to give a residue. The crude product was triturated with the solution of Petro ether and EtOAc (10:1.11 mL) at 25° C. for 20 min. The suspension was filtered and filter cake was concentrated under reduced pressure to give a residue. Compound 6-nitro-2-oxo-3,4-dihydro-1H-quinoline-8-carbonitrile (220 mg, 1.01 mmol, 72.67% yield) was obtained as a white solid. LCMS: (M+H)$^+$: 218.1.

Step 3: To a solution of 6-nitro-2-oxo-3,4-dihydro-1H-quinoline-8-carbonitrile (220 mg, 1.01 mmol, 1 eq) in H$_2$O (3 mL) and EtOH (3 mL) was added Fe (282.87 mg, 5.06 mmol, 5 eq) and NH$_4$Cl (270.92 mg, 5.06 mmol, 5 eq). The mixture was stirred at 50° C. for 2 hrs. The reaction mixture was filtered and filter concentrated under reduced pressure to give a residue. The residue was purified by prep-TLC (SiO$_2$, Petro ether:EtOAc=0:1). The crude product was triturated with the mixture solution of Petro ether and EtOAc (10:1, 11 mL). The suspension was filtered and filter cake was concentrated under reduced pressure to give a residue. Compound 6-amino-2-oxo-3,4-dihydro-1H-quinoline-8-carbonitrile (120 mg, 641.03 umol, 63.28% yield) was obtained as a white solid. LCMS (M+H)$^+$: 188.1.

Step 4: To a mixture of 6-amino-2-oxo-3,4-dihydro-1H-quinoline-8-carbonitrile (120 mg, 641.03 umol, 1 eq) and 3-ethylpyridine-4-carboxylic acid (106.59 mg, 705.14 umol, 1.1 eq) in Py. (2 mL) was added EDCI (122.89 mg, 641.03 umol, 1 eq) in one portion at 40° C. The mixture was stirred at 40° C. for 2 hrs. The reaction mixture was concentrated under reduced pressure to give a residue. The residue was purified by prep-TLC (SiO$_2$, Ethyl acetate:Methanol=5:1). Compound N-(8-cyano-2-oxo-3,4-dihydro-1H-quinolin-6-yl)-3-ethyl-pyridine-4-carboxamide (75.6 mg, 227.74 umol, 35.53% yield, 96.5% purity) was obtained as white solid. LCMS: (M+H)$^+$: 321.0. $^1$H NMR (400 MHz, MeOD): δ 8.56 (s, 1H), 8.51 (d, J=4.8 Hz, 1H), 7.92 (s, 1H), 7.77 (s, 1H), 7.48 (d, J=5.2 Hz, 1H), 3.02-3.06 (m, 2H), 2.85 (q, J=7.6 Hz, 2H), 2.63-2.67 (m, 2H), 1.27 (t, J=7.6 Hz, 3H).

Example 6. Synthesis of Compound 140

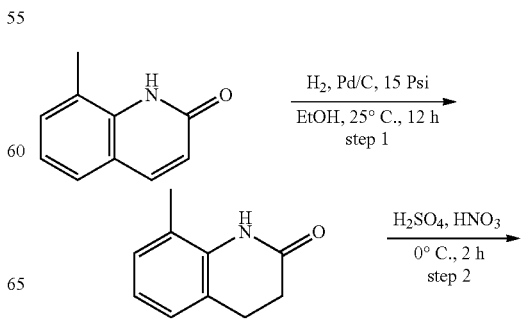

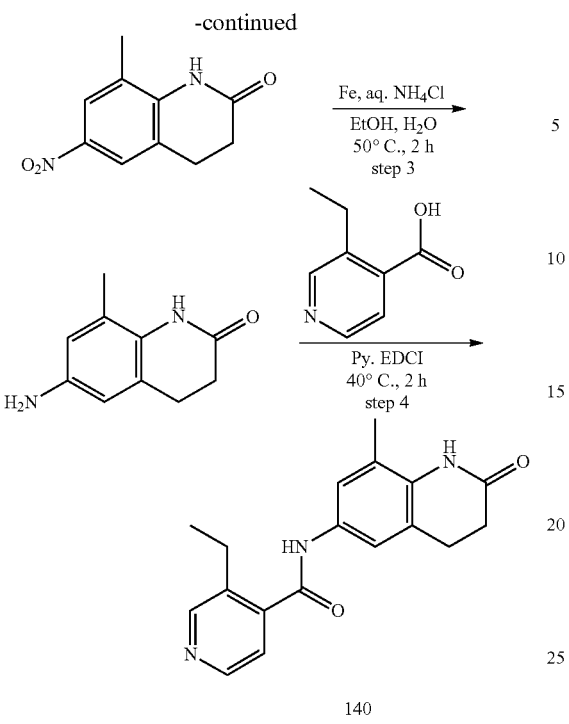

Step 1: The suspension of 8-methyl-1H-quinolin-2-one (200 mg, 1.26 mmol, 1 eq) and 10% Pd/C (80 mg) in EtOH (10 mL) was degassed and purged with $H_2$ for 3 times. The mixture was stirred under $H_2$ (15 Psi) at 25° C. for 12 hrs. The reaction mixture was filtered and filtrates were concentrated under reduced pressure to give a residue. The crude product 8-methyl-3,4-dihydro-1H-quinolin-2-one (180 mg, 1.12 mmol, 88.87% yield) was obtained as a white solid. It was used into the next step without further purification.

Step 2: To a solution of 8-methyl-3,4-dihydro-1H-quinolin-2-one (180 mg, 1.12 mmol, 1 eq) in conc·$H_2SO_4$ (3 mL) was added $KNO_3$ (112.89 mg, 1.12 mmol, 1 eq) at 0° C. The mixture was stirred at 0° C. for 2 hrs. The reaction mixture was cooled at 0° C. and the resulting solution was quenched by adding 20 mL of $H_2O$/ice. The suspension was filtered and filter cake was concentrated under reduced pressure to give a residue. The crude product 8-methyl-6-nitro-3,4-dihydro-1H-quinolin-2-one (150 mg, 727.46 umol, 65.15% yield) was obtained as a white solid.

Step 3: To a solution of 8-methyl-6-nitro-3,4-dihydro-1H-quinolin-2-one (150 mg, 727.46 umol, 1 eq) in $H_2O$ (3 mL) and EtOH (3 mL) was added Fe (203.12 mg, 3.64 mmol, 5 eq) and $NH_4Cl$ (194.56 mg, 3.64 mmol, 5 eq). The mixture was stirred at 50° C. for 2 hrs. The reaction mixture was filtered and filtrates were concentrated under reduced pressure to give a residue. The residue was purified by prep-TLC ($SiO_2$, Petro ether:EtOAc=0:1) to give crude product. The crude product was triturated with the mixture solution of Petro ether and EtOAc (10:1, 11 mL). The suspension was filtered and filter cake was concentrated under reduced pressure to give a residue. Compound 6-amino-8-methyl-3,4-dihydro-1H-quinolin-2-one (105 mg, 595.86 umol, 81.91% yield) was obtained as a white solid. LCMS (M+H)$^+$: 177.1.

Step 4: To a mixture of 6-amino-8-methyl-3,4-dihydro-1H-quinolin-2-one (105 mg, 595.86 umol, 1 eq) and 3-ethylpyridine-4-carboxylic acid (90.07 mg, 480.07 umol, 8.06e-1 eq, HCl) in Py. (2 mL) was added EDCI (137.07 mg, 715.04 umol, 1.2 eq) in one portion. The mixture was stirred at 40° C. for 2 hrs. The reaction mixture was concentrated under reduced pressure to give a residue. The residue was purified by prep-TLC ($SiO_2$, Ethyl acetate:Methanol=5:1). Then the crude product was triturated with the mixture solution of Petroleum ether and Ethyl acetate (8:1, 9 mL). The mixture was stirred at 20° C. for 1 h. The suspension was filtered and filter cake was concentrated under reduced pressure to give a residue. Compound 3-ethyl-N-(8-methyl-2-oxo-3,4-dihydro-1H-quinolin-6-yl)pyridine-4-carboxamide (71.3 mg, 95.7% purity) was obtained. LCMS: (M+H)$^+$: 310.0. $^1$H NMR (400 MHz, MeOD): δ 8.55 (s, 1H), 8.50 (d, J=4.8 Hz, 1H), 7.45 (d, J=4.8 Hz, 1H), 7.41 (s, 1H), 7.34 (s, 1H), 2.94-2.97 (m, 2H), 2.85 (q, J=7.6 Hz, 2H), 2.55-2.59 (m, 2H), 2.27 (s, 3H), 1.27 (t, J=7.6 Hz, 3H).

Example 7. Synthesis of Compound 141

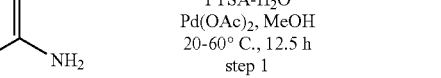

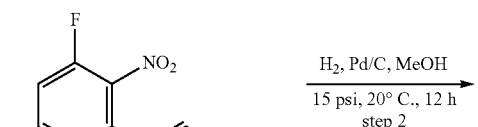

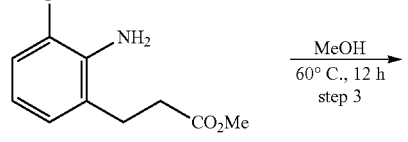

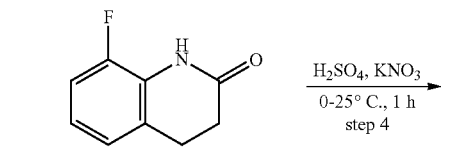

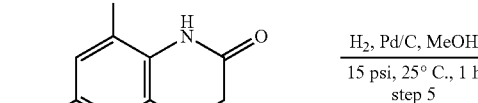

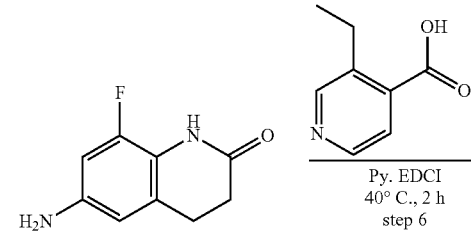

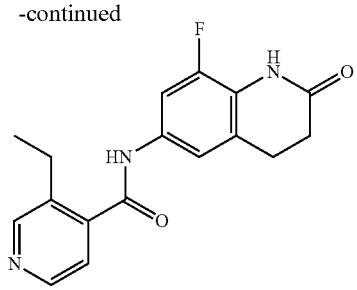

141

Step 1: Step A: To a mixture of NaNO$_2$ (25.87 g, 374.99 mmol, 8.72 eq) and Amberlyst A26 (38 g) in H$_2$O (520 mL) in one portion at 20° C. under N$_2$. The mixture was stirred at 20° C. for 30 min. The suspension was filtered and filter cake were washed with H$_2$O until the pH of filtrate to 7. Step B: To a mixture of the product from step A, 1-fluoro-2,3-dinitro-benzene (8 g, 42.99 mmol, 1 eq), 4-methylbenzenesulfonic acid (24.43 g, 141.86 mmol, 3.3 eq) and diacetoxypalladium (965.13 mg, 4.30 mmol, 0.1 eq) in MeOH (80 mL) was added methyl prop-2-enoate (18.50 g, 214.94 mmol, 19.36 mL, 5 eq) in one portion at 60° C. under N$_2$. The mixture was stirred at 60° C. for 12 hrs. The reaction mixture was filtered and filtrates were concentrated under reduced pressure to give a residue. The residue was purified by column chromatography (SiO$_2$, Petroleum ether/Ethyl acetate=15/1 to 2/1). Compound methyl (E)-3-(3-fluoro-2-nitro-phenyl)prop-2-enoate (5.5 g, 24.43 mmol, 56.82% yield) was obtained as a white solid. LCMS: (M+H)$^+$: 226.0.

Step 2: The suspension of methyl (E)-3-(3-fluoro-2-nitrophenyl)prop-2-enoate (600 mg, 2.66 mmol, 1 eq) and 10% Pd/C (100 mg) in MeOH (10 mL) was degassed and purged with H$_2$ for 3 times. The mixture was stirred under H$_2$ (15 Psi) at 20° C. for 12 hrs. The reaction mixture was filtered and filtrates were concentrated under reduced pressure to give a residue. The crude product methyl 3-(2-amino-3-fluoro-phenyl)propanoate (400 mg) was obtained as a white solid. LCMS: (M+H)$^+$: 198.1.

Step 3: The mixture of methyl 3-(2-amino-3-fluoro-phenyl)propanoate (400 mg, 2.03 mmol, 1 eq) in MeOH (50 mL) was stirred at 60° C. for 12 hrs. The reaction mixture was concentrated under reduced pressure to remove MeOH. The residue was purified by column chromatography (SiO$_2$, Petroleum ether/Ethyl acetate=10/1 to 3/1). Compound 8-fluoro-3,4-dihydro-1H-quinolin-2-one (190 mg, 1.15 mmol, 56.71% yield) was obtained as a white solid.

Step 4: To a solution of 8-fluoro-3,4-dihydro-1H-quinolin-2-one (1.1 g, 6.66 mmol, 1 eq) in conc. H$_2$SO$_4$ (5 mL) was added KNO$_3$ (673.33 mg, 6.66 mmol, 1 eq) at 0° C. The mixture was stirred at 25° C. for 1 hr. The reaction mixture was cooled at 0° C. and the resulting solution was stirred for 15 min at 0° C. Then the mixture was quenched by adding 100 mL of H$_2$O/ice. The suspension was filtered and filter cake was concentrated under reduced pressure to give a residue. The crude product was diluted with the mixture solution of Petroleum ether and Ethyl acetate (10:1, 11 mL). The mixture was stirred at 25° C. for 20 min. The suspension was filtered and filter cake was concentrated under reduced pressure to give a residue. Compound 8-fluoro-6-nitro-3,4-dihydro-1H-quinolin-2-one (800 mg, 3.81 mmol, 57.16% yield) was obtained as a white solid.

Step 5: The suspension of 8-fluoro-6-nitro-3,4-dihydro-1H-quinolin-2-one (189 mg, 899.31 umol, 1 eq) and 10% Pd/C (50 mg) in MeOH (10 mL) was degassed and purged with H$_2$ for 3 times. The mixture was stirred under H$_2$ (15 psi) at 25° C. for 1 hr. The reaction mixture was filtered and filtrates were concentrated under reduced pressure to give a residue. The crude product was triturated with the mixture solution of Petroleum ether/Ethyl acetate (10:1, 11 mL) at 25° C. for 10 min. The suspension was filtered and filter cake was concentrated under reduced pressure to give a residue. Compound 6-amino-8-fluoro-3,4-dihydro-1H-quinolin-2-one (150 mg, 832.51 umol, 92.57% yield) was obtained as a white solid.

Step 6: To a mixture of 6-amino-8-fluoro-3,4-dihydro-1H-quinolin-2-one (100 mg, 555.00 umol, 1 eq) and 3-ethylpyridine-4-carboxylic acid (100.67 mg, 666.00 umol, 1.2 eq) in Py. (2 mL) was added EDCI (127.67 mg, 666.00 umol, 1.2 eq) in one portion. The mixture was stirred at 40° C. for 2 hrs. The residue was purified by prep-HPLC (column: Waters Xbridge Prep OBD C18 150*40 mm*10 um; mobile phase: [water (0.05% NH$_3$·H$_2$O+10 mM NH$_4$HCO$_3$)-ACN]; B %: 15%-35%, 8 min). Compound 3-ethyl-N-(8-fluoro-2-oxo-3,4-dihydro-1H-quinolin-6-yl)pyridine-4-carboxamide (79 mg, 252.13 umol, 45.43% yield, 100% purity) was obtained. LCMS: (M+H)$^+$: 314.1. $^1$H NMR (400 MHz, MeOD): δ 8.55 (s, 1H), 8.50 (d, J=4.4 Hz, 1H), 7.55 (dd, J=12.4 and 2.4 Hz, 1H), 7.45 (d, J=5.2 Hz, 1H), 7.26 (d, J=1.2 Hz, 1H), 2.99-3.03 (m, 2H), 2.83 (q, J=8.0 Hz, 2H), 2.60-2.63 (m, 2H), 1.27 (t, J=7.6 Hz, 3H).

Compound 67 (14 mg) was also obtained from this Example 7.

Example 8. Synthesis of Compound 147

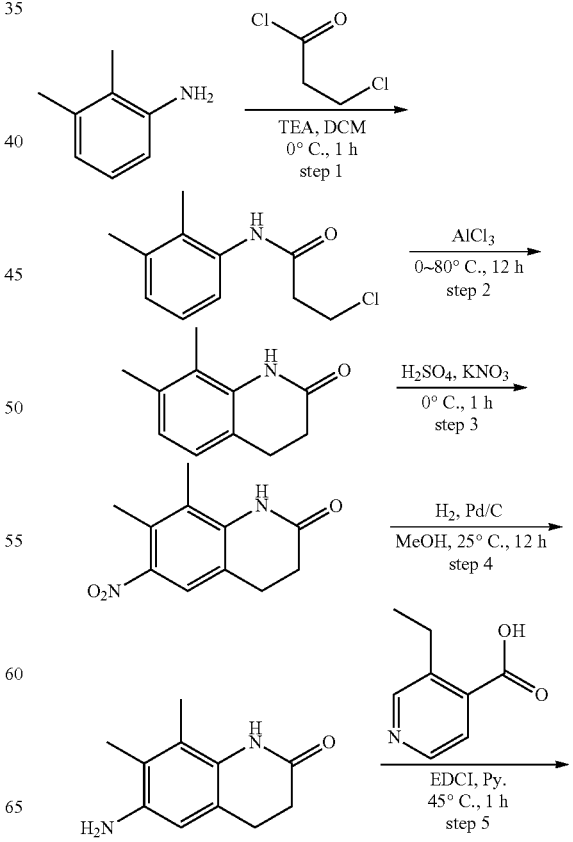

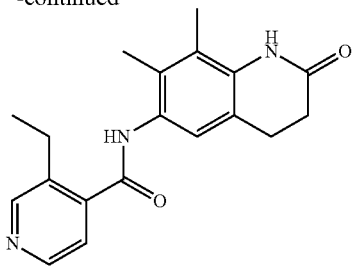

147

Step 1: To the mixture of 2,3-dimethylaniline (10 g, 82.52 mmol, 10.08 mL, 1 eq) and TEA (9.19 g, 90.77 mmol, 12.63 mL, 1.1 eq) in DCM (100 mL) was added 3-chloropropanoyl chloride (10.48 g, 82.52 mmol, 7.94 mL, 1 eq) at 0° C. The mixture was stirred at 0° C. for 1 hr. To the mixture was added H2O (50 mL). The aqueous phase was extracted with DCM (50 mL*3). The combined organic phase was washed with brine (50 mL*2), dried with Na$_2$SO$_4$, filtered and concentrated in vacuum. 3-chloro-N-(2,3-dimethylphenyl)propanamide (15 g, crude) was obtained as off-white solid.

Step 2: To the mixture of 3-chloro-N-(2,3-dimethylphenyl)propanamide (2 g, 9.45 mmol, 1 eq) in PhCl (20 mL) was added AlCl$_3$ (3.78 g, 28.34 mmol, 1.55 mL, 3 eq) at 0° C. The mixture was stirred at 80° C. for 12 hr. The reaction mixture was added to ice (20 mL). Then the mixture was extracted with ethyl acetate (30 mL*3). The combined organic phase was washed with brine (20 mL), dried with anhydrous Na$_2$SO$_4$, filtered and concentrated in vacuum. The residue was purified by column chromatography (SiO2, Petroleum ether/Ethyl acetate=100/1 to 2/1). The residue was purified by prep-HPLC (column: Waters Xbridge Prep OBD C18 150*40 mm*10 um; mobile phase: [water (0.050% NH3H2O+10 mM NH4HCO3)-ACN]; B %: 15%-35%, 8 min). Compound 7,8-dimethyl-3,4-dihydro-1H-quinolin-2-one (115 mg, 656.29 umol, 23.96% yield) was obtained as a white solid.

Step 3: To the mixture of 7,8-dimethyl-3,4-dihydro-1H-quinolin-2-one (0.1 g, 570.69 umol, 1 eq) in H$_2$SO$_4$ (1 mL) was added KNO$_3$ (57.70 mg, 570.69 umol, 1.0 eq) in portions at 0° C. The mixture was stirred at 0° C. for 1 h. The mixture was added to ice (20 mL) slowly. Then the mixture was filtered. The filter cake was washed with water (2 mL) and concentrated in vacuum. 7,8-dimethyl-6-nitro-3,4-dihydro-1H-quinolin-2-one (112 mg, 508.57 umol, 89.12% yield) was obtained as yellow solid.

Step 4: To a solution of 7,8-dimethyl-6-nitro-3,4-dihydro-1H-quinolin-2-one (101.41 mg, 460.49 umol, 1 eq) in MeOH (10 mL) was added 10% Pd/C (0.05 g) under N$_2$. The suspension was degassed under vacuum and purged with H$_2$ several times. The mixture was stirred under H$_2$ (15 Psi) at 25° C. for 12 hours. The mixture was filtered and concentrated in vacuum. 6-amino-7,8-dimethyl-3,4-dihydro-1H-quinolin-2-one (67 mg, 352.18 umol, 76.48% yield) was obtained as yellow solid.

Step 5: To the mixture of 6-amino-7,8-dimethyl-3,4-dihydro-1H-quinolin-2-one (55 mg, 289.11 umol, 1 eq) and 3-ethylpyridine-4-carboxylic acid (65.09 mg, 346.93 umol, 1.2 eq, HCl) in Py (1 mL) was added EDCI (66.51 mg, 346.93 umol, 1.2 eq). The mixture was stirred at 45° C. for 1 hr. The mixture was concentrated in vacuum. The residue was purified by prep-TLC (SiO2, Petroleum ether:Ethyl acetate=0:1). N-(7,8-dimethyl-2-oxo-3,4-dihydro-1H-quinolin-6-yl)-3-ethyl-pyridine-4-carboxamide (16 mg, 48.49 umol, 98% purity) was obtained. LCMS: (M+H)$^+$: 324.1. $^1$H NMR (400 MHz, MeOD): δ 8.56 (s, 1H), 8.52 (d, J=5.2 Hz, 1H), 7.54 (d, J=5.2 Hz, 1H), 7.08 (s, 1H), 2.88-2.97 (m, 4H), 2.55-2.59 (m, 2H), 2.25 (s, 3H), 2.24 (s, 3H), 1.32 (t, J=7.6 Hz, 3H).

Example 9. Synthesis of Compound 149

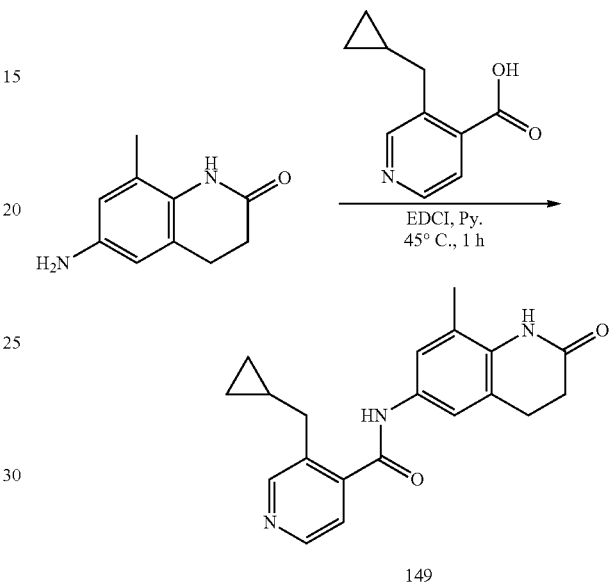

149

To a solution of 6-amino-8-methyl-3,4-dihydro-1H-quinolin-2-one (100 mg, 567.49 umol, 1 eq) and 3-(cyclopropylmethyl)pyridine-4-carboxylic acid (218.25 mg, 1.02 mmol, 1.8 eq, HCl) in Py (1 mL) was added EDCI (130.55 mg, 680.99 umol, 1.2 eq). The mixture was stirred at 45° C. for 1 hr. The reaction mixture was concentrated under reduced pressure to give a residue. The residue was purified by prep-TLC (SiO$_2$, Ethyl acetate:MeOH=10:1). Compound 3-(cyclopropylmethyl)-N-(8-methyl-2-oxo-3,4-dihydro-1H-quinolin-6-yl)pyridine-4-carboxamide (0.065 g, 189.92 umol, 63.70% yield, 98% purity) was obtained. LCMS: (M+H)$^+$: 336.1. $^1$H NMR (400 MHz, MeOD): δ 8.63 (s, 1H), 8.52 (d, J=5.2 Hz, 1H), 7.46 (d, J=5.2 Hz, 1H), 7.41 (s, 1H), 7.34 (s, 1H), 2.94-2.97 (m, 2H), 2.74 (d, J=7.2 Hz, 2H), 2.56-2.59 (m, 2H), 2.27 (s, 3H), 1.02-1.08 (m, 1H), 0.50-0.55 (m, 2H), 0.24-0.26 (m, 2H).

Example 10. Synthesis of Compound 150

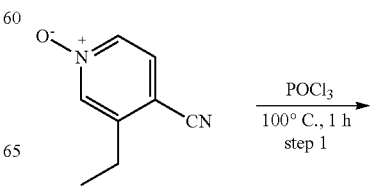

-continued

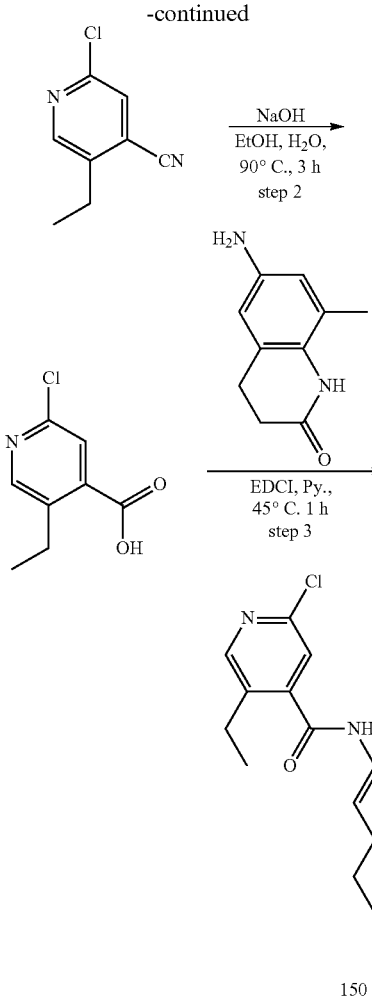

Step 1: To the solution of POCl₃ (10 mL) was added 3-ethyl-1-oxido-pyridin-1-ium-4-carbonitrile (1 g, 6.75 mmol, 1 eq). The mixture was stirred at 100° C. for 1 hr. The reaction mixture was concentrated under reduced pressure to give a residue. The reaction mixture was diluted with EtOAc (30 mL). Then the solution was added to water (100 mL) slowly at 25° C. The mixture was adjusted pH to 8 with sat·Na₂CO₃. And the mixture was extracted with Ethyl acetate 60 mL (20 ml*3). Then the combined organic phase was concentrated under reduced pressure to give a residue. The residue was purified by flash silica gel chromatography (ISCO®; 12 g SepaFlash® Silica Flash Column, Eluent of 0-10% Ethyl acetate/Petroleum ethergradient @40 mL/min). Compound 2-chloro-5-ethyl-pyridine-4-carbonitrile (0.9 g, 5.40 mmol, 80.04% yield) was obtained as a white solid. LCMS: (M+H)⁺: 167.1.

Step 2: To a solution of 2-chloro-5-ethyl-pyridine-4-carbonitrile (0.9 g, 5.40 mmol, 1 eq) in EtOH (5 mL) and H₂O (5 mL) was added NaOH (648.18 mg, 16.21 mmol, 3 eq). The mixture was stirred at 90° C. for 3 hrs. The crude reaction mixture was concentrated under reduced pressure to remove EtOH, and then the mixture was adjusted to pH=3 with 6N HCl(2 ml). And then the mixture was filtered. The filter cake was concentrated in vacuum. Compound 2-chloro-5-ethyl-pyridine-4-carboxylic acid (485 mg, HCl, crude) was obtained as a white solid. LCMS: (M+H)⁺: 186.1.

Step 3: To a solution of 6-amino-8-methyl-3,4-dihydro-1H-quinolin-2-one (100 mg, 567.49 umol, 1 eq) and 2-chloro-5-ethyl-pyridine-4-carboxylic acid (151.23 mg, 680.99 umol, 1.2 eq, HCl) in Py (1 mL) was added EDCI (130.55 mg, 680.99 umol, 1.2 eq). The mixture was stirred at 45° C. for 1 hr. The reaction mixture was concentrated under reduced pressure to give a residue. The residue was purified by prep-TLC (SiO₂, Ethyl acetate:MeOH=10:1). Compound 2-chloro-5-ethyl-N-(8-methyl-2-oxo-3,4-dihydro-1H-quinolin-6-yl)pyridine-4-carboxamide (28 mg, 78.18 umol, 13.78% yield, 96% purity) was obtained. LCMS: (M+H)⁺: 344.1. ¹H NMR (400 MHz, MeOD): δ 8.36 (s, 1H), 7.51 (s, 1H), 7.40 (s, 1H), 7.34 (s, 1H), 2.93-2.97 (m, 2H), 2.81 (q, J=7.6 Hz, 2H), 2.55-2.59 (m, 2H), 2.27 (s, 3H), 1.25 (t, J=7.6 Hz, 3H).

Example 11. Synthesis of Compound 151

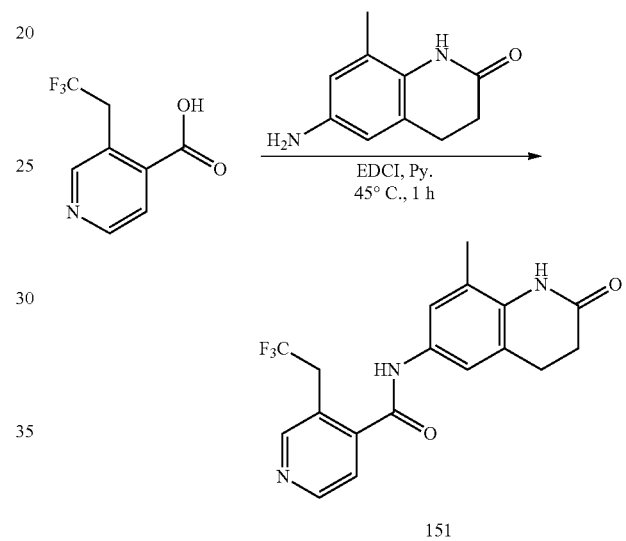

To a mixture of 3-(2,2,2-trifluoroethyl)pyridine-4-carboxylic acid (50 mg, 243.74 umol, 1 eq) and 6-amino-8-methyl-3,4-dihydro-1H-quinolin-2-one (42.95 mg, 243.74 umol, 1 eq) in Py (1 mL) was added EDCI (56.07 mg, 292.49 umol, 1.2 eq). The mixture was stirred at 45° C. for 1 hr. The reaction mixture was concentrated under reduced pressure to give a residue. The residue was purified by prep-TLC (SiO₂, Ethyl acetate:MeOH=10:1). Compound N-(8-methyl-2-oxo-3,4-dihydro-1H-quinolin-6-yl)-3-(2,2,2-trifluoroethyl)pyridine-4-carboxamide (35 mg, 96.33 umol, 39.52% yield, 100% purity) was obtained. LCMS: (M+H)⁺: 364.1. ¹H NMR (400 MHz, MeOD): δ 8.68-8.70 (m, 2H), 7.62 (d, J=4.8 Hz, 1H), 7.41 (s, 1H), 7.34 (s, 1H), 3.94 (q, J=11.2 Hz, 2H), 2.94-2.98 (m, 2H), 2.56-2.60 (m, 2H), 2.28 (s, 3H).

Example 12. Synthesis of Compound 145

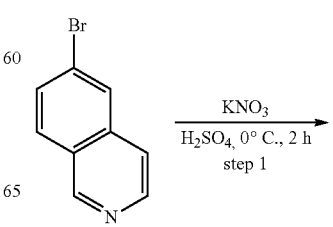

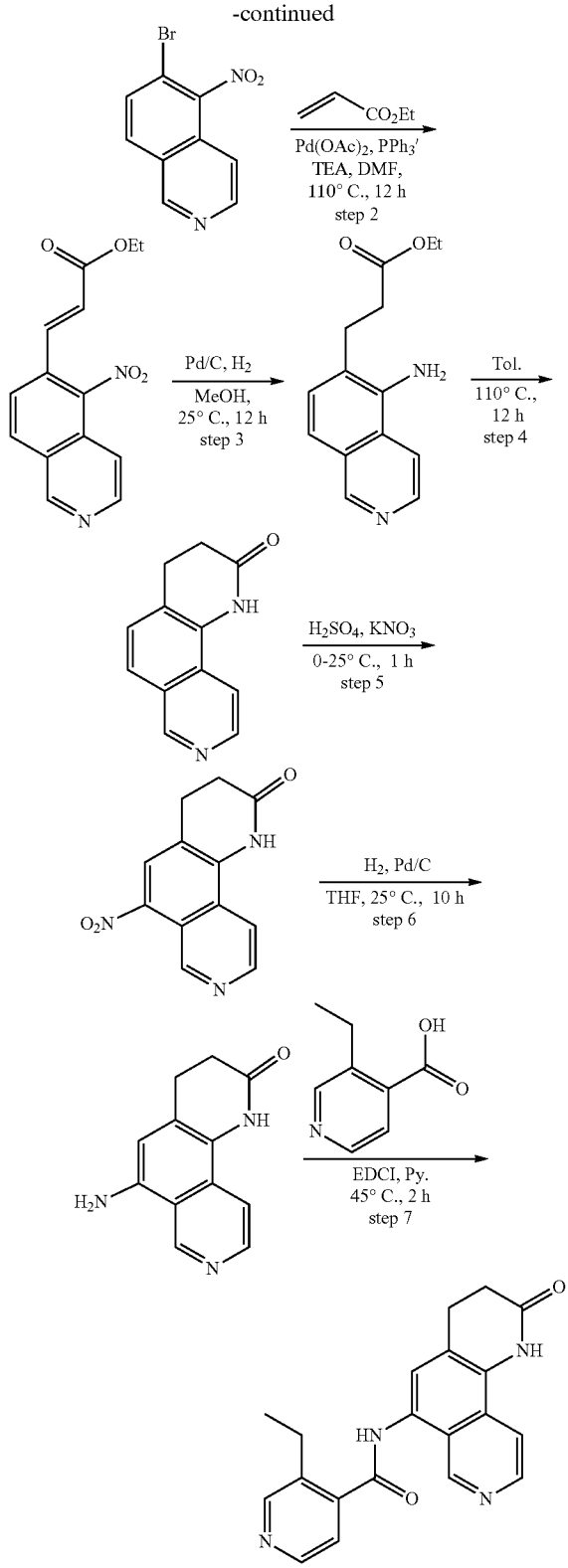

145

Step 1: To the mixture of 6-bromoisoquinoline (10 g, 48.06 mmol, 1 eq) in $H_2SO_4$ (70 mL) was added $KNO_3$ (6.12 g, 60.53 mmol, 1.26 eq) in portions at 0° C. Then the mixture was stirred at 0° C. for 2 hr. The mixture was added to ice (350 mL) slowly. The solution was adjusted to pH=8-9 by 33% $NH_4OH$ aq. The aqueous phase was extracted with ethyl acetate (100 mL*3). The combined organic phase was washed with brine (100 mL), dried with anhydrous $Na_2SO_4$, filtered and concentrated in vacuum. 6-bromo-5-nitro-isoquinoline (10 g, 39.52 mmol, 82.22% yield) was obtained as off-white solid. LCMS: $(M+H)^+$: 252.9, 254.9.

Step 2: To the mixture of ethyl prop-2-enoate (3.4 g, 33.96 mmol, 3.69 mL, 2.86 eq) and 6-bromo-5-nitro-isoquinoline (3 g, 11.86 mmol, 1 eq) in DMF (40 mL) was added $Pd(OAc)_2$ (532.32 mg, 2.37 mmol, 0.2 eq), $PPh_3$ (621.89 mg, 2.37 mmol, 0.2 eq) and TEA (1.80 g, 17.78 mmol, 2.48 mL, 1.5 eq). The mixture was stirred at 110° C. for 12 hr. The mixture was cooled to 25° C. The mixture was added to water (150 mL). The aqueous phase was extracted with ethyl acetate (50 mL*3). The combined organic phase was washed with brine (30 mL*4), dried with anhydrous $Na_2SO_4$, filtered and concentrated in vacuum. The residue was purified by column chromatography ($SiO_2$, Petroleum ether/Ethyl acetate=100/1 to 3/1). Ethyl (E)-3-(5-nitro-6-isoquinolyl)prop-2-enoate (1.1 g, 4.04 mmol, 34.08% yield) was obtained as yellow solid.

Step 3: To a solution of ethyl (E)-3-(5-nitro-6-isoquinolyl)prop-2-enoate (1 g, 3.67 mmol, 1 eq) in MeOH (20 mL) was added 10% Pd/C (0.1 g) under $N_2$. The suspension was degassed under vacuum and purged with $H_2$ several times. The mixture was stirred under $H_2$ (15 psi) at 25° C. for 12 hours. The mixture was filtered and concentrated in vacuum. Ethyl 3-(5-amino-6-isoquinolyl)propanoate (0.72 g, 2.95 mmol, 80.24% yield) was obtained as yellow solid. LCMS: $(M+H)^+$: 245.1.

Step 4: The mixture of ethyl 3-(5-amino-6-isoquinolyl)propanoate (0.72 g, 2.95 mmol, 1 eq) in Tol. (5 mL) was stirred at 110° C. for 12 hr. The mixture was concentrated in vacuum. The residue was purified by flash silica gel chromatography (ISCO®; 12 g SepaFlash® Silica Flash Column, Eluent of 0~50% Ethylacetate/Petroleum ethergradient @40 mL/min). 3,4-dihydro-1H-1,8-phenanthrolin-2-one (0.3 g, 1.51 mmol, 51.35% yield) was obtained as yellow solid.

Step 5: The mixture of 3,4-dihydro-1H-1,8-phenanthrolin-2-one (0.1 g, 504.49 umol, 1 eq) in $H_2SO_4$ (1 mL) was added $KNO_3$ (56.11 mg, 554.94 umol, 1.1 eq) in portions at 0° C. Then the mixture was stirred at 0° C. for 1 hr. The mixture was added to ice (10 mL) slowly. The mixture was filtered. The filter cake was washed with $H_2O$ (5 mL) and concentrated in vacuum. 6-nitro-3,4-dihydro-1H-1,8-phenanthrolin-2-one (45 mg, 185.02 umol, 36.67% yield) was obtained as yellow solid. LCMS: $(M+H)^+$: 244.0.

Step 6: To a solution of 6-nitro-3,4-dihydro-1H-1,8-phenanthrolin-2-one (45 mg, 185.02 umol, 1 eq) in THF (30 mL) was added 10% Pd/C (0.02 g). The mixture was stirred at 25° C. for 10 hr under $H_2$ (15 Psi). The reaction mixture was filtered and concentrated under reduced pressure to give a residue. Compound 6-amino-3,4-dihydro-1H-1,8-phenanthrolin-2-one (20 mg, crude) was obtained as a white solid.

Step 7: To a solution of 6-amino-3,4-dihydro-1H-1,8-phenanthrolin-2-one (15 mg, 70.34 umol, 1 eq) and 3-ethylpyridine-4-carboxylic acid (15.84 mg, 84.41 umol, 1.2 eq, HCl) in Py (5 mL) was added EDCI (16.18 mg, 84.41 umol, 1.2 eq). The mixture was stirred at 45° C. for 2 hr. The reaction mixture was concentrated under reduced pressure to give a residue. The residue was purified by prep-HPLC (column: Phenomenex Gemini-NX 80*40 mm*3 um; mobile phase: [water (10 mM $NH_4HCO_3$)-ACN]; B %: 5%-25%, 8 min). Compound 3-ethyl-N-(2-oxo-3,4-dihydro- 1H-1,8-phenanthrolin-6-yl)pyridine-4-carboxamide (4 mg, 11.55 umol, 100% purity) was obtained. LCMS: (M+H)+: 347.2. ¹H NMR (400 MHz, MeOD): δ 9.37 (s, 1H), 8.63 (s, 1H), 8.60 (d, J=4.8 Hz, 1H), 8.53 (d, J=6.4 Hz, 1H), 8.13 (d, J=6.0, 1H), 7.77 (s, 1H), 7.72 (d, J=4.8 Hz, 1H), 3.22-3.25 (m, 2H), 2.97 (q, J=7.6 Hz, 2H), 2.74-2.77 (m, 2H), 1.36 (t, J=7.6 Hz, 3H).

Example 13. Synthesis of Compound 160

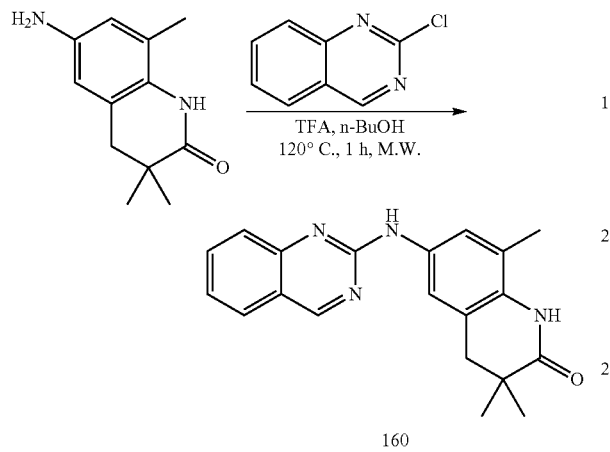

160

To a solution of 6-amino-3,3,8-trimethyl-1,4-dihydroquinolin-2-one (35 mg, 171.34 umol, 1.5 eq) and 2-chloroquinazoline (18.80 mg, 114.23 umol, 1 eq) in TFA (0.01 mL) and n-BuOH (3 mL) was taken up into a microwave tube. The sealed tube was heated at 120° C. for 60 min under microwave. The reaction mixture was concentrated under reduced pressure to give a residue. The residue was purified by prep-HPLC (column: Welch Xtimate C18 100*25 mm*3 um; mobile phase: [water(0.05% HCl)-ACN]; B %: 10%-30%, 8 min) to give 3,3,8-trimethyl-6-(quinazolin-2-ylamino)-1,4-dihydroquinolin-2-one (8 mg, 19.09 umol, 16.71% yield, 88% purity, HCl). LCMS: (M+H)+: 333.1. ¹H NMR (400 MHz, DMSO): δ 9.77 (bs, 1H), 9.28 (s, 1H), 7.90 (d, J=6.8 Hz, 1H), 7.79 (m, 1H), 7.63-7.65 (m, 2H), 7.57 (s, 1H), 7.38 (m, 1H), 2.76 (s, 2H), 2.24 (s, 3H), 1.07 (s, 6H).

Example 14. Synthesis of Compound 161

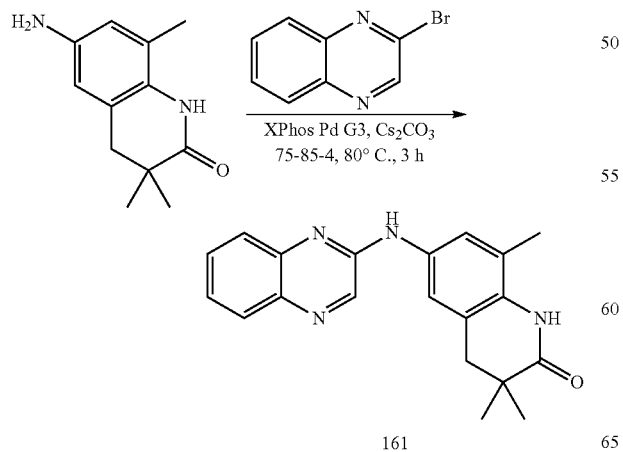

161

A mixture of 6-amino-3,3,8-trimethyl-1,4-dihydroquinolin-2-one (80 mg, 391.64 umol, 1.8 eq), 2-bromoquinoxaline (45.48 mg, 217.58 umol, 1 eq), [2-(2-aminophenyl)phenyl] palladium(2+)-dicyclohexyl-[2-(2,4,6-triisopropylphenyl) phenyl]phosphane methanesulfonate (18.42 mg, 21.76 umol, 0.1 eq), Cs₂CO₃ (141.78 mg, 435.16 umol, 2 eq) in 2-methylbutan-2-ol (4 mL) was degassed and purged with N₂ for 3 times, and then the mixture was stirred at 80° C. for 3 hr under N₂ atmosphere. The reaction mixture was filtered and the filtrate concentrated under reduced pressure to give a residue. The crude product was purified by reversed-phase HPLC(column: Waters Xbridge BEH C18 100*25 mm*5 um; mobile phase: [water(10 mM NH₄HCO₃)-ACN]; B %: 30%-55%, 10 min) to give 3,3,8-trimethyl-6-(quinoxalin-2-ylamino)-1,4-dihydroquinolin-2-one (39 mg, 111.46 umol, 51.23% yield, 95% purity). LCMS: (M+H)+: 333.1. ¹H NMR (400 MHz, DMSO): δ 9.77 (s, 1H), 9.31 (s, 1H), 8.51 (s, 1H), 7.82 (d, J=8.0 Hz, 1H), 7.70 (m, 2H), 7.60-7.62 (m, 2H), 7.43 (m, 1H), 2.77 (s, 2H), 2.26 (s, 3H), 1.07 (s, 6H).

Example 15. Synthesis of Compound 152

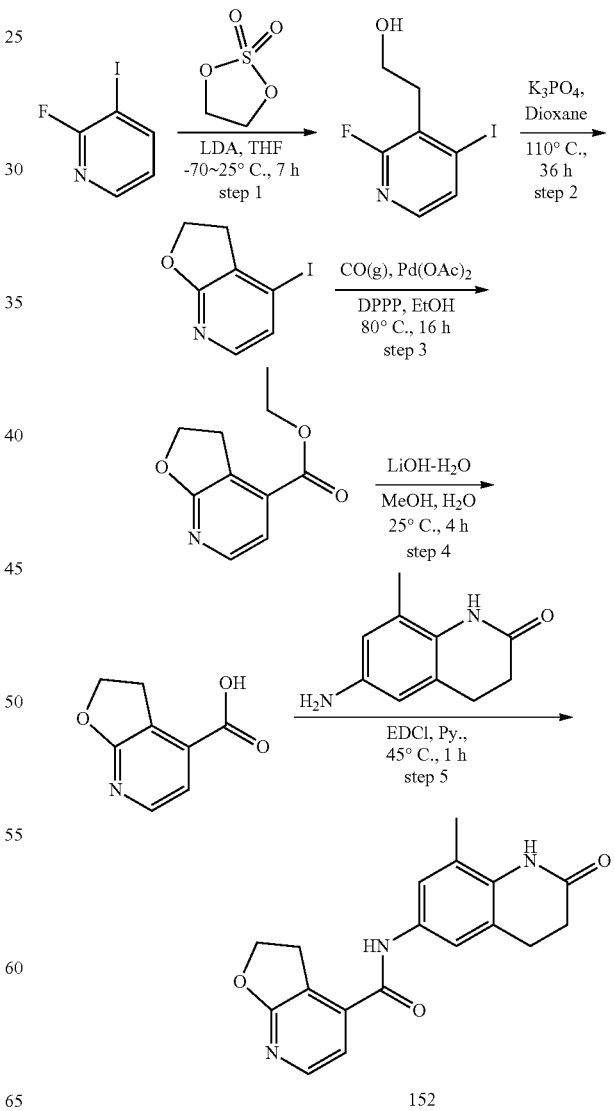

152

Step 1: To the mixture of 2-fluoro-3-iodo-pyridine (5 g, 22.42 mmol, 1 eq) in THF (60 mL) was added LDA (2 M, 13.45 mL, 1.2 eq) drop-wise at −70° C. Then the mixture was stirred at −70° C. for 1.5 h under N₂. To the mixture was added the solution of 1,3,2-dioxathiolane 2,2-dioxide (3.62 g, 29.15 mmol, 1.3 eq) in THF (30 mL) drop-wise at −70° C. The mixture was stirred at −70° C. for 0.5 h and at 25° C. for 2 hr. Then to the mixture was added HCl (12 M, 8.41 mL, 4.5 eq) at 0° C. The mixture was stirred at 25° C. for 3 h. The mixture was added to sat·NaHCO₃ (300 ml) slowly. The aqueous phase was extracted with ethyl acetate (100 mL*3). The combined organic phase was washed with brine (50 mL), dried with anhydrous Na₂SO₄, filtered and concentrated in vacuum. The residue was purified by flash silica gel chromatography (ISCO®; 20 g SepaFlash® Silica Flash Column, Eluent of 0-35% Ethyl acetate/Petroleum ethergradient @40 mL/min). 2-(2-fluoro-4-iodo-3-pyridyl)ethanol (2.5 g, 9.36 mmol, 41.75% yield) was obtained as off-white solid. LCMS: (M+H)⁺: 268.0.

Step 2: The mixture of 2-(2-fluoro-4-iodo-3-pyridyl)ethanol (1 g, 3.74 mmol, 1 eq) and K₃PO₄ (3.97 g, 18.72 mmol, 5 eq) in 1,4-dioxane (30 mL) was stirred at 110° C. for 36 hr. The mixture was filtered. The filter cake was washed with EtOAc (50 mL). The filtrate was washed with brine (10 mL) and dried with anhydrous Na₂SO₄, filtered and concentrated in vacuum. 4-iodo-2,3-dihydrofuro[2,3-b]pyridine (0.8 g, crude) was obtained as yellow solid.

Step 3: To the mixture of 4-iodo-2,3-dihydrofuro[2,3-b]pyridine (0.8 g, 3.24 mmol, 1 eq) in EtOH (20 mL) was added Pd(OAc)₂ (72.71 mg, 323.84 umol, 0.1 eq), DPPP (133.57 mg, 323.84 umol, 0.1 eq) and TEA (983.08 mg, 9.72 mmol, 1.35 mL, 3 eq). The suspension was degassed under vacuum and purged with CO several times. Then the mixture was stirred under CO (50 psi) at 80° C. for 16 hours. The mixture was filtered and concentrated in vacuum. The residue was purified by flash silica gel chromatography (ISCO®; 12 g SepaFlash® Silica Flash Column, Eluent of 0-25% Ethyl acetate/Petroleum ethergradient @40 mL/min). Ethyl 2,3-dihydrofuro[2,3-b]pyridine-4-carboxylate (0.3 g, 1.55 mmol, 47.95% yield) was obtained as white solid. LCMS: (M+H)⁺: 194.0.

Step 4: To the mixture of ethyl 2,3-dihydrofuro[2,3-b]pyridine-4-carboxylate (0.1 g, 517.60 umol, 1 eq) in THF (1 mL) and H₂O (1 mL) was added LiOH·H₂O (32.58 mg, 776.40 umol, 1.5 eq). The mixture was stirred at 25° C. for 1 h. The mixture was concentrated in vacuum to remove THF. The aqueous phase was adjusted to pH=3 by 6N HCl. The mixture was concentrated in vacuum. 2,3-dihydrofuro[2,3-b]pyridine-4-carboxylic acid (110 mg, crude) was obtained as white solid. LCMS: (M+H)⁺: 166.0.

Step 5: To a mixture of 2,3-dihydrofuro[2,3-b]pyridine-4-carboxylic acid (0.09 g, 446.41 umol, 1.2 eq, HCl) and 6-amino-8-methyl-3,4-dihydro-1H-quinolin-2-one (65.55 mg, 372.01 umol, 1 eq) in Py (1 mL) was added EDCI (85.58 mg, 446.41 umol, 1.2 eq). The mixture was stirred at 45° C. for 1 hr. The reaction mixture was concentrated under reduced pressure to give a residue. The residue was purified by prep-TLC (SiO₂, Ethyl acetate:MeOH=10:1). Then the residue was washed by the solution of (3 mL, petroleum ether:ethyl acetate=10:1). Compound N-(8-methyl-2-oxo-3,4-dihydro-1H-quinolin-6-yl)-2,3-dihydrofuro[2,3-b]pyridine-4-carboxamide (30 mg, 88.33 umol, 25.2% yield, 95.2% purity) was obtained. LCMS: (M+H)⁺: 324.0. ¹H NMR (400 MHz, CD3OD): δ 8.02 (d, J=5.6 Hz, 1H), 7.42 (s, 1H), 7.36 (s, 1H), 7.18 (d, J=5.6 Hz, 1H), 4.69 (t, J=8.4 Hz, 2H), 3.53 (t, J=8.4 Hz, 2H), 2.93-2.97 (m, 2H), 2.55-2.59 (m, 2H), 2.27 (s, 3H).

Example 16. Synthesis of Compound 153

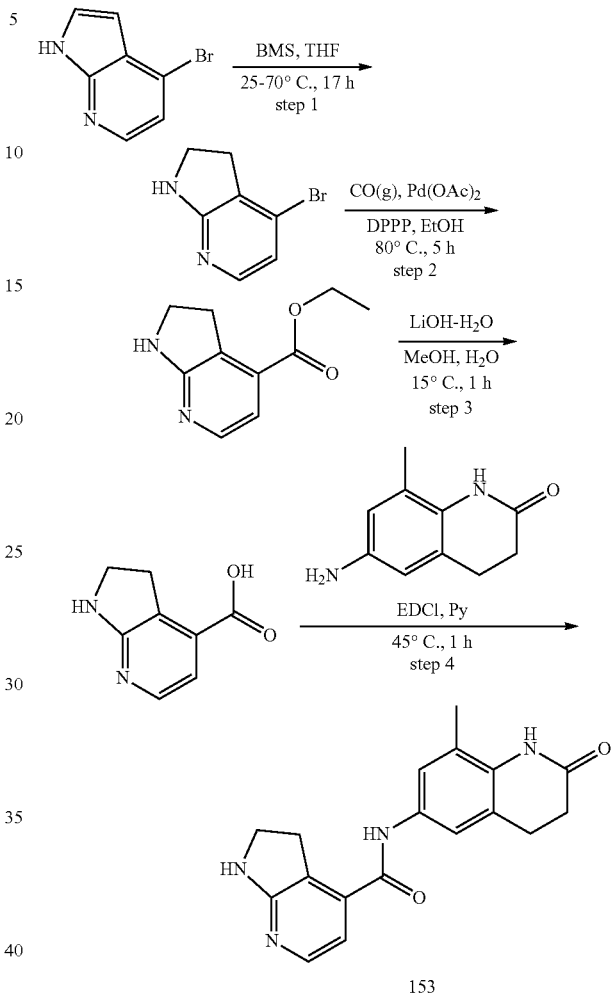

Step 1: To a mixture of 4-bromo-1H-pyrrolo[2,3-b]pyridine (5 g, 25.38 mmol, 1 eq) in THF (80 mL) was added BMS (10 M, 14.46 mL, 5.7 eq) drop-wise at 25° C. The mixture was stirred at 25° C. for 1 hr. Then the mixture was stirred at 70° C. for 16 hr. To the mixture was added water (30 mL) drop-wise at 0° C. Then the mixture was stirred at 25° C. for 1 hr. The mixture was extracted with ethyl acetate (30 mL*3). The combined organic phase was washed with brine (30 mL), dried with anhydrous Na₂SO₄, filtered and concentrated in vacuum. Compound 4-bromo-2,3-dihydro-1H-pyrrolo[2,3-b]pyridine (1.4 g, crude) was obtained as white solid.

Step 2: To a solution of 4-bromo-2,3-dihydro-1H-pyrrolo[2,3-b]pyridine (0.5 g, 2.51 mmol, 1 eq) in EtOH (15 mL) was added Pd(OAc)₂ (56.40 mg, 251.20 umol, 0.1 eq), DPPP (103.60 mg, 251.20 umol, 0.1 eq), TEA (762.55 mg, 7.54 mmol, 1.05 mL, 3 eq). The suspension was degassed under vacuum and purged with CO several times. The mixture was stirred under CO (50 Psi) at 80° C. for 5 hours. The reaction mixture was filtered and concentrated under reduced pressure to give a residue. The residue was purified by column chromatography (SiO₂, Petroleum ether/Ethyl acetate=5/1 to 2/1). Compound ethyl 2,3-dihydro-1H-pyrrolo[2,3-b]pyridine-4-carboxylate (0.1 g, 447.42 umol, 15.2% yield, 86% purity) was obtained white solid. LCMS: (M+H)⁺: 193.0.

Step 3: To a mixture of ethyl 2,3-dihydro-1H-pyrrolo[2,3-b]pyridine-4-carboxylate (0.1 g, 520.25 umol, 1 eq) in THF (1 mL) was added LiOH·H₂O (43.66 mg, 1.04 mmol, 2 eq) in H₂O (1 mL). The mixture was stirred at 15° C. for 1 hr. The mixture was concentrated to remove THF. Then the mixture was adjusted to pH=3 with HCl(1N), filtered to give the residue. Compound 2,3-dihydro-1H-pyrrolo[2,3-b]pyridine-4-carboxylic acid (0.09 g, crude) was obtained as a white solid. LCMS: (M+H)⁺: 165.1.

Step 4: To a mixture of 2,3-dihydro-1H-pyrrolo[2,3-b]pyridine-4-carboxylic acid (0.045 g, 274.12 umol, 1.1 eq) and 6-amino-8-methyl-3,4-dihydro-1H-quinolin-2-one (43.91 mg, 249.20 umol, 1 eq) in Py (1 mL) was added EDCI (57.33 mg, 299.04 umol, 1.2 eq). The mixture was stirred at 45° C. for 1 hr. The reaction mixture was concentrated under reduced pressure to give a residue. The residue was purified by prep-TLC (SiO₂, Ethyl acetate:MeOH=10:1). Compound N-(8-methyl-2-oxo-3,4-dihydro-1H-quinolin-6-yl)-2,3-dihydro-1H-pyrrolo[2,3-b]pyridine-4-carboxamide (25 mg, 76.31 umol, 31.12% yield, 98.4% purity) was obtained. LCMS: (M+H)⁺: 323.2. H NMR (400 MHz, CD3OD): δ 7.76 (d, J=5.6 Hz, 1H), 7.40 (s, 1H), 7.34 (s, 1H), 6.73 (d, J=6.0 Hz, 1H), 3.64 (t, J=8.4 Hz, 2H), 3.34 (overlap with peak at 3.31, presumed 2H), 2.93-2.97 (m, 2H), 2.55-2.59 (m, 2H), 2.27 (s, 3H).

Example 17. Synthesis of Compound 155

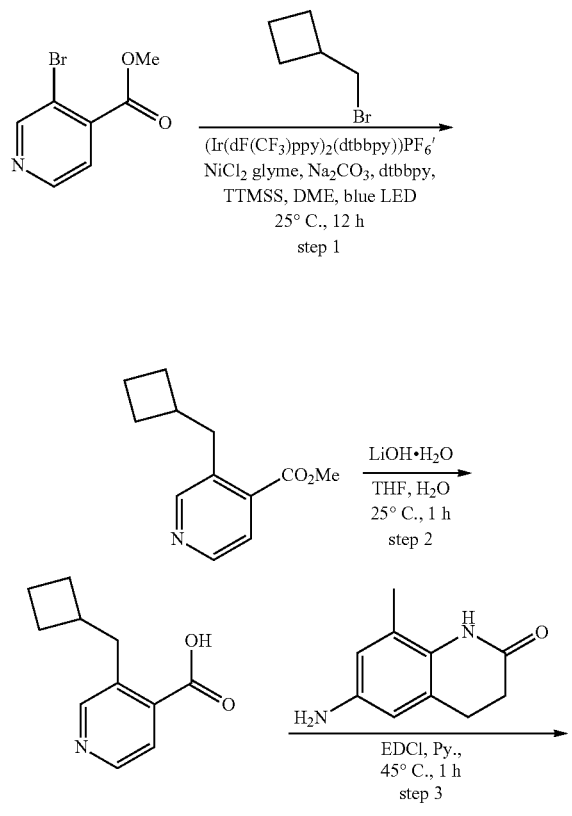

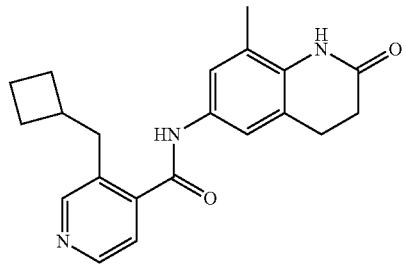

155

Step 1: To the solution of methyl 3-bromopyridine-4-carboxylate (0.5 g, 2.31 mmol, 1 eq) and bromomethylcyclobutane (517.39 mg, 3.47 mmol, 389.01 uL, 1.5 eq) in DME (10 mL) was added bis[3,5-difluoro-2-[5-(trifluoromethyl)-2-pyridyl]phenyl]iridium (1+); 4-tert-butyl-2-(4-tert-butyl-2-pyridyl)pyridine; hexafluorophosphate (25.97 mg, 23.14 umol, 0.01 eq), 4-tert-butyl-2-(4-tert-butyl-2-pyridyl)pyridine (3.11 mg, 11.57 umol, 0.005 eq), bis(trimethylsilyl)silyl-trimethyl-silane (575.52 mg, 2.31 mmol, 714.04 uL, 1 eq) and Na₂CO₃ (490.62 mg, 4.63 mmol, 2 eq), dichloronickel; 1,2-dimethoxyethane (2.54 mg, 11.57 umol, 0.005 eq). The mixture was stirred at 25° C. under Ar and blue LED for 12 h. The mixture was filtered. The filter cake was washed with EtOAc (10 mL). The filtrate was concentrated in vacuum. The residue was purified by flash silica gel chromatography (ISCO®; 12 g SepaFlash® Silica Flash Column, Eluent of 0~20% Ethyl acetate/Petroleum ethergradient @40 mL/min). Methyl 3-(cyclobutylmethyl)pyridine-4-carboxylate (200 mg, 974.41 umol, 42.10% yield) was obtained as yellow oil. LCMS: (M+H)⁺: 206.0.

Step 2: To the mixture of methyl 3-(cyclobutylmethyl)pyridine-4-carboxylate (100 mg, 487.21 umol, 1 eq) in THF (1 mL) and H₂O (1 mL) was added LiOH·H₂O (30.67 mg, 730.81 umol, 1.5 eq). The mixture was stirred at 25° C. for 1 hr. The mixture was concentrated in vacuum to remove THF. The aqueous phase was adjusted to pH=3 by 6N HCl. The aqueous phase was concentrated in vacuum. 3-(cyclobutylmethyl)pyridine-4-carboxylic acid (120 mg, crude, HCl) was obtained as white solid. LCMS: (M+H)⁺: 192.2.

Step 3: To a solution of 3-(cyclobutylmethyl)pyridine-4-carboxylic acid (80 mg, 351.36 umol, 1.55 eq, HCl) and 6-amino-8-methyl-3,4-dihydro-1H-quinolin-2-one (0.04 g, 227.00 umol, 1 eq) in Py (1 mL) was added EDCI (52.22 mg, 272.39 umol, 1.2 eq). The mixture was stirred at 45° C. for 1 hr. The reaction mixture was concentrated under reduced pressure to give a residue. The residue was purified by prep-TLC (SiO₂, Ethyl acetate:MeOH=10:1). Compound 3-(cyclobutylmethyl)-N-(8-methyl-2-oxo-3,4-dihydro-1H-quinolin-6-yl)pyridine-4-carboxamide (20 mg, 65.82 umol, 29.00% yield, 99.2% purity) was obtained as a white solid. LCMS: (M+H)⁺: 350.1. ¹H NMR (400 MHz, MeOD): 8.48 (m, 2H), 7.44 (d, J=5.2 Hz, 1H), 7.41 (s, 1H), 7.34 (s, 1H), 2.91-2.97 (m, 4H), 2.55-2.62 (m, 3H), 2.27 (s, 3H), 2.00-2.02 (m, 2H), 1.74-1.84 (m, 4H).

Example 18. Synthesis of Compound 165

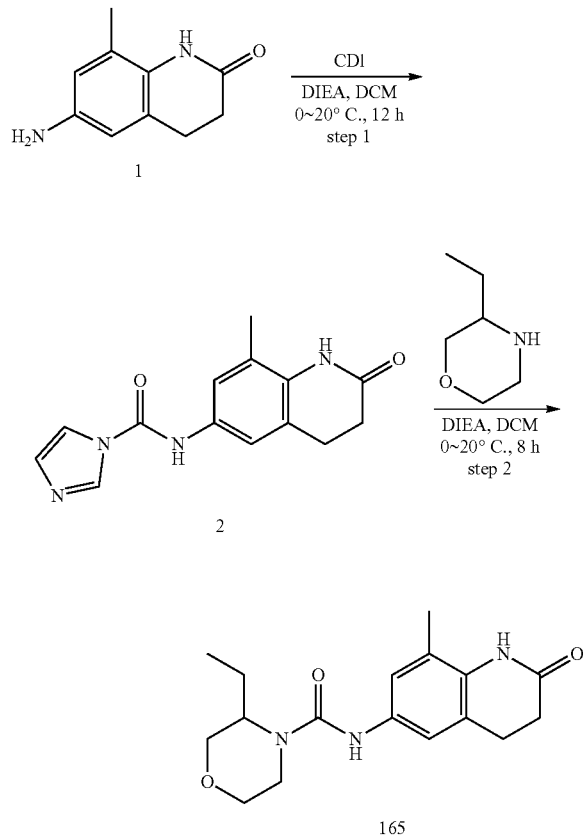

Example 19. Synthesis of Compound 154

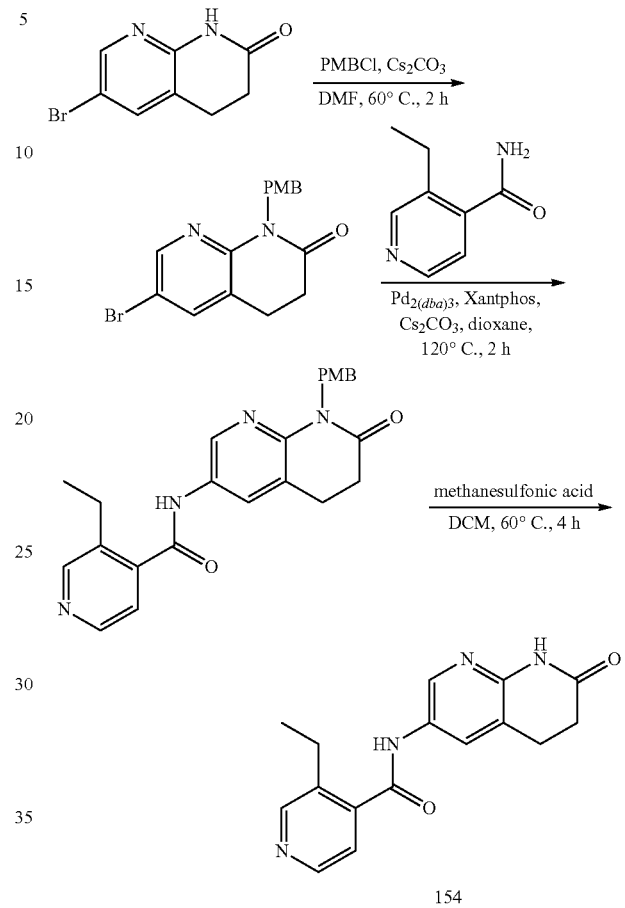

Step 1: To a solution of CDI (92.02 mg, 567.49 umol, 1 eq) and DIEA (110.02 mg, 851.23 umol, 148.27 uL, 1.5 eq) in DCM (10 mL) was added 6-amino-8-methyl-3,4-dihydro-1H-quinolin-2-one (100 mg, 567.49 umol, 1 eq) in one portion at 0° C. The mixture was stirred at 20° C. for 12 hr. TLC showed the reaction was consumed completely. The mixture was concentrated in vacuum. N-(8-methyl-2-oxo-3,4-dihydro-1H-quinolin-6-yl) imidazole-1-carboxamide (250 mg, crude) was obtained as a white solid.

Step 2: To a solution of N-(8-methyl-2-oxo-3,4-dihydro-1H-quinolin-6-yl) imidazole-1-carboxamide (250 mg, 277.48 umol, 1 eq) and DIEA (119.41 mg, 277.48 umol, 48.33 uL, 1 eq) in DCM (10 mL) was added 3-ethylmorpholine (117.05 mg, 305.23 umol, 1.1 eq) at 0° C. The mixture was stirred at 20° C. for 8 hr. LC-MS showed the reaction was consumed completely. The mixture was concentrated in vacuum. The crude product was purified by reversed-phase HPLC (column: Waters Xbridge Prep OBD C18 150*40 mm*10 um; mobile phase: [water (NH$_4$HCO$_3$)-ACN]; B %: 10%-40%, 8 min). The product of 3-ethyl-N-(8-methyl-2-oxo-3,4-dihydro-1H-quinolin-6-yl) morpholine-4-carboxamide (44 mg, 138.63 umol, 49.96% yield, 100% purity) was obtained as a white solid. (M+H)$^+$: 318.1. $^1$H NMR (400 MHz, METHANOL-d4) δ ppm 7.03 (d, J=11.6 Hz, 2H), 3.90-4.10 (m, 3H), 3.75-3.85 (m, 1H), 3.57-3.65 (m, 1H), 3.48-3.49 (m, 1H), 3.20-3.28 (m, 1H), 2.88-2.92 (m, 2H), 2.51-2.55 (m, 2H), 2.22 (s, 3H), 1.75-1.84 (m, 2H), 0.92-0.96 (m, 3H).

Step 1: A mixture of 6-bromo-3,4-dihydro-1H-1,8-naphthyridin-2-one (1 g, 4.40 mmol, 1 eq), Cs$_2$CO$_3$ (2.87 g, 8.81 mmol, 2 eq), PMB-Cl (827.68 mg, 5.29 mmol, 719.72 uL, 1.2 eq) in DMF (10 mL) was degassed and purged with N$_2$ for 3 times, and then the mixture was stirred at 60° C. for 2 hr under N$_2$ atmosphere. The mixture was added to water (50 ml). Then the mixture was filtered and concentrated in vacuum. 6-bromo-1-[(4-methoxyphenyl)methyl]-3,4-dihydro-1,8-naphthyridin-2-one (1.3 g, 3.52 mmol, 79.83% yield, 93.9% purity) was obtained as off-white solid.

Step 2: To the mixture of 6-bromo-1-[(4-methoxyphenyl)methyl]-3,4-dihydro-1,8-naphthyridin-2-one (200 mg, 576.03 umol, 1 eq), 3-ethylpyridine-4-carboxamide (95.16 mg, 633.63 umol, 1.1 eq), Cs$_2$CO$_3$ (375.36 mg, 1.15 mmol, 2 eq) in dioxane (10 mL) was added Pd$_2$(dba)$_3$ (52.75 mg, 57.60 umol, 0.1 eq) and Xantphos (33.33 mg, 57.60 umol, 0.1 eq). The mixture was stirred at 120° C. for 2 hr. The mixture was concentrated in vacuum. The residue was purified by flash silica gel chromatography (ISCO®; 12 g SepaFlash® Silica Flash Column, Eluent of 0~75% Ethyl acetate/Petroleum ethergradient @40 mL/min). 3-ethyl-N-[8-[(4-methoxyphenyl)methyl]-7-oxo-5,6-dihydro-1,8-naphthyridin-3-yl]pyridine-4-carboxamide (112 mg, 268.93 umol, 46.69% yield) was obtained as yellow solid. LCMS: (M+H)$^+$: 417.1.

Step 3: The mixture of 3-ethyl-N-[8-[(4-methoxyphenyl)methyl]-7-oxo-5,6-dihydro-1,8-naphthyridin-3-yl]pyridine- 4-carboxamide (112 mg, 268.93 umol, 1 eq) in DCM (2 mL) and methanesulfonic acid (0.2 mL) was stirred at 60° C. for 4 hr. The mixture was concentrated in vacuum. The residue was purified by prep-HPLC (column: Phenomenex luna C18 80*40 mm*3 um; mobile phase: [water (0.04% HCl)-ACN]; B %: 1%-25%, 7 min). 3-ethyl-N-(7-oxo-6,8-dihydro-5H-1,8-naphthyridin-3-yl)pyridine-4-carboxamide (15 mg, 45.07 umol, 16.76% yield, 100% purity, HCl) was obtained. LCMS: (M+H)$^+$: 297.1. $^1$H NMR (400 MHz, DMSO): 10.91 (s, 1H), 10.49 (s, 1H), 8.85 (s, 1H), 8.81 (d, J=5.6 Hz, 1H), 8.38 (d, J=2.4 Hz, 1H), 7.97 (d, J=2.0 Hz, 1H), 7.90 (d, J=5.2 Hz, 1H), 2.90-2.94 (m, 2H), 2.83 (q, J=7.6 Hz, 2H), 2.52 (overlap with peak at 2.50, presumed 2H), 1.22 (t, J=7.6 Hz, 3H).

Example 20. Synthesis of Compound 159

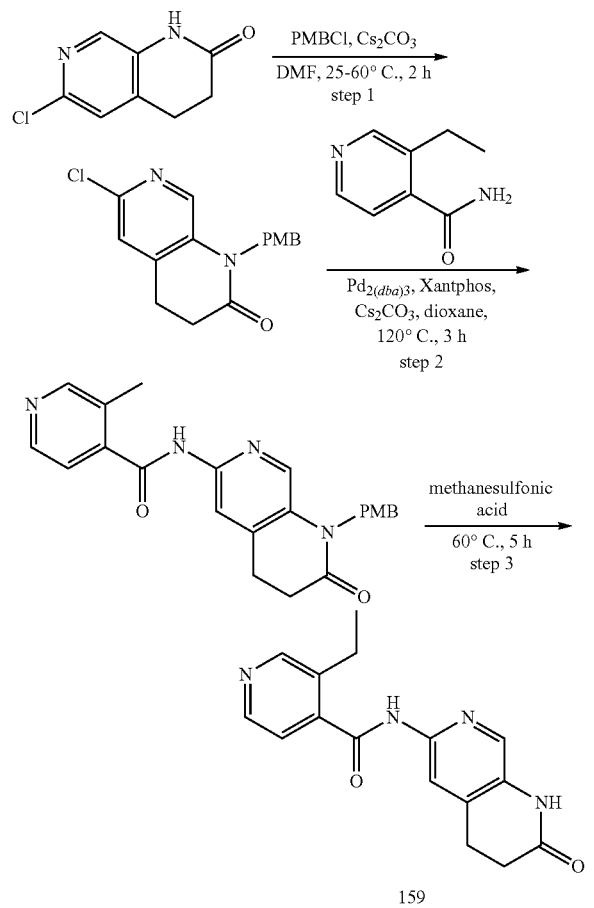

Step 1: To a solution of 6-chloro-3,4-dihydro-1H-1,7-naphthyridin-2-one (0.14 g, 639.07 umol, 1 eq, HCl) and 1-(chloromethyl)-4-methoxy-benzene (200.17 mg, 1.28 mmol, 174.06 uL, 2 eq) in DMF (1 mL) was added Cs$_2$CO$_3$ (624.67 mg, 1.92 mmol, 3 eq) at 25° C. The mixture was stirred at 60° C. for 2 hr. The mixture was poured into water (5 mL) and stirred for 10 min. The mixture was filtered to give a residue. Compound 6-chloro-1-[(4-methoxyphenyl)methyl]-3,4-dihydro-1,7-naphthyridin-2-one (0.144 g, crude) was obtained as a white solid. LCMS: (M+H)$^+$: 303.0.

Step 2: To a mixture of 6-chloro-1-[(4-methoxyphenyl)methyl]-3,4-dihydro-1,7-naphthyridin-2-one (220 mg, 726.66 umol, 1 eq) and 3-ethylpyridine-4-carboxamide (120 mg, 799.33 umol, 1.1 eq) in dioxane (1 mL) was added Xantphos (42.03 mg, 72.67 umol, 0.1 eq), Cs$_2$CO$_3$ (710.04 mg, 2.18 mmol, 3 eq) and Pd$_2$(dba)$_3$ (66.52 mg, 72.67 umol, 0.1 eq). The mixture was stirred at 120° C. for 3 hr. The reaction mixture was filtered and concentrated under reduced pressure to give a residue. The residue was purified by flash silica gel chromatography (ISCO®; 10 g Sepa-Flash® Silica Flash Column, Eluent of 0~79% Ethyl acetate/Petroleum ethergradient @40 mL/min). Compound 3-ethyl-N-[1-[(4-methoxyphenyl)methyl]-2-oxo-3,4-dihydro-1,7-naphthyridin-6-yl]pyridine-4-carboxamide (0.17 g, 408.19 umol, 56.17% yield) was obtained as a brown solid. LCMS: (M+H)$^+$: 417.1.

Step 3: The mixture of 3-ethyl-N-[1-[(4-methoxyphenyl)methyl]-2-oxo-3,4-dihydro-1,7-naphthyridin-6-yl]pyridine-4-carboxamide (170 mg, 408.19 umol, 1 eq) in DCM (2 mL) and methanesulfonic acid (0.2 mL) was stirred at 60° C. for 5 hr. The mixture was concentrated in vacuum. The residue was purified by prep-HPLC (column: Welch Xtimate C18 100*25 mm*3 um; mobile phase: [water (0.04% HCl)-ACN]; B %: 1%-25%, 8 min). 3-ethyl-N-(2-oxo-3,4-dihydro-1H-1,7-naphthyridin-6-yl)pyridine-4-carboxamide (25 mg, 75.12 umol, 18.40% yield, 100% purity, HCl) was obtained. LCMS: (M+H)$^+$: 297.1. $^1$H NMR (400 MHz, DMSO): 11.12 (s, 1H), 10.29 (s, 1H), 8.72 (s, 1H), 8.67 (d, J=5.2 Hz, 1H), 8.03 (s, 1H), 7.88 (s, 1H), 7.68 (d, J=5.2 Hz, 1H), 2.96-3.01 (m, 2H), 2.78 (q, J=7.6 Hz, 2H), 2.50 (overlap with peak at 2.50, presumed 2H), 1.20 (t, J=7.6 Hz, 3H).

Example 21. Synthesis of Compound 166

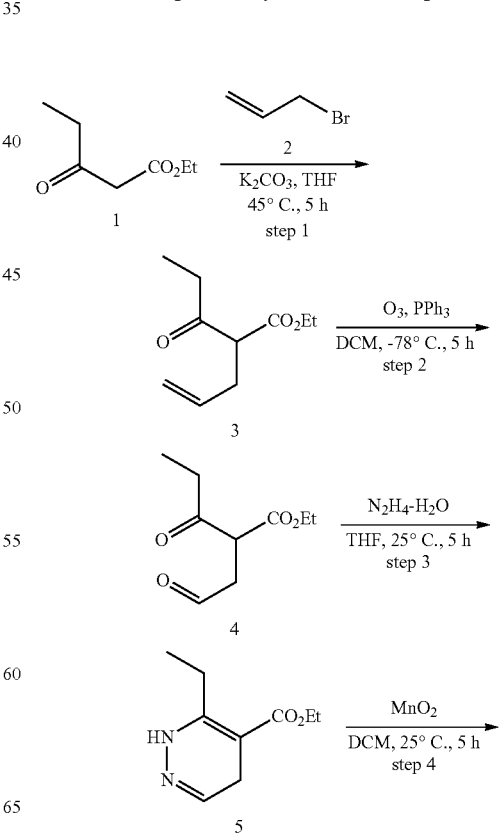

-continued

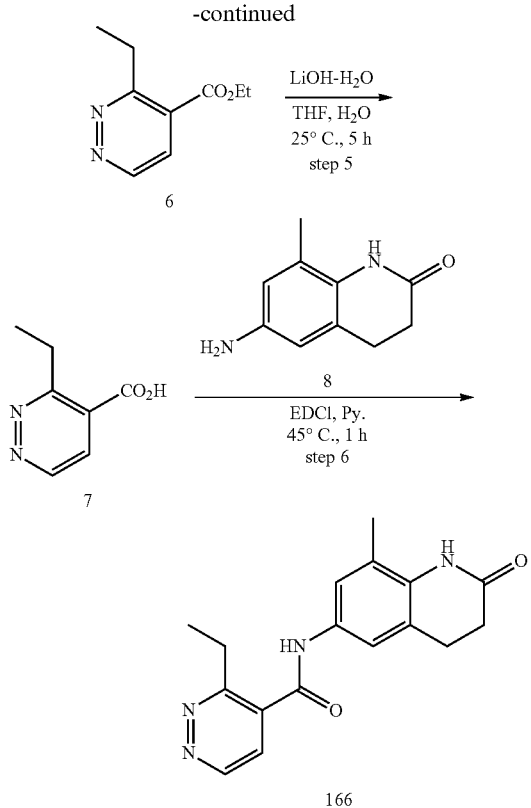

Step 1: To a solution of ethyl 3-oxopentanoate (3 g, 20.81 mmol, 1 eq) and 3-bromoprop-1-ene (2.52 g, 20.81 mmol, 1 eq) in THF (50 mL) was added K₂CO₃ (8.63 g, 62.43 mmol, 3 eq). The mixture was stirred at 45° C. for 5 hr. TLC indicated ethyl 3-oxopentanoate was consumed completely. The reaction mixture was diluted with H₂O (100 mL) and extracted with EtOAc (50 mL*3). The combined organic layers were washed with brine (50 mL*3), dried over Na₂SO₄, filtered and concentrated under reduced pressure to give a residue. The product of ethyl 2-propanoylpent-4-enoate (1.2 g, 6.51 mmol, 31.30% yield) was obtained as a white solid.

Step 2: OZONE was bubbled into a solution of ethyl 2-propanoylpent-4-enoate (1.2 g, 6.51 mmol, 1 eq) in DCM (20 mL) at −78° C. for 2 h. After excess O₃ was purged by 02, PPh₃ (1.71 g, 6.51 mmol, 1 eq) was added at −78° C. stirred for 3 h. TLC indicated ethyl 2-propanoylpent-4-enoate was consumed completely. The mixture was filtered. The filtrate was concentrated. The residue was purified by column chromatography (SiO₂, Petroleum ether/Ethyl acetate=50/1 to 6/1). Compound ethyl 3-oxo-2-(2-oxoethyl) pentanoate (500 mg, 2.69 mmol, 41.23% yield) was obtained as a white solid.

Step 3: To a solution of ethyl 3-oxo-2-(2-oxoethyl) pentanoate (500 mg, 1.24 mmol, 1 eq) in THF (10 mL) was added N₂H₄-H₂O (177.98 mg, 1.61 mmol, 79.64 uL, 98% purity, 1.3 eq) drop-wise at 25° C. The mixture was stirred at 25° C. for 5 hr. TLC indicated ethyl 3-oxo-2-(2-oxoethyl) pentanoate was consumed completely. To the mixture was added water (10 mL). The mixture was extracted with ethyl acetate (10 mL*3). The combined organic phase was washed with brine (10 mL), dried with anhydrous Na₂SO₄, filtered and concentrated in vacuum. Compound ethyl 6-ethyl-1,4-dihydropyridazine-5-carboxylate (200 mg, crude) was obtained as a white solid.

Step 4: To a solution of ethyl 6-ethyl-1,4-dihydropyridazine-5-carboxylate (190 mg, 1.04 mmol, 1 eq) in DCM (8 mL) was added MnO₂ (142.76 mg, 2.09 mmol, 2 eq). The mixture was stirred at 25° C. for 5 hr. TLC indicated ethyl 6-ethyl-1,4-dihydropyridazine-5-carboxylate was consumed completely. The reaction mixture was filtered and concentrated under reduced pressure to give a residue. The residue was purified by column chromatography (SiO₂, Petroleum ether/Ethyl acetate=10/1 to 5/1). Compound ethyl 3-ethylpyridazine-4-carboxylate (40 mg, crude) was obtained as a white solid.

Step 5: To a solution of ethyl 3-ethylpyridazine-4-carboxylate (40 mg, 166.48 umol, 1 eq) in THF (1 mL) and H₂O (1 mL) was added LiOH. H₂O (18.58 mg, 332.96 umol, 2 eq). The mixture was stirred at 25° C. for 5 hr. TLC indicated ethyl 3-ethylpyridazine-4-carboxylate was consumed completely. The reaction mixture was adjusted pH to 3-4 by 1N HCl. Then the reaction mixture was filtered and the solid was concentrated under reduced pressure to give a residue. Compound 3-ethylpyridazine-4-carboxylic acid (40 mg, crude) was obtained as a white solid.

Step 6: To a solution of 3-ethylpyridazine-4-carboxylic acid (40 mg, 197.17 umol, 1 eq) and 6-amino-8-methyl-3,4-dihydro-1H-quinolin-2-one (46.21 mg, 197.17 umol, 1 eq) in Pyridine (2 mL) was added EDCI (75.41 mg, 295.76 umol, 1.5 eq). The mixture was stirred at 45° C. for 1 hr. TLC indicated 3-ethylpyridazine-4-carboxylic acid was consumed completely and one new spot formed. The reaction mixture was concentrated under reduced pressure to give a residue. The residue was purified by prep-TLC (SiO₂, Ethyl acetate/MeOH=10/1). Compound 3-ethyl-N-(8-methyl-2-oxo-3,4-dihydro-1H-quinolin-6-yl) pyridazine-4-carboxamide (7.8 mg, 23.88 umol, 12.11% yield) was obtained as a white solid. [M+H]⁺: 311.1. ¹H NMR (400 MHz, METHANOL-d4) δ ppm 9.20 (d, J=5.2 Hz, 1H), 7.73 (d, J=5.2 Hz, 1H), 7.41 (s, 1H), 7.34 (s, 1H), 3.12-3.18 (m, 2H), 2.93-2.97 (m, 2H), 2.57-2.59 (m, 2H), 2.27 (s, 3H), 1.35 (t, J=7.6 Hz, 3H).

Example 22. Synthesis of Compound 167

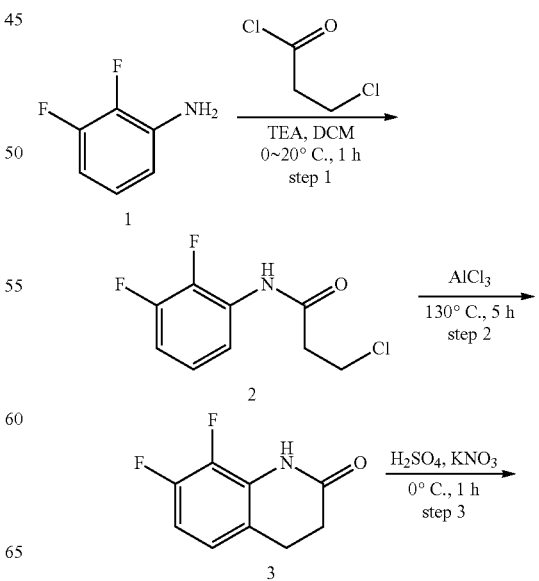

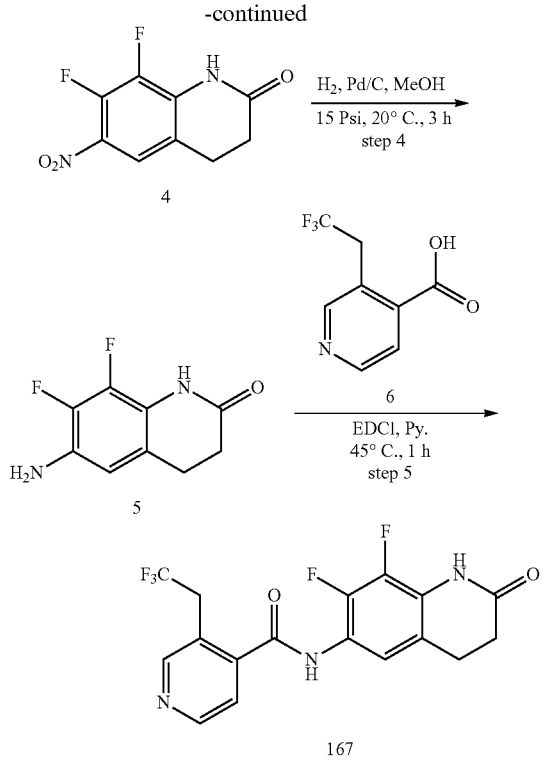

Step 1: To the mixture 3-chloropropanoyl chloride (4.67 g, 36.79 mmol, 3.54 mL, 0.95 eq) and TEA (3.92 g, 38.73 mmol, 5.39 mL, 1 eq) in DCM (20 mL) was added 2,3-difluoroaniline (5 g, 38.73 mmol, 3.94 mL, 1 eq) drop-wise at 0° C. Then the reaction mixture was stirred at 20° C. for 1 hr. LC-MS showed the reaction was consumed completely. The reaction mixture was quenched by addition H₂O (50 mL) at 0° C., then diluted with H₂O (20 mL) and extracted with EtOAc (30 mL*3). The combined organic layers were washed with brine (15 mL*3), dried over Na₂SO₄, filtered and concentrated under reduced pressure to give a residue. Compound 3-chloro-N-(2,3-difluorophenyl) propanamide (7 g, crude) was obtained as a white solid. (M+H⁺): 220.1

Step 2: The mixture of 3-chloro-N-(2,3-difluorophenyl) propanamide (6 g, 27.32 mmol, 1 eq) in AlCl₃ (10.93 g, 81.96 mmol, 4.48 mL, 3 eq) was stirred at 130° C. for 5 hr. TLC (PE:EtOAc=2:1) indicated some of 3-chloro-N-(2,3-difluorophenyl) propanamide was remained, and one major new spot with larger polarity was detected. The mixture was added to ice-water (100 mL). Then the mixture was extracted with ethyl acetate (50 mL*3). The combined organic phase was washed with brine (150 mL), dried with anhydrous Na₂SO₄, filtered and concentrated in vacuum. The residue was purified by column chromatography (SiO₂, Petroleum ether/Ethyl acetate=20/1 to 5/1). Compound 7,8-difluoro-3,4-dihydro-1H-quinolin-2-one (1.3 g, 4.12 mmol, 15.07% yield) was obtained as a white solid. ¹H NMR (400 MHz, DMSO-d6) δ ppm 10.35 (s, 1H), 6.93-7.03 (m, 2H), 2.88-2.91 (m, 2H), 2.46-2.50 (m, 2H).

Step 3: To the mixture of 7,8-difluoro-3,4-dihydro-1H-quinolin-2-one (400 mg, 2.18 mmol, 1 eq) in H₂SO₄ (7.51 g, 75.04 mmol, 4.08 mL, 98% purity, 34.36 eq) was added KNO₃ (410 mg, 4.06 mmol, 1.86 eq) in portions at 0° C. Then the reaction mixture was stirred at 0° C. for 1 hr. TLC showed the starting material was consumed completely. The mixture was poured into ice (10 mL) slowly. Then the mixture was filtered. Compound 7,8-difluoro-6-nitro-3,4-dihydro-1H-quinolin-2-one (380 mg, crude) was obtained as a brown solid.

Step 4: To a solution of 7,8-difluoro-6-nitro-3,4-dihydro-1H-quinolin-2-one (180 mg, 788.95 umol, 1 eq) in MeOH (5 mL) was added Pd/C (0.05 g 10% purity) under N₂ atmosphere. The suspension was degassed and purged with H₂ for 5 times. The mixture was stirred under H₂ (15 Psi) at 20° C. for 3 hr. LC-MS showed 7,8-difluoro-6-nitro-3,4-dihydro-1H-quinolin-2-one was consumed completely and one main peak with desired m/z mass was detected. The reaction mixture was filtered and filter liquor concentrated under reduced pressure to give a residue. Compound 6-amino-7,8-difluoro-3,4-dihydro-1H-quinolin-2-one (100 mg, crude) was obtained as a black solid. (M+H⁺): 199.2

Step 5: A mixture of 6-amino-7,8-difluoro-3,4-dihydro-1H-quinolin-2-one (150 mg, 756.93 umol, 1 eq), 3-(2,2,2-trifluoroethyl) pyridine-4-carboxylic acid (259.82 mg, 908.32 umol, 1.2 eq, HBr), EDCI (174.13 mg, 908.32 umol, 1.2 eq) in Pyridine (2.94 g, 37.17 mmol, 3.00 mL, 49.10 eq) was degassed and purged with N₂ for 3 times, and then the mixture was stirred at 45° C. for 1 hr under N₂ atmosphere. TLC showed the starting material was consumed completely. The reaction mixture was concentrated. The residue was purified by prep-HPLC (column: Phenomenex C18 75*40 mm*3 um; mobile phase: [water (NH₄HCO₃)-ACN]; B %: 5%-40%, 8 min). Compound N-(7,8-difluoro-2-oxo-3,4-dihydro-1H-quinolin-6-yl)-3-(2,2,2-trifluoroethyl) pyridine-4-carboxamide (58 mg, 150.54 umol, 19.89% yield) was obtained as a white solid. (M+H⁺): 386.0. ¹H NMR (400 MHz, MeOD-d4) δ ppm 8.70-8.72 (m, 2H), 7.67 (d, J=5.2 Hz, 1H), 7.36-7.38 (m, 1H), 3.91-3.99 (m, 2H), 3.00-3.04 (m, 2H), 2.62-2.65 (m, 2H).

Example 23. Synthesis of Compound 168

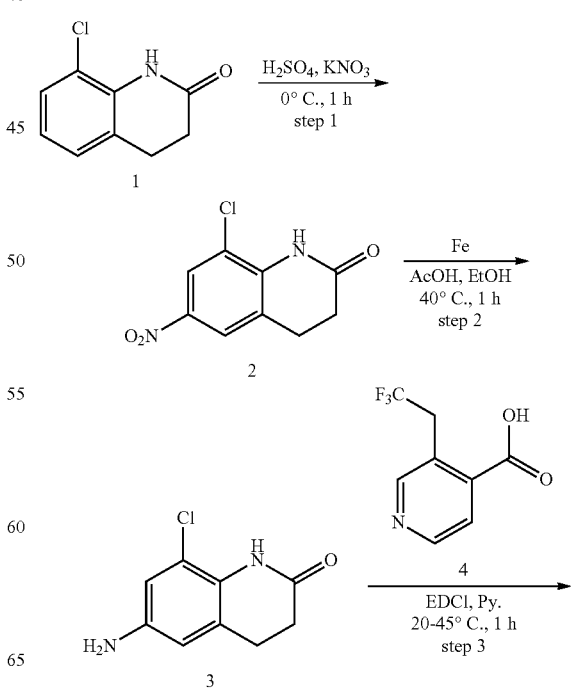

-continued

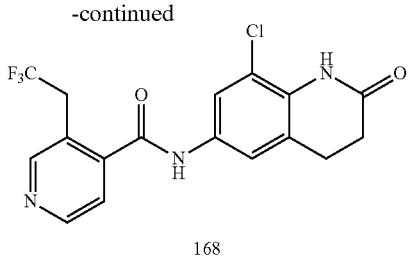

168

Step 1: To the mixture of 8-chloro-3,4-dihydro-1H-quinolin-2-one (0.3 g, 1.65 mmol, 1 eq) in H$_2$SO$_4$ (3.76 g, 37.52 mmol, 2.04 mL, 98% purity, 22.72 eq) was added KNO$_3$ (200.40 mg, 1.98 mmol, 1.2 eq) in portions at 0° C. Then the mixture was stirred at 0° C. for 1 hr. TLC showed the starting material was consumed completely. The mixture was added to ice (20 mL) slowly. Then the mixture was filtered. The filter cake was washed with water (5 mL). Compound 8-chloro-6-nitro-3,4-dihydro-1H-quinolin-2-one (200 mg, crude) was obtained as a white solid. $^1$H NMR (400 MHz, DMSO-d$_6$) δ ppm 10.19 (s, 1H), 8.14 (d, J=2.4 Hz, 1H), 8.19 (d, J=2.4 Hz, 1H) 3.08 (m, 2H), 2.50-2.60 (m, 2H).

Step 2: To the mixture of 8-chloro-6-nitro-3,4-dihydro-1H-quinolin-2-one (100 mg, 441.27 umol, 1 eq) in EtOH (3 mL) was added AcOH (264.99 mg, 4.41 mmol, 252.38 uL, 10 eq) and Fe (123.21 mg, 2.21 mmol, 5 eq) in portions at 20° C. Then the reaction mixture was stirred at 40° C. for 1 hr. TLC showed the starting material was consumed completed and one major new spot with larger polarity was detected. The mixture filtered and concentrated under reduced pressure to give a residue. The residue was purified by prep-TLC (SiO$_2$, Petroleum ether:Ethyl acetate=1:1). Compound 6-amino-8-chloro-3,4-dihydro-1H-quinolin-2-one (70 mg) was obtained as a white solid.

Step 3: To the mixture of 6-amino-8-chloro-3,4-dihydro-1H-quinolin-2-one (50 mg, 254.28 umol, 1 eq) and 3-(2,2,2-trifluoroethyl) pyridine-4-carboxylic acid (87.28 mg, 305.14 umol, 1.2 eq, HBr) in Py. (980.00 mg, 12.39 mmol, 1 mL, 48.72 eq) was added EDCI (58.50 mg, 305.14 umol, 1.2 eq) at 20° C. Then the reaction mixture was stirred at 45° C. for 1 hr. TLC indicated the starting material consumed completely and the desired production was detected. The crude production was concentrated under reduced pressure to give a residue. The residue was purified by prep-TLC (SiO$_2$, =Petroleum ether:Ethyl acetate 1:1). Compound N-(8-chloro-2-oxo-3,4-dihydro-1H-quinolin-6-yl)-3-(2,2,2-trifluoroethyl) pyridine-4-carboxamide (28.7 mg, 73.97 umol, 29.09% yield) was obtained as a white solid. (M+H)$^+$: 384.0. $^1$H NMR (400 MHz, MeOD-d$_4$) δ ppm 8.68-8.70 (m, 2H), 7.75 (s, 1H), 7.63 (d, J=4.8 Hz, 1H), 7.46 (d, J=2.0 Hz, 1H), 3.90-3.98 (m, 2H), 3.0-03.04 (m, 2H), 2.60-2.64 (m, 2H).

Example 24. Synthesis of Compound 169

 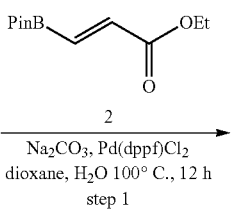

-continued

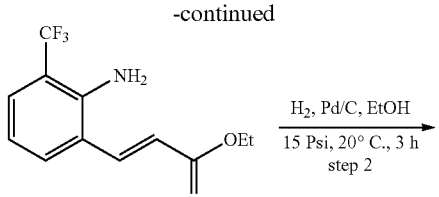

3

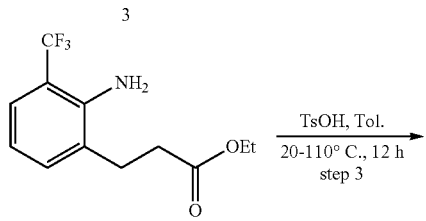

4

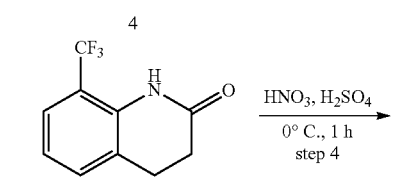

5

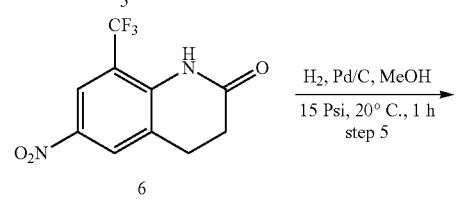

6

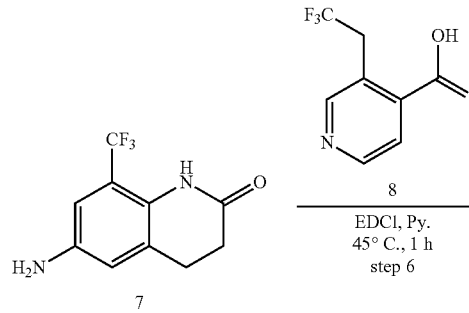

7

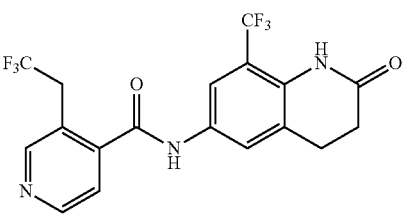

169

Step 1: A mixture of 2-bromo-6-(trifluoromethyl)aniline (0.8 g, 3.33 mmol, 1 eq), ethyl (E)-3-(4,4,5,5-tetramethyl-1,3,2-dioxaborolan-2-yl) prop-2-enoate (904.23 mg, 4.00 mmol, 1.2 eq) and Na$_2$CO$_3$ (706.53 mg, 6.67 mmol, 2 eq) in dioxane (16 mL) and H$_2$O (1.6 mL) was added Pd(dppf)Cl$_2$ (24.39 mg, 33.33 umol, 0.01 eq) under N$_2$. The reaction mixture was stirred at 100° C. for 12 hr. TLC indicated the starting material was consumed completely. To the mixture was added H$_2$O (10 mL) then the mixture was extracted with ethyl acetate (10 mL*3). The combined organic phase was washed with brine (50 mL*2), dried with anhydrous Na$_2$SO$_4$, filtered and concentrated in vacuum. The residue was purified by column chromatography (SiO$_2$, Petroleum ether/Ethyl acetate=15/1 to 5/1). Compound ethyl (E)-3-[2-amino-3-(trifluoromethyl) phenyl]prop-2-enoate (780 mg, 3.01 mmol, 90.28% yield) was obtained as a yellow oil.

Step 2: To a solution of ethyl (E)-3-[2-amino-3-(trifluoromethyl) phenyl]prop-2-enoate (780 mg, 3.01 mmol, 1 eq) in EtOH (10 mL) was added Pd/C (70 mg, 10% purity) under N$_2$ atmosphere. The suspension was degassed and purged with H$_2$ for 3 times. The mixture was stirred under H$_2$ (15 Psi) at 20° C. for 3 hr. TLC showed the reaction was completed. The mixture was filtered and the filter liquor was concentrated under reduced pressure to give a residue. Compound ethyl 3-[2-amino-3-(trifluoromethyl) phenyl]propanoate (720 mg, 2.76 mmol, 91.60% yield) was obtained as a yellow oil.

Step 3: To the mixture of ethyl 3-[2-amino-3-(trifluoromethyl) phenyl]propanoate (720 mg, 2.76 mmol, 1 eq) in Tol. (10 mL) was added TsOH (47.46 mg, 275.61 umol, 0.1 eq) at 20° C. Then the reaction mixture was stirred at 110° C. for 12 hr. TLC showed the starting material was consumed completely. The reaction mixture was diluted with H$_2$O (10 mL) and extracted with EtOAc (10 mL*3). The combined organic layers were washed with brine (30 mL), dried over Na$_2$SO$_4$, filtered and concentrated under reduced pressure to give a residue. Compound 8-(trifluoromethyl)-3,4-dihydro-1H-quinolin-2-one (520 mg, 2.42 mmol, 87.68% yield) was obtained as a yellow oil. $^1$H NMR (400 MHz, DMSO-d$_6$) δ ppm 9.13 (s, 1H), 7.56-7.62 (m, 2H), 7.17-7.21 (m, 1H), 3.01-3.04 (m, 2H), 2.57-2.61 (m, 2H).

Step 4: A mixture of 8-(trifluoromethyl)-3,4-dihydro-1H-quinolin-2-one (520 mg, 2.42 mmol, 1 eq) in H$_2$SO$_4$ (18.40 g, 183.85 mmol, 10 mL, 98% purity, 76.08 eq) at 100 mL three neek bottle was added KNO$_3$ (293.20 mg, 2.90 mmol, 1.2 eq) in portions at 0° C. Then the reaction mixture was stirred at 0° C. for 1 hr. TLC showed the starting material was consumed completely. The reaction mixture was poured into ice (20 mL), filtered and the filter cake was concentrated. Compound 6-nitro-8-(trifluoromethyl)-3,4-dihydro-1H-quinolin-2-one (427 mg, 1.64 mmol, 67.91% yield) was obtained as a yellow solid.

Step 5: To a solution of 6-nitro-8-(trifluoromethyl)-3,4-dihydro-1H-quinolin-2-one (420 mg, 1.61 mmol, 1 eq) in MeOH (1 mL) was added Pd/C (10%, 20 mg) under N$_2$ atmosphere. The suspension was degassed and purged with H$_2$ for 3 times. The mixture was stirred under H$_2$ (15 Psi) at 20° C. for 1 hr. TLC showed the starting material was consumed completely. The reaction mixture was filtered and filter liquor was concentrated. Compound 6-amino-8-(trifluoromethyl)-3,4-dihydro-1H-quinolin-2-one (320 mg, 1.39 mmol, 86.11% yield) was obtained as a yellow solid.

Step 6: A mixture of 6-amino-8-(trifluoromethyl)-3,4-dihydro-1H-quinolin-2-one (80 mg, 347.54 umol, 1 eq) and 3-(2,2,2-trifluoroethyl)pyridine-4-carboxylic acid (119.30 mg, 417.05 umol, 1.2 eq, HBr) in Py. (2 mL) was added EDCI (79.95 mg, 417.05 umol, 1.2 eq). Then the reaction mixture was stirred at 45° C. for 1 hr. TLC showed the starting material was consumed completely. The reaction mixture was concentrated under reduced pressure to give a residue. The residue was purified by prep-TLC (SiO2, DCM:MeOH=10:1). Compound N-[2-oxo-8-(trifluoromethyl)-3,4-dihydro-1H-quinolin-6-yl]-3-(2,2,2-trifluoroethyl) pyridine-4-carboxamide (50 mg, 119.82 umol, 34.48% yield) was obtained as a white solid. (M+H$^+$): 418.1. $^1$H NMR (400 MHz, MeOD-d$_4$) δ ppm 8.69-8.71 (m, 2H), 7.92 (d, J=2.0 Hz, 1H), 7.81 (d, J=1.6 Hz, 1H), 7.65 (d, J=4.8 Hz, 1H), 3.91-3.99 (m, 2H) 3.04-3.08 (m, 2H), 2.63-2.67 (m, 2H).

Example 25. Synthesis of Compound 182

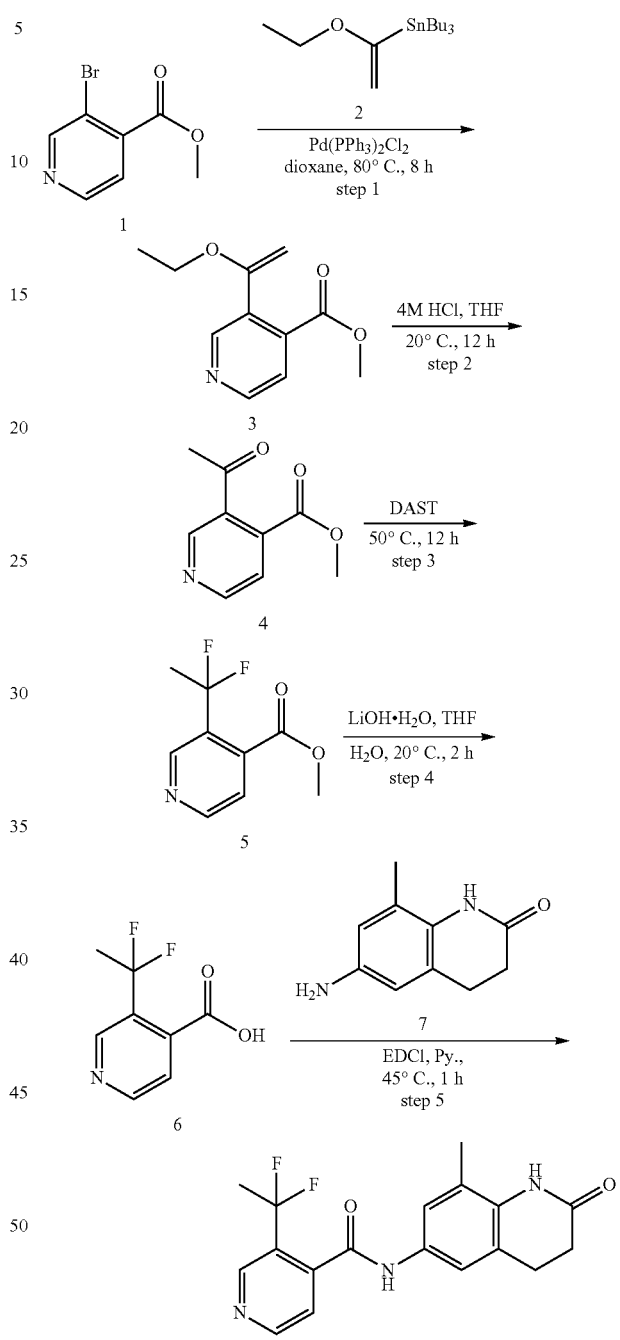

Step 1: A mixture of methyl 3-bromopyridine-4-carboxylate (5 g, 23.14 mmol, 1 eq), tributyl (1-ethoxyvinyl) stannane (9.27 g, 25.67 mmol, 8.66 mL, 1.11 eq) and Pd(PPh$_3$)$_2$Cl$_2$ (649.81 mg, 925.79 umol, 0.04 eq) in dioxane (50 mL) was degassed and purged with N$_2$ for 3 times, and then the mixture was stirred at 80° C. for 8 hr under N$_2$. LC-MS showed the reaction was consumed completely. The reaction mixture was quenched by addition dropwise to sat. KF solution 25 mL at 0° C., and then diluted with H$_2$O 30 mL and extracted with EtOAc (25 mL*4). The combined organic layers were washed with brine (100 mL), dried over Na₂SO₄, filtered and concentrated under reduced pressure to give a residue. The residue was purified by column chromatography (SiO₂, Petroleum ether/Ethyl acetate=20/1 to 1/1). Compound methyl 3-(1-ethoxyvinyl) pyridine-4-carboxylate (4 g, 14.86 mmol, 64.22% yield) was obtained as a yellow oil. (M+H)⁺: 208.2. ¹H NMR (400 MHz, CDCl₃) δ ppm 8.69 (s, 1H), 8.58 (d, J=4.8 Hz, 1H), 7.39 (d, J=5.2 Hz, 1H), 4.42 (d, J=2.8 Hz, 1H), 4.37 (d, J=2.4 Hz, 1H), 4.29 (d, J=2.8 Hz, 1H), 3.83 (s, 3H) 3.78-3.81 (m, 2H), 1.24-1.27 (m, 3H).

Step 2: To a solution of methyl 3-(1-ethoxyvinyl)pyridine-4-carboxylate (4 g, 19.30 mmol, 1 eq) in THF (40 mL) was added HCl (4 M, 4.83 mL, 1 eq). The mixture was stirred at 20° C. for 12 hr. LC-MS showed the starting material was consumed completely and one main peak with desired was detected. The reaction mixture was adjusted to pH=7 by saturated NaHCO₃. The reaction mixture was extracted with EtOAc (25 mL*3). The combined organic layers were washed with brine (100 mL), dried over Na₂SO₄, filtered and concentrated under reduced pressure to give a residue. The residue was purified by column chromatography (SiO₂, Petroleum ether/Ethyl acetate=10/1 to 0/1). Compound methyl 3-acetylpyridine-4-carboxylate (1.8 g, 8.74 mmol, 45.28% yield) was obtained as a yellow oil. (M+H)⁺: 180.2. ¹H NMR (400 MHz, CDCl₃) δ ppm 8.83 (s, 1H), 8.80-8.81 (m, 1H), 7.58-7.60 (m, 1H), 3.92 (s, 3H), 2.59 (s, 3H).

Step 3: A mixture of methyl 3-acetylpyridine-4-carboxylate (0.5 g, 2.79 mmol, 1 eq) in DAST (10 mL) was degassed and purged with N₂ for 3 times, and then the mixture was stirred at 50° C. for 12 hr under N₂ atmosphere. LC-MS showed ~13% of the starting material remained. The reaction mixture was diluted with addition dichloromethane (50 mL) at 20° C., and then the mixture was added to sat. NaHCO₃ solution (100 mL) dropwise at 20° C. The reaction mixture was extracted with dichloromethane (30 mL*3). The combined organic layers were washed with brine (100 mL), dried over Na₂SO₄, filtered and concentrated under reduced pressure to give a residue. The residue was purified by column chromatography (SiO₂, Petroleum ether/Ethyl acetate=10/1 to 0/1). Compound methyl 3-(1,1-difluoroethyl) pyridine-4-carboxylate (0.26 g, 853.01 umol, 30.57% yield) was obtained as a yellow oil. (M+H)⁺: 202.2. ¹H NMR (400 MHz, CDCl₃) δ ppm 8.84 (s, 1H), 8.76 (d, J=4.8 Hz, 1H), 7.42 (d, J=4.8 Hz, 1H), 3.94 (s, 3H), 2.09 (d, J=18.4 Hz, 3H).

Step 4: A mixture of methyl 3-(1,1-difluoroethyl) pyridine-4-carboxylate (150 mg, 745.64 umol, 1 eq) and LiOH·H₂O (62.58 mg, 1.49 mmol, 2 eq) in THF (2 mL) and H₂O (2 mL) was degassed and purged with N₂ for 3 times, and then the mixture was stirred at 20° C. for 2 hr under N₂ atmosphere. LC-MS showed the starting material was consumed completely and one main peak with desired was detected. The reaction mixture was concentrated under reduced pressure to remove THF. The reaction mixture was adjusted to pH=4 by 1N HCl solution. The reaction mixture was concentrated under reduced pressure to give a residue. Compound 3-(1,1-difluoroethyl) pyridine-4-carboxylic acid (150 mg, 670.83 umol, 89.97% yield, HCl) was obtained as a yellow solid. (M+H)⁺: 188.2. ¹H NMR (400 MHz, MeOD-d4) δ ppm 8.68 (s, 1H), 8.63 (d, J=5.2 Hz, 1H), 7.46 (d, J=5.2 Hz, 1H), 2.08 (m, 3H).

Step 5: A mixture of 3-(1,1-difluoroethyl)pyridine-4-carboxylic acid (125.62 mg, 561.81 umol, 1.50 eq, HCl), 6-amino-8-methyl-3,4-dihydro-1H-quinolin-2-one (66 mg, 374.54 umol, 1 eq), EDCI (86.16 mg, 449.45 umol, 1.2 eq) in Py. (3 mL) was degassed and purged with N₂ for 3 times, and then the mixture was stirred at 45° C. for 1 hr under N₂ atmosphere. LC-MS showed the reaction was consumed completely and one main peak with desired was detected. The reaction mixture was concentrated under reduced pressure to give a residue. The residue was purified by prep-HPLC (column: Phenomenex Luna 80*30 mm*3 um; mobile phase: [water (HCl)-ACN]; B %: 15%-45%, 8 min) to give the compound 3-(1,1-difluoroethyl)-N-(8-methyl-2-oxo-3,4-dihydro-1H-quinolin-6-yl) pyridine-4-carboxamide (29 mg, 99.7% purity, 8.4% yield) as a light yellow solid. (M+H)⁺: 346.1. ¹H NMR (400 MHz, MeOD-d4) δ ppm 9.01 (s, 1H), 8.95 (d, J=5.6 Hz, 1H), 7.93 (d, J=5.2 Hz, 1H), 7.37 (s, 1H), 7.30 (s, 1H), 2.94-2.97 (m, 3H), 2.55-2.59 (m, 2H), 2.27 (s, 3H), 2.08-2.18 (m, 3H).

Example 26. Synthesis of Compound 185

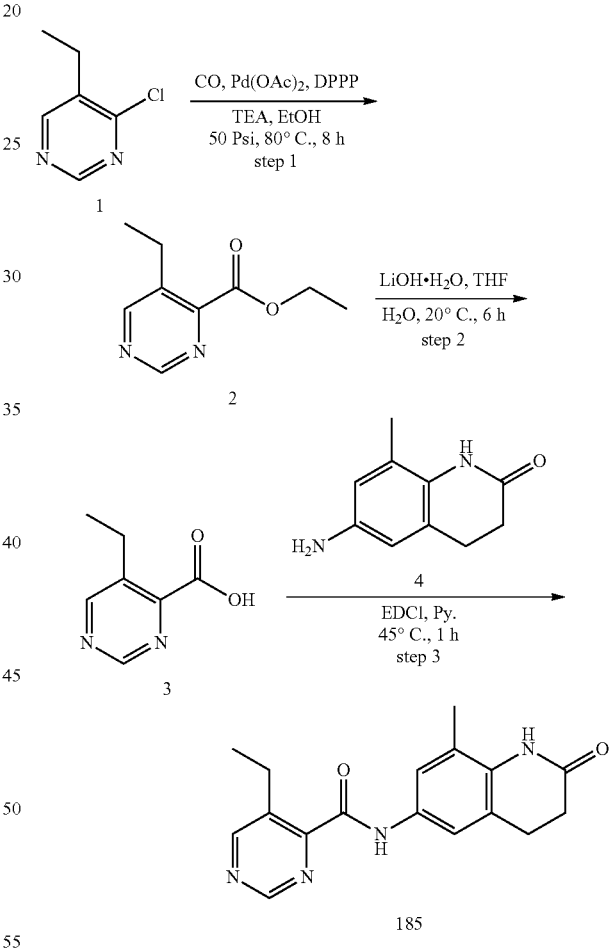

Step 1: To a solution of 4-chloro-5-ethyl-pyrimidine (0.9 g, 6.31 mmol, 1 eq) in EtOH (200 mL) was added TEA (2.55 g, 25.25 mmol, 3.51 mL, 4 eq), DPPP (260.33 mg, 631.20 umol, 0.1 eq), Pd(OAc)₂ (141.71 mg, 631.20 umol, 0.1 eq) under N₂ atmosphere. The suspension was degassed and purged with CO for 3 times. The mixture was stirred under CO (50 Psi) at 80° C. for 8 hr. LC-MS showed the starting material was consumed completely. The reaction mixture was filtered and concentrated under reduced pressure to give a residue. The residue was purified by column chromatography (SiO₂, Petroleum ether/Ethyl acetate=20/1 to 1/1).

Compound ethyl 5-ethylpyrimidine-4-carboxylate (500 mg, 2.00 mmol, 31.65% yield) was obtained as a yellow oil. (M+H)+: 181.2. $^1$H NMR (400 MHz, CDCl$_3$) δ ppm 9.17 (s, 1H), 8.75 (s, 1H), 4.44-4.50 (m, 2H), 2.87-2.93 (m, 2H), 1.43 (m, 3H), 1.28 (m, 3H).

Step 2: A mixture of ethyl 5-ethylpyrimidine-4-carboxylate (200 mg, 1.11 mmol, 1 eq) and LiOH·H$_2$O (93.15 mg, 2.22 mmol, 2 eq) in THF (5 mL) and H$_2$O (5 mL) was degassed and purged with N$_2$ for 3 times, and then the mixture was stirred at 20° C. for 6 hr under N$_2$ atmosphere. LC-MS showed the starting material was consumed completely. The reaction mixture was concentrated under reduced pressure to remove THF. The reaction mixture was adjusted to pH=4 by 1N HCl solution. The reaction mixture was concentrated under reduced pressure to give a residue. Compound 5-ethylpyrimidine-4-carboxylic acid (150 mg, crude, HCl) was obtained as a white solid. (M+H)+: 153.2.

Step 3: The mixture of 5-ethylpyrimidine-4-carboxylic acid (40 mg, 212.08 umol, 1 eq, HCl), 6-amino-8-methyl-3,4-dihydro-1H-quinolin-2-one (33.63 mg, 190.87 umol, 0.9 eq) and EDCI (48.79 mg, 254.49 umol, 1.2 eq) in Py. (2 mL) was stirred at 45° C. for 1 hr. LC-MS showed 5-ethylpyrimidine-4-carboxylic acid was consumed completely. The reaction mixture was concentrated under reduced pressure to give a residue. The batch was combined with this page for purification. The residue was purified by prep-TLC (SiO$_2$, Ethyl acetate:Methanol=10:1). The product of 5-ethyl-N-(8-methyl-2-oxo-3,4-dihydro-1H-quinolin-6-yl) pyrimidine-4-carboxamide (18 mg, 96.6% purity, 7.1% yield) was obtained as a yellow solid. (M+H)+: 311.3. $^1$H NMR (400 MHz, MeOD-d4) δ ppm 9.14 (s, 1H), 8.86 (s, 1H), 7.15 (s, 1H), 7.45 (s, 1H), 3.08-3.14 (m, 2H), 2.97-3.00 (m, 3H), 2.58-2.61 (m, 2H), 2.30 (s, 3H), 1.31-1.34 (m, 3H).

Example 27. Synthesis of Compound 186

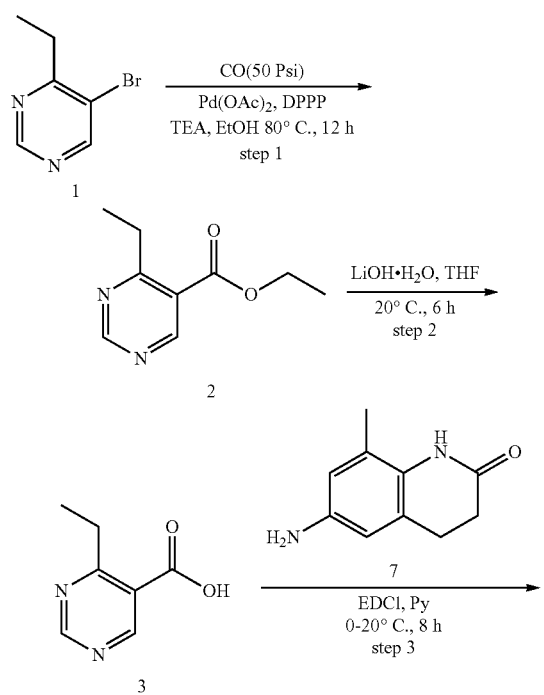

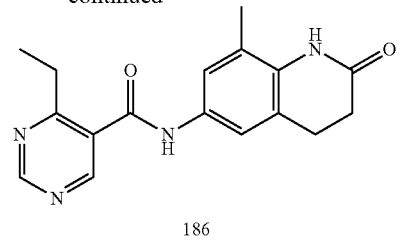

186

Step 1: To a solution of 5-bromo-4-ethyl-pyrimidine (2 g, 10.69 mmol, 1 eq) in EtOH (20 mL) was added Pd(OAc)$_2$ (240.07 mg, 1.07 mmol, 0.1 eq), TEA (2.16 g, 21.39 mmol, 2.98 mL, 2 eq) and DPPP (882.06 mg, 2.14 mmol, 0.2 eq). The mixture was stirred at 80° C. for 12 hr under CO atmosphere (50 psi). The reaction mixture was filtered and concentrated under reduced pressure to give a residue. The residue was purified by column chromatography (SiO$_2$, Petroleum ether/Ethyl acetate=I/O to 5/1). Compound ethyl 4-ethylpyrimidine-5-carboxylate (1 g, 5.27 mmol, 49.30% yield, 95% purity) as a yellow oil. (M+H)+: 180.9. $^1$H NMR (400 MHz, CDCl$_3$) δ ppm 9.20 (s, 1H), 9.12 (s, 1H), 4.46-4.40 (q, J=7.2 Hz, 2H), 3.21-3.16 (q, J=7.6 Hz, 2H), 1.43 (t, J=6.8 Hz, 3H), 1.30 (t, J=7.6 Hz, 3H).

Step 2: To a solution of ethyl 4-ethylpyrimidine-5-carboxylate (1 g, 5.55 mmol, 1 eq) in THF (8 mL) was added LiOH·H$_2$O (465.74 mg, 11.10 mmol, 2 eq) in H$_2$O (8 mL). The mixture was stirred at 20° C. for 6 hr under N$_2$. The mixture was adjusted to PH<6 with 2M HCl. The mixture was filtered and the cake was collected. Compound 4-ethylpyrimidine-5-carboxylic acid (0.4 g, 2.60 mmol, 46.90% yield, 99% purity) as a white solid. (M+H)+: 153.1. $^1$H NMR (400 MHz, DMSO-d$_6$) δ ppm 13.71 (br s, 1H), 9.20 (s, 1H), 9.05 (s, 1H), 3.12-3.07 (q, J=7.6 Hz, 2H), 1.22 (t, J=7.6 Hz, 3H).

Step 3: To a solution of 6-amino-8-methyl-3,4-dihydro-1H-quinolin-2-one (130 mg, 737.74 umol, 1 eq) 4-ethylpyrimidine-5-carboxylic acid (134.70 mg, 885.28 umol, 1.2 eq) in Py. (3 mL) was added EDCI (282.85 mg, 1.48 mmol, 2 eq) at 0° C. under N$_2$. The mixture was stirred at 20° C. for 8 hr under N$_2$. The reaction mixture was concentrated under reduced pressure to remove solvent. The residue was diluted with H$_2$O (10 mL) and extracted with EtOAc 20 mL (10 mL*2). The combined organic layers were dried over Na$_2$SO$_4$, filtered and the filtrate was concentrated under reduced pressure to give a residue. The residue was purified by column chromatography (SiO$_2$, Petroleum ether/Ethyl acetate=I/O to 1/1). Compound 4-ethyl-N-(8-methyl-2-oxo-3,4-dihydro-1H-quinolin-6-yl)pyrimidine-5-carboxamide (120 mg, 385.89 umol, 52.31% yield, 99.8% purity) as a light yellow solid. (M+H)+: 311.1. $^1$H NMR (400 MHz, MeOD-d$_4$) δ ppm 9.14 (s, 1H), 8.81 (s, 1H), 7.42 (s, 1H), 7.36 (s, 1H), 2.99-2.94 (m, 4H), 2.54-2.60 (q, J=5.6 Hz, 2H), 2.28 (s, 3H), 1.33 (t, J=7.2 Hz, 3H).

Example 28. Synthesis of Compound 188

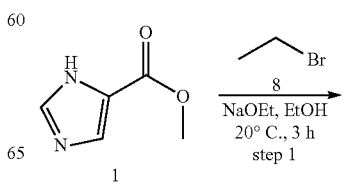

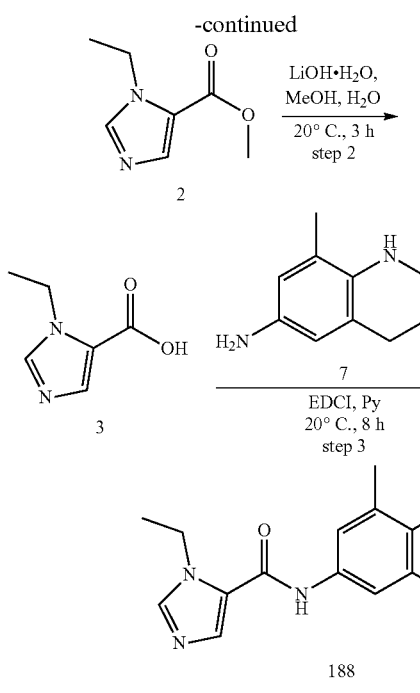

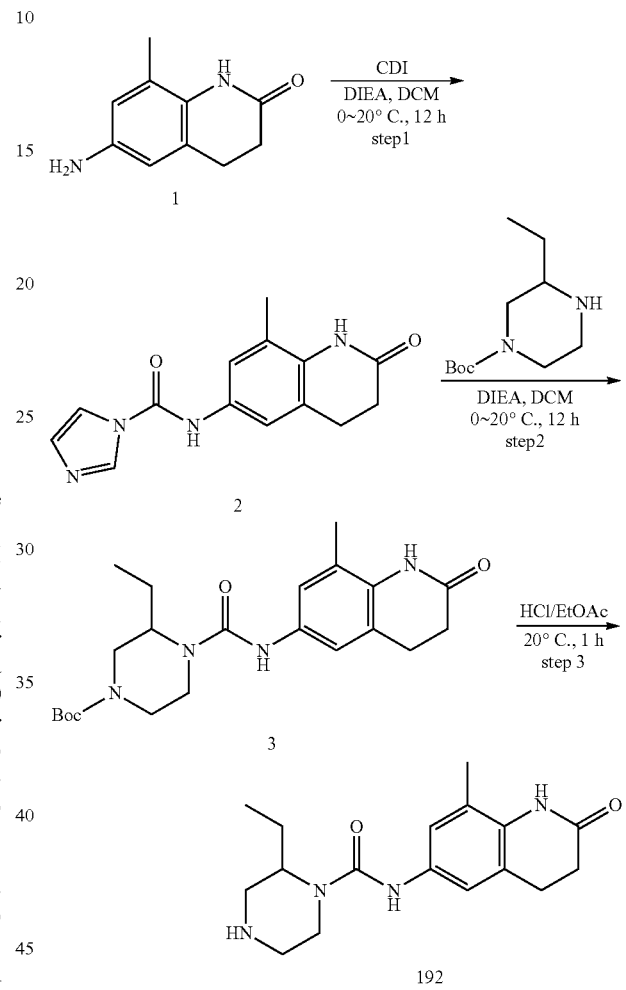

Step 1: A mixture of methyl 1H-imidazole-5-carboxylate (5 g, 39.65 mmol, 1 eq), bromoethane (5.18 g, 47.58 mmol, 3.55 mL, 1.2 eq), EtONa (5.40 g, 79.29 mmol, 2 eq) in EtOH (100 mL) was degassed and purged with $N_2$ for 3 times, and then the mixture was stirred at 20° C. for 3 hr under $N_2$ atmosphere. The reaction mixture was concentrated under reduced pressure to remove solvent. The residue was diluted with $H_2O$ (100 mL) and extracted with EtOAc 200 mL (100 mL*2). The combined organic layers were dried over $Na_2SO_4$, filtered and concentrated under reduced pressure to give a residue. The residue was purified by column chromatography ($SiO_2$, Petroleum ether:Ethyl acetate=20/1 to 0/1). Compound methyl 3-ethylimidazole-4-carboxylate (1 g, 6.49 mmol, 16.36% yield) was obtained as a yellow solid.

Step 2: To a solution of methyl 3-ethylimidazole-4-carboxylate (1 g, 6.49 mmol, 1 eq) in MeOH (80 mL) and $H_2O$ (10 mL) was added LiOH·$H_2O$ (408.30 mg, 9.73 mmol, 1.5 eq). The mixture was stirred at 20° C. for 3 hr. The reaction mixture was added 1N HCl to adjust pH<6 and concentrated under reduced pressure to give a residue. The obtained compound used for next step without purification. Compound 3-ethylimidazole-4-carboxylic acid (0.5 g, crude) was obtained as a yellow solid. $^1$H NMR (400 MHz, DMSO-$d_6$) δ ppm 7.91 (s, 1H), 7.56 (s, 1H), 4.28 (q, J=7.2 Hz, 2H), 1.30 (t, J=7.2 Hz, 3H).

Step 3: To a solution of 6-amino-8-methyl-3,4-dihydro-1H-quinolin-2-one (0.2 g, 777.83 umol, 1 eq) and 3-ethyl-imidazole-4-carboxylic acid (130 mg, 927.65 umol, 1.19 eq) in Py. (3 mL) was added EDCI (298.22 mg, 1.56 mmol, 2 eq). The mixture was stirred at 20° C. for 8 hr. The reaction mixture was concentrated under reduced pressure to remove solvent. The residue was diluted with $H_2O$ (30 mL) and extracted with DCM 100 mL (50 mL*2). The combined organic layers were dried over $Na_2SO_4$, filtered and concentrated under reduced pressure to give a residue. The residue was purified by column chromatography by prep-TLC ($SiO_2$, DCM:MeOH=10:1). Compound 3-ethyl-N-(8-methyl-2-oxo-3,4-dihydro-1H-quinolin-6-yl)imidazole-4-carboxamide (60 mg, 201.11 umol, 25.86% yield) was obtained as a yellow solid. (M+H)$^+$: 299.1. $^1$H NMR (400 MHz, MeOD-d4) δ ppm 7.86 (s, 1H), 7.73 (s, 1H), 7.36 (s, 1H), 7.31 (s, 1H), 4.47-4.41 (q, J=7.2 Hz, 2H), 2.94 (t, J=7.2 Hz, 2H), 2.57 (t, J=5.6 Hz, 2H), 2.26 (s, 3H), 1.43 (t, J=6.8 Hz, 3H).

Example 29. Synthesis of Compound 192

Step 1: To a solution of di(imidazol-1-yl) methanone (92.02 mg, 567.49 umol, 1 eq) and DIEA (110.01 mg, 851.23 umol, 148.27 uL, 1.5 eq) in DCM (10 mL) was added 6-amino-8-methyl-3,4-dihydro-1H-quinolin-2-one (100 mg, 567.49 umol, 1 eq) in DCM (3 mL) drop-wise at 0° C. The mixture was stirred at 20° C. for 12 h. LC-MS showed 6-amino-8-methyl-3,4-dihydro-1H-quinolin-2-one was consumed completely and the desired m/z was detected. The reaction mixture was concentrated in vacuum. N-(8-methyl-2-oxo-3,4-dihydro-1H-quinolin-6-yl) imidazole-1-carboxamide (453 mg, crude) was obtained as yellow solid. (M+H)$^+$: 271.2.

Step 2: To a solution of N-(8-methyl-2-oxo-3,4-dihydro-1H-quinolin-6-yl) imidazole-1-carboxamide (453 mg, 1.68 mmol, 1 eq) and DIEA (216.61 mg, 1.68 mmol, 291.93 uL, 1 eq) in THF (10 mL) was added tert-butyl 3-ethylpiperazine-1-carboxylate (395.09 mg, 1.84 mmol, 1.1 eq) at 0° C. The mixture was stirred at 20° C. for 12 hr. LC-MS showed N-(8-methyl-2-oxo-3,4-dihydro-1H-quinolin-6-yl) imidazole-1-carboxamide was consumed completely and one main peak with desired mass was detected. The reaction mixture was diluted with water (10 mL) and extracted with EtOAc (10 mL*3). The combined organic layers were washed with brine (30 mL*3), dried over anhydrous $Na_2SO_4$, filtered and concentrated under reduced pressure to give a residue. The residue was purified by flash silica gel chromatography (ISCO; 12 g SepaFlash Silica Flash Column, Eluent of 0-71% Ethyl acetate/Petroleum ether gradient 40 mL/min). Compound tert-butyl 3-ethyl-4-[(8-methyl-2-oxo-3,4-dihydro-1H-quinolin-6-yl) carbamoyl] piperazine-1-carboxylate (30 mg, crude) was obtained as a light yellow solid. (M−tBu)+: 361.2.

Step 3: The mixture of tert-butyl 3-ethyl-4-[(8-methyl-2-oxo-3,4-dihydro-1H-quinolin-6-yl)carbamoyl]piperazine-1-carboxylate (30 mg, 72.03 umol, 1 eq) in HCl/EtOAc (4 M, 2 mL, 111.07 eq) was stirred at 20° C. for 1 h. TLC showed the starting material was consumed completely. The reaction mixture was concentrated under reduced pressure to give a residue. The crude product was purified by re-crystallization by EtOAc (1 mL) at 25° C. Compound 2-ethyl-N-(8-methyl-2-oxo-3,4-dihydro-1H-quinolin-6-yl) piperazine-1-carboxamide (18 mg, 48.51 umol, 67.35% yield, 95.100% purity, HCl) was obtained as a white solid. (M+H)+: 317.2. 1H NMR (400 MHz, MeOD-d4) δ ppm 7.04 (d, J=12 Hz, 1H), 4.43-4.45 (m, 1H), 4.17-4.21 (m, 1H), 3.36-3.42 (m, 2H), 3.26-3.28 (m, 2H), 3.10-3.20 (m, 1H), 2.88-2.92 (m, 2H), 2.52-2.55 (m, 2H), 2.23 (s, 3H), 1.71-1.76 (m, 2H), 0.97-1.01 (m, 3H). Compounds of the present disclosure can be generally prepared by those skilled in the art in view of the present disclosure. See also methods described in PCT/US2019/044278, which has an international filing date of Jul. 31, 2019, and PCT/US2021/014883, which has an international filing date of Jan. 25, 2021, the content of which is incorporated by reference in its entirety.

By following similar procedures above, other disclosed compounds herein were or can be prepared.

Example 30. Synthesis of Compound 170

Compound 170 can be prepared according to the following scheme:

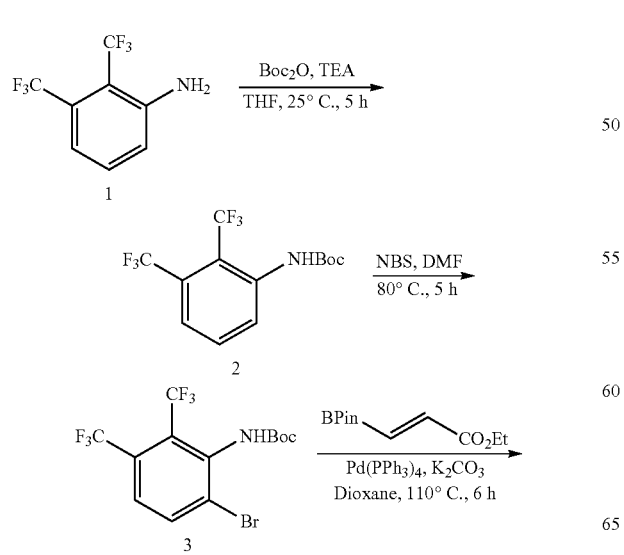

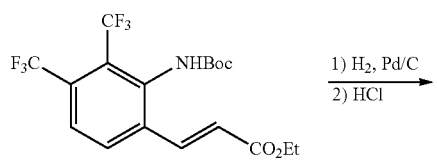

Example 31. Synthesis of Compound 171
Compound 171 can be prepared according to the following scheme:
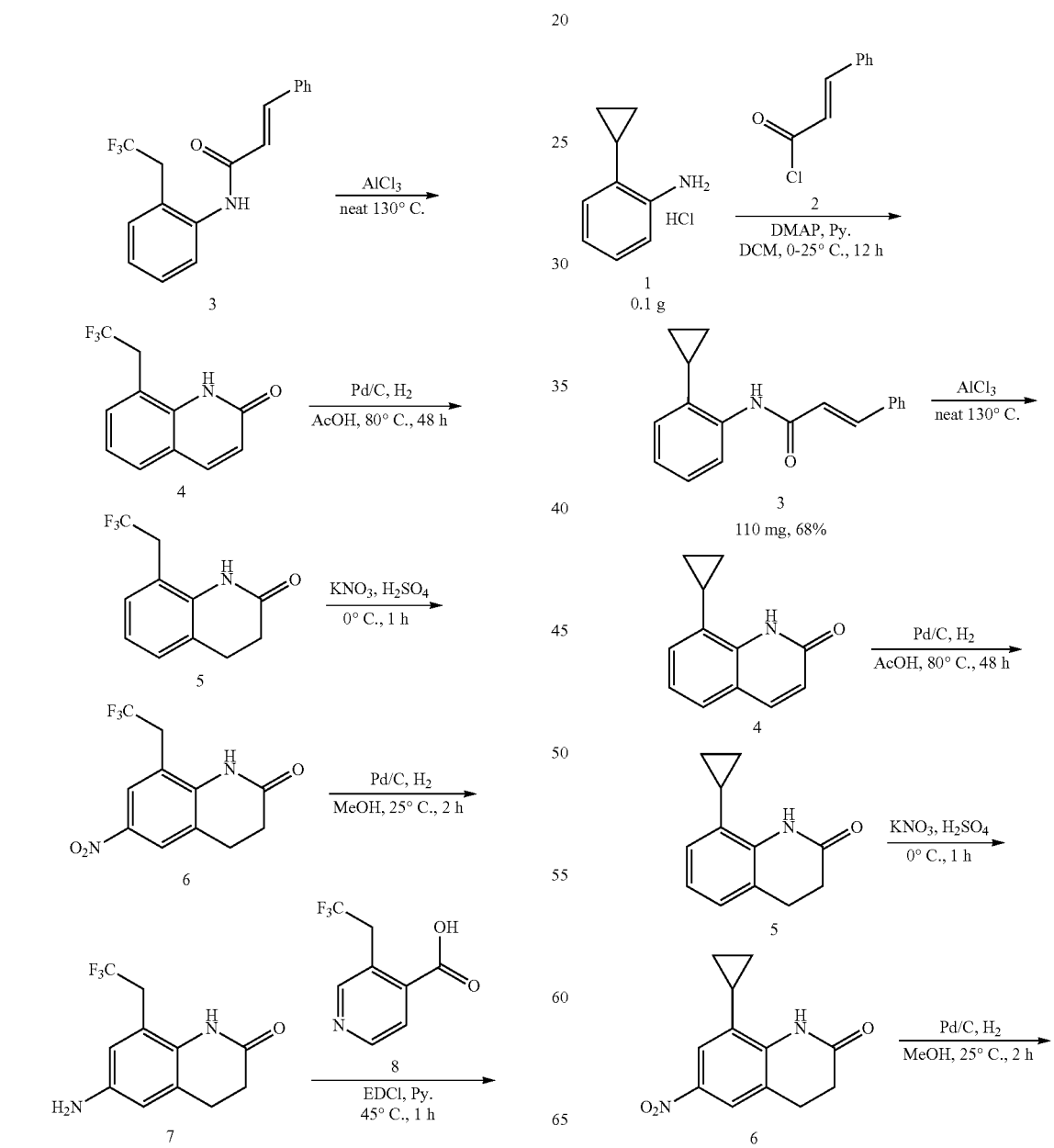

167
-continued
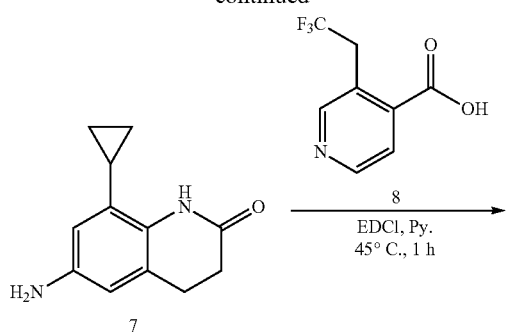
172
Example 33. Synthesis of Compound 173
Compound 173 can be prepared according to the following scheme:
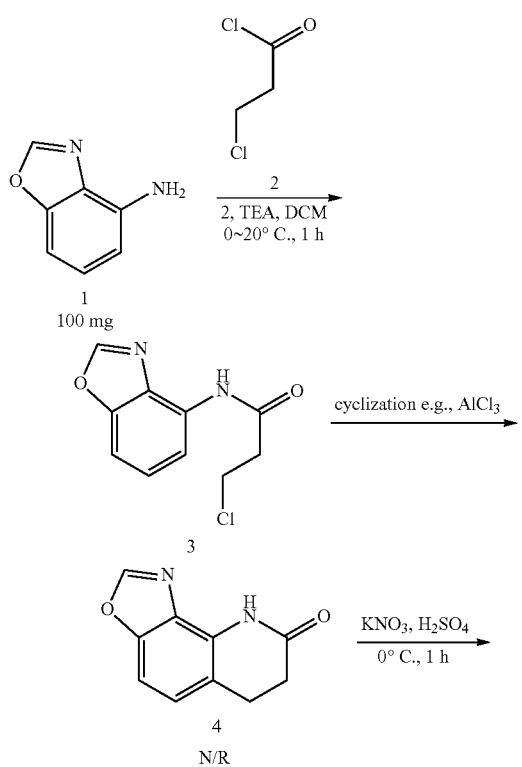
168
-continued
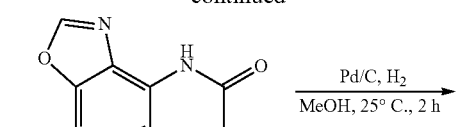
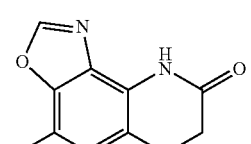
173
Example 34. Synthesis of Compound 174
Compound 174 can be prepared according to the following scheme:
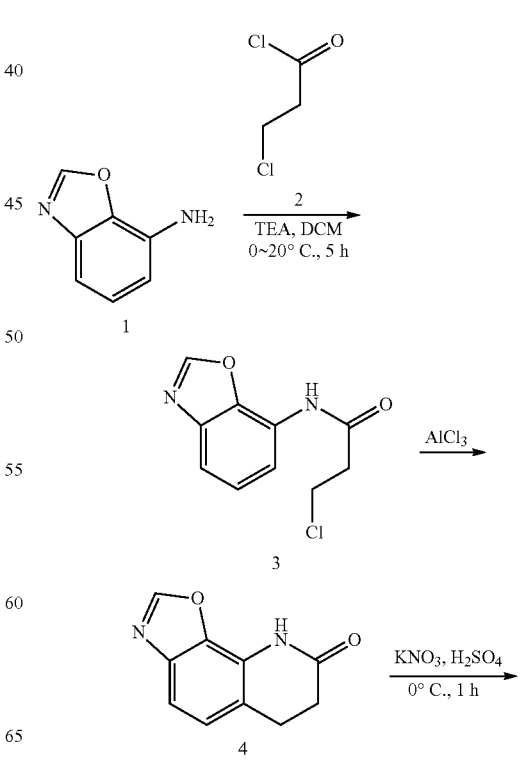

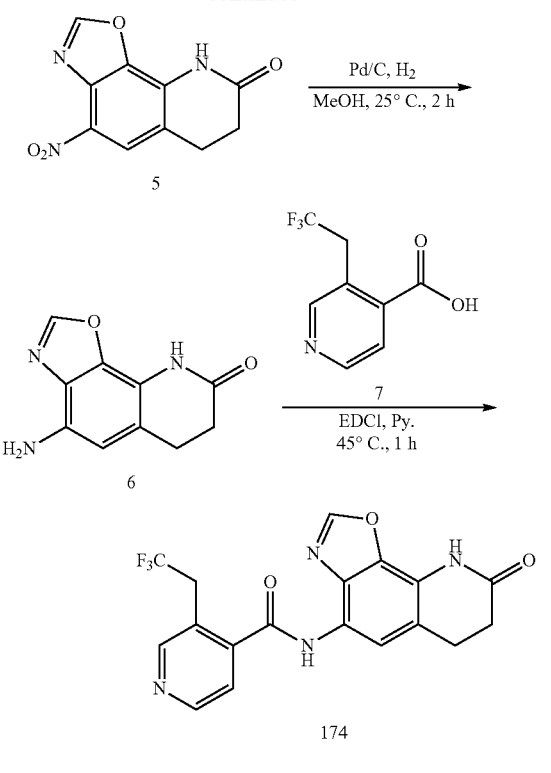
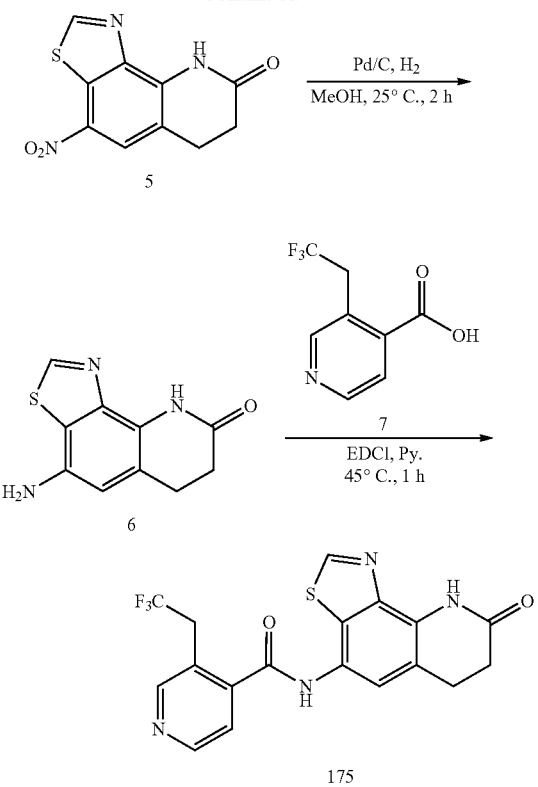
Example 35. Synthesis of Compound 175
Compound 174 can be prepared according to the following scheme:
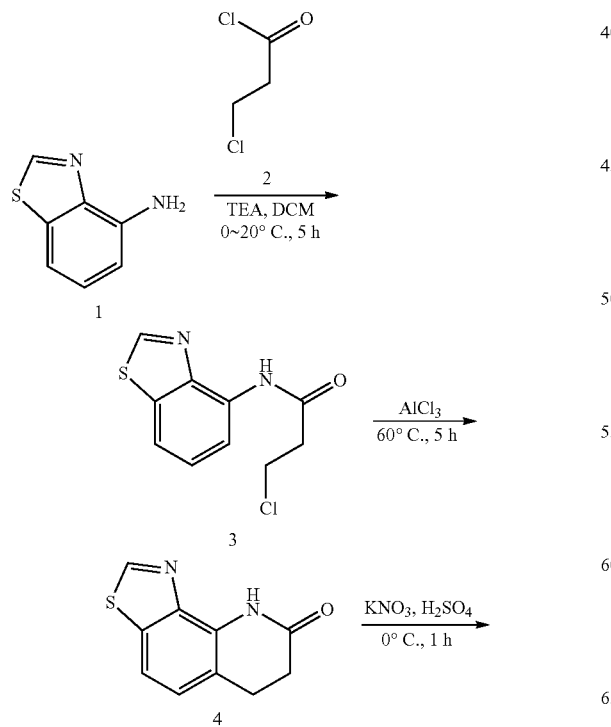
Example 36. Synthesis of Compound 176
Compound 176 can be prepared according to the following scheme:
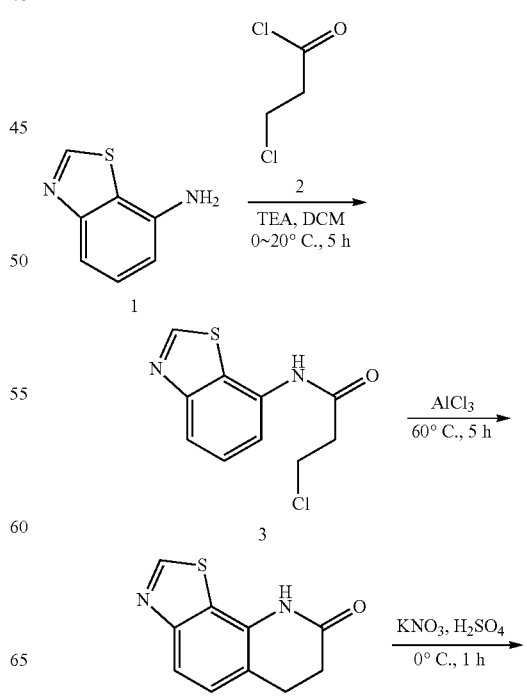

171
-continued
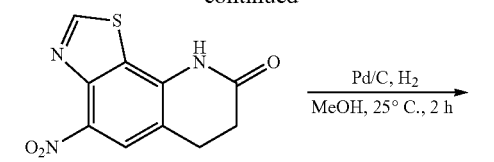
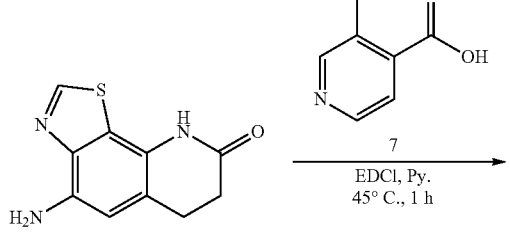
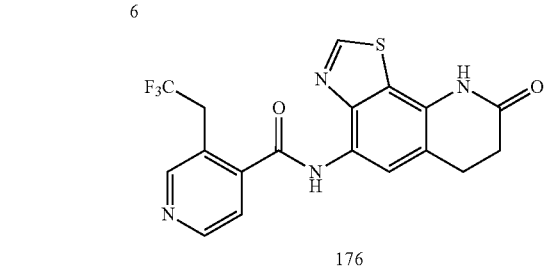
176
Example 37. Synthesis of Compound 177
Compound 177 can be prepared according to the following scheme:
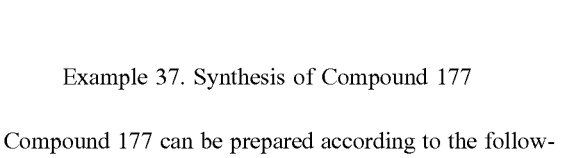
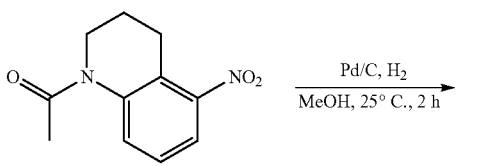
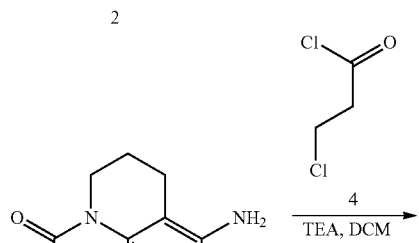
172
-continued
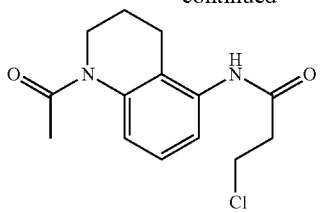
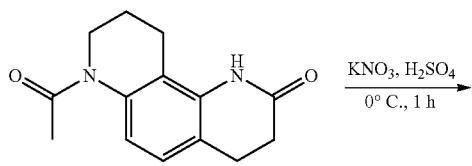
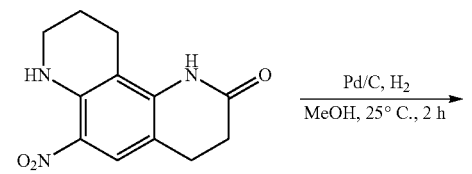
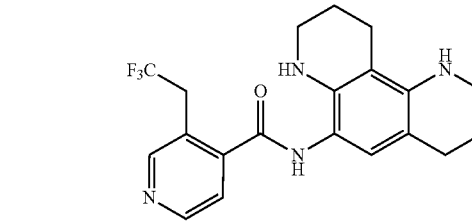
177
Example 38. Synthesis of Compound 178
Compound 178 can be prepared according to the following scheme:
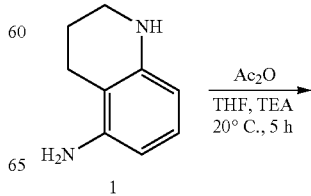

-continued
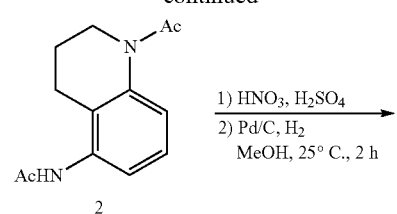
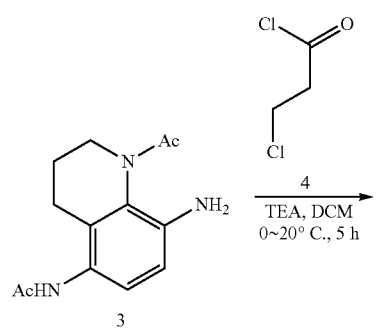
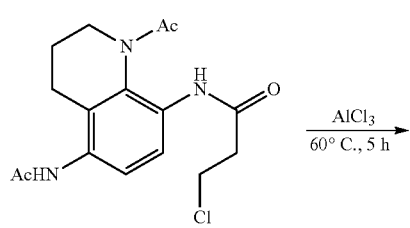
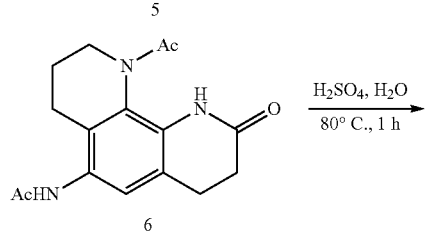
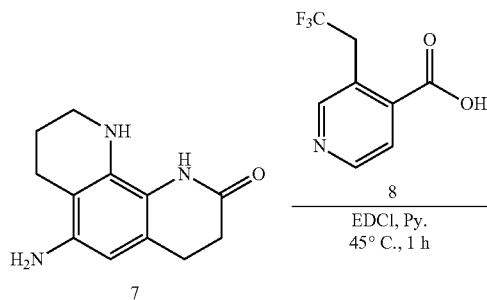
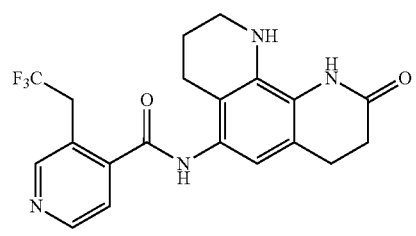
Example 40. Synthesis of Compound 180
Compound 180 can be prepared according to the following scheme:
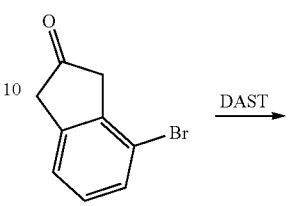
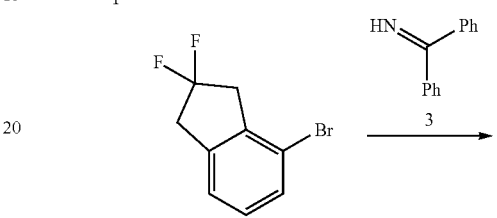
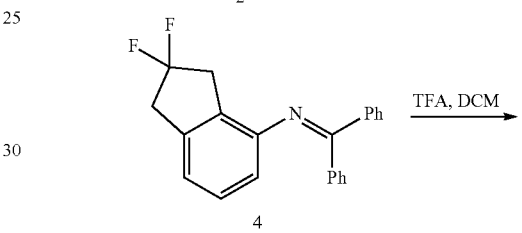
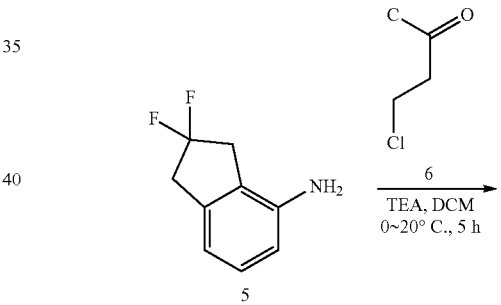
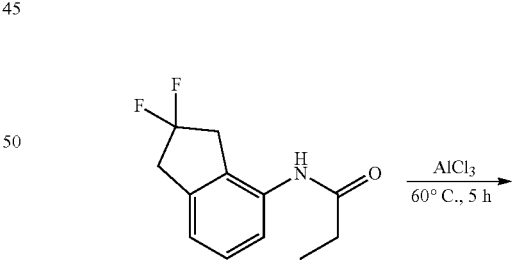
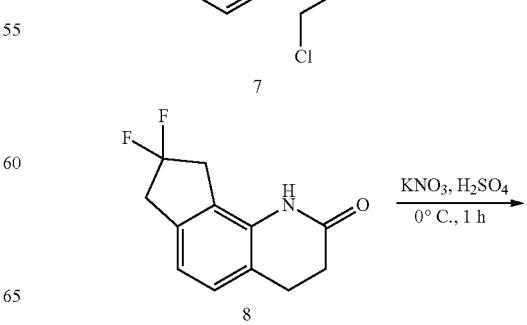

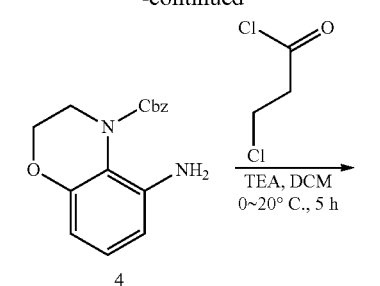
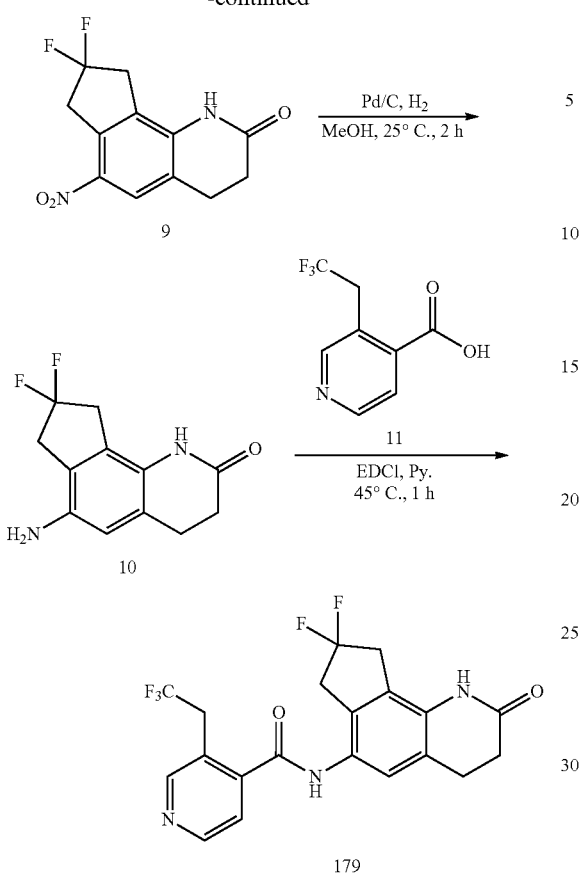
Example 40. Synthesis of Compound 180ID-71C
Compound 180 can be prepared according to the following scheme:
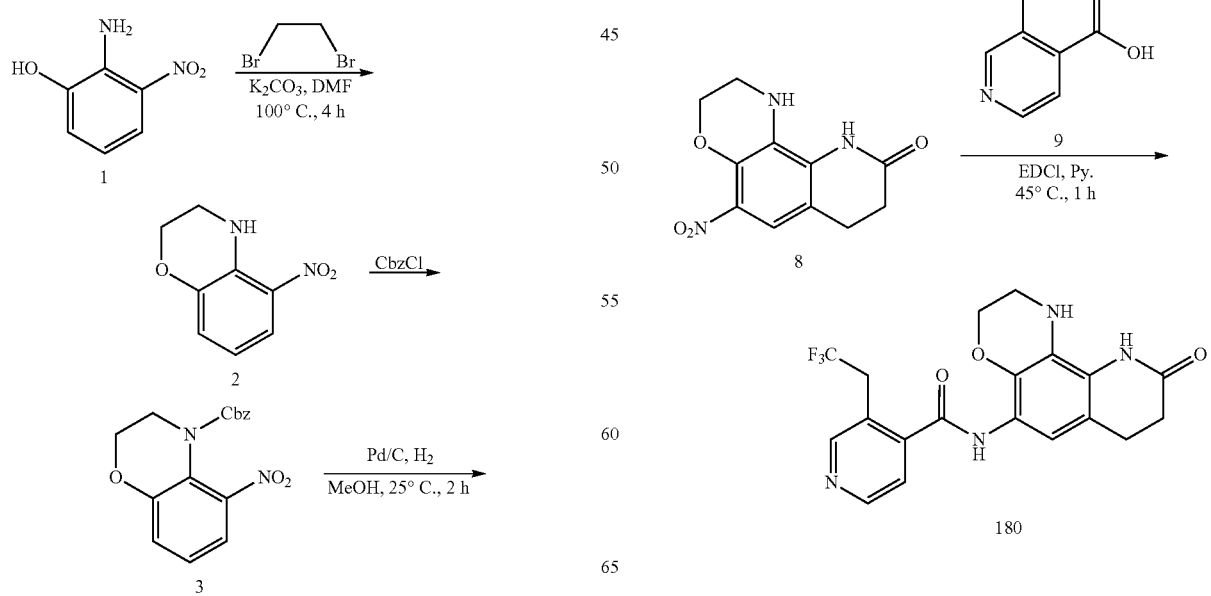

Example 41. Synthesis of Compound 183
Compound 183 can be prepared according to the following scheme:
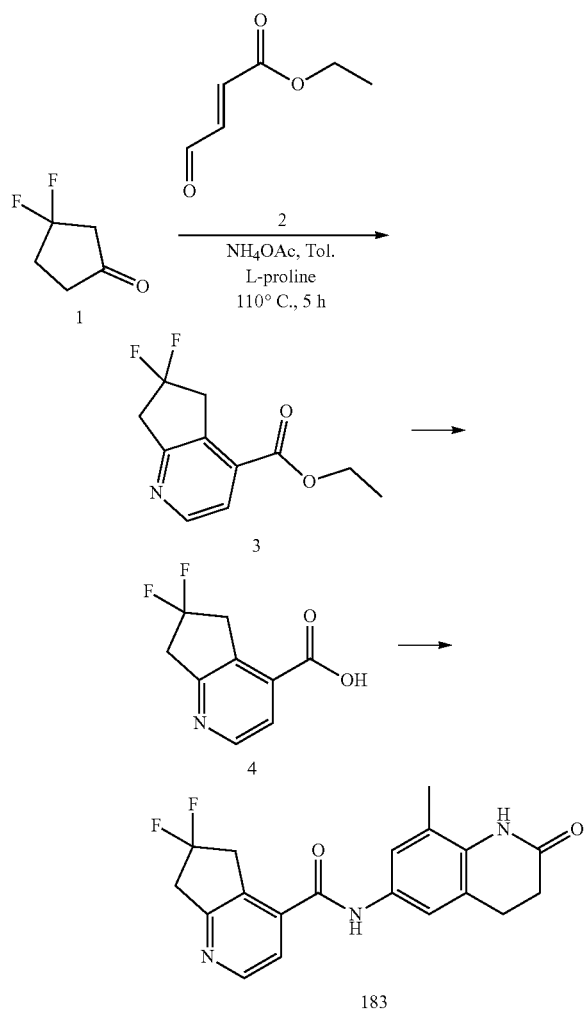
Example 42. Synthesis of Compound 184
Compound 184 can be prepared according to the following scheme:
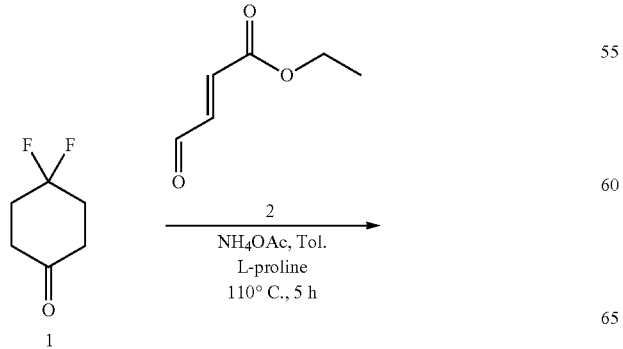
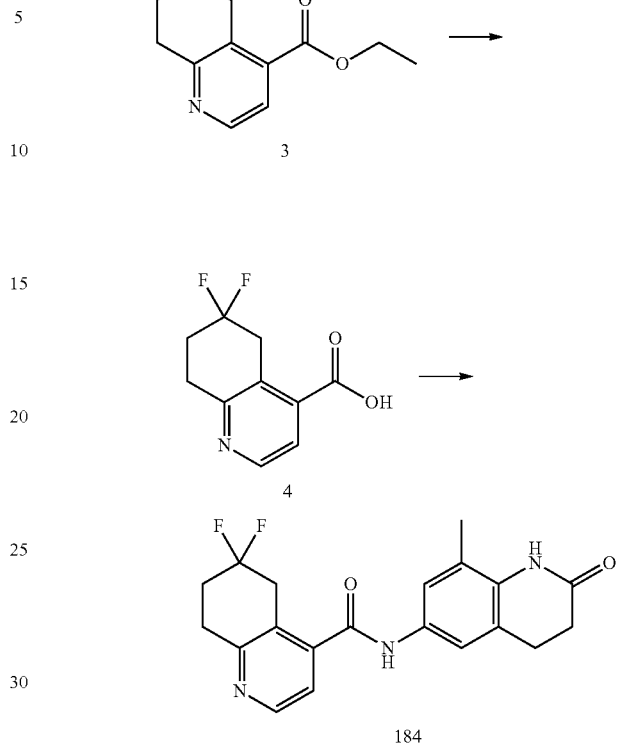
Example 43. Synthesis of Compound 187
Compound 187 can be prepared according to the following scheme:
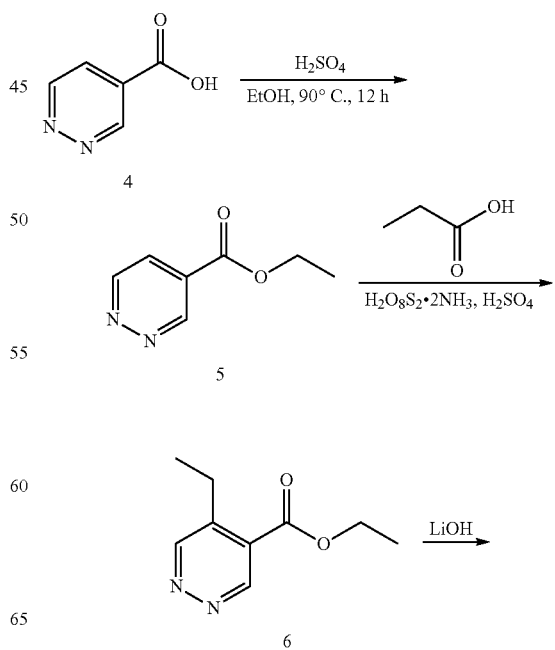

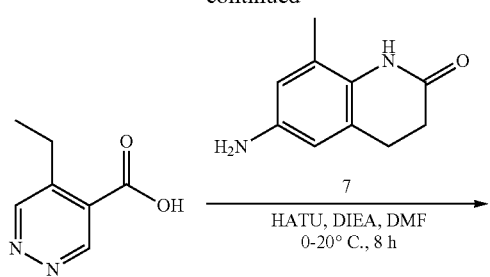
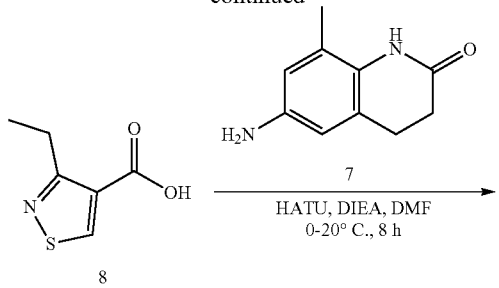
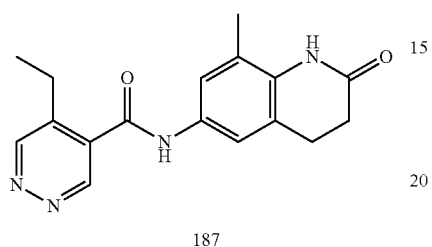
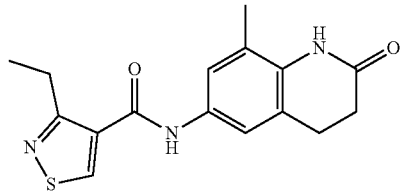
Example 44. Synthesis of Compound 189
Compound 189 can be prepared according to the following scheme:
Example 45. Synthesis of Compound 190
Compound 190 can be prepared according to the following scheme:
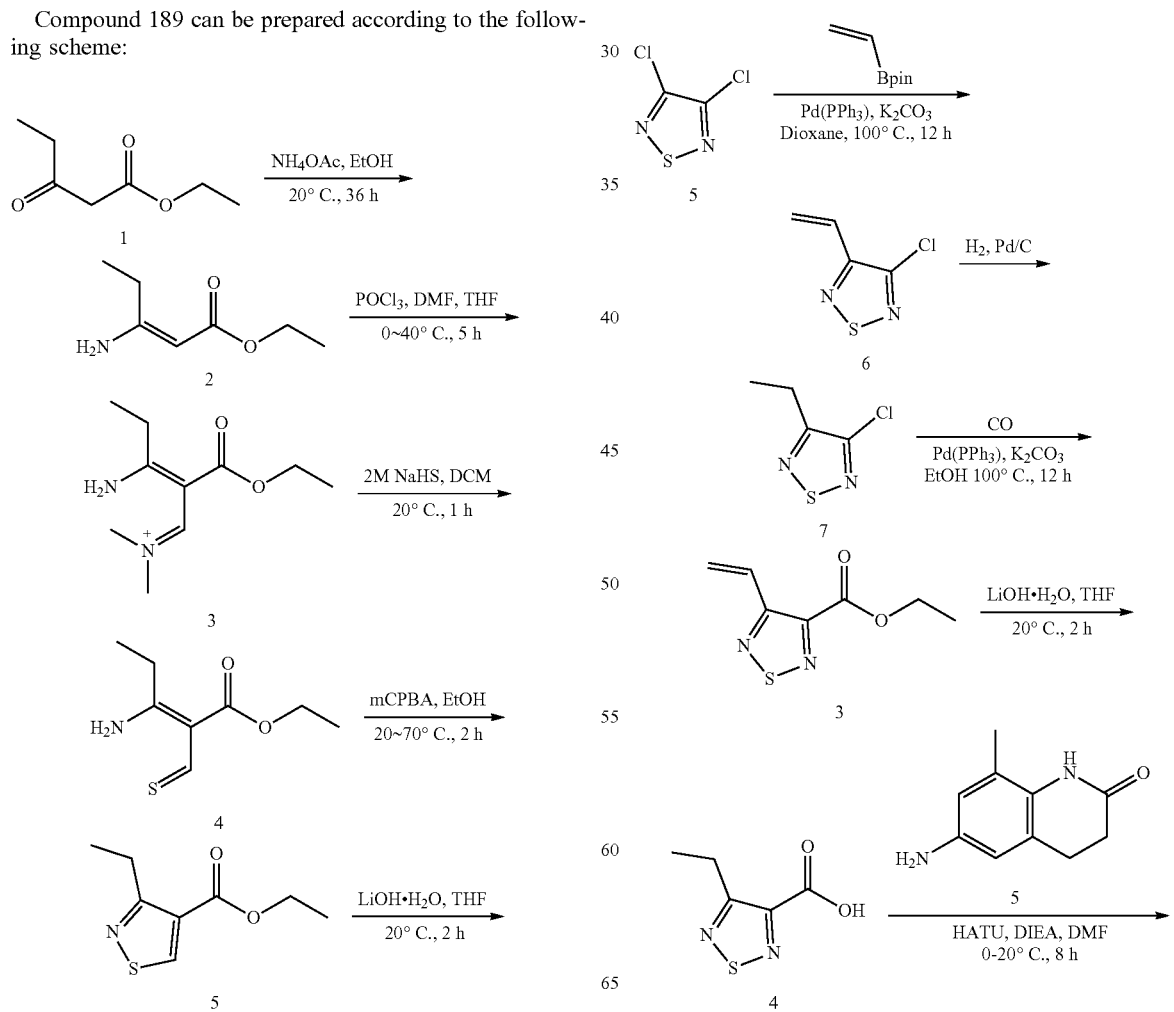

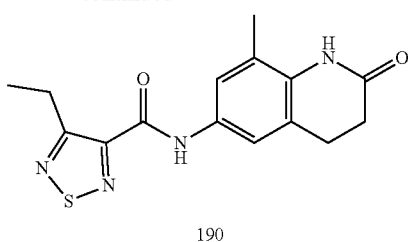
190
Example 46. Synthesis of Compound 191
Compound 191 can be prepared according to the following scheme:
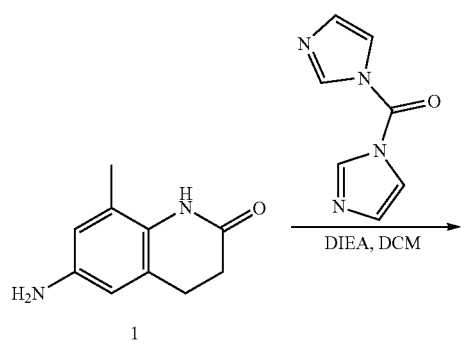
191
Example 47. Synthesis of Compound 192 and 193
Compound 192 and 193 can be prepared according to the following scheme:
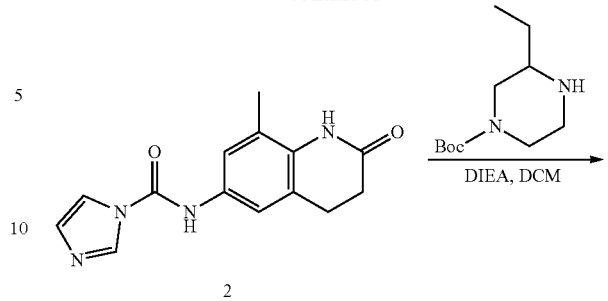
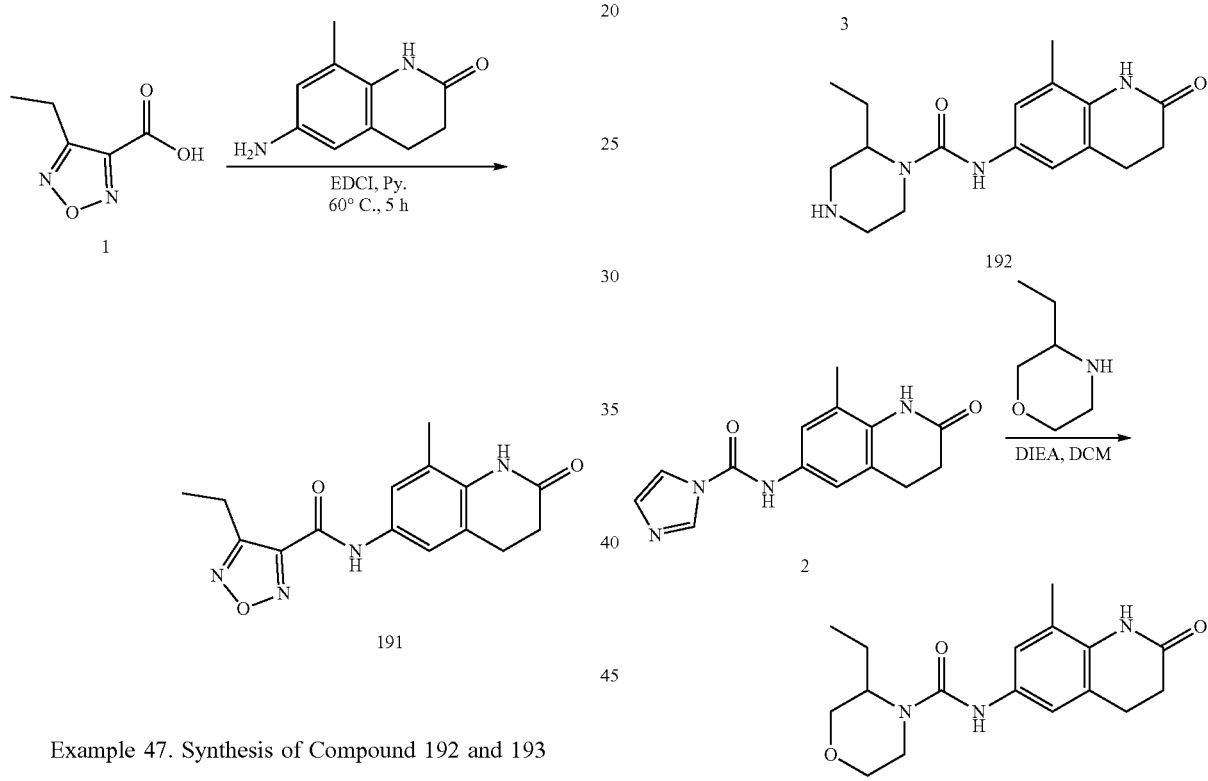
Example 48. Synthesis of Compound 194
Compound 194 can be prepared according to the following scheme:
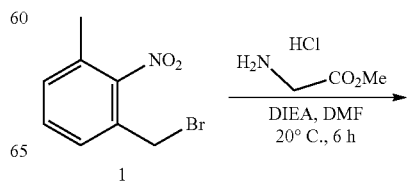

-continued
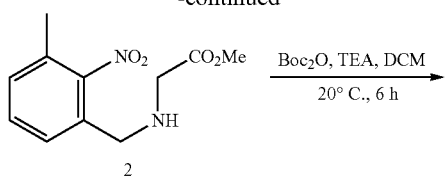
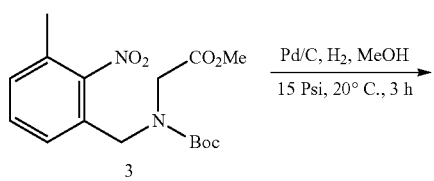
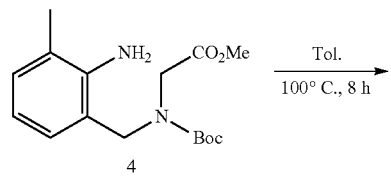
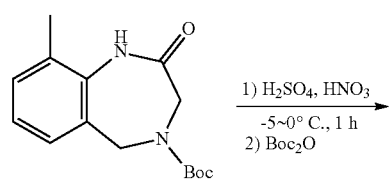
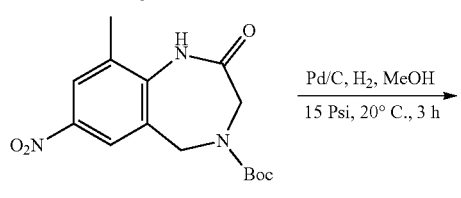
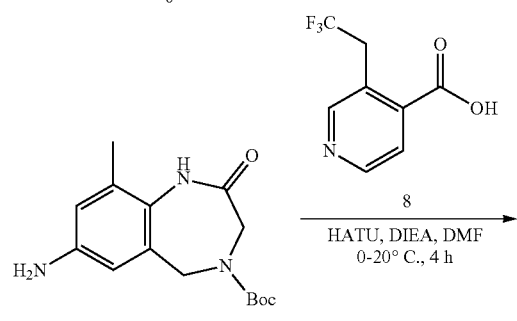
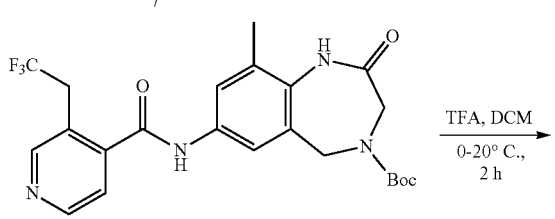
-continued
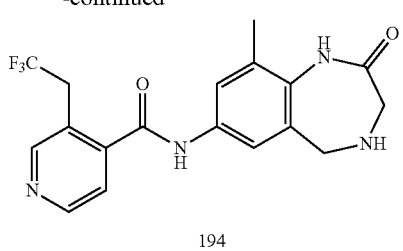
Example 49. Synthesis of Compound 195
Compound 195 can be prepared according to the following scheme:
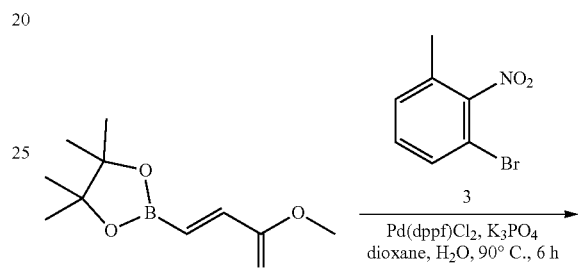
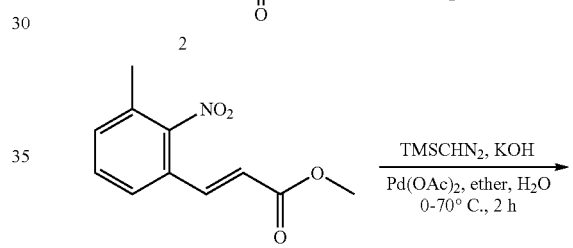

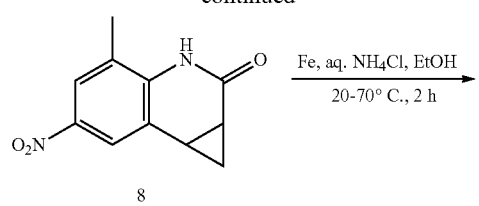
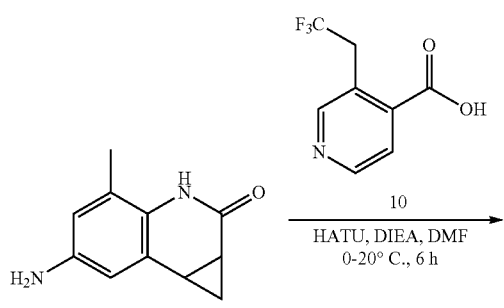
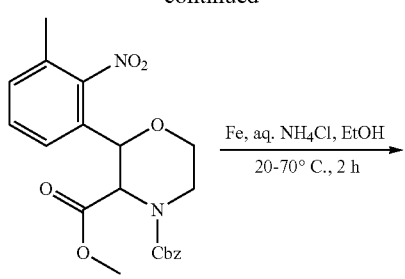
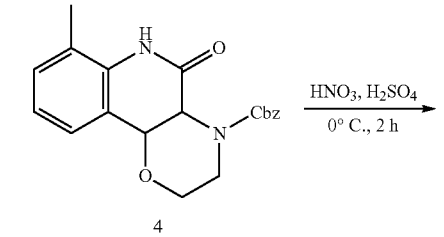
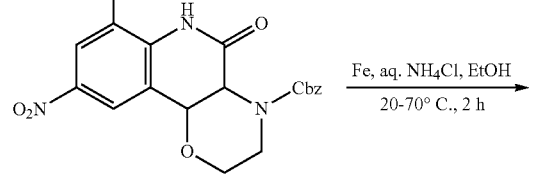
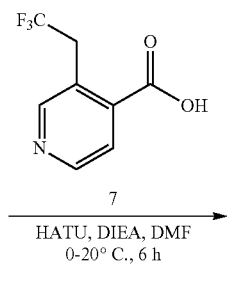
Example 50. Synthesis of Compound 196
Compound 196 can be prepared according to the following scheme:
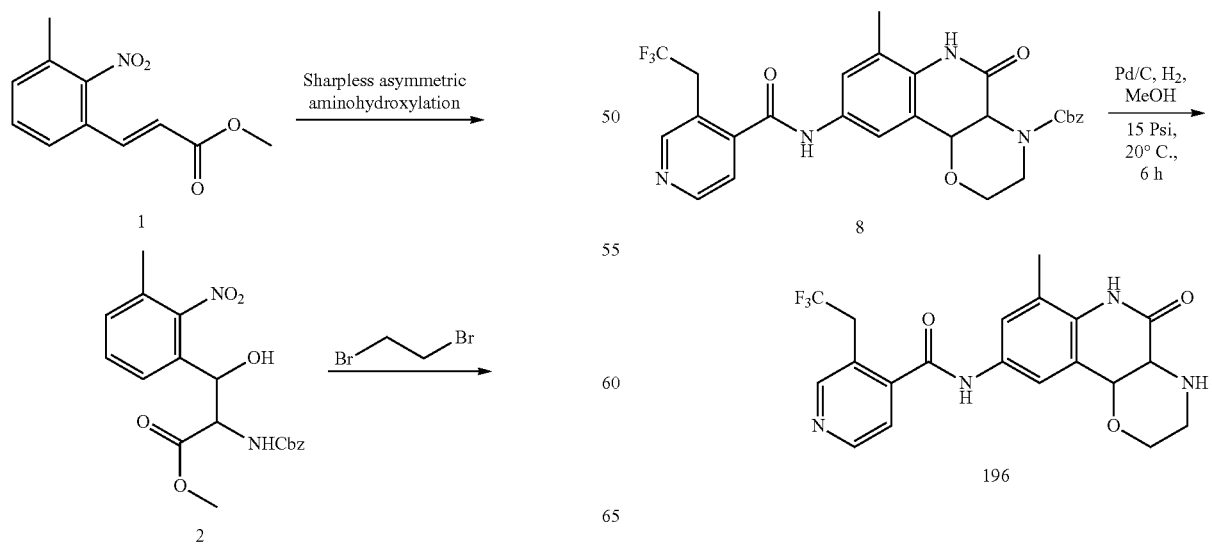

187
Example 51. Synthesis of Compound 197
Compound 197 can be prepared according to the following scheme:
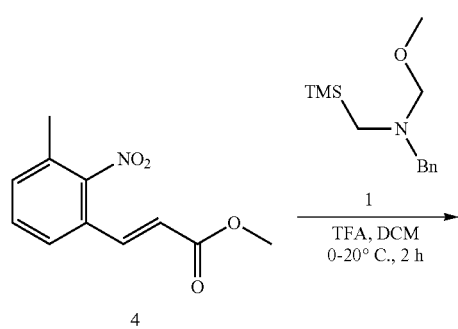
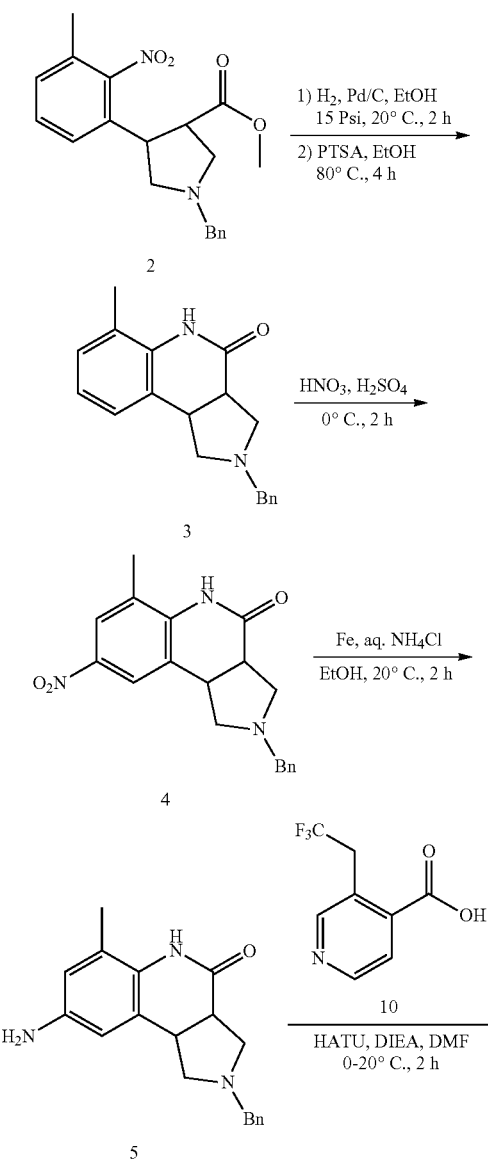
188
-continued
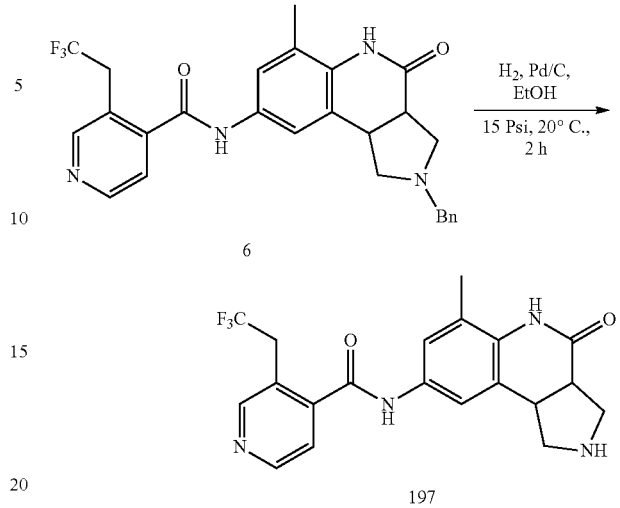
Example 52. Synthesis of Compound 201
Compound 201 can be prepared according to the following scheme:
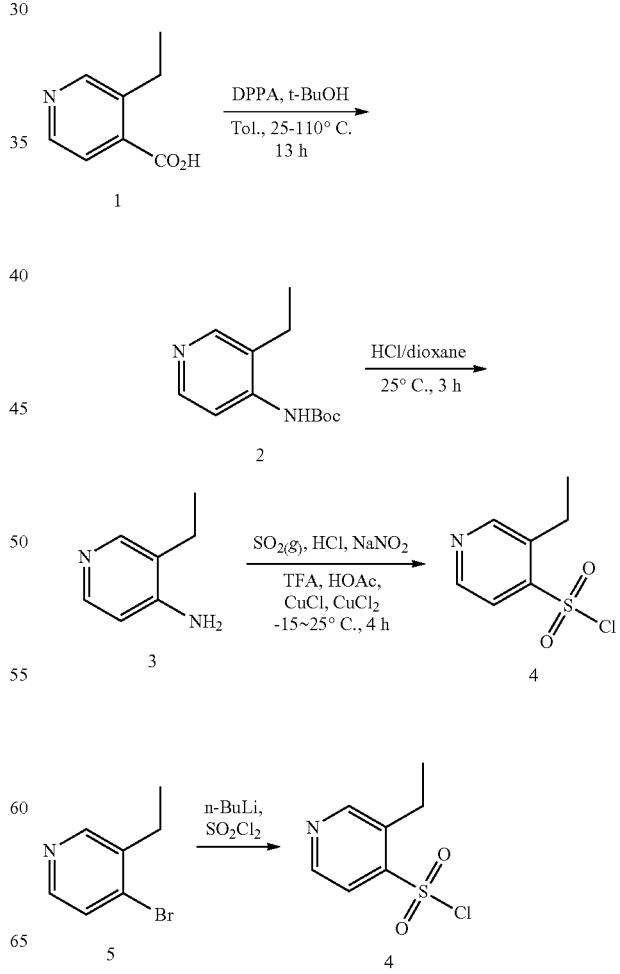

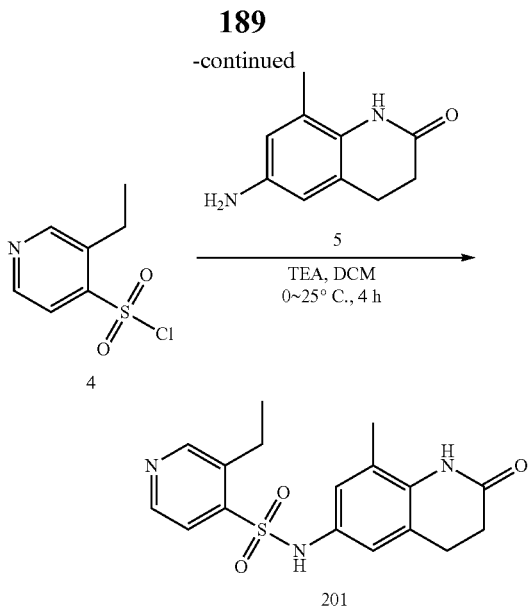

Example 53. Synthesis of Compound 202

Compound 202 can be prepared according to the following scheme:

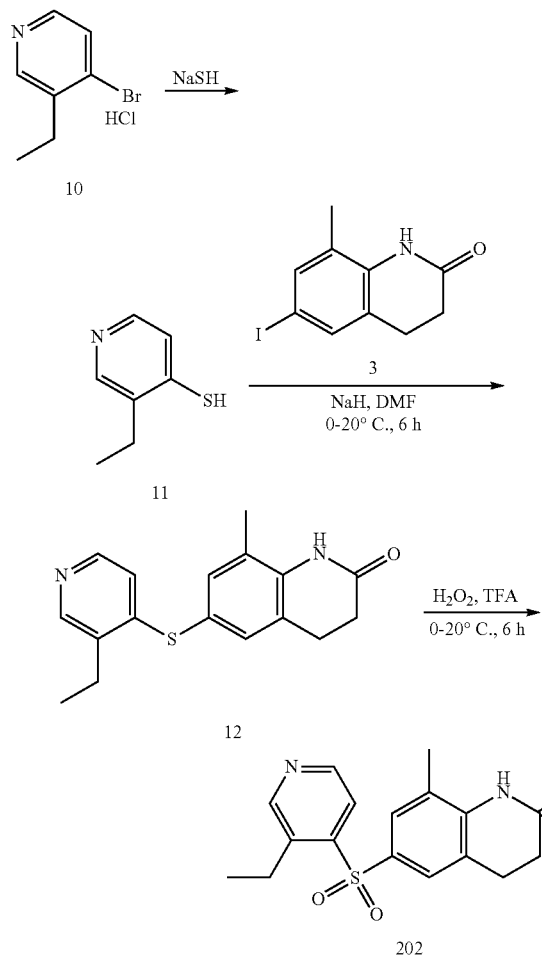

Biological Example 1. Material and General Methods

Cell Lines and Cell Culture:

MDA-MB-468, MCF7, 293T, B16F10, HCT 116, HepG2, LN229, HTB140 and SW480 cells were cultured in DMEM+10% FBS; DU145 cells and its derivatives, PC3, AsPC-1, NCI-H358 were cultured in RPMI-1640+10% FBS; and SUM159 cells and its derivatives were cultured in F12 media supplemented with 10% FBS, 10 μg/mL Insulin and 20 ng/mL EGF. Cell lines were labeled with retroviral vectors with bi-cistronic expression of GFP/firefly luciferase to facilitate imaging and flow cytometry experiments. All cell lines were verified negative for *mycoplasma* contamination by monthly PCR analysis. No cells lines used here appear in the database of commonly misidentified cell lines (ICLAC). All cell lines were validated with STR analysis and compared to NCBI repository data.

Cloning, Viral Production, and Transduction:

The coding sequences of Aldh1a1, Aldh1a2, Aldh1a3 and Aldh3a1 were cloned from cDNA made from pooled human reference RNA samples. Cloned sequences flanked by Age1 and Xho1 restriction sites were inserted into the pLex lentiviral plasmid. Clones were sequenced and compared against NCBI expressed sequence tags (ESTs) for accuracy. Viral production of each enzyme was performed by transfection into the 293T packaging cell line using PEI along with PsPax2 and VSVG packaging vectors. Viruses were collected and filtered at 0.45 μm, then cells were transduced using polybrene (8 μg/mL) for 12 hours, followed by culture with 1 μg/mL puromycin for the duration of experiments. All viral transduction and selection was performed on a cell population-wide basis.

Biological Example 2. Genetic Knockout Studies

CRISPR-Cas9 vectors containing both the Cas9 gene and gRNA sequences containing homologous sequences to genomic Aldh1a3 were transduced into MDA-MB-468 cells by lentiviral infection followed by puromycin selection for viral integration, and the resulting cells were analyzed by ALDEFLUOR™ assay. Two ALDH1a3-targeting gRNA vectors were used to create two derivative cell lines, and one gRNA with a scrambled sequence was used to generate a control derivative cell line. ALDH1a3 targeting gRNA vectors were compared to a non-target gRNA.

Aldh1a3 knockout or control cells were implanted into the mammary fat pad of female NSG mice and were treated with either PBS or Paclitaxel at 25 mg/kg for 6 doses. Tumor mass from each group was measured at the experimental endpoint. The results were shown in FIGS. 1A-1C.

Figure 1A:
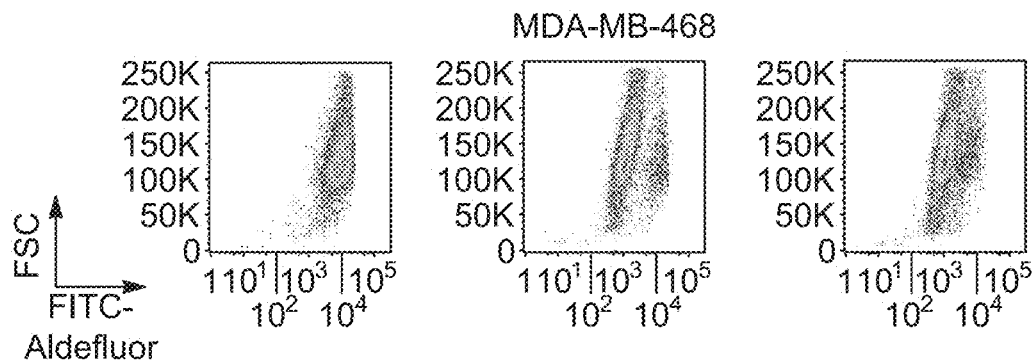
FIG. 1A is flow cytometry spectra, and shows that genetic knockout of ALDH1a3 (middle and rightmost spectra, two distinct ALDH1a3-targeting CRISPR gRNAs) in MDA-MB-468 breast cancer cells substantially decreases ALDEFLUOR™ activity compared to control MDA-MB-468 cells (leftmost spectra).
Figure 1B:
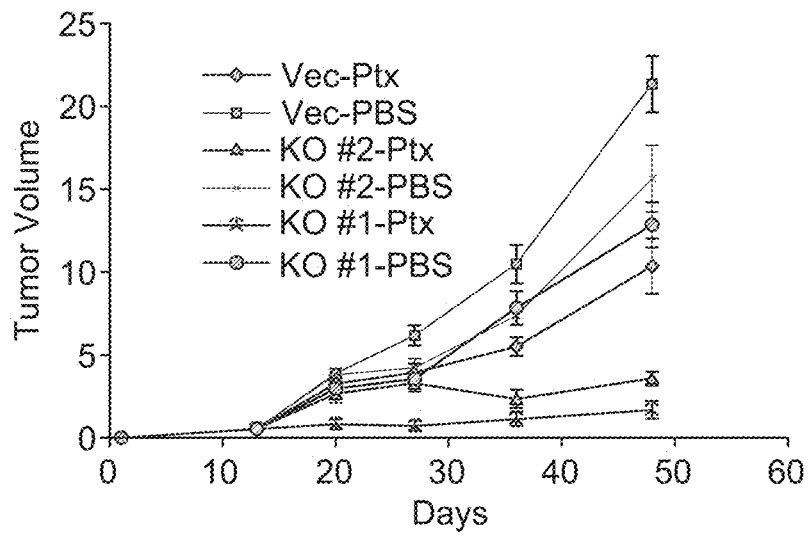
FIG. 1B is a line graph of tumor volume ($mm^3$) versus time (days), and shows that genetic knockout of ALDH1a3 (KO #1 and KO #2) in MDA-MB-468 breast cancer cells slows primary tumor growth and sensitizes tumors to paclitaxel (ptx) compared to control cells (Vec).
Figure 1C:
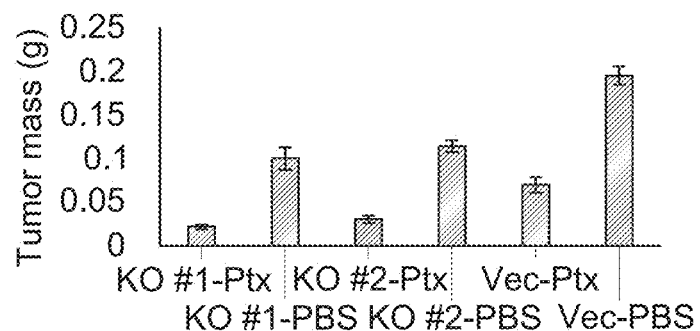
FIG. 1C is a bar graph of tumor mass (g) versus ALDH1a3 genetic knockout (KO #1 and KO #2), and shows that genetic knockout of ALDH1a3 in MDA-MB-468 breast cancer cells slows primary tumor growth compared to control (Vec) and sensitizes tumors to paclitaxel (ptx).

FIG. 1A is flow cytometry spectra, and shows that genetic knockout of ALDH1a3 (middle and rightmost spectra) in MDA-MB-468 breast cancer cells substantially decreases ALDEFLUOR™ activity compared to control MDA-MB-468 cells (leftmost spectra). FIG. 1B is a line graph of tumor volume (mm$^3$) versus time (days), and shows that genetic knockout of ALDH1a3 in MDA-MB-468 breast cancer cells slows primary tumor growth and sensitizes tumors to paclitaxel. FIG. 1C is a bar graph of tumor mass (g) versus genetic knockout, and shows that genetic knockout of ALDH1a3 in MDA-MB-468 breast cancer cells slows primary tumor growth and sensitizes tumors to paclitaxel. Thus, these results show that genetic knockout of Aldh1a3 in MDA-MB-468 breast cancer cells slows primary tumor growth and sensitizes tumors to paclitaxel.

In another experiment, CRISPR-Cas9 vectors targeting the ALDH1a3 gene were transduced into the Sum159-M1a cell line followed by a rescue or control vector and analyzed by the Aldefluor assay. CRISPR-Cas9 vectors containing both the Cas9 gene and gRNA sequences containing homologous sequences to genomic Aldh1a3 were transduced into Sum159-M1a cells followed by selection for positively transfected cells by flow cytometry. Positively transfected cells were then virally transduced with lentiviral vectors containing either the vector backbone or full-length human Aldh1a3. Positive transductants were selected by puromycin, and the resulting cells were analyzed by ALDEFLUOR™ assay. In a xenograft experiment, the knockout-vector or knockout-Aldh1a3 or wild-type vector or wild-type-Aldh1a3 cells were injected by intracardiac injection into mice, and bone metastasis growth was tracked by intravital bioluminescent imaging. Bone metastasis-free survival was tracked by bioluminescence, and plotted using the Kaplan-Meier model. The results were shown in FIGS. 2A-2C.

Figure 2A:
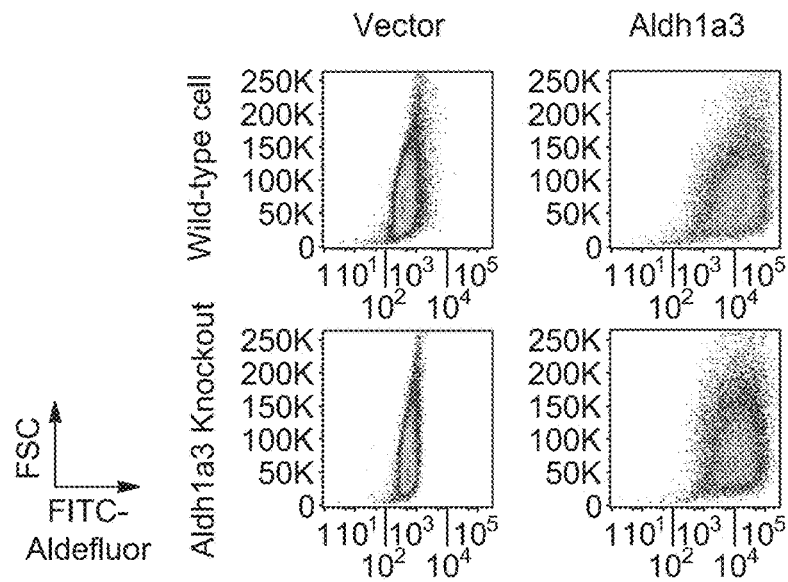
FIG. 2A is flow cytometry spectra, and shows that genetic knockout of ALDH1a3 in Sum159-M1a breast cancer cells nearly abolishes ALDEFLUOR™ activity in the cells, and that ALDEFLUOR™ activity can be rescued by transducing the cells with a rescue vector encoding ALDH1a3 compared to empty vector.
Figure 2B:
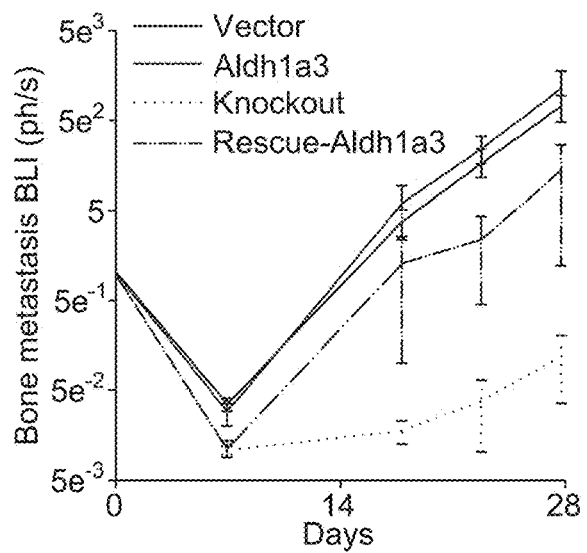
FIG. 2B is a line graph of bone metastasis, as measured by bioluminescence (ph/s), versus time (days), and shows that knockout of ALDH1a3 in Sum159-M1a breast cancer cells slows bone metastasis growth.
Figure 2C:
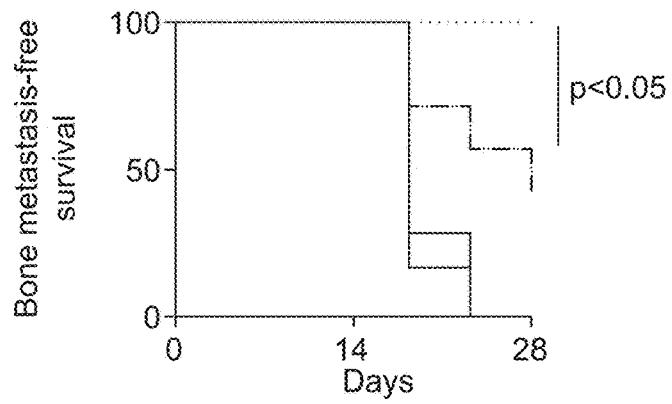
FIG. 2C is a Kaplan-Meier plot of bone metastasis-free survival over time, and shows that knockout of ALDH1a3 in Sum159-M1a breast cancer cells significantly increases survival time. Statistics by Cox's proportional hazards model.
Figure 4A:
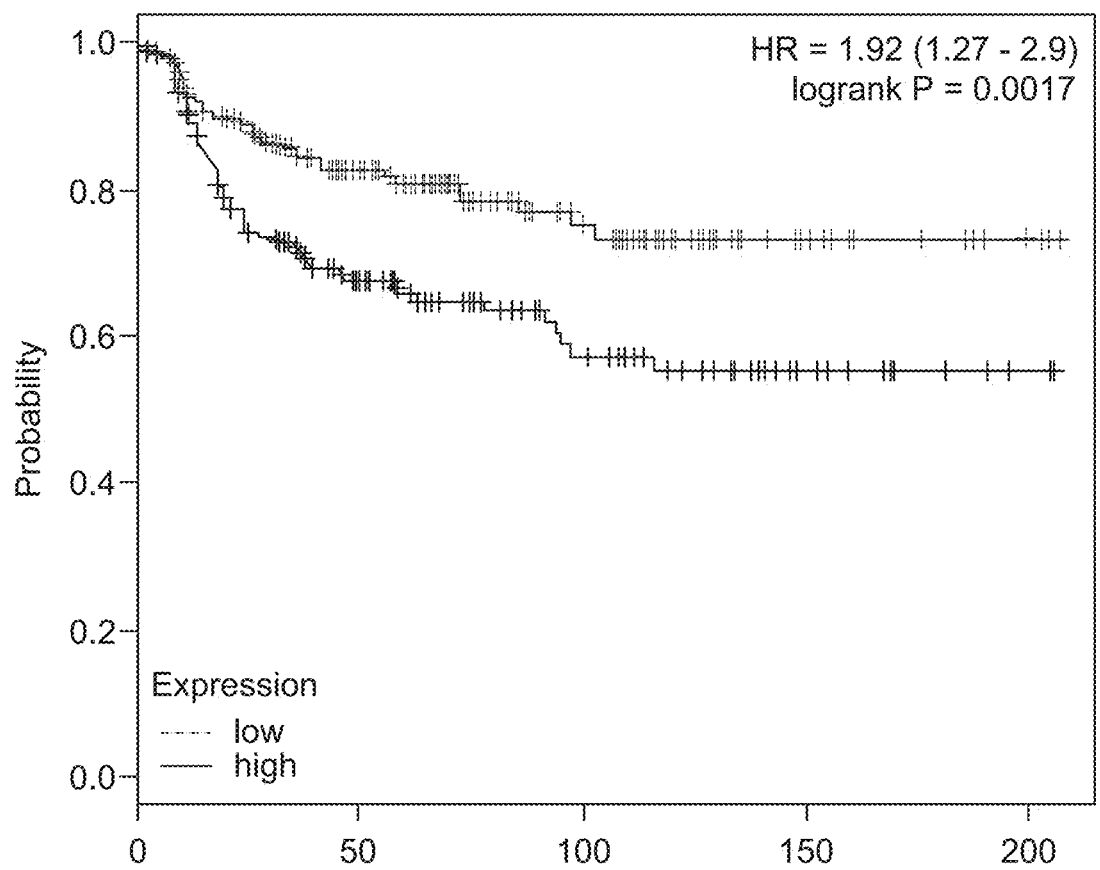
FIG. 4A is a patient survival curve stratified by high (red) and low (black) Aldh1a3 expression based on the data analysis tool hosted at kmplot.com, and shows the distant metastasis-free survival for breast cancer patients as a function of ALDH1a3 expression level.
Figure 4B:
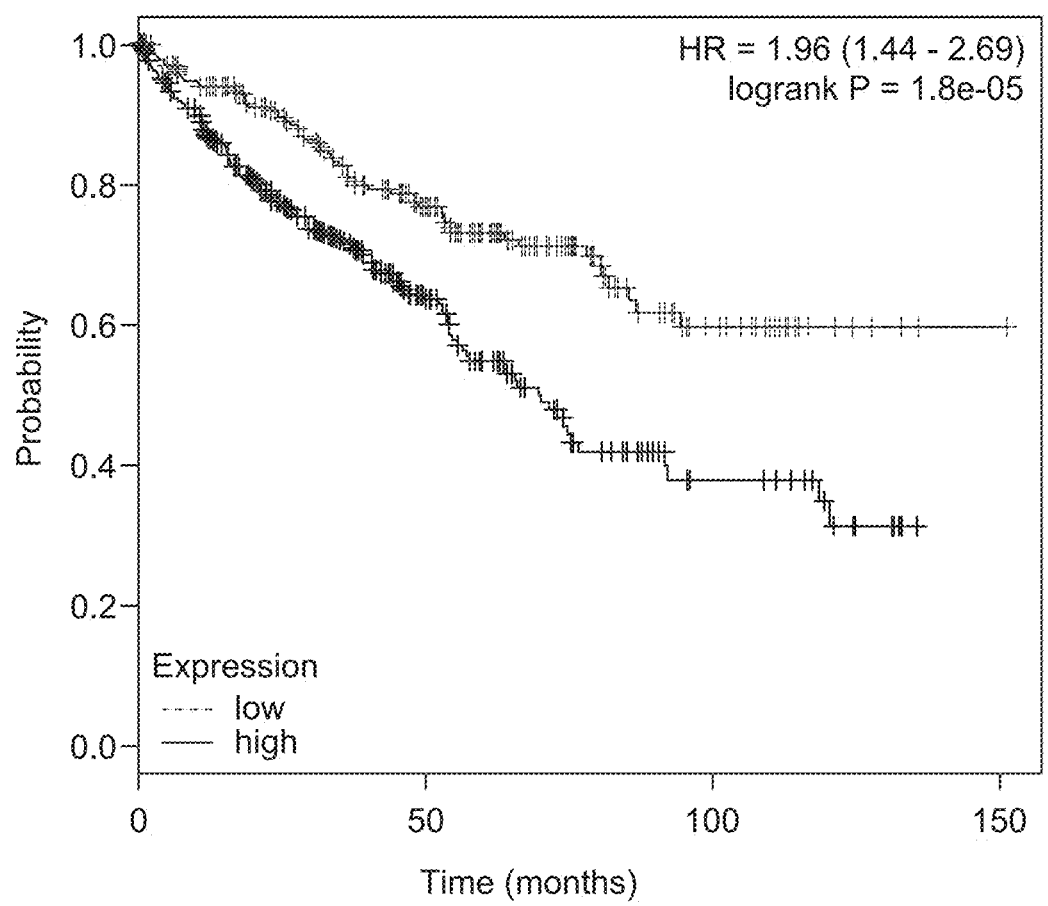
FIG. 4B is a patient survival curve stratified by high (red) and low (black) Aldh1a3 expression based on the data analysis tool hosted at kmplot.com, and shows the overall survival for renal clear cell cancer patients as a function of ALDH1a3 expression level.
Figure 4C:
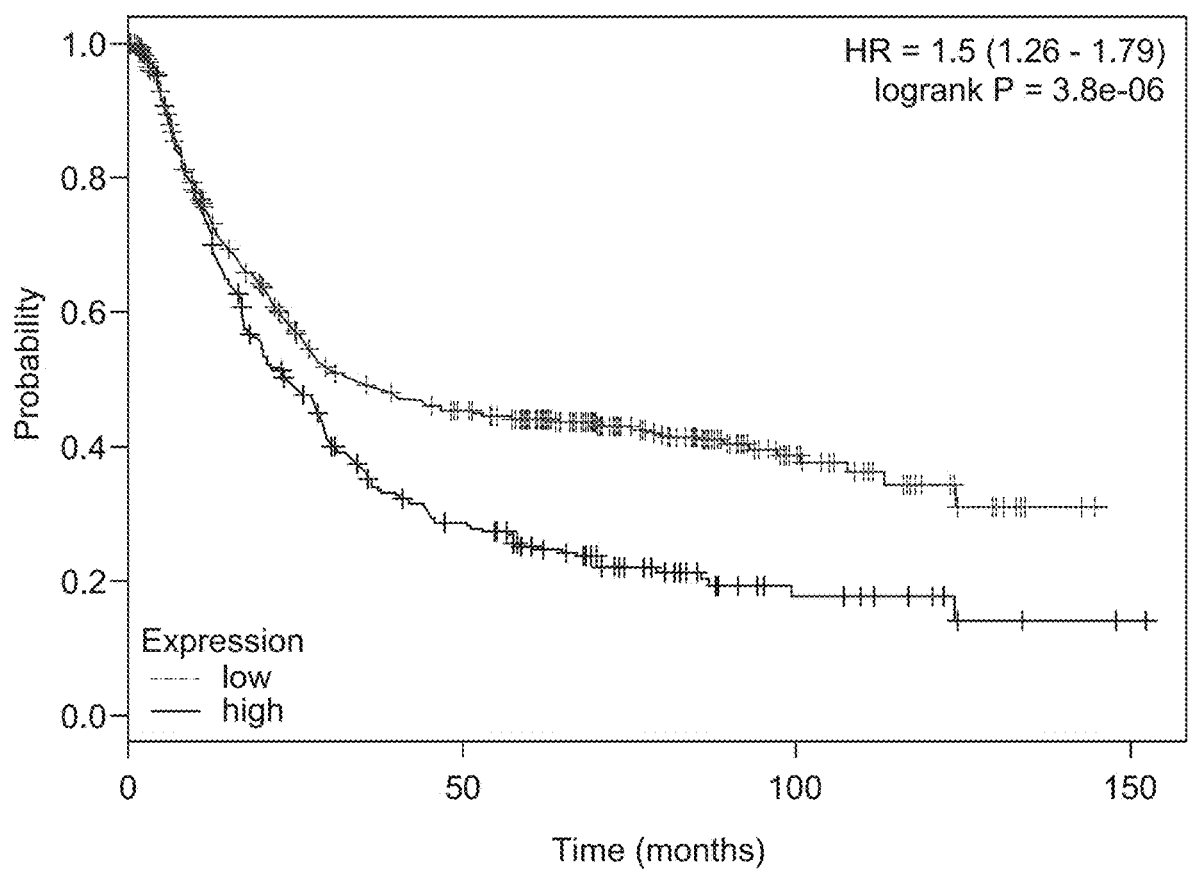
FIG. 4C is a patient survival curve stratified by high (red) and low (black) Aldh1a3 expression based on the data analysis tool hosted at kmplot.com, and shows the overall survival for gastric cancer patients as a function of ALDH1a3 expression level.
Figure 4D:
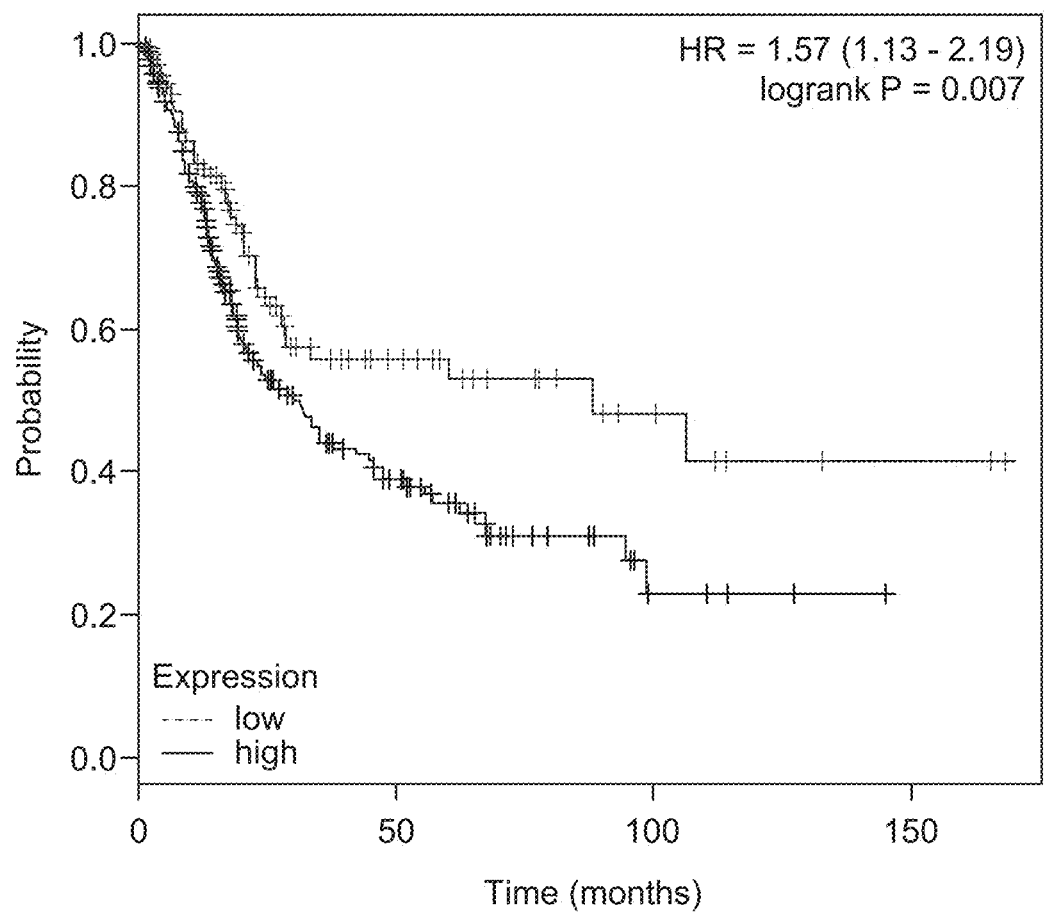
FIG. 4D is a patient survival curve stratified by high (red) and low (black) Aldh1a3 expression based on the data analysis tool hosted at kmplot.com, and shows the overall survival for bladder cancer patients as a function of ALDH1a3 expression level.
Figure 4E:
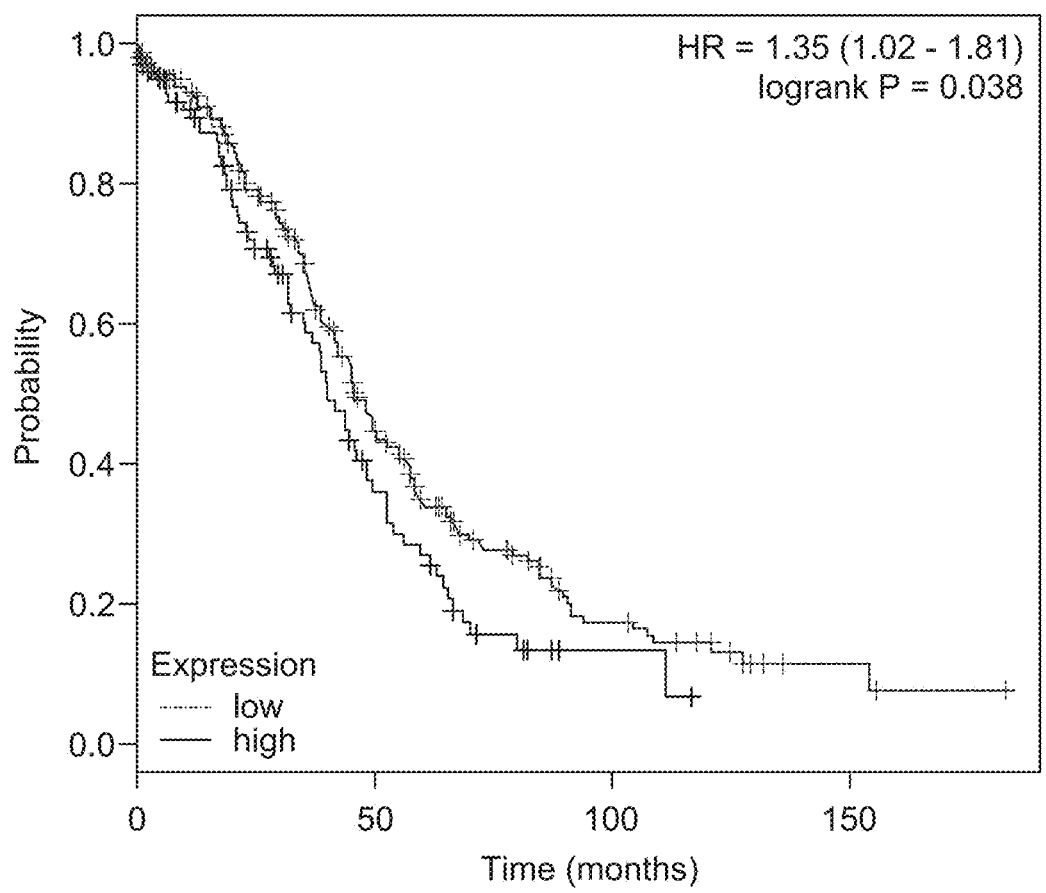
FIG. 4E is a patient survival curve stratified by high (red) and low (black) Aldh1a3 expression based on the data analysis tool hosted at kmplot.com, and shows the overall survival for ovarian cancer patients as a function of ALDH1a3 expression level.
Figure 4F:
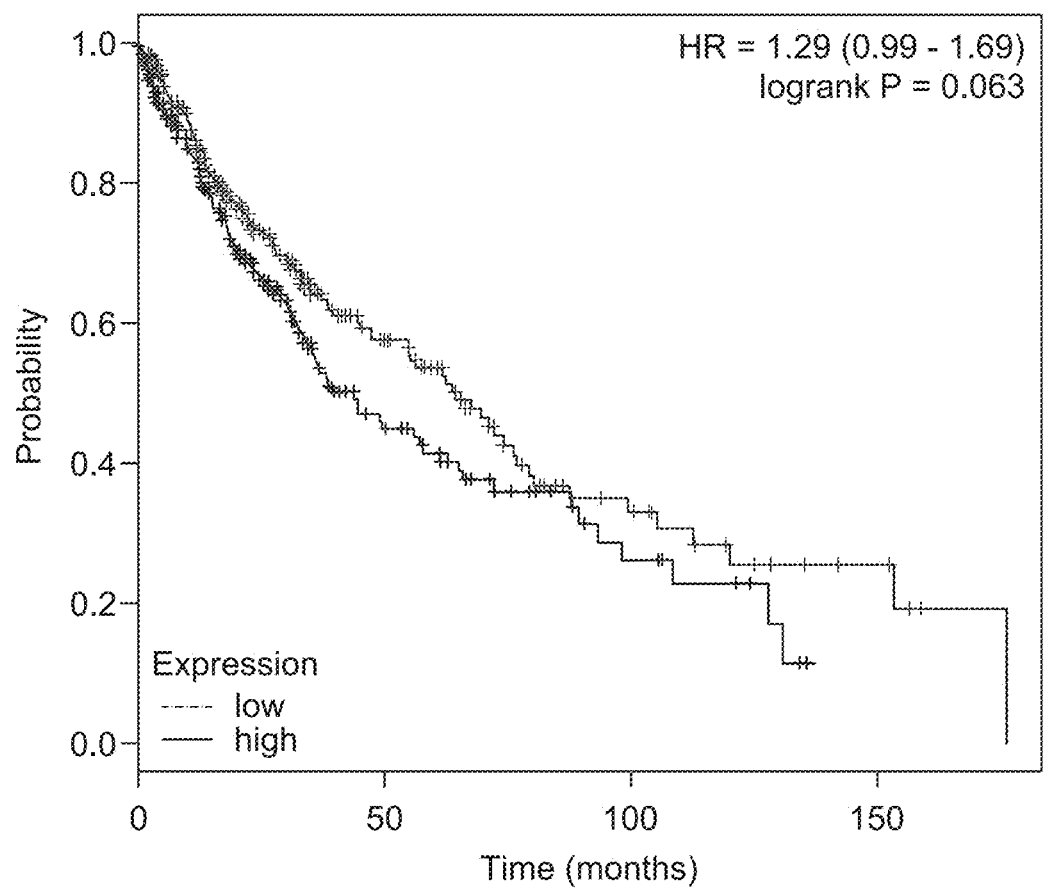
FIG. 4F is a patient survival curve stratified by high (red) and low (black) Aldh1a3 expression based on the data analysis tool hosted at kmplot.com, and shows the overall survival for lung squamous cancer patients as a function of ALDH1a3 expression level.
Figure 4G:
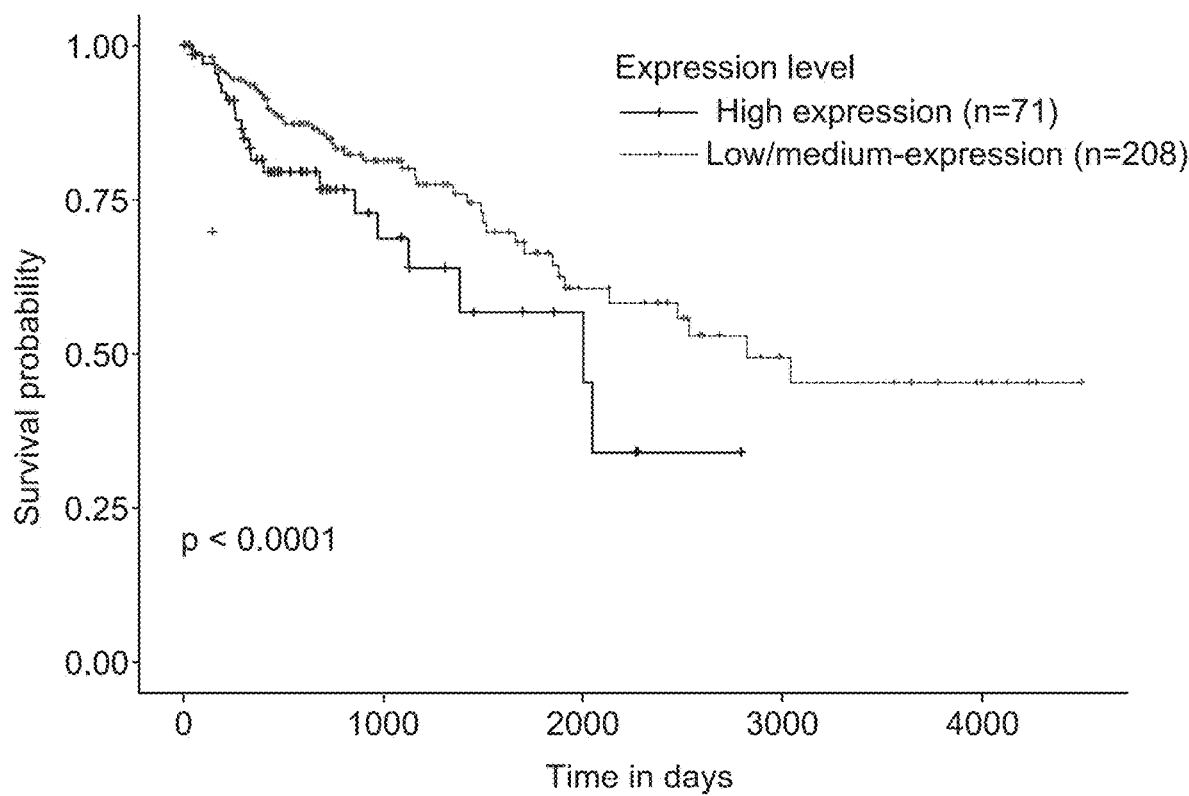
FIG. 4G is a patient survival curve stratified by high (red) and low (blue) Aldh1a3 expression based on survival time series data and patient-level RNA expression data from The Cancer Genome Atlas, and shows the overall survival for colorectal cancer patients as a function of ALDH1a3 expression level.
Figure 4H:
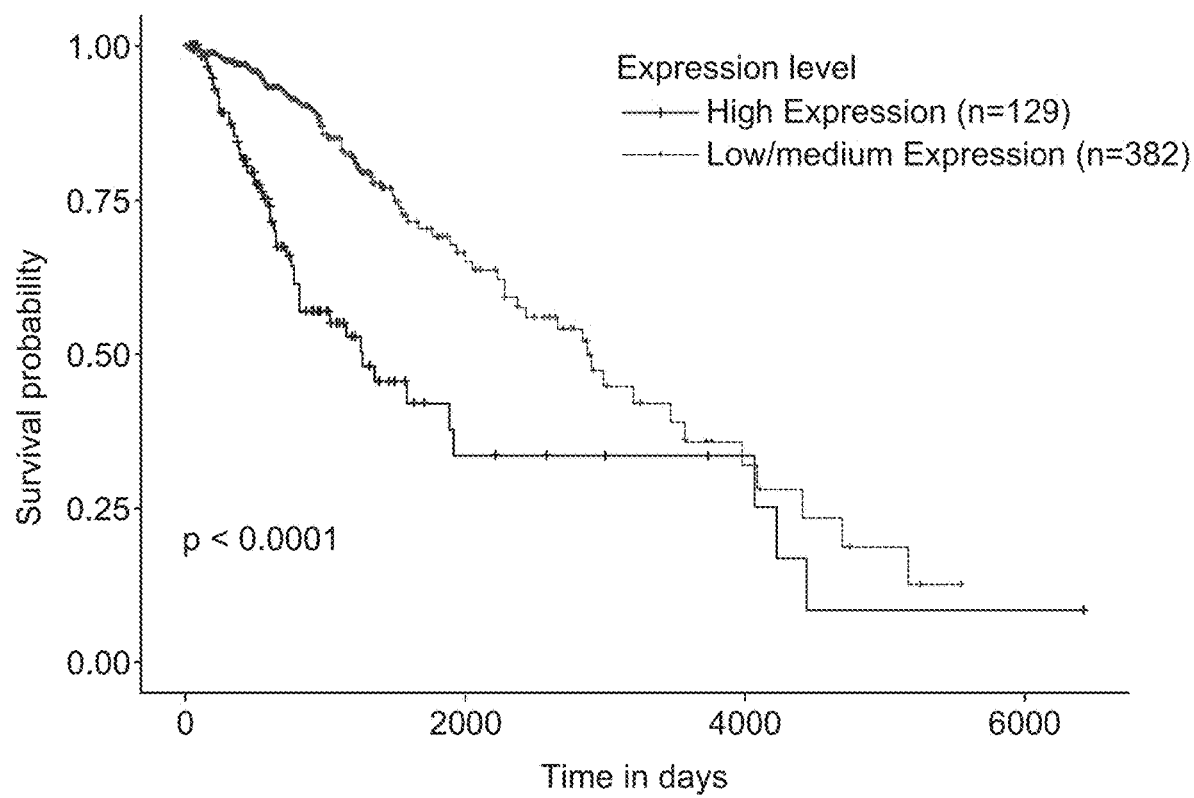
FIG. 4H is a patient survival curve stratified by high (red) and low (blue) Aldh1a3 expression based on survival time series data and patient-level RNA expression data from The Cancer Genome Atlas, and shows the overall survival for low-grade glioma patients as a function of ALDH1a3 expression level.

FIG. 2A is flow cytometry spectra, and shows that genetic knockout of ALDH1a3 in Sum159-M1a breast cancer cells nearly abolishes ALDEFLUOR™ activity in the cells, and that ALDEFLUOR™ activity can be rescued by transducing the cells with a rescue vector. FIG. 2B is a line graph of bone metastasis, as measured by bioluminescence (ph/s), versus time (days), and shows that knockout of ALDH1a3 in Sum159-M1a breast cancer cells slows bone metastasis growth. FIG. 2C is a Kaplan-Meier plot of bone metastasis-free survival over time, and shows that knockout of ALDH1a3 in Sum159-M1a breast cancer cells significantly increases survival time. Thus, genetic knockout of Aldh1a3 in Sum159-M1a breast cancer cells slows bone metastasis growth.

In sum, the above results show that genetic knockout of Aldh1a3 in cancer cells can slow primary tumor growth, sensitize tumors to chemotherapy, slow metastasis, and enhance survival time.

Biological Example 3. Genetic Expression Studies

Genetic Expression of ALDH1a3

Lentiviral vectors encoding one of three human ALDH genes, ALDH1a1, ALDH1a3 or ALDH3a1, were introduced by viral transduction into luciferase-labeled Sum159-M1b cells followed by positive selection with puromycin, and the transduced cells were injected by tail-vein injection into mice. Growth of lung metastasis was tracked by intravital bioluminescence imaging once weekly. Lung nodes were counted ex vivo. The results were shown in FIGS. 3A-3C.

FIG. 3A is a line graph of bioluminescence (ph/s) versus time (days), and shows the development of lung metastasis in mice injected with SUM159-M1b cells transfected with vectors encoding three ALDH enzymes, ALDH1a1, ALDH1a3 and ALDH3a1. FIG. 3B is a plot of lung nodes counted ex vivo at the endpoint of the experiment described in FIG. 3A. FIG. 3C shows sample images of bioluminescence at Day1 (left) and endpoint (right). As can be seen from the figures, genetic expression of Aldh1a3 in Sum159-M1b breast cancer cells enhances lung metastasis growth.

Biological Example 4. Survival Predictions

TCGA and Kaplan-Meier plotter (kmplot.com) data was used to generate expression data and survival curves for various cancers as a function of ALDH1a3 expression level. Cancer patients from each dataset were stratified by high or low Aldh1a3 expression according to either median expression value or the optimal stratification value. Kaplan-Meier analysis was then used to plot patient survival, whether measuring distant metastasis-free or overall survival, to assess the relationship between relative levels of Aldh1a3 between patients and corresponding survival metrics. The results were shown in FIGS. 4A-4H.

FIGS. 4A-4H are prognostic patient survival curves stratified by high (red) and low (black) Aldh1a3 expression based on the data analysis tool hosted at kmplot.com, and show the distant metastasis free survival for triple negative breast cancer patients (FIG. 4A) and overall survival for renal clear cell, gastric, bladder cancer, ovarian cancer, lung squamous cancer, colorectal cancer and low-grade glioma cancer patients (FIGS. 4B-4H, respectively) as a function of ALDH1a3 expression level. The data shows that high Aldh1a3 expression predicts worse overall survival in cancer patients.

In another set of predictions, mRNA expression of Aldh1a3 from the METABRIC clinical breast cancer dataset was segregated by tumor type and prior treatment with chemotherapy. Survival curves in the EMC-MSK dataset were generated by splitting patients according to subtype, and stratifying by median Aldh1a3 expression.

Figure 5A:
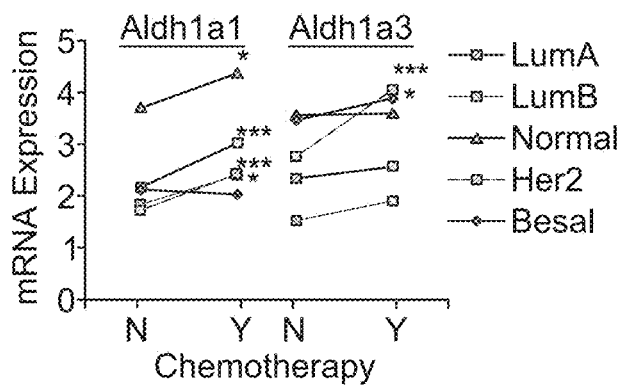
FIG. 5A is graph of mRNA expression of Aldh1a3 from the METABRIC clinical breast cancer dataset, and shows expression of Aldh1a3 by breast cancer subtype and history of chemotherapy. Statistics by Student's t-test, two sided.
Figure 5B:
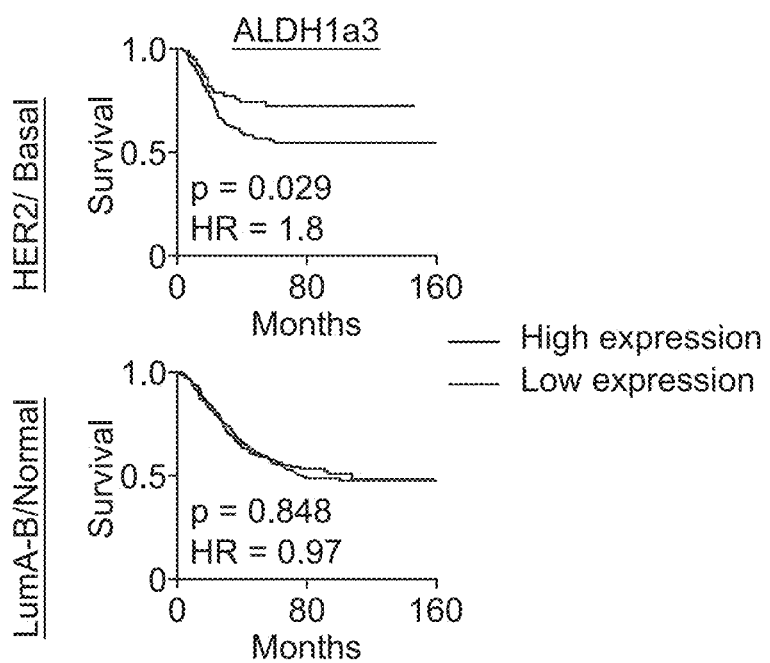
FIG. 5B is a set of survival curves based on the Erasmus Medical Center-Memorial Sloan-Kettering (EMC-MSK) dataset, and shows the survival time of breast cancer patients by subtype and stratification by median ALDH1a3 expression level. Statistics by Cox's proportional hazards model.

FIG. 5A is graph of mRNA expression of ALDH1a3 from the METABRIC clinical breast cancer dataset, and shows expression of ALDH1a3 by breast cancer subtype and history of chemotherapy. FIG. 5B is predicted survival curves based on the EMC-MSK dataset, and shows the predicted survival time of breast cancer patients by subtype and median ALDH1a3 expression level. The data shows that high Aldh1a3 expression predicts worse overall survival in breast cancer patients.

Table 1 reports the hazard ratio (p-value) of patients expressing high ALDH1a1 or ALDH1a3 in estrogen receptor-negative (ER) breast cancer derived from the Kaplan-Meier plotter database, and includes the Her2 and triple negative breast cancer (TNBC) populations that are at high risk for developing metastasis. ALDH1a3 is a poor prognosis predictor in ER-negative breast cancer patients, the population most likely to develop metastasis. Table 1. Hazard ratio (p-value) of patients expressing high ALDH1a1 or ALDH1a3 in ER-negative breast cancer patient populations derived from the Kaplan-Meier plotter database

| Gene | All | Chemotherapy | No Chemotherapy |
|---|---|---|---|
| ALDH1a1 | 0.48 (0.00039) | 2.34 (0.065) | 0.48 (0.0071) |
| ALDH1a3 | 1.85 (0.004) | 3.3 (0.026) | 1.81 (0.032) |

Biological Example 5A. ALDEFLUOR™ Assay

The ALDEFLUOR™ assay assesses the ability of cells to oxidize bodipy-aminoacetaldehyde (BAAA) to bodipy-aminoacetate (BAA). This activity can be used to sort live cells and thereby discriminate between ALDH activity levels within heterogenous populations. When it was first discovered in 2007 that ALDEFLUOR™-positive cancer cells were more tumorigenic and predicted worse clinical outcome, it was assumed that ALDEFLUOR™ activity was a marker of a broader transcriptional program that promoted tumor aggressiveness. Since these early studies, ALDEFLUOR™ activity has become the most cited method for assessing the "stemness" or aggressiveness of tumor cell populations.

Following this seminal discovery, ALDEFLUOR™ activity was often assessed with little consideration for the function of ALDH1 enzymes. Rather, publications showed that the ALDEFLUOR™ assay isolated aggressive or metastatic cancer cells, regardless of the site of the primary tumor. Since, hundreds of papers have used the ALDEFLUOR™ assay in assessing cancer cell traits across almost all cancer types. Only beginning with Marcato and colleagues in 2011 was it shown that ALDH1a3 is responsible for ALDEFLUOR™ activity in most breast cancer cell lines.

Since Marcato's and colleagues' publication, an accelerating rate of emerging studies has established that ALDH1a3 is not only responsible for ALDEFLUOR™ activity across most cancer types, but that it also functionally promotes cancer growth, therapeutic resistance, and metastasis. Research of varying quality has established that ALDH1a3 is expressed and important for growth in melanoma patient-derived xenografts or cell lines, metabolism, chemoresistance and radioresistance in mesenchymal-like glioma or glioblastoma, tumorigenicity and cisplatin resistance in lung cancer, growth and radio-resistance in pancreatic cancer, FAK inhibitor resistance in colon and thyroid cells, cisplatin resistance in mesothelioma, Gleason score and growth in prostate cancer, apoptosis-resistance and metastasis in breast cancer and prognosis in cholangiocarcinoma. It is shown herein that ALDH1a3 is the dominant ALDEFLUOR™-inducing enzyme across most solid tumor types.

Expression and prognosis studies have further shown that ALDH1a3 is strongly predictive of poor outcomes across cancer types. Hypermethylation of the ALDH1a3 promoter leading to lower ALDH1a3 expression was the strongest predictor of favorable outcome in a set of primary glioblastoma patients. High ALDH1a3 predicted lymph node metastasis in cholangiocarcinoma patients. ALDH1a3 expression is driven by androgen in prostate cancer, where androgen is the major mitogen for prostate cancer cells, while mir187 targets ALDH1a3 in prostate cancer and high mir187 was correlated to favorable prognosis.

In the ALDEFLUOR™ assay used herein, cells were grown until they reached 50-80% confluence, harvested with 0.25% Trypsin/EDTA (Sigma), and washed once with PBS by centrifugation/resuspension (190 g for 5 min at 4° C.). Cells were counted, centrifuged and resuspended at 1,000,000 cells/mL in ALDEFLUOR™ buffer (Stemcell Technologies). ALDEFLUOR™ substrate (Stemcell Technologies, 1:200) and test compound or 1 mM DEAB were added to cell suspension and incubated at 37° C. for 45 minutes with vortexing every 15 minutes. Cells were centrifuged and resuspended in ALDEFLUOR™ buffer with DAPI at 5 μg/mL. Samples were analyzed with the BD LSR2 flow cytometry platform. Gating was performed using DEAB as a negative control.

Biological Example 5B. Aldh1a3 Enzyme Inhibition Assay

Recombinant protein extraction: pET-Aldh1a3 transformed BL21-DE3 cultures induced at 20° C. for 19 h with 0.3 mM IPTG rocking. Cultures were spun at 3500 g for 10 min, supernatants were poured off and allowed to drain fully. Cells were resuspended in 10 mM HTEPES pH 7.4, 10 mM KCl. Cells were freeze-thawed in liquid nitrogen and then a 37° C. water bath for 10 cycles followed by ultrasonication at 50% amplitude, 3 sec on, 9 sec off for 10 cycles at 4° C. Cell extracts were spun at 16000×g for 5 minutes.

Reaction performed at 20° C. in reaction buffer (10 mM HTEPES pH 7.4, 10 mM KCl, 0.1 M Resazurin, 1 mg/mL BSA, 200 uM NAD+, diaphorase and aldehyde substrate). Recombinant enzyme and inhibitor added immediately before assay. Reaction rate measured by resorufin fluorescence.

The structures of compounds 1, 9, 49, 53, 59, 77, 82, and 83, are shown in Table 3 below and disclosed in PCT/US2021/014883 which is incorporated by reference herein.

TABLE 3

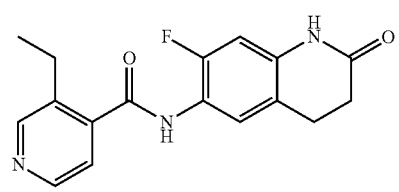

1

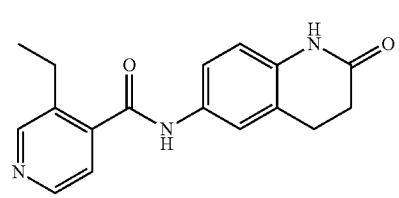

9

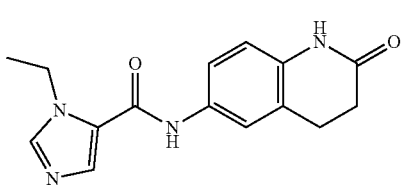

49

TABLE 3-continued

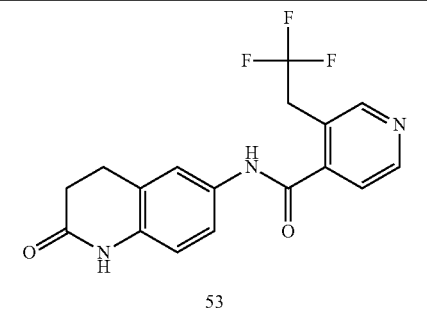

53

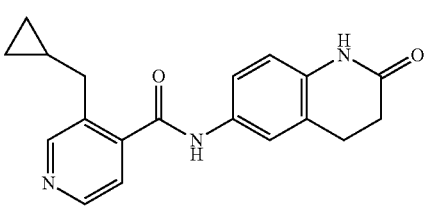

59

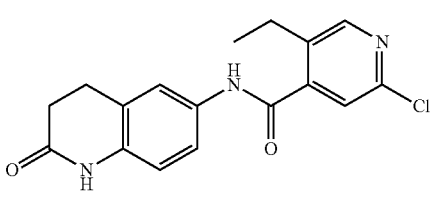

77

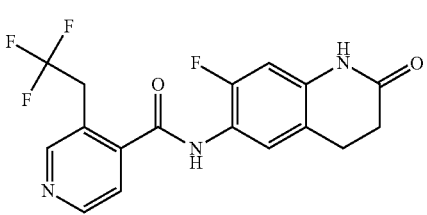

82

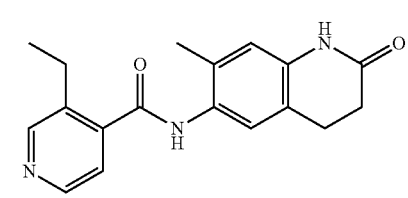

83

The IC$_{50}$ values of selected tested compounds are shown in Table 3A below.

TABLE 3A

IC$_{50}$ values* for inhibition of hALDH1a3 and mALDH1a3 of selected compounds

| Cmpd. No. | hAldh1a3 IC$_{50}$ | mAldh1a3 IC$_{50}$ | Cmpd. No. | hAldh1a3 IC$_{50}$ | mAldh1a3 IC$_{50}$ |
|---|---|---|---|---|---|
| 1 | B | B | 77 | B | C |
| 9 | A | C | 83 | B | D |
| 49 | E | E | 53 | A | A |
| 59 | A | A | 82 | A | B |

TABLE 3A-continued

IC$_{50}$ values* for inhibition of hALDH1a3 and mALDH1a3 of selected compounds

| Cmpd. No. | hAldh1a3 IC$_{50}$ | mAldh1a3 IC$_{50}$ | Cmpd. No. | hAldh1a3 IC$_{50}$ | mAldh1a3 IC$_{50}$ |
|---|---|---|---|---|---|
| 139 | B | A | 140 | A | A |
| 142 | A | A | 141 | A | A |
| 144 | A | A | 143 | A | A |
| 146 | A | A | 145 | A | A |
| 149 | A | A | 147 | B | C |
| 151 | A | A | 150 | A | A |
| 153 | D | C | 152 | D | C |
| 155 | C | D | 154 | D | C |
| 160 | E | E | 159 | C | C |
| 168 | A | A | 161 | E | C |
| 192 | E | E | 167 | A | A |
| 166 | A | C | 193 | E | E |

*The IC$_{50}$ values are reported herein according to the Activity Level: A < 100 nM; B: 100 nM-250 nM; C: 250 nM-1 uM (micromolar); D: 1 uM-5 uM; E: > 5 uM.

Biological Example 5C. Aldh1a2 Enzyme Inhibition Assay

Recombinant protein extraction: pET-Aldh1a2 transformed BL21-DE3 cultures induced at 20° C. for 19 h with 0.3 mM IPTG rocking. Cultures were spun at 3500 g for 10 min, supernatants were poured off and allowed to drain fully. Cells were resuspended in 10 mM HEPES pH 7.4, 10 mM KCl. Cells were freeze-thawed in liquid nitrogen and then a 37° C. water bath for 10 cycles followed by ultrasonication at 50% amplitude, 3 sec on, 9 sec off for 10 cycles at 4° C. Cell extracts were spun at 16000×g for 5 minutes.

Reaction performed at 20° C. in reaction buffer (10 mM HEPES pH 7.4, 10 mM KCl, 0.1 M Resazurin, 1 mg/mL BSA, 200 uM NAD+, diaphorase and aldehyde substrate). Recombinant enzyme and inhibitor added immediately before assay. Reaction rate measured by resorufin fluorescence.

Compounds 1-138 are disclosed in PCT/US2021/014883 which is incorporated by reference herein.

The IC$_{50}$ values of selected tested compounds are shown in Table 3B below.

TABLE 3B

IC$_{50}$ values (nM) for inhibition of hALDH1a2 and mALDH1a2 of selected compounds

| Cmpd. No. | hAldh1a2 IC$_{50}$ | mAldh1a2 IC$_{50}$ | Cmpd. No. | hAldh1a2 IC$_{50}$ | mAldh1a2 IC$_{50}$ |
|---|---|---|---|---|---|
| 1 | 3333 | 3333 | 70 | >10000 | 2963 |
| 2 | >10000 | 10000 | 71 | 963 | 747 |
| 3 | 4000 | 3333 | 72 | >10000 | >10000 |
| 4 | 5000 | 4000 | 73 | >10000 | >10000 |
| 5 | 9000 | 10000 | 76 | 6560 | 4311 |
| 6 | >10000 | 10000 | 77 | 415 | 333 |
| 7 | 3500 | 9000 | 78 | 460 | 366 |
| 8 | 9000 | 5000 | 79 | 1455 | 849 |
| 9 | 587 | 1111 | 80 | 384 | 324 |
| 10 | 9000 | 3500 | 81 | 376 | 522 |
| 11 | >10000 | >10000 | 83 | 9000 | 3500 |
| 12 | >10000 | >10000 | 84 | >10000 | >10000 |
| 13 | 5000 | 2949 | 86 | 10000 | 84 |
| 14 | 10000 | 10000 | 87 | 419 | 149 |
| 15 | 10000 | 10000 | 88 | >10000 | >10000 |
| 16 | 10000 | 10000 | 89 | 10000 | 489 |
| 17 | 10000 | 10000 | 90 | 10000 | 6381 |
| 18 | 2130 | 1740 | 91 | 998 | 594 |
| 19 | 650 | 1046 | 92 | 40 | 31 |
| 20 | >10000 | >100000 | 93 | 80 | 63 |

TABLE 3B-continued

IC$_{50}$ values (nM) for inhibition of
hALDH1a2 and mALDH1a2 of selected compounds

| Cmpd. No. | hAldh1a2 IC$_{50}$ | mAldh1a2 IC$_{50}$ | Cmpd. No. | hAldh1a2 IC$_{50}$ | mAldh1a2 IC$_{50}$ |
|---|---|---|---|---|---|
| 21 | 30000 | 32000 | 94 | 809 | 921 |
| 22 | 20000 | 25000 | 95 | 10000 | 1768 |
| 24 | 100000 | 100000 | 96 | >10000 | >10000 |
| 30 | 9000 | 11110 | 97 | 466 | 294 |
| 33 | 258 | 143 | 98 | 3076 | 1292 |
| 34 | 39220 | 30950 | 99 | 316 | 184 |
| 35 | 148 | 100 | 100 | >10000 | >10000 |
| 37 | >10000 | >10000 | 101 | 1892 | 935 |
| 38 | >10000 | >10000 | 103 | >10000 | 5000 |
| 39 | 3500 | 8000 | 104 | >10000 | >10000 |
| 40 | 1042 | 3333 | 105 | >10000 | >10000 |
| 42 | 6358 | 2604 | 106 | >10000 | >10000 |
| 43 | 1200 | 3000 | 108 | 120 | 100 |
| 45 | 293 | 3333 | 109 | 42 | 45 |
| 46 | 248 | 162 | 111 | 196 | 145 |
| 47 | 99 | 72 | 112 | 346 | 300 |
| 48 | 99 | 97 | 113 | >10000 | >10000 |
| 49 | >10000 | >10000 | 114 | >10000 | >10000 |
| 50 | >10000 | >10000 | 115 | >10000 | >10000 |
| 52 | 320 | 117 | 116 | 305 | 337 |
| 53 | 374 | 494 | 118 | >10000 | >10000 |
| 54 | 1057 | 224 | 119 | >10000 | 10000 |
| 55 | >10000 | >10000 | 120 | 10000 | >10000 |
| 56 | 10000 | 1263 | 122 | >10000 | >10000 |
| 59 | 530 | 487 | 123 | >10000 | >10000 |
| 60 | 1534 | 935 | 125 | 4495 | 4047 |
| 61 | 2041 | 1815 | 126 | 214 | 165 |
| 62 | >10000 | >10000 | 127 | 894 | 1287 |
| 63 | 538 | 297 | 132 | 71 | 53 |
| 64 | 2789 | 5000 | 134 | 125 | 97 |
| 68 | >10000 | 3442 | 135 | >10000 | >10000 |
| 69 | >10000 | >10000 | 136 | >10000 | >10000 |
| 57 | >10000 | >10000 | 137 | >10000 | >100000 |
| 82 | 620 | 941 | 41 | 9000 | 11110 |
| 140 | 99 | 96 | 51 | >10000 | >10000 |
| 142 | 57 | 63 | 58 | >10000 | >10000 |
| 144 | 304 | 462 | 102 | >10000 | >10000 |
| 146 | 356 | 405 | 139 | 10000 | 1484 |
| 149 | 87 | 118 | 141 | 289 | 180 |
| 151 | 75 | 86 | 143 | 674 | 594 |
| 153 | 492 | 362 | 145 | 120 | 172 |
| 155 | 835 | 1294 | 147 | 431 | 358 |
| 160 | 163 | 177 | 150 | 121 | 131 |
| 152 | 807 | 824 | 159 | 2748 | 3182 |
| 154 | 4746 | 8171 | 161 | 89 | 114 |
| 168 | 70 | 92 | 167 | 754 | 815 |
| 192 | >10000 | >10000 | 193 | >10000 | >10000 |
| 166 | 1600 | >10000 | | | |

Biological Example 5D. Cell Based Assay

MCF7 cells were stably transduced with lentiviral vectors encoding human ALDH1a1, ALDH1a2 or ALDH1a3 or Vector control and selected by puromycin to establish stable cultures that were verified for overexpression by western blotting and Aldefluor activity. Cells were plated into 6 cm plates in regular DMEM media supplement with 1000 FBS. At the beginning of the assay, cells were washed with PBS for 5 minutes followed by addition of compound solvated into DMEM media with 10% FBS or corresponding DMSO controls, maintaining DMSO at a constant concentration of 0.1% across all samples. Following 20 hours of incubation at 37 C, cells were lysed and RNA was extracted using a Qiagen RNAeasy kit. cDNA was synthesized using the Superscript IV kit and retinoid activation was measured using STRA6 mRNA levels as a proxy as measured by q-rtPCR.

Figure 10A:
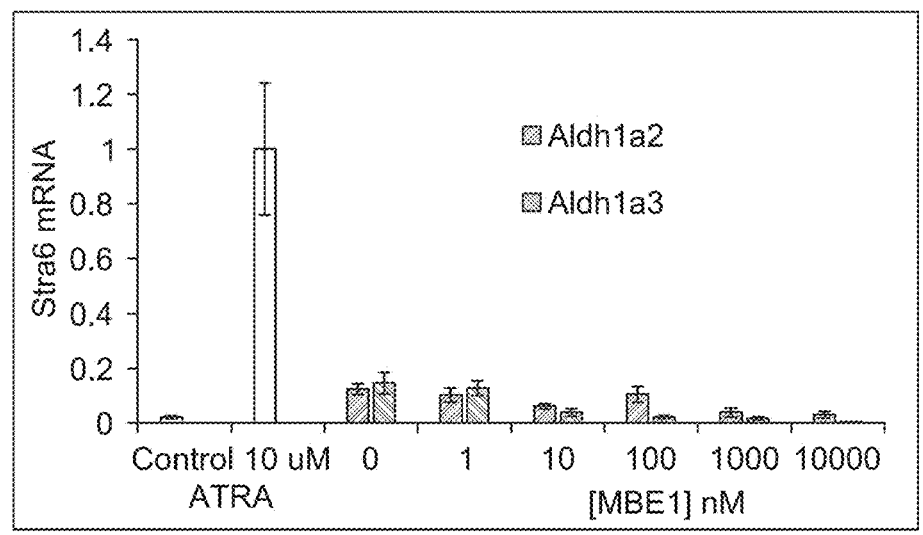
FIGS. 10A-10C. q-rtPCR of STRA6 levels in MCF7 cells stably expressing vector control treated with DMSO or all-trans retinoic acid (10 uM) treated with various doses of MBE1 (10A), Compound 140 (10B) or Compound 151 (1° C.) demonstrate that compounds 140 and 151 effectively inhibit both ALDH1a2 and ALDH1a3 in cell-based assays at therapeutically advantageous levels (<50 nM) with IC50 values for MBE1 at 1666 nM (ALDH1a2) and 3.67 nM (Aldh1a3), IC50 values for 140 of 27.6 nM (Aldh1a2) and 6.97 nM (Aldh1a3) and IC50 values for 151 of 55.3 nM (Aldh1a2) and 1.25 nM (Aldh1a3).
Figure 10B:
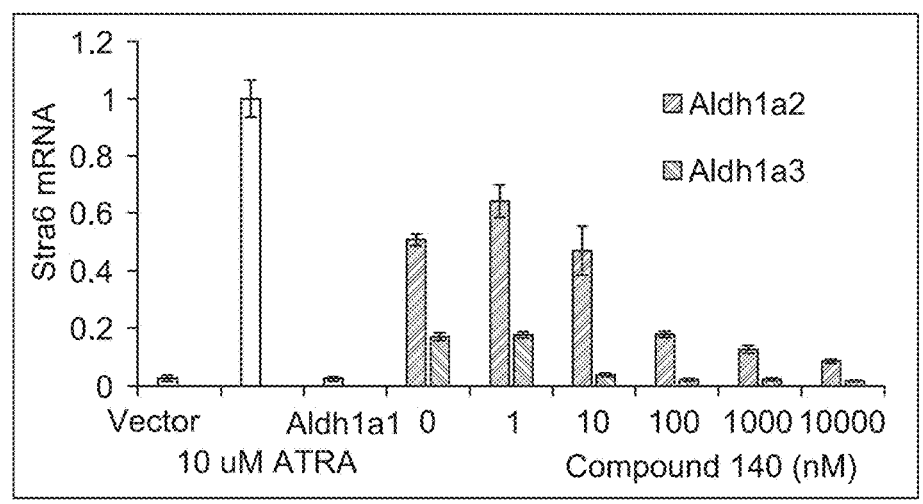
Figure 10C:
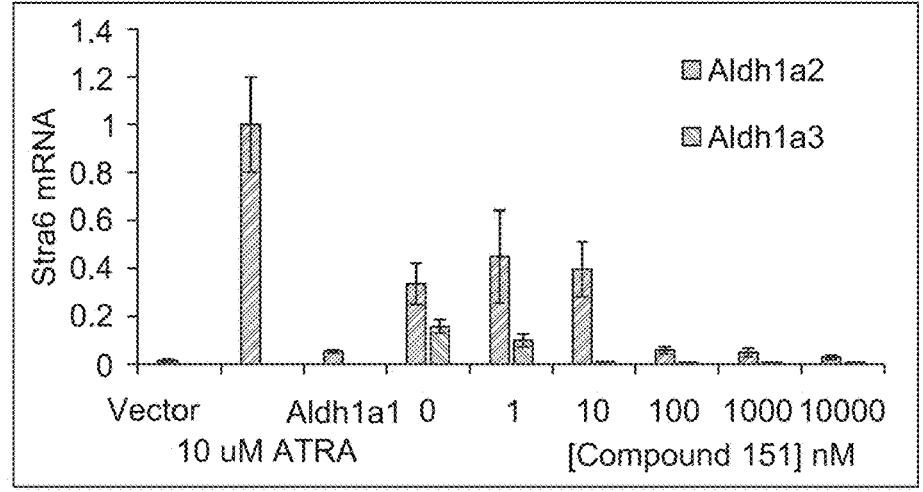

MCF7 cells stably expressing vector control were treated with DMSO or all-trans retinoic acid (10 uM) treated with various doses of MBE1, Compound 140 or Compound 151. q-rtPCR of STRA6 expression levels were measured by q-rtPCR. The results were shown in FIGS. 10A-10C. Based on this assay, IC50 values for MBE1 are 1666 nM (ALDH1a2) and 3.67 nM (Aldh1a3), IC50 values for 140 are 27.6 nM (Aldh1a2) and 6.97 nM (Aldh1a3) and IC50 values for 151 are 55.3 nM (Aldh1a2) and 1.25 nM (Aldh1a3). Compounds 140 and 151 inhibit both ALDH1a2 and ALDH1a3 with IC50 less than 50 nM.

Biological Example 6A. In Vivo Allografts Studies

Figure 11A:
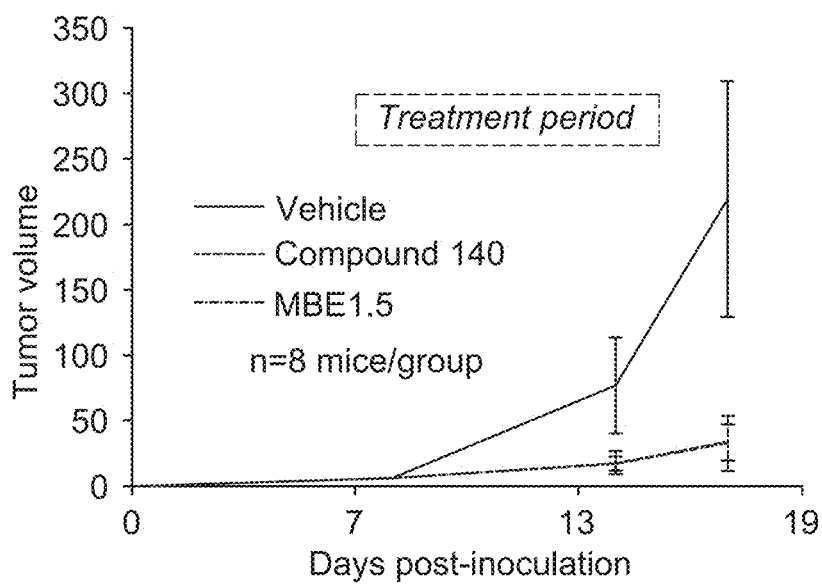
FIGS. 11A and 11B. Treatment of the T3-MCA fibrosarcoma cell line allografts implanted subcutaneously into C57BL6 syngeneic mice with compounds Compound 140 or MBE1.5 once daily for the indicated treatment period show successful inhibition of tumor growth as a single agent as shown by caliper measurement (11A) and tumor mass at endpoint (11B).
Figure 11B:
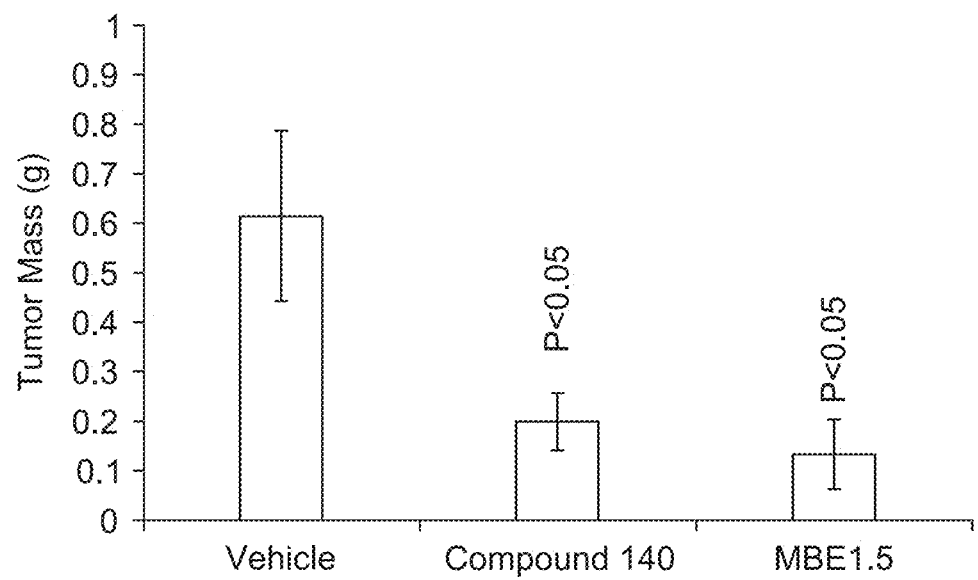

In one allograft study, T3-MCA fibrosarcoma cell line allografts were implanted subcutaneously into C57BL6 syngeneic mice. The mice were then treated with Compound 140 at 40 mg/kg by intraperitoneal injection suspended in a 5% DMSO, 0.5% methocel, 0.5% Tween-80 in saline solution or MBE1.5 formulated into diet for oral administration at a 25 mg/kg daily equivalent dose or vehicle, n=10 mice/group, injections of Compound 140 were administered once daily for 9 days while MBE1.5 medicated diet was introduced for the same time period of 9 days. Tumor volume were measured on day 8, 14, and 17 post inoculation for each group, and tumor mass were measured at the end of the study. The results are shown in FIGS. 11A and 11B.

Figure 12A:
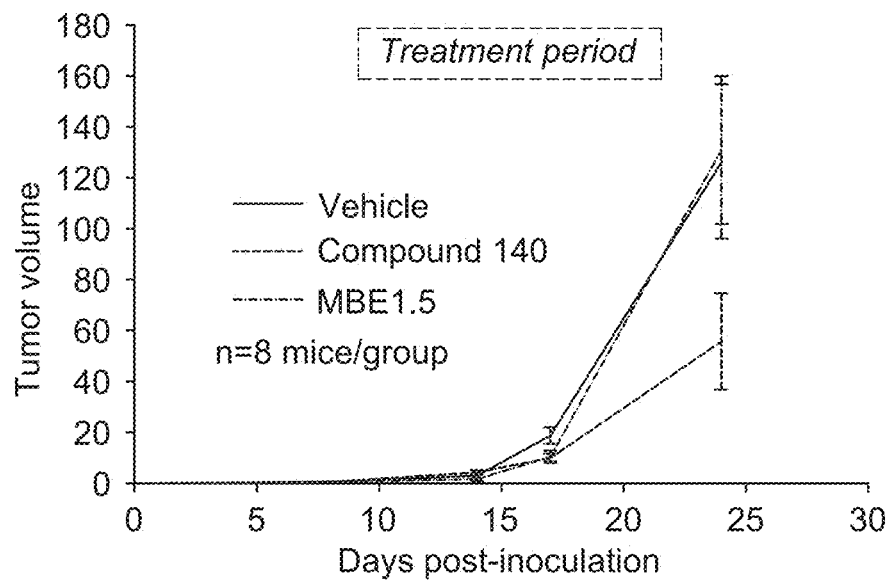
FIGS. 12A and 12B. Treatment of the K-Ras, p53 −/− undifferentiated pleiomorphic sarcoma cell line allografts implanted subcutaneously into C57BL6 syngeneic mice with compounds Compound 140 or MBE1.5 once daily for the indicated treatment period show successful inhibition of tumor growth as a single agent for Compound 140 and not MBE1.5 as shown by caliper measurement (12A) and tumor mass at endpoint (12B).
Figure 12B:
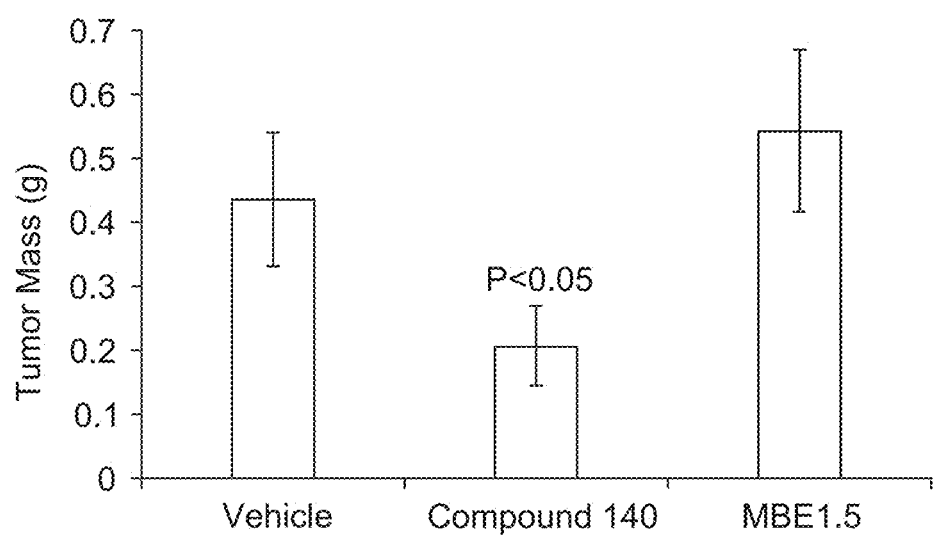
Figure 13A:
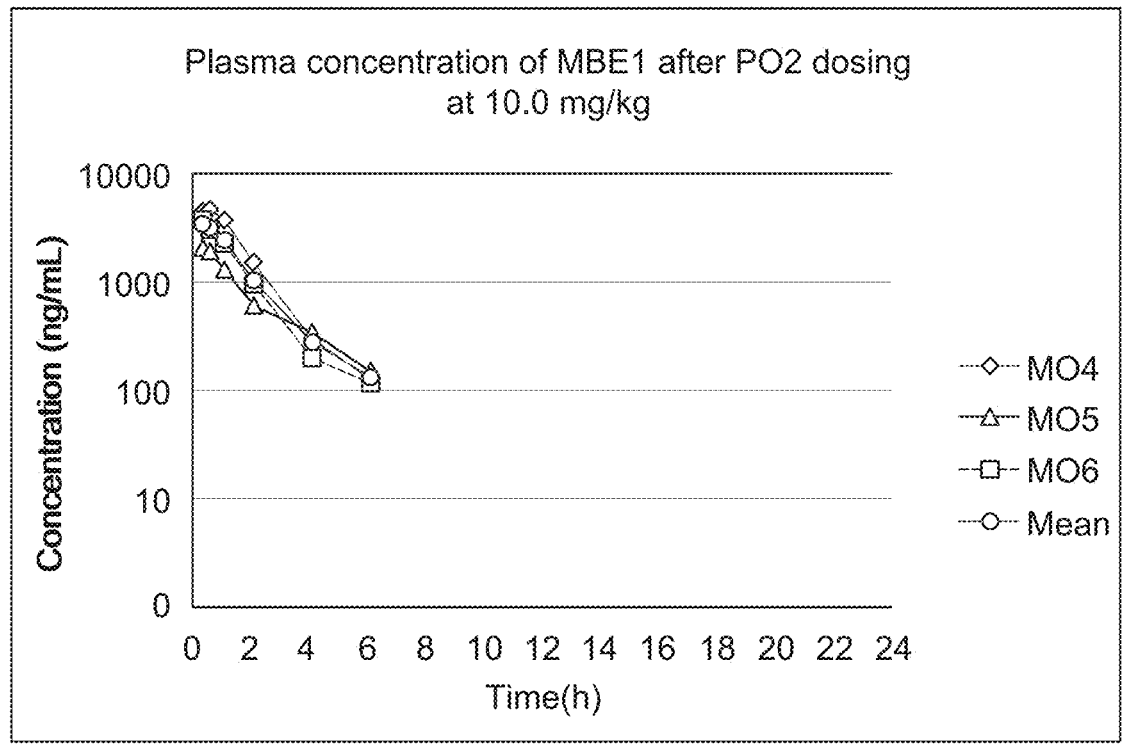
FIGS. 13A-13D. Pharmacokinetics analysis of plasma half-life in CD-1 mice after 10 mg/kg single oral dose of compounds MBE1 (13A), MBE1.5 (13B), Compound 140 (13C), and Compound 151 (13D) demonstrates superior pharmacokinetic dosing for compounds with 8' methyl substitution.
Figure 13B:
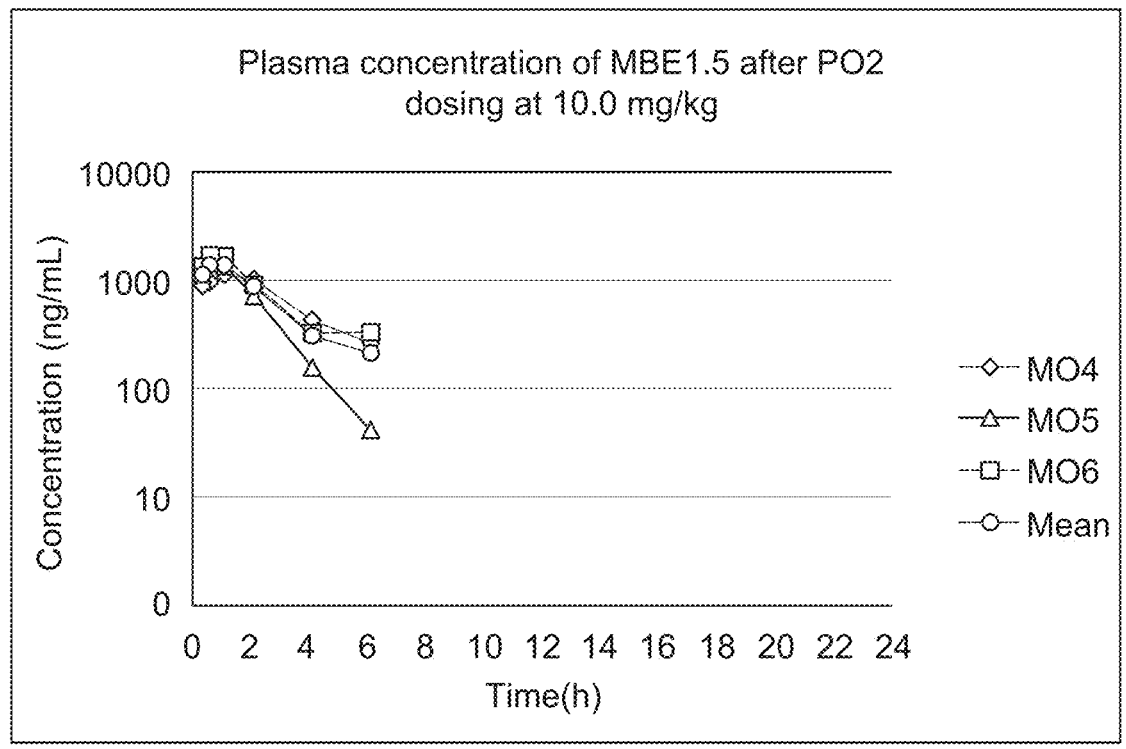
Figure 13C:
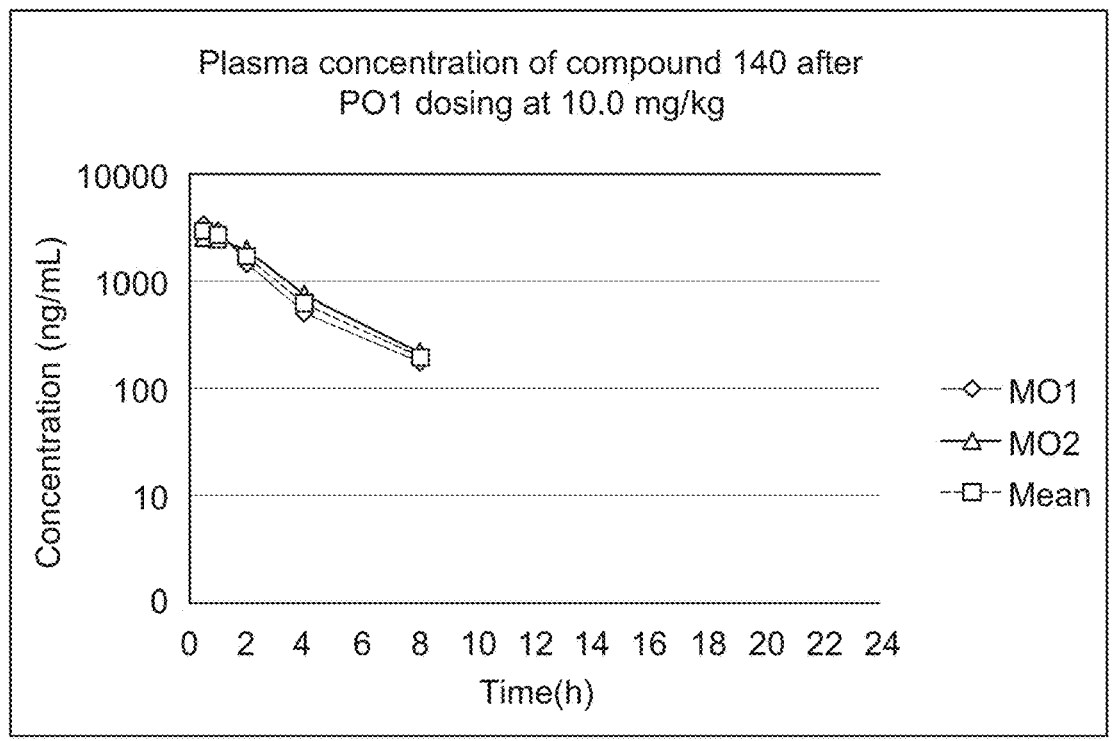
Figure 13D:
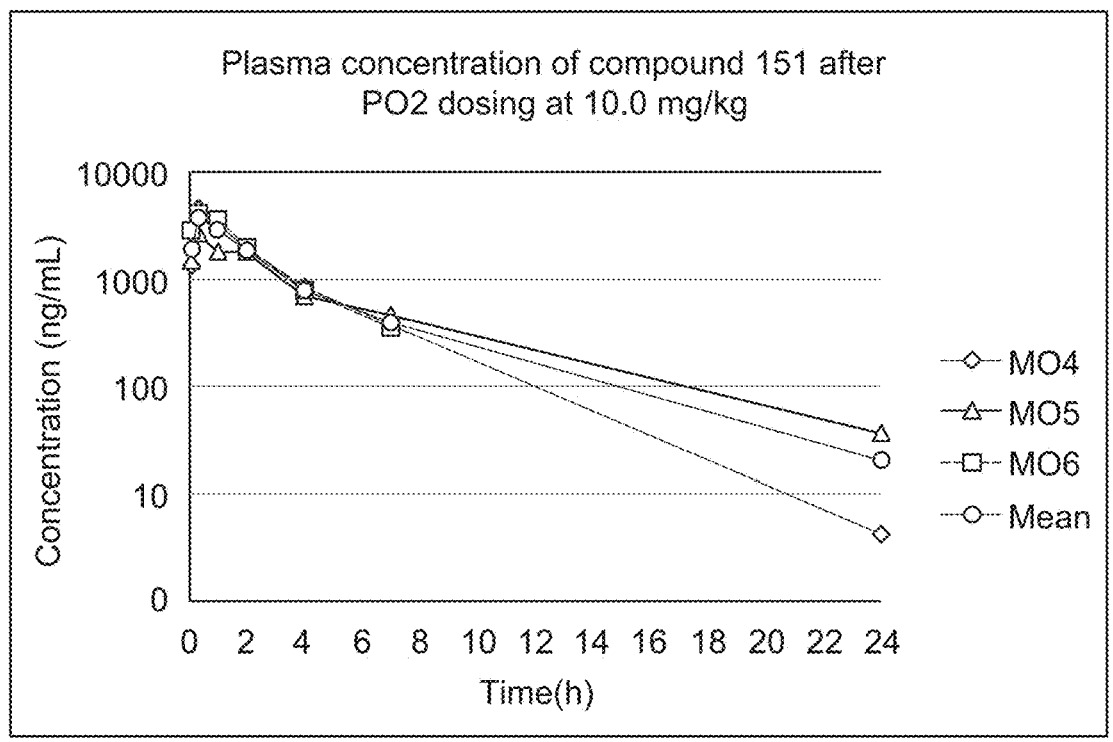

In another allograft study, K-Ras, p53 −/− undifferentiated pleiomorphic sarcoma cell line allografts were implanted subcutaneously into C57BL6 syngeneic mice. The mice were then treated with Compound 140 at 40 mg/kg by intraperitoneal injection suspended in a 5% DMSO, 0.5% methocel, 0.5% Tween-80 in saline solution or MBE1.5 formulated into diet for oral administration at a 25 mg/kg daily equivalent dose or vehicle, n=8 mice/group, injections of Compound 140 were administered once daily for 20 days while MBE1.5 medicated diet was introduced for the same time period of 20 days. Tumor volume were measured on day 14, 17, and 24 post inoculation for each group, and tumor mass were measured at the end of the study. The results are shown in FIGS. 12A and 12B.

Figure 15A:
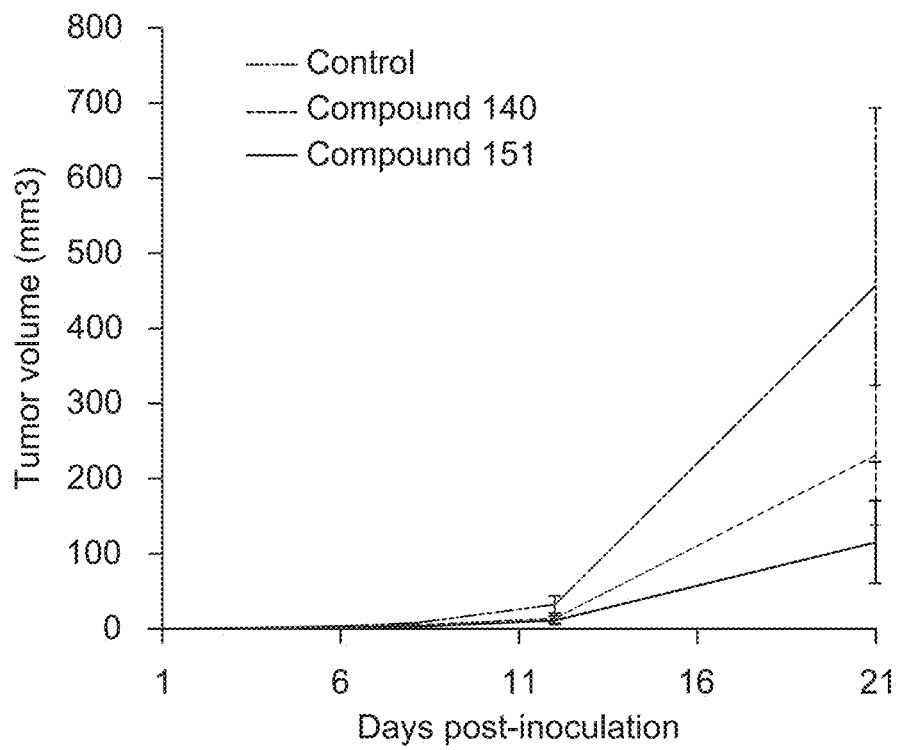
FIG. 15A & FIG. 15B. Treatment of the T3-MCA fibrosarcoma cell line allografts implanted subcutaneously into C57BL6 syngeneic mice with oral Compound 140 or Compound 151 at 40 mg/kg once daily for twelve days show successful inhibition of tumor growth (FIG. 15A) while showing excellent tolerability (FIG. 15B).
Figure 15B:
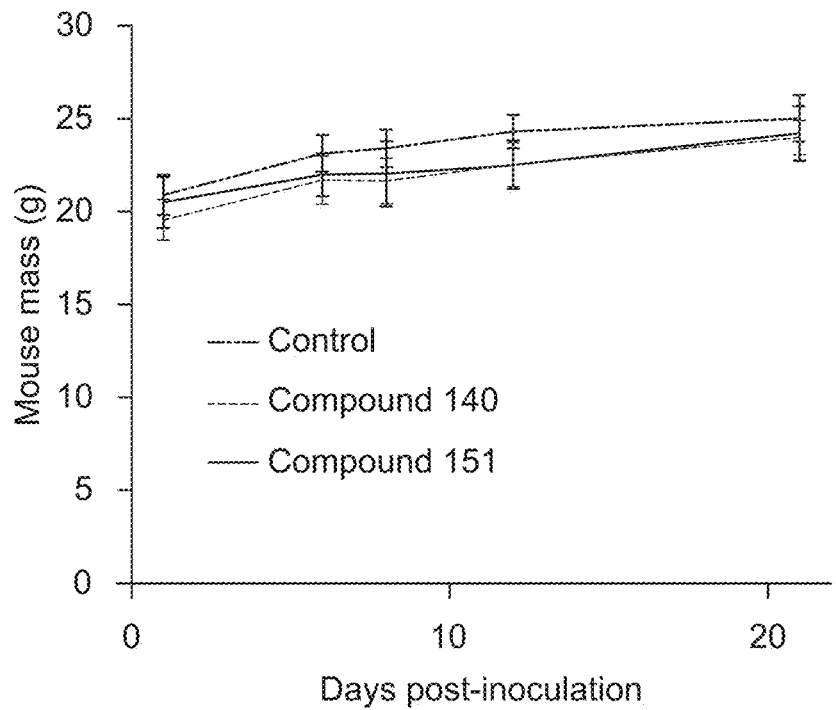

In another allograft study, T3-MCA fibrosarcoma cell line allografts were implanted subcutaneously into C57BL6 syngeneic mice. The mice were then treated with vehicle or oral Compound 140 or Compound 151 at 40 mg/kg once daily for 12 days, n=10 mice/group. The results are shown in FIGS. 15A and 15B.

Biological Example 6B. Combination with Anti-PD-1

Figure 14:
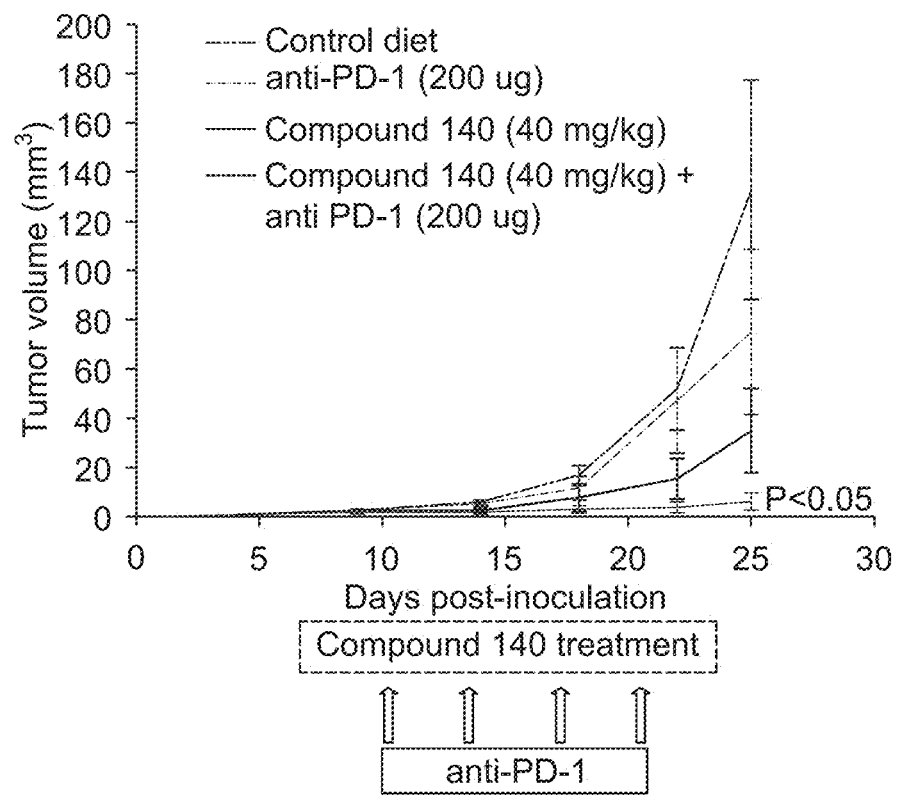
FIG. 14. Treatment of the T3-MCA fibrosarcoma cell line allografts implanted subcutaneously into C57BL6 syngeneic mice with oral Compound 140 and/or anti-PD-1 antibody for the indicated treatment period at the indicated doses show successful inhibition of tumor growth as a single agent as well as synergy with anti-PD-1 antibody in causing tumor regression. From the top line to the bottom line, control diet, anti-PD-1, Compound 140, and compound 140+ anti-PD-1.

This example studies the effect of combined treatment of compound 140 with an anti-PD-1 antibody (Bio-X-cel InVivoMAb anti-mouse PD-1 (CD279)). T3-MCA fibrosarcoma cell line allografts were implanted subcutaneously into C57BL6 syngeneic mice. The mice were then treated with Compound 140 (40 mg/kg daily equivalent, oral formulation into medicated diet picolabs diet 5053), anti-PD-1 (200 microgram), combined treatment with anti-PD-1 (200 microgram) and Compound 140 (40 mg/kg daily equivalent, oral formulation into medicated diet picolabs diet 5053) or diet control. Medicated diet was initiated at Day 9 after mice were randomized and continued until termination at Day 25. Anti-PD-1 antibody was administered by intraperitoneal injection at Day 11, 14, 18 and 21 by a 200 uL injection of a 1 mg/mL solution in saline. Tumor volume were measured on day 14, 18, 22, and 25 post inoculation for each group. The results were shown in FIG. 14. The results show that compound 140 inhibits tumor growth as a single agent and also achieved synergy with anti-PD-1 antibody in causing tumor regression.

Biological Example 7. Pharmacokinetic Prolifing of Test Compounds

Three male CD-1/C57BL/6 mice per group were dosed with compound MBEI (alternatively referred to herein as Compound No. 1) or MBE1.5 (alternatively referred to herein as Compound No. 4) at 10 mg/kg for oral gavage or 1 mg/kg for intravenous dosing. Cage side observations were performed and no adverse reactions to either MBE1 or MBE1.5 treatment were observed from 0 hours to 24 hours post-dosing. Blood was drawn from subjects and plasma was extracted at 6 timepoints. Plasma concentrations of each compound was profiled by LC-MS and absolute concentrations were derived by comparison to a reference standard. Linear regression was performed to calculate oral bioavailability of 88% and a plasma half-life of 1.79 hours for IV bolus dosing and 1.37 hours from PO oral gavage dosing for compound MBE1. For compound MBE1-5, oral bioavailability of 62.5% was calculated with a plasma half-life of 1.22 hours for IV bolus dosing and 1.70 hours from PO oral gavage dosing.

Figure 6A:
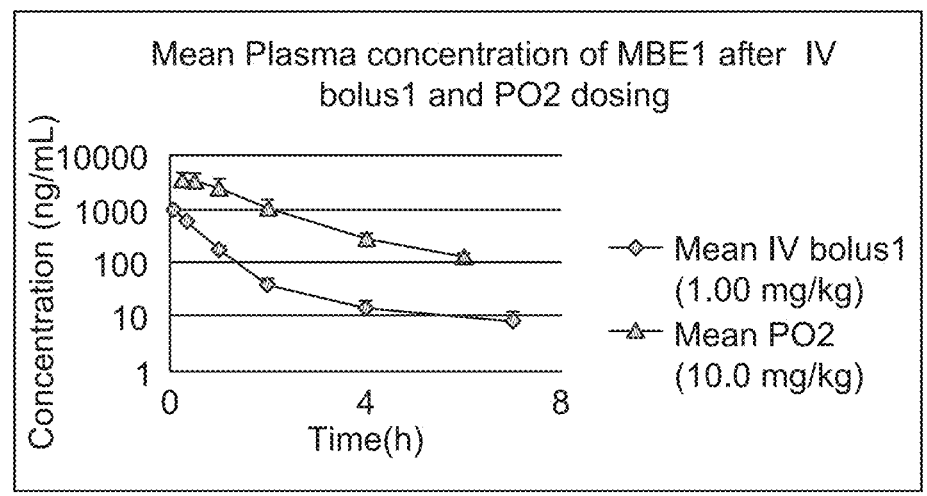
FIG. 6A is a line graph of the pharmacokinetics of compounds MBE1 that shows that oral gavage (PO) and intravenous (IV) administration of compound MBE1 leads to plasma concentrations that exceed 5-fold the IC50 for for >10 hours. Data points are the average of biological replicates, n=3 mice per group.
Figure 6B:
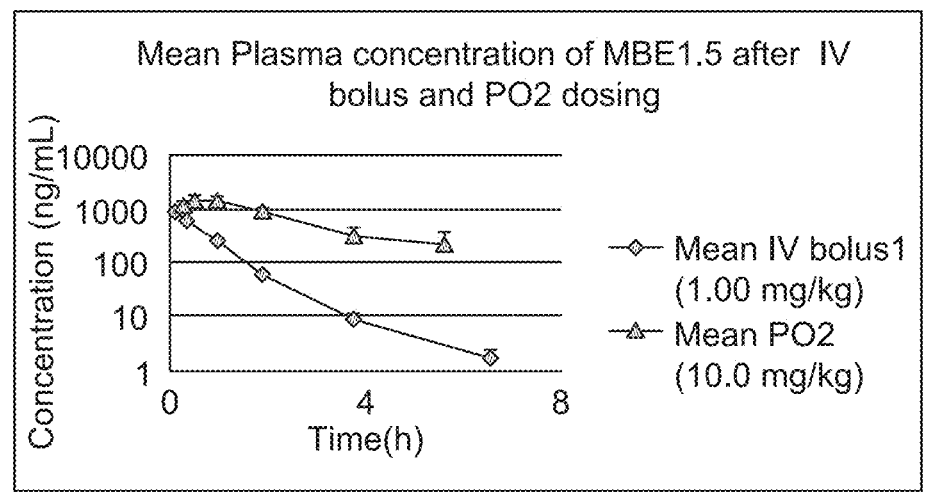
FIG. 6B is a line graph of the pharmacokinetics of compounds MBE1.5 that shows that oral gavage (PO) and intravenous (IV) administration of compound MBE1.5 leads to plasma concentrations that exceed 5-fold the IC50 for for >10 hours. Data points are the average of biological replicates, n=3 mice per group.

FIG. 6A and FIG. 6B demonstrate plasma concentrations of MBE1 at each bioanalysis time point demonstrating sufficient stability to therapeutically inhibit Aldh1a3 for in vivo models following treatment at once or twice per day.

Similar pharmacokinetics studies were also performed with three CD-1 mice after 10 mg/kg single oral dose of MBE1, MBE1.5, Compound 140 or 151. The results were shown in FIGS. 13A-13D. As shown in FIGS. 13A-13D, compounds 140 and 151, both have a 8'-methyl group, have a superior pharmacokinetic profile with a much improved plasma half-life.

Biological Example 8. ALDH1a2 and ALDH1a3 and Retinoid Pathway Activation

This example studies the relationship between retinoid pathway activation and various ALDH isoforms.

Figure 8:
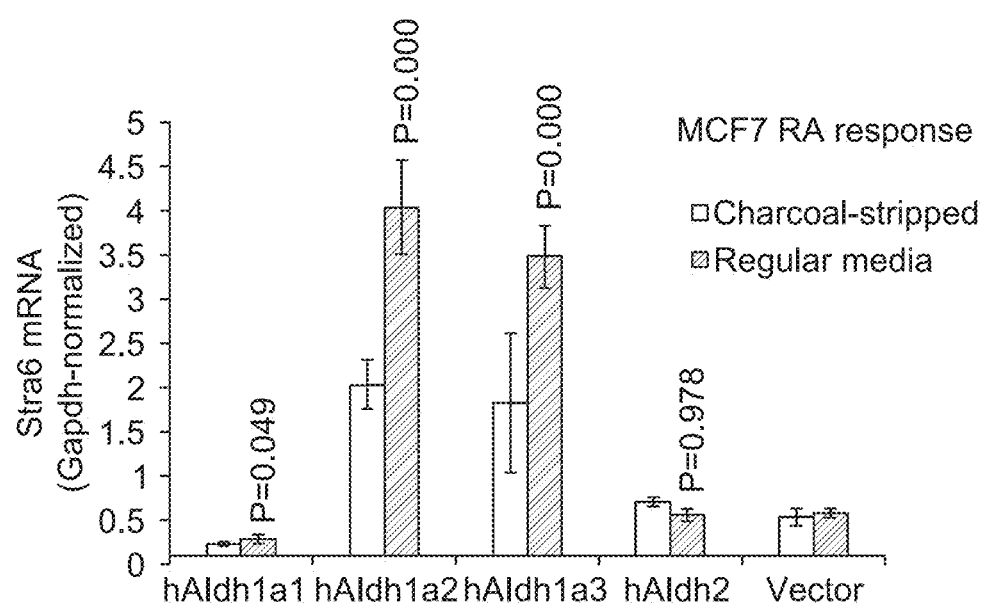
FIG. 8. q-rtPCR of STRA6 mRNA to measure retinoid pathway activity in MCF7 cells expressing each ALDH isoform of interest, which demonstrates that only ALDH1a2 and ALDH1a3 induce retinoid pathway activation. Results were tested in both regular DMEM+ FBS as well as DMEM+ charcoal-stripped FBS.

STRA6 mRNA levels of MCF7 cells expressing each ALDH isoform of interest 1a1, 1a2, 1a3, or 2, or vector control were measured by q-rtPCR. Results were tested in both regular DMEM+ FBS as well as DMEM+ charcoal-stripped FBS. The results are shown in FIG. 8. This study shows that only ALDH1a2 and ALDH1a3 induce retinoid pathway activation.

Figure 9:
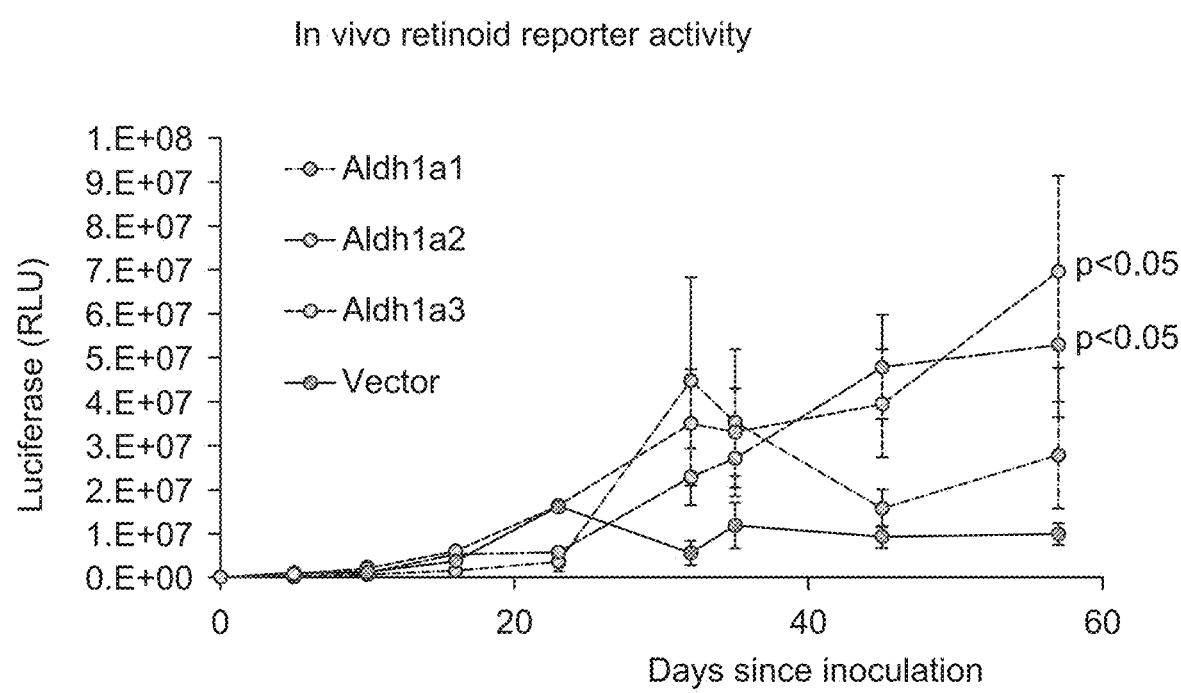
FIG. 9. In vivo imaging of SCP28 cells containing a retinoid response element driven firefly luciferase reporter were stably transduced with ALDH1a1, 1a2, 1a3 or vector control and then injected into the mammary gland of Nu/Nu female mice. Intravital imaging shows that ALDH1a2 and ALDH1a3 drive retinoid pathway activation in solid tumors in vivo. In the figure, based on the last data point, from top to the bottom, Aldh1a3, Aldh1a2, Aldh1a1, and vector control.

In an in vivo study, SCP28 cells containing a retinoid response element driven firefly luciferase reporter were stably transduced with ALDH1a1, 1a2, 1a3 or vector control and then injected into the mammary gland of Nu/Nu female mice. Intravital imaging shows that ALDH1a2 and ALDH1a3 drive retinoid pathway activation in solid tumors in vivo. See also FIG. 9.

Biological Example 9. Cytochrome P450 Inhibition Assay

The five main cytochrome P450 isoforms (CYP1A2, CYP2C9, CYP2C19, CYP2D6 and CYP3A4 were investigated in a Cytochrome P450 Inhibition assay. Isoform-specific substrates (Acetaminophen, 4'-hydroxy diclofenac, 4'-hydroxy mephenytoin, Dextrorphan, 1'-hydroxy midazolam) were incubated individually with human liver microsomes and inhibitors administered at a concentration of 10 µM. The reaction proceeded for 10 minutes. At the end of the incubation, the formation of metabolite was monitored by LC-MS/MS using standard protocols.

FIG. 29 shows the results of the Cytochrome P450 inhibition assay for compounds MBE1, Compound 140 and Compound 151.

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

Embodiments

1. A compound of Formula I, or a pharmaceutically acceptable salt thereof:

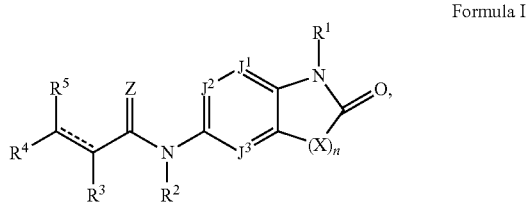

Formula I wherein:
- X at each occurrence is independently selected from O, $NR^{10}$, and $CR^{20}R^{21}$ provided that at most one X is selected from O and $NR^{10}$;
- n is 1, 2, 3, or 4;
- $J^1$, $J^2$, and $J^3$ are each independently selected from $CR^{22}$ or N, preferably, at least one of $J^1$, $J^2$, and $J^3$ is not N;
- $R^1$ and $R^2$ are each independently hydrogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_2$-6 alkynyl), or a nitrogen protecting group;
- $R^3$ and $R^4$ are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring);
- Z is O, and $R^5$ is hydrogen, $-NR^{11}R^{12}$, $-CR^{23}R^{24}R^{25}$, or $-OR^{30}$;
- or Z is O, and $R^3$, $R^4$ and $R^5$ are joined to form an optionally substituted bicyclic or polycyclic ring system, wherein the ring system is an aryl, heteroaryl, carbocyclic, or heterocyclic ring system;
- or $R^5$ and Z are joined to form an optionally substituted aryl, an optionally substituted heteroaryl, an optionally substituted carbocyclic (e.g., $C_{3-8}$ carbocyclic), or an optionally substituted heterocyclic ring (e.g., 3-8 membered heterocyclic ring); and
- "⩵" in Formula I indicates the bond is an aromatic bond, a double bond or a single bond as valance permits, and when a single bond, the two carbons forming the bond can be optionally further substituted as valance permits;

wherein:
- $R^{10}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring;
- $R^{20}$ and $R^{21}$ at each occurrence are each independently hydrogen, halogen, $-OR^{31}$, $-NR^1R^{14}$ an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or
- $R^{10}$ and one of $R^{20}$ and $R^{21}$ are joined to form a bond, an optionally substituted 4-8 membered heterocyclic ring or an optionally substituted 5 or 6 membered heteroaryl ring, wherein the other of $R^{20}$ and $R^{21}$ is defined above;
- $R^{20}$ and $R^{21}$ together with the carbon they are both attached to form $-C(O)-$, an optionally substituted $C_{3-8}$ carbocyclic ring, or an optionally substituted 3-8 membered heterocyclic ring; or
- one of $R^{20}$ and $R^{21}$ in one $CR^{20}R^{21}$ is joined with one of $R^{20}$ and $R^{21}$ in a different $CR^{20}R^{21}$ to form a bond, an optionally substituted $C_{3-8}$ carbocyclic ring, an optionally substituted 3-8 membered heterocyclic ring, wherein the others of $R^{20}$ and $R^{21}$ are defined above;
- $R^{22}$ at each occurrence is independently hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), $-CN$, $-S(O)$-alkyl, $-S(O)_2$-alkyl, or $-OR^{31}$; or two adjacent $R^{22}$ are joined to form an optionally substituted ring structure, such as an optionally substituted $C_{3-8}$ carbocyclic ring, optionally substituted 4-8 membered heterocyclic ring, optionally substituted phenyl, or optionally substituted 5 or 6 membered heteroaryl ring;
- one of $R^{11}$ and $R^{12}$ is hydrogen or a nitrogen protecting group, and the other of $R^{11}$ and $R^{12}$ is hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl;
- one of $R^{23}$, $R^{24}$, and $R^{25}$ is hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, an optionally substituted 5-10 membered heteroaryl, $-OR^{31}$, or $-NR^{13}R^{14}$, and the other two of $R^{23}$, $R^{24}$, and $R^{25}$ are independently selected from hydrogen, fluorine, or methyl, preferably, $-CR^{23}R^{24}R^{25}$ is not $-CH_3$;
- $R^{30}$ is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring; and wherein:
- each of $R^{13}$ and $R^{14}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{13}$ and $R^{14}$ are joined to form a 3-8 membered optionally substituted heterocyclic or a 5-10 membered optionally substituted heteroaryl; and $R^{31}$ at each occurrence is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl.

2. The compound of embodiment 1, or a pharmaceutically acceptable salt thereof, characterized as having Formula I-1 or I-2:

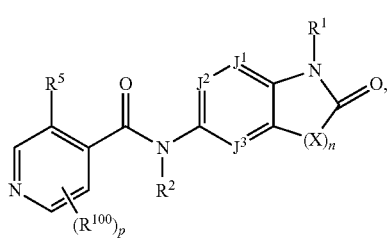

Formula I-1

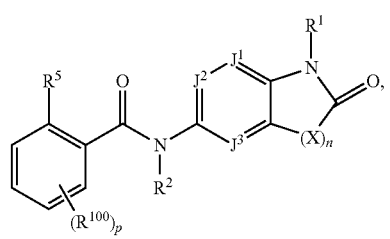

Formula I-2 wherein:

$R^{100}$ at each occurrence is independently selected from halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), —CN, or —$OR^{31}$, wherein $R^{31}$ is defined in embodiment 1; and p is 0, 1, 2, or 3, preferably, p is 0 or 1.

3. The compound of embodiment 2, or a pharmaceutically acceptable salt thereof, characterized as having Formula I-1-A or Formula I-2-A:

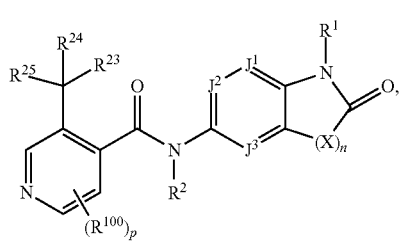

Formula I-1-A

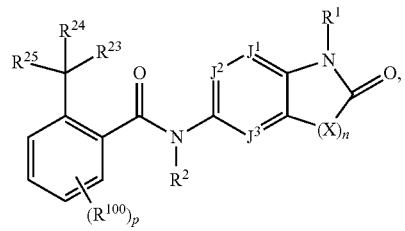

Formula I-2-A wherein:

$R^{23}$ is hydrogen or fluorine;

$R^{24}$ is hydrogen or fluorine;

$R^{25}$ is hydrogen; fluorine; $C_{1-4}$ alkyl optionally substituted with 1-3 fluorines and/or a $C_{3-6}$ cycloalkyl; a $C_{1-4}$ alkoxy optionally substituted with 1-3 fluorines and/or a $C_{3-6}$ cycloalkyl; a $C_{3-6}$ cycloalkoxy optionally substituted with 1-3 substituents independently selected from fluorine and methyl; a $C_{3-6}$ cycloalkyl optionally substituted with 1-3 substituents independently selected from fluorine and methyl; or a 3-6 membered heterocyclic ring optionally substituted with 1-3 substituents independently selected from fluorine and methyl; and at least one of $R^{23}$, $R^{24}$, and $R^{25}$ is not hydrogen.

4. The compound of embodiment 3, or a pharmaceutically acceptable salt thereof, characterized as having Formula I-1-A1, Formula I-1-A2, Formula I-1-A3, Formula I-2-A1, Formula I-2-A2; Formula I-2-A3:

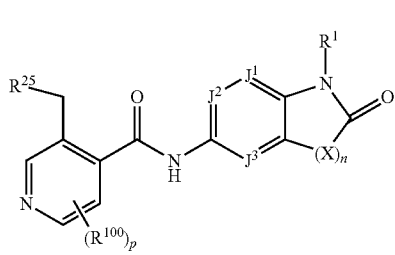

Formula I-1-A1

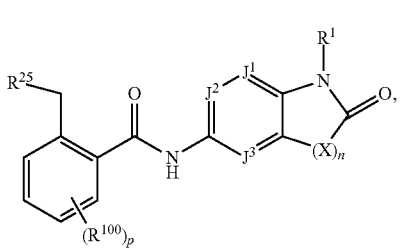

Formula I-2-A1

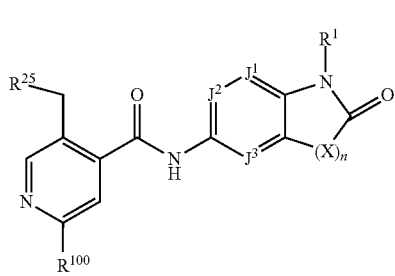

Formula I-1-A2

Formula I-2-A2

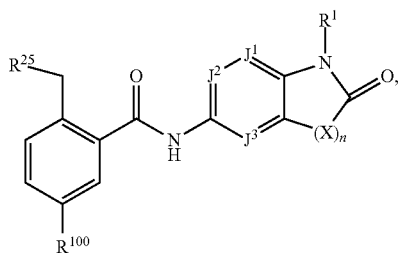

Formula I-1-A3

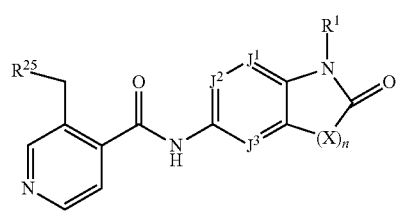

Formula I-2-A3

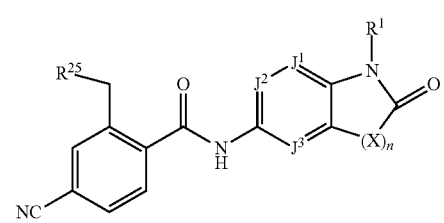

wherein:
$R^{25}$ is $C_{1-4}$ alkyl optionally substituted with 1-3 fluorines and/or a $C_{3-6}$ cycloalkyl, preferably, methyl, ethyl, n-propyl, isopropyl, or —$CF_3$; or a $C_{3-6}$ cycloalkyl optionally substituted with 1-3 substituents independently selected from fluorine and methyl, preferably, cyclopropyl or cyclobutyl; for example, $R^{25}$ is methyl, ethyl, n-propyl, isopropyl, difluoromethyl, trifluoromethyl, —$CH_2$—$CF_3$, —$CH_2$-cyclopropyl, cyclopropyl or cyclobutyl.

5. The compound of embodiment 2, or a pharmaceutically acceptable salt thereof, characterized as having Formula I-1-B, I-1-C, I-2-B, or I-2-C:

Formula I-1-B

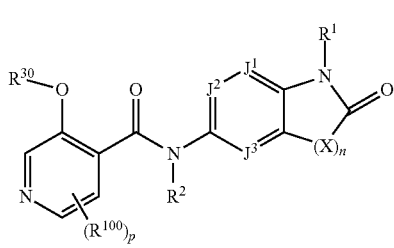

Formula I-2-B

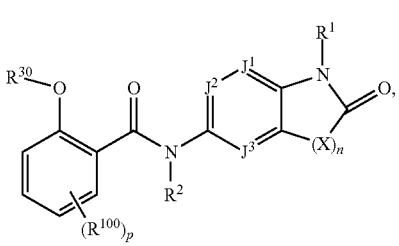

Formula I-1-C

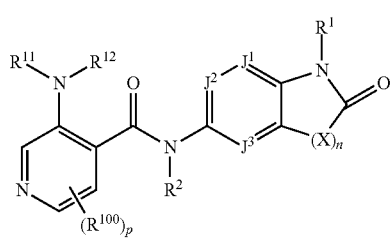

Formula I-2-C

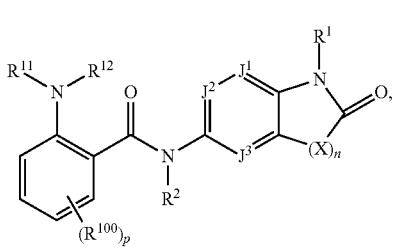

wherein:
$R^{30}$ is hydrogen; $C_{1-4}$ alkyl optionally substituted with 1-3 fluorines or a $C_{3-6}$ cycloalkyl, preferably, methyl, ethyl, n-propyl, isopropyl, difluoromethyl, trifluoromethyl, —$CH_2$—$CF_3$, or —$CH_2$-cyclopropyl; a $C_{3-6}$ cycloalkyl optionally substituted with 1-3 substituents independently selected from fluorine and methyl, preferably, cyclopropyl or cyclobutyl; or a 3-6 membered heterocyclic ring optionally substituted with 1-3 substituents independently selected from fluorine and methyl, preferably,

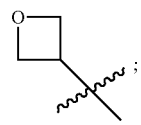

wherein one of $R^{11}$ and $R^{12}$ is hydrogen or a nitrogen protecting group, and the other of $R^{11}$ and $R^{12}$ is hydrogen, a nitrogen protecting group, $C_{1-4}$ alkyl optionally substituted with 1-3 fluorines or a $C_{3-6}$ cycloalkyl, preferably, methyl, ethyl, n-propyl, isopropyl, difluoromethyl, trifluoromethyl, —$CH_2$—$CF_3$, or —$CH_2$-cyclopropyl; a $C_{3-6}$ cycloalkyl optionally substituted with 1-3 substituents independently selected from fluorine and methyl, preferably, cyclopropyl or cyclobutyl; or a 3-6 membered heterocyclic ring optionally substituted with 1-3 substituents independently selected from fluorine and methyl, preferably,

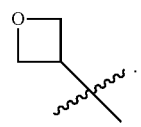

6. The compound of embodiment 2, or a pharmaceutically acceptable salt thereof, characterized as having Formula I-1-B1, Formula I-1-B2, Formula I-2-B1, Formula I-2-B2:

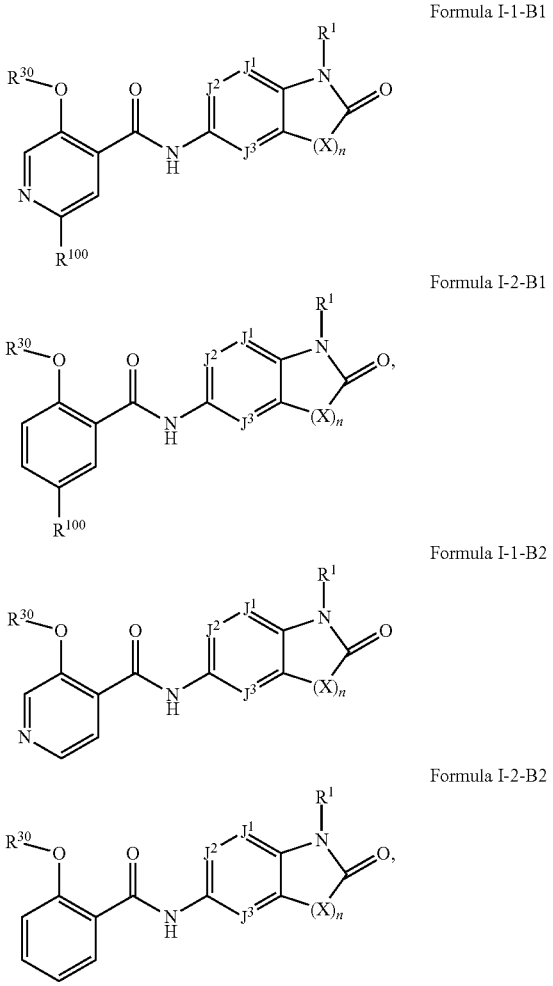

Formula I-1-B1

Formula I-2-B1

Formula I-1-B2

Formula I-2-B2 wherein $R^{30}$ is hydrogen, methyl, ethyl, n-propyl, isopropyl, difluoromethyl, trifluoromethyl, —CH$_2$—CF$_3$, —CH$_2$-cyclopropyl, cyclopropyl or cyclobutyl.

7. The compound of any one of embodiments 2-6, or a pharmaceutically acceptable salt thereof, wherein $R^{100}$ at each occurrence is independently selected from F; Cl; $C_{1-4}$ alkyl optionally substituted with 1-3 fluorines, preferably, methyl, ethyl, n-propyl, isopropyl, or —CF$_3$; a $C_{1-4}$ alkoxy optionally substituted with 1-3 fluorines, preferably, methoxy, ethoxy, n-propoxy, isopropoxy, or —OCF$_3$; a $C_{3-6}$ cycloalkyl optionally substituted with 1-3 substituents independently selected from fluorine and methyl, preferably, cyclopropyl or cyclobutyl; and —CN.

8. The compound of any one of embodiments 2-6, or a pharmaceutically acceptable salt thereof, wherein p is 1, and $R^{100}$ is F, Cl, methyl, ethyl, n-propyl, isopropyl, —CF$_3$, methoxy, ethoxy, n-propoxy, isopropoxy, —OCF$_3$, cyclopropyl, or —CN.

9. The compound of embodiment 1, or a pharmaceutically acceptable salt thereof, wherein Z is O;
$R^3$ and $R^4$ are joined to form an optionally substituted phenyl, an optionally substituted 5 or 6-membered heteroaryl, e.g., having one or two ring nitrogen atoms, an optionally substituted $C_{4-7}$ cycloalkyl group (preferably cyclopentyl or cyclohexyl), or an optionally substituted 4 to 7-membered (preferably 6-membered) heterocyclic ring having one or two ring heteroatoms; and
$R^5$ is —O—$R^{30}$ or —CR$^{23}$R$^{24}$R$^{25}$ 10. The compound of embodiment 9, or a pharmaceutically acceptable salt thereof, wherein $R^3$ and $R^4$ are joined to form a phenyl optionally substituted with one or two substituents independently selected from F; Cl; $C_{1-4}$ alkyl optionally substituted with 1-3 fluorines, preferably, methyl, ethyl, n-propyl, isopropyl, or —CF$_3$; a $C_{1-4}$ alkoxy optionally substituted with 1-3 fluorines, preferably, methoxy, ethoxy, n-propoxy, isopropoxy, or —OCF$_3$; a $C_{3-6}$ cycloalkoy optionally substituted with 1-3 substituents independently selected from fluorine and methyl; a $C_{3-6}$ cycloalkyl optionally substituted with 1-3 substituents independently selected from fluorine and methyl, preferably, cyclopropyl or cyclobutyl; and —CN.

11. The compound of embodiment 9, or a pharmaceutically acceptable salt thereof, wherein $R^3$ and $R^4$ are joined to form a 5 or 6-membered heteroaryl, preferably, pyrazole, imidazole, oxazole, thiazole, isoxazole, isothiazole, pyridyl, pyrimidinyl, pyridazinyl, or pyrazinyl, which is optionally substituted with one or two (preferably one) substituents independently selected from F; Cl; $C_{1-4}$ alkyl optionally substituted with 1-3 fluorines, preferably, methyl, ethyl, n-propyl, isopropyl, or —CF$_3$; a $C_{1-4}$ alkoxy optionally substituted with 1-3 fluorines, preferably, methoxy, ethoxy, n-propoxy, isopropoxy, or —OCF$_3$; a $C_{3-6}$ cycloalkoy optionally substituted with 1-3 substituents independently selected from fluorine and methyl; a $C_{3-6}$ cycloalkyl optionally substituted with 1-3 substituents independently selected from fluorine and methyl, preferably, cyclopropyl or cyclobutyl; and —CN.

12. The compound of embodiment 9, or a pharmaceutically acceptable salt thereof, wherein $R^3$ and $R^4$ are joined to form a 5 or 6-membered saturated ring system optionally containing one or two (preferably one) ring heteroatoms selected from O or N, which is optionally substituted with one or two substituents independently selected from F and $C_{1-4}$ alkyl, wherein the $C_{1-4}$ alkyl is optionally substituted with 1-3 fluorines.

13. The compound of any one of embodiments 1-12, or a pharmaceutically acceptable salt thereof, wherein $R^5$ is ethyl, n-propyl, isopropyl, n-butyl, isobutyl, sec-butyl, —CH$_2$—CHF$_2$, —CH$_2$—CF$_3$, —CF$_3$, —CH$_2$-cyclopropyl, —CH$_2$-cyclobutyl, —CH$_2$—O—CH$_3$, —CH$_2$—O—C$_2$H$_5$, —CH$_2$-0-n-propyl, —CH$_2$—O-isopropyl, —C$_2$H$_4$-cyclopropyl, —C$_2$H$_4$-cyclobutyl, methoxy, ethoxy, n-propoxy, isopropoxy, n-butoxy, isobutoxy, sec-butoxy, —O—CH$_2$—CF$_3$, —O—CF$_3$, —O—CH$_2$-cyclopropyl, —O—CH$_2$-cyclobutyl, —O—C$_2$H$_4$-cyclopropyl, or —O—C$_2$H$_4$-cyclobutyl.

14. The compound of any one of embodiments 1-13, or a pharmaceutically acceptable salt thereof, wherein $J^1$ is N.

15. The compound of any one of embodiments 1-13, or a pharmaceutically acceptable salt thereof, wherein $J^1$ is CR$^{22}$ and $R^{22}$ is hydrogen, F, Cl, CN, or $C_{1-4}$ alkyl (preferably methyl).

16. The compound of any one of embodiments 1-15, or a pharmaceutically acceptable salt thereof, wherein $J^2$ is N.

17. The compound of any one of embodiments 1-15, or a pharmaceutically acceptable salt thereof, wherein $J^2$ is CR$^{22}$. 18. The compound of embodiment 17, or a pharmaceutically acceptable salt thereof, wherein $J^2$ is $CR^{22}$ and $R^{22}$ is hydrogen, F, Cl, CN, or methyl.

19. The compound of any one of embodiments 1-18, or a pharmaceutically acceptable salt thereof, wherein $J^3$ is N.
20. The compound of any one of embodiments 1-18, or a pharmaceutically acceptable salt thereof, wherein $J^3$ is CH.
21. The compound of any one of embodiments 1-20, or a pharmaceutically acceptable salt thereof, wherein $R^1$ is hydrogen.
22. The compound of any one of embodiments 1-21, or a pharmaceutically acceptable salt thereof, wherein n is 1.
23. The compound of any one of embodiments 1-21, or a pharmaceutically acceptable salt thereof, wherein n is 2.
24. The compound of any one of embodiments 1-21, or a pharmaceutically acceptable salt thereof, wherein n is 3.
25. The compound of any one of embodiments 1-24, or a pharmaceutically acceptable salt thereof, wherein at least one instance of X is $CR^{20}R^{21}$, wherein $R^{20}$ and $R^{21}$ are independently hydrogen or $C_{1-4}$ alkyl, or $R^{20}$ and $R^{21}$, together with the carbon they are both attached to, form a $C_{3-6}$ cycloalkyl (preferably, cyclopropyl, cyclobutyl, or cyclopentyl) or an oxetanyl ring.
26. The compound of any one of embodiments 1-25, or a pharmaceutically acceptable salt thereof, wherein one instance of X is O.
27. The compound of any one of embodiments 1-25, or a pharmaceutically acceptable salt thereof, wherein one instance of X is $NR^{10}$, wherein $R^{10}$ is hydrogen or $C_{1-4}$ alkyl.
28. The compound of any one of embodiments 1-21, or a pharmaceutically acceptable salt thereof, wherein the

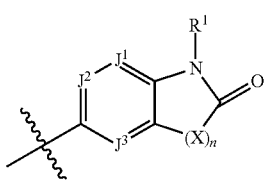

is selected from the following:

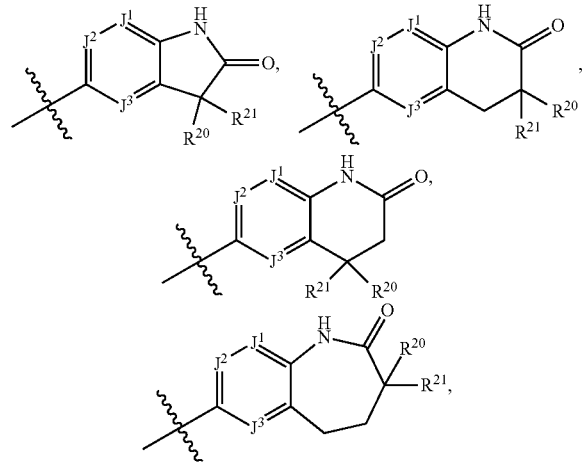

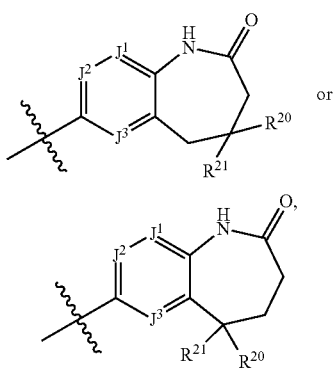

wherein $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl-ring.

29. The compound of any one of embodiments 1-13, or a pharmaceutically acceptable salt thereof, wherein the

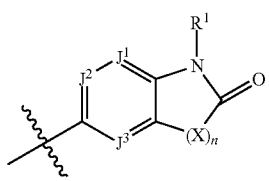

is selected from the following:

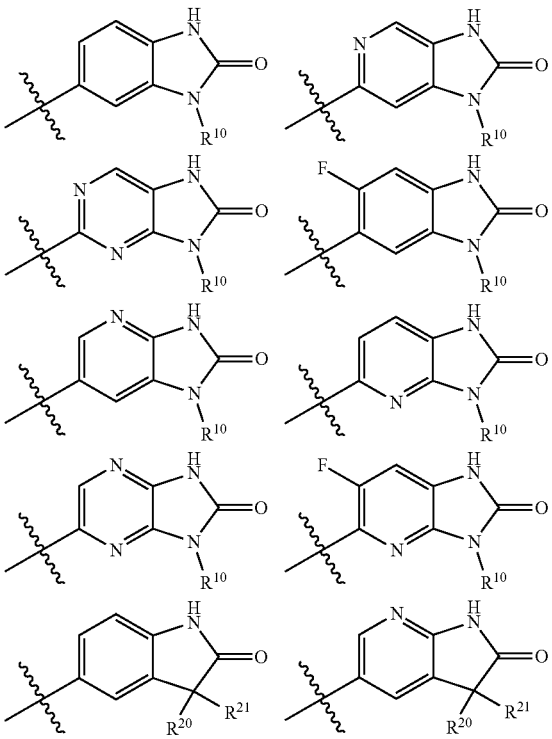

211
-continued

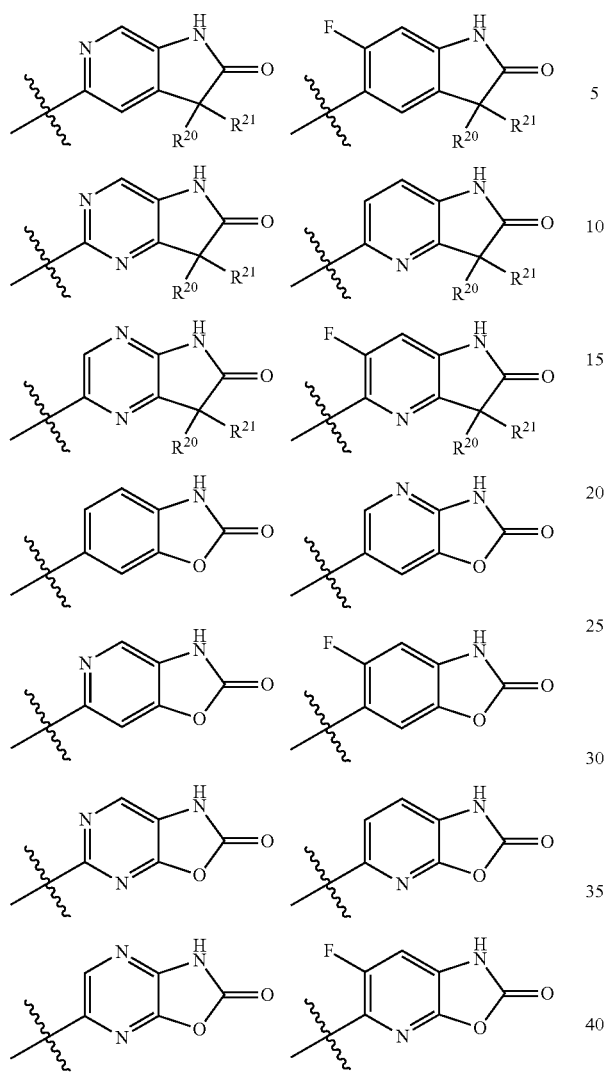

wherein:
- $R^{10}$ is independently hydrogen or $C_{1-4}$ alkyl (e.g., methyl, ethyl, etc.);
- $R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring.

30. The compound of any one of embodiments 1-13, or a pharmaceutically acceptable salt thereof, wherein the

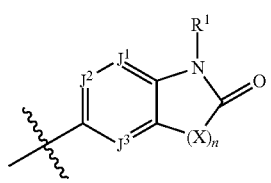

212
is selected from the following:

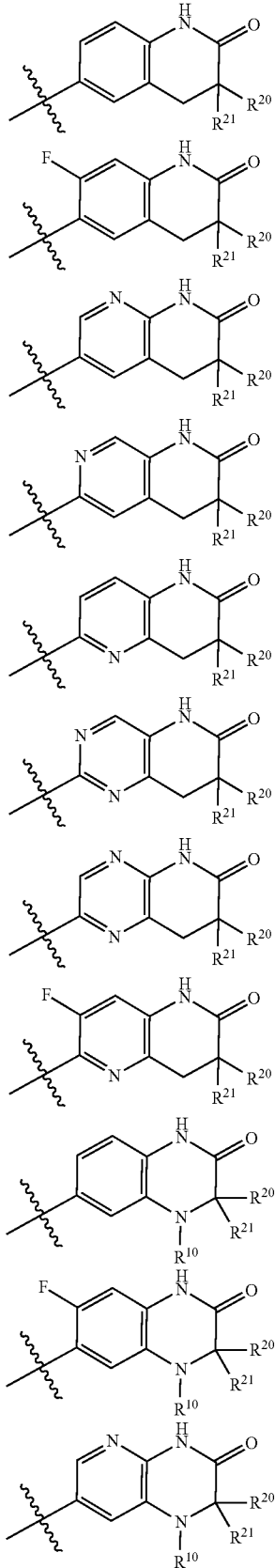

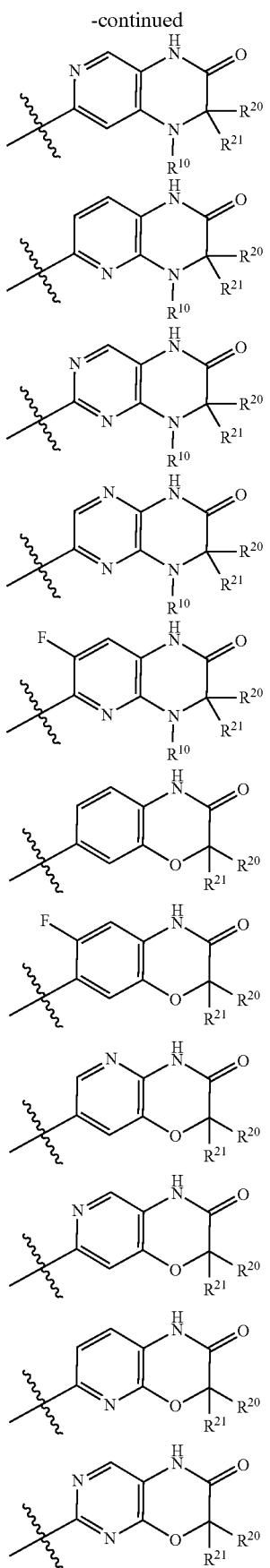
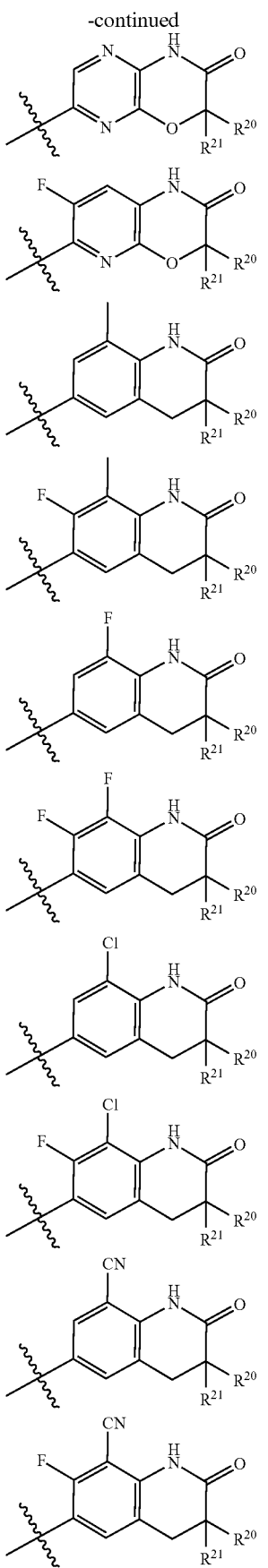

-continued

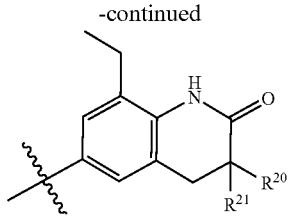

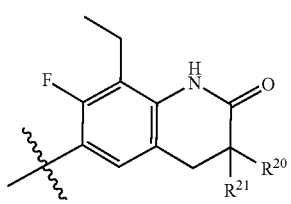

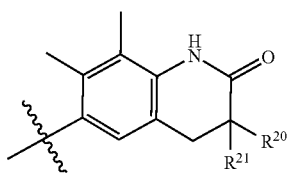

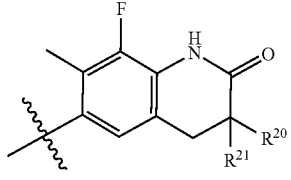

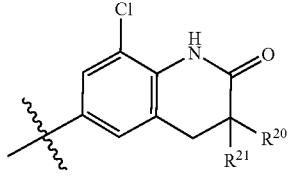

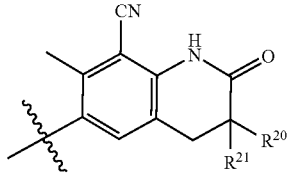

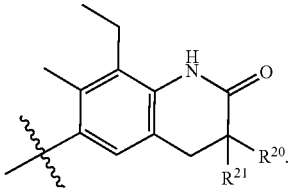

wherein:

$R^{10}$ is independently hydrogen or $C_{1-4}$ alkyl (e.g., methyl, ethyl, etc.);

$R^{20}$ and $R^{21}$ are independently hydrogen or $C_{1-4}$ alkyl (e.g., methyl, ethyl, etc.), or $R^{20}$ and $R^{21}$, together with the carbon they are both attached to, form a cyclopropyl, cyclobutyl, cyclopentyl, or an oxetanyl ring.

31. The compound of any one of embodiments 1-13, or a pharmaceutically acceptable salt thereof, wherein the

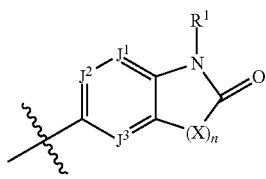

is selected from the following:

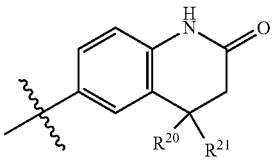 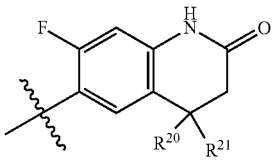

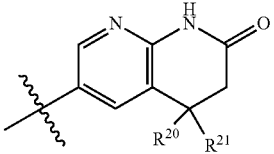 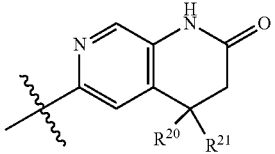

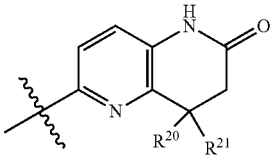 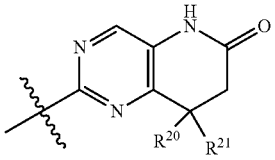

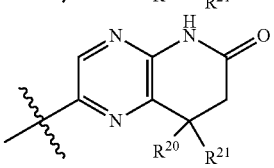 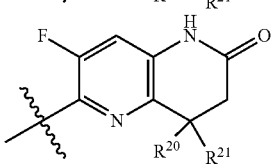

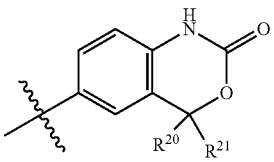 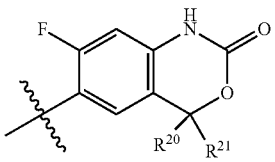

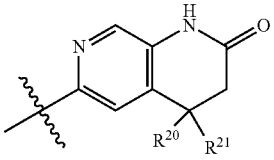 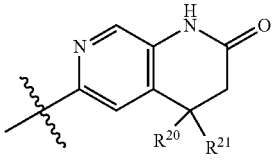

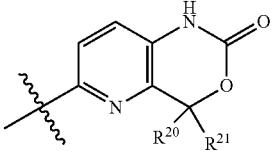 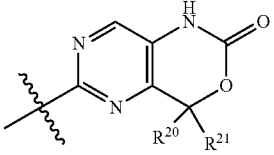

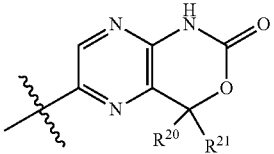 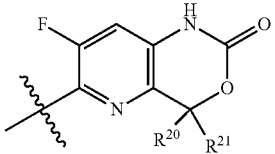

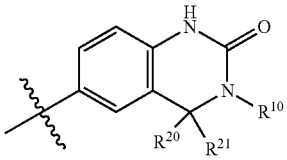 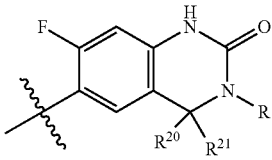

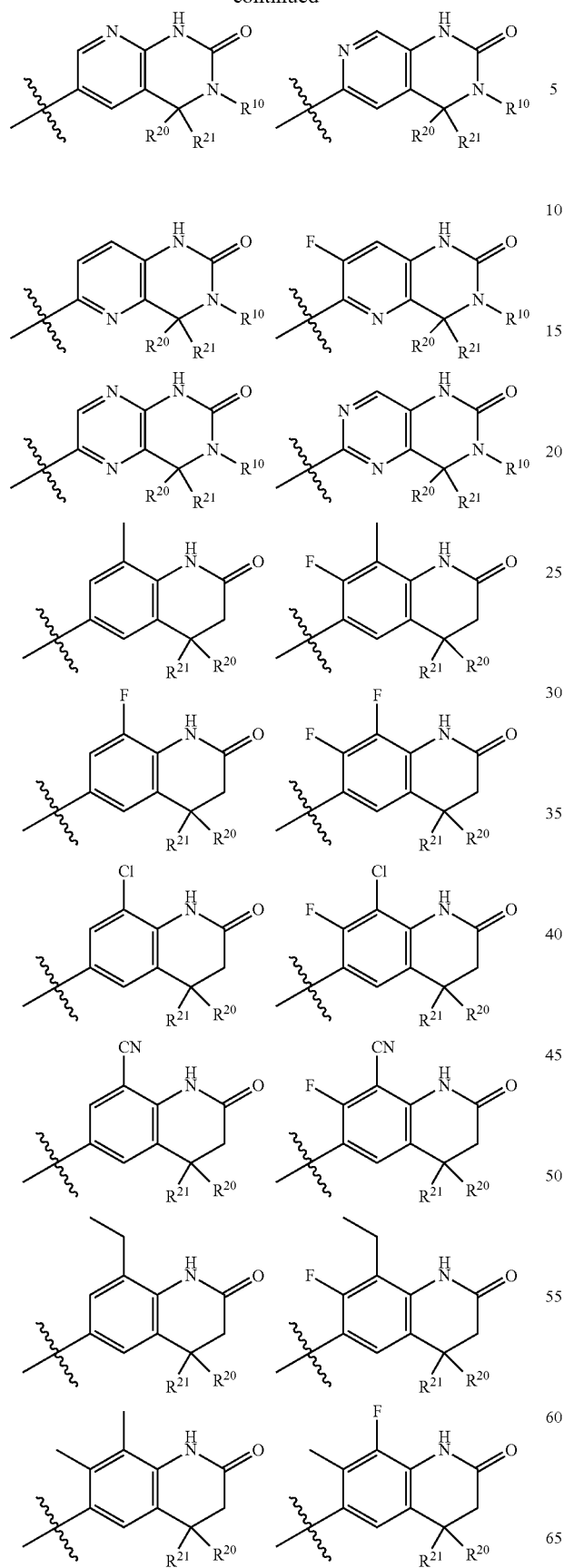

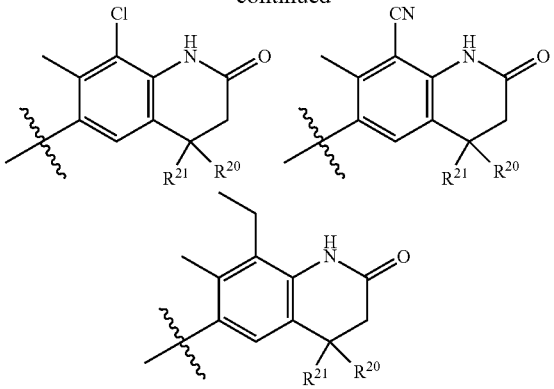

wherein:

R[10] is independently hydrogen or $C_{1-4}$ alkyl (e.g., methyl, ethyl, etc.);

R[20] and R[21] are independently hydrogen or $C_{1-4}$ alkyl (e.g., methyl, ethyl, etc.), or R[20] and R[21], together with the carbon they are both attached to, form a cyclopropyl, cyclobutyl, cyclopentyl, or an oxetanyl ring.

32. The compound of any one of embodiments 1-13, or a pharmaceutically acceptable salt thereof, wherein the

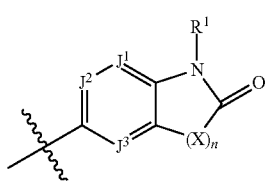

is selected from the following:

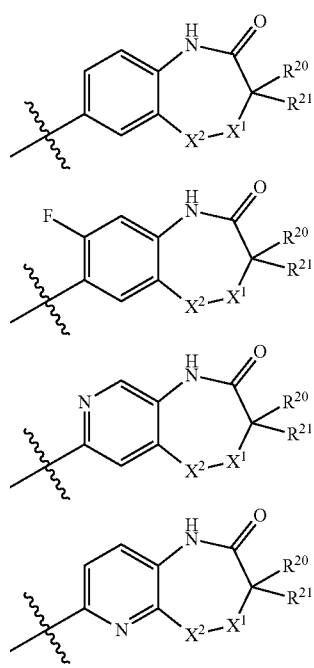

-continued
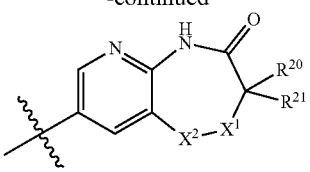
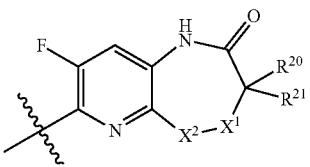
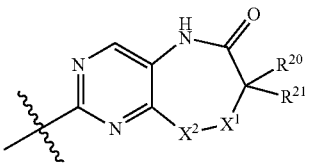
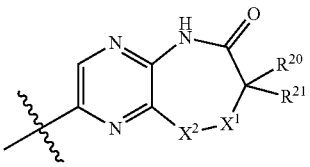
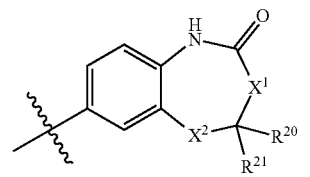
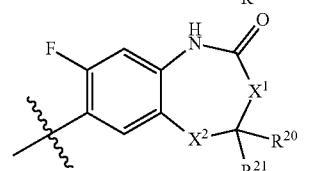
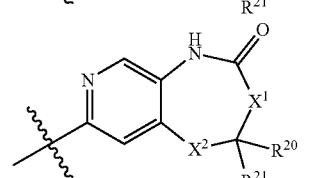
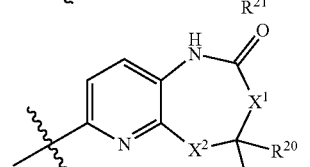
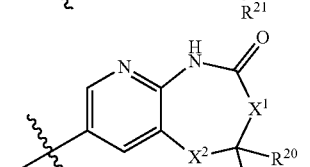
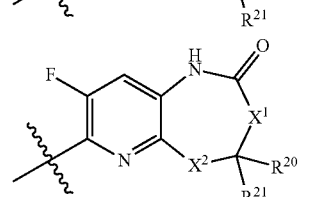
-continued
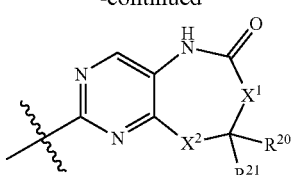
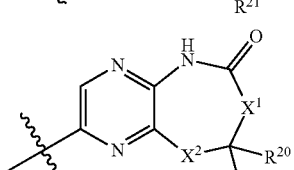
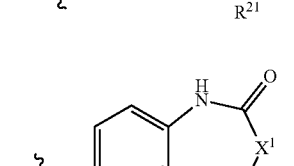
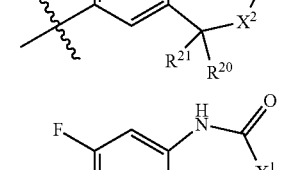
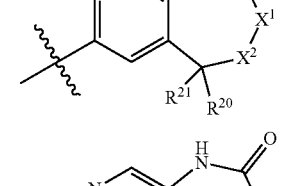
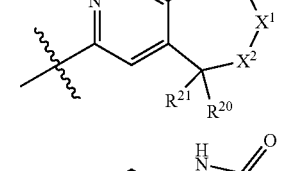
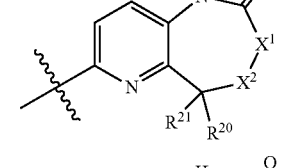
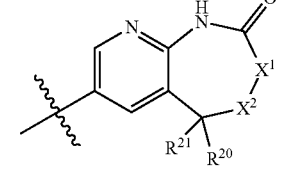
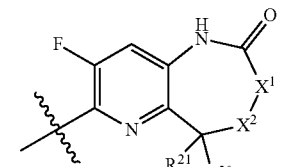
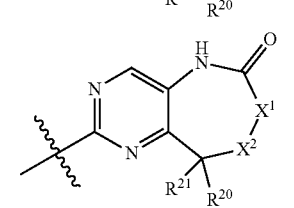

-continued

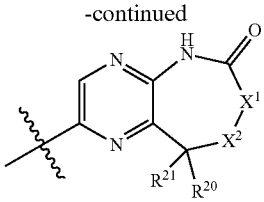

wherein:
X¹ and X² are independently O, NR¹⁰, or CH₂, provided that at least one of X¹ and X² is CH₂;
R¹⁰ is hydrogen or $C_{1-4}$ alkyl (e.g., methyl, ethyl, etc.);
R²⁰ and R²¹ are independently hydrogen or $C_{1-4}$ alkyl (e.g., methyl, ethyl, etc.), or R²⁰ and R²¹, together with the carbon they are both attached to, form a cyclopropyl, cyclobutyl, cyclopentyl, or an oxetanyl ring.

33. The compound of any one of embodiments 1-21, or a pharmaceutically acceptable salt thereof, wherein:
$(X)_n$ in the formula includes 1-3 $CR^{20}R^{21}$ units, wherein for at least one $CR^{20}R^{21}$ unit, R²⁰ and R²¹ are both methyl;
one of R²⁰ and R²¹ is methyl, and the other of R²⁰ and R²¹ is ethyl or methoxy; or R²⁰ and R²¹, together with the carbon they are both attached to, form a cyclopropyl, cyclobutyl, or an oxetanyl ring.

34. The compound of any one of embodiments 1-13, or a pharmaceutically acceptable salt thereof, wherein the

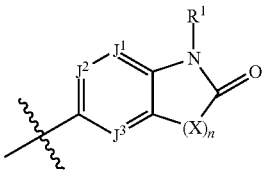

in Formula I is selected from the following:

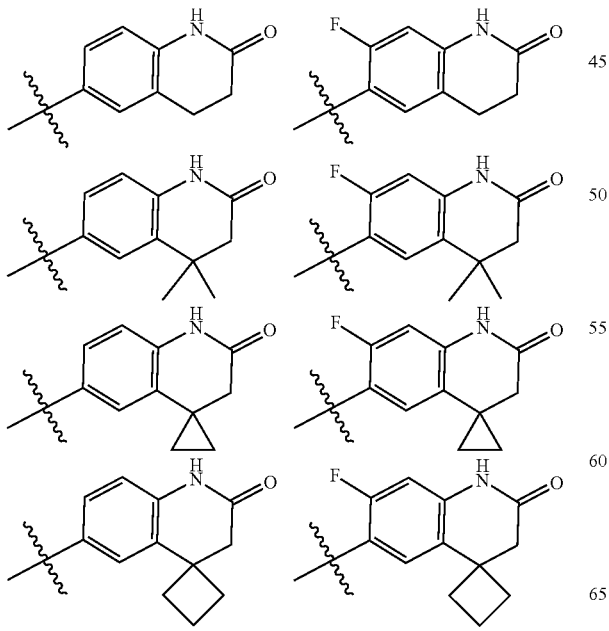

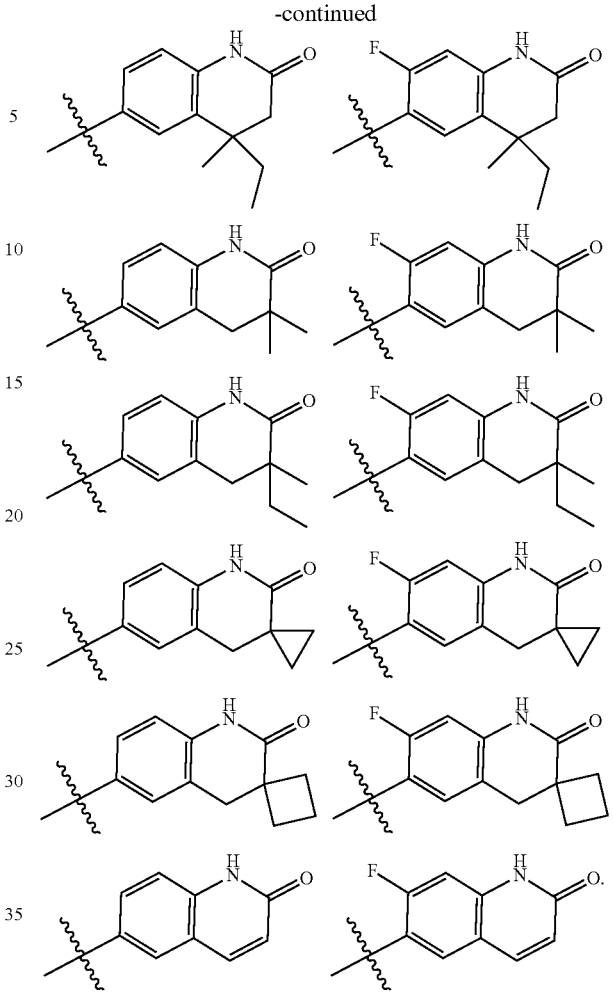

35. The compound of any one of embodiments 1-13, or a pharmaceutically acceptable salt thereof, wherein the

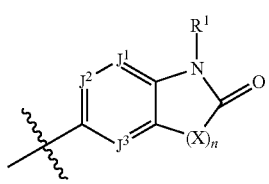

in Formula I is selected from the following:

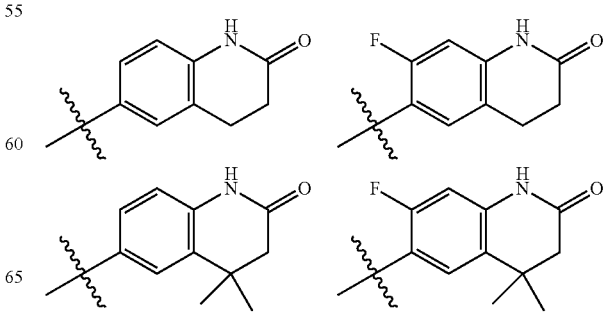

-continued

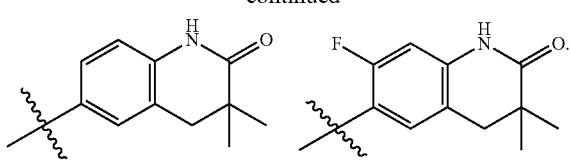

36. The compound of any one of embodiments 1-13, or a pharmaceutically acceptable salt thereof, wherein the

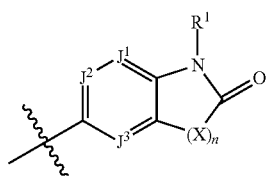

in Formula I is selected from the following:

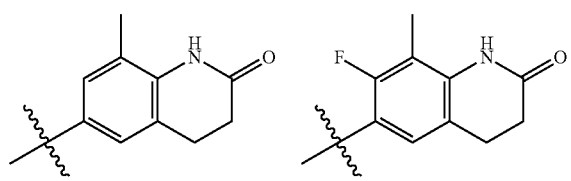

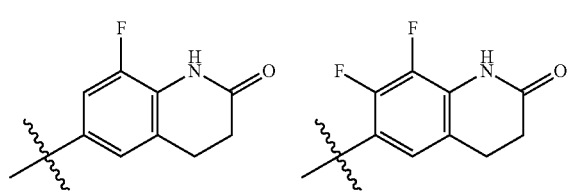

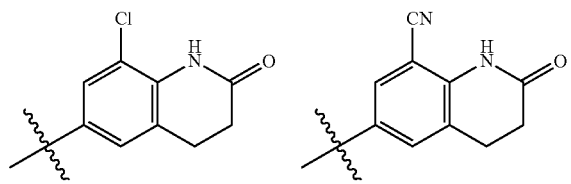

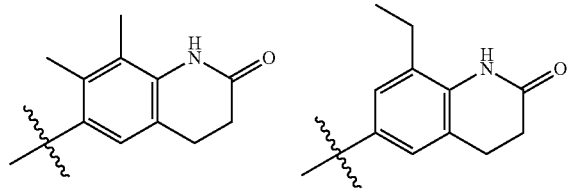

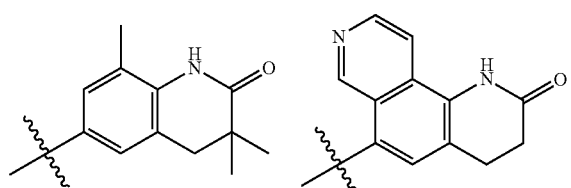

37. The compound of any one of embodiments 1-13, or a pharmaceutically acceptable salt thereof, wherein the

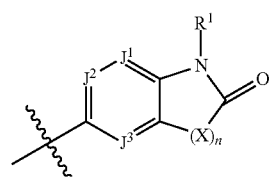

in Formula I is

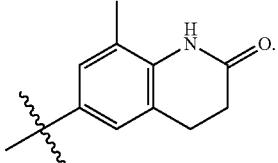 [SMILES: *c1cc(C)c2c(c1)CCC(=O)N2]

38. The compound of any one of embodiments 1-13, or a pharmaceutically acceptable salt thereof, wherein the

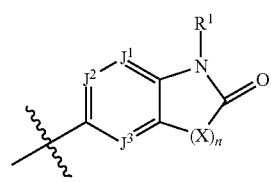

in Formula I is selected from the following:

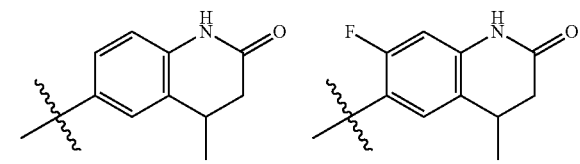

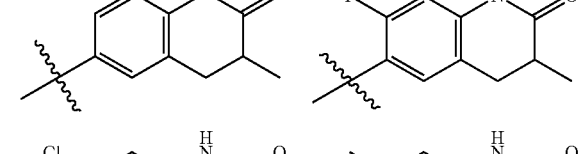

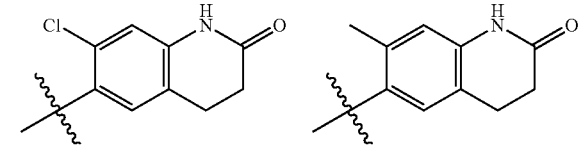

39. A compound of Formula II, or a pharmaceutically acceptable salt thereof:

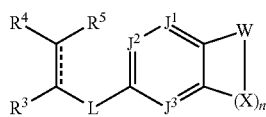

Formula II wherein:
W is —N(R$^1$)—C(O)—, —N(R$^1$)—S(O)—, or —N(R$^1$)—S(O)$_2$—;
L is —(CR$^{A1}$R$^{B1}$)$_{t1}$-Q$^1$-Q$^2$-Q$^3$-(CR$^{A2}$R$^{B2}$)$_{t2}$—, wherein:
Q$^1$ and Q$^3$ are independently null, O or NR$^2$;
Q$^2$ is null, —C(O)—, —C(=Z)—, —S(O)—, or —S(O)$_2$—;
t1 is 0, 1, 2, or 3;
t2 is 0, 1, 2, or 3; and
R$^{A1}$, R$^{B1}$, R$^{A2}$, and R$^{B2}$ at each occurrence are independently hydrogen, C$_{1-4}$ alkyl (e.g., methyl), or fluorine, or
two adjacent CR$^{A1}$R$^{B1}$ or two adjacent CR$^{A2}$R$^{B2}$ can form —C(R$^{A1}$)=C(R$^{B1}$)—, —C(R$^{A2}$)=C(R$^{B2}$)—, or

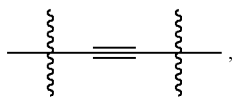

wherein R$^{A1}$, R$^{B1}$, R$^{A2}$, and R$^{B2}$ at each occurrence are independently hydrogen, C$_{1-4}$ alkyl (e.g., methyl), or fluorine;
X at each occurrence is independently selected from O, NR$^{10}$, and CR$^{20}$R$^{21}$ provided that at most one X is selected from O and NR$^{10}$;
n is 1, 2, 3, or 4;
J$^1$, J$^2$, and J$^3$ are each independently selected from CR$^{22}$ or N, preferably, at least one of J$^1$, J$^2$, and J$^3$ is not N;
R$^1$ and R$^2$ at each occurrence are each independently hydrogen, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), or a nitrogen protecting group;
R$^3$ and R$^4$ are joined to form an optionally substituted aryl, an optionally substituted heteroaryl, an optionally substituted carbocyclic (e.g., C$_{3-8}$ carbocyclic), or an optionally substituted heterocyclic ring (e.g., 3-8 membered heterocyclic ring);
R$^5$ is hydrogen, —NR$^{11}$R$^{12}$, —CR$^{23}$R$^{24}$R$^{25}$, or —OR$^{30}$;
R$^3$, R$^4$ and R$^5$ are joined to form an optionally substituted bicyclic or polycyclic ring system, wherein the ring system is an aryl, heteroaryl, carbocyclic, or heterocyclic ring system;
or when Q$^2$ is —C(=Z)—, R$^5$ and Z are joined to form an optionally substituted aryl, an optionally substituted heteroaryl, an optionally substituted carbocyclic (e.g., C$_{3-8}$ carbocyclic), or an optionally substituted heterocyclic ring (e.g., 3-8 membered heterocyclic ring);

"═" in Formula II indicates the bond is an aromatic bond, a double bond or a single bond as valance permits, and when a single bond, the two carbons forming the bond can be optionally further substituted as valance permits;
wherein:
R$^{10}$ at each occurrence is independently hydrogen, a nitrogen protecting group, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), an optionally substituted C$_{3-8}$ carbocyclic ring, or an optionally substituted 3-8 membered heterocyclic ring;
R$^{20}$ and R$^{21}$ at each occurrence are each independently hydrogen, halogen, —OR$^{31}$, —NR$^{13}$R$^{14}$, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), an optionally substituted C$_{3-8}$ carbocyclic ring, an optionally substituted 3-8 membered heterocyclic ring, an optionally substituted phenyl, or an optionally substituted 5-10 membered heteroaryl; or
R$^{10}$ and one of R$^{20}$ and R$^{21}$ are joined to form a bond, an optionally substituted 4-8 membered heterocyclic ring or an optionally substituted 5 or 6 membered heteroaryl ring, wherein the other of R$^{20}$ and R$^{21}$ is defined above;
R$^{20}$ and R$^{21}$ together with the carbon they are both attached to form —C(O)—, an optionally substituted C$_{3-8}$ carbocyclic ring, or an optionally substituted 3-8 membered heterocyclic ring; or
one of R$^{20}$ and R$^{21}$ in one CR$^{20}$R$^{21}$ is joined with one of R$^{20}$ and R$^{21}$ in a different CR$^{20}$R$^{21}$ to form a bond, an optionally substituted C$_{3-8}$ carbocyclic ring, an optionally substituted 3-8 membered heterocyclic ring, wherein the others of R$^{20}$ and R$^{21}$ are defined above;
R$^{22}$ at each occurrence is independently hydrogen, halogen, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), —CN, —S(O)-alkyl, —S(O)$_2$-alkyl, or —OR$^{31}$; or two adjacent R$^{22}$ are joined to form an optionally substituted ring structure, such as an optionally substituted C$_{3-8}$ carbocyclic ring, optionally substituted 4-8 membered heterocyclic ring, optionally substituted phenyl, or optionally substituted 5 or 6 membered heteroaryl ring;
one of R$^{11}$ and R$^{12}$ is hydrogen or a nitrogen protecting group, and the other of R$^{11}$ and R$^{12}$ is hydrogen, a nitrogen protecting group, an optionally substituted alkyl (e.g., optionally substituted C$_{1-6}$ alkyl), an optionally substituted alkenyl (e.g., optionally substituted C$_{2-6}$ alkenyl), an optionally substituted alkynyl (e.g., optionally substituted C$_{2-6}$ alkynyl), an optionally substituted C$_{3-8}$ carbocyclic ring, an optionally substituted 3-8 membered heterocyclic ring, an optionally substituted phenyl, or an optionally substituted 5-10 membered heteroaryl;

one of $R^{23}$, $R^{24}$, and $R^{25}$ is hydrogen, halogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, an optionally substituted 5-10 membered heteroaryl, —$OR^{31}$, or —$NR^{13}R^{14}$, and the other two of $R^{23}$, $R^{24}$, and $R^{25}$ are independently selected from hydrogen, fluorine, or methyl, preferably, —$CR^{23}R^{24}R^{25}$ is not —$CH_3$;

$R^{30}$ is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring; and wherein:
each of $R^{13}$ and $R^{14}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or $R^{13}$ and $R^{14}$ are joined to form a 3-8 membered optionally substituted heterocyclic or a 5-10 membered optionally substituted heteroaryl; and $R^{31}$ at each occurrence is hydrogen, an oxygen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl.

40. The compound of embodiment 39, or a pharmaceutically acceptable salt thereof, wherein W is —NH—C(O)— or —NH—S(O)$_2$—.

41. The compound of embodiment 39 or 40, or a pharmaceutically acceptable salt thereof, wherein L is —(CR$^{A1}$R$^{B1}$)$_{t1}$—N(R$^2$)—, wherein t1 is 1 or 2.

42. The compound of embodiment 39 or 40, or a pharmaceutically acceptable salt thereof, wherein L is —(CR$^{A1}$R$^{B1}$)$_{t1}$—, wherein t1 is 1 or 2.

43. The compound of embodiment 39 or 40, or a pharmaceutically acceptable salt thereof, wherein L is —(CR$^{A1}$R$^{B1}$)$_{t1}$—N(R$^2$)—C(O)—, wherein t1 is 1 or 2.

44. The compound of embodiment 39 or 40, or a pharmaceutically acceptable salt thereof, wherein L is —N(R$^2$)—C(O)—(CR$^{A2}$R$^{B2}$)$_{t2}$—, wherein t2 is 1 or 2.

45. The compound of embodiment 39 or 40, or a pharmaceutically acceptable salt thereof, wherein L is —(CR$^{A1}$R$^{B1}$ t-N(R$^2$)—C(O)—(CR$^{A2}$R$^{B2}$)$_{t2}$—, wherein t1 and t2 are independently 0, 1 or 2.

46. A compound of Formula III, or a pharmaceutically acceptable salt thereof,

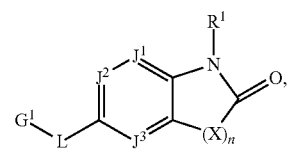

Formula III wherein:
X at each occurrence is independently selected from O, NR$^{10}$, and CR$^{20}$R$^{21}$ provided that at most one X is selected from O and NR$^{10}$;
n is 1, 2, 3, or 4;
J$^1$, J$^2$, and J$^3$ are each independently selected from CR$^{22}$ or N, preferably, at least one of J$^1$, J$^2$, and J$^3$ is not N;
R$^1$ is hydrogen, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), or a nitrogen protecting group;
L is NH, O, or selected from:

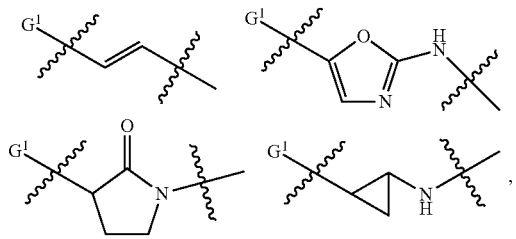

G$^1$ is an optionally substituted phenyl, optionally substituted heteroaryl (e.g., 5- or 6-membered heteroaryl, or 8-10 membered bicyclic heteroaryl), or an optionally substituted heterocyclyl,
wherein:
R$^{10}$ at each occurrence is independently hydrogen, a nitrogen protecting group, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, or an optionally substituted 3-8 membered heterocyclic ring;
R$^{20}$ and R$^{21}$ at each occurrence are each independently hydrogen, halogen, —OR$^{31}$, —NR$^{13}$R$^{14}$, an optionally substituted alkyl (e.g., optionally substituted $C_{1-6}$ alkyl), an optionally substituted alkenyl (e.g., optionally substituted $C_{2-6}$ alkenyl), an optionally substituted alkynyl (e.g., optionally substituted $C_{2-6}$ alkynyl), an optionally substituted $C_{3-8}$ carbocyclic ring, an optionally substituted 3-8 membered heterocyclic ring, an optionally substituted phenyl, or an optionally substituted 5-10 membered heteroaryl; or R$^{10}$ and one of R$^{20}$ and R$^{21}$ are joined to form a bond, an optionally substituted 4-8 membered heterocyclic ring or an optionally substituted 5 or 6 membered heteroaryl ring, wherein the other of R$^{20}$ and R$^{21}$ is defined above;

R²⁰ and R²¹ together with the carbon they are both attached to form —C(O)—, an optionally substituted C₃₋₈ carbocyclic ring, or an optionally substituted 3-8 membered heterocyclic ring; or one of R²⁰ and R²¹ in one CR²⁰R²¹ is joined with one of R²⁰ and R²¹ in a different CR²⁰R²¹ to form a bond, an optionally substituted C₃₋₈ carbocyclic ring, an optionally substituted 3-8 membered heterocyclic ring, wherein the others of R²⁰ and R²¹ are defined above;

R²² at each occurrence is independently hydrogen, halogen, an optionally substituted alkyl (e.g., optionally substituted C₁₋₆ alkyl), an optionally substituted alkenyl (e.g., optionally substituted C₂₋₆ alkenyl), an optionally substituted alkynyl (e.g., optionally substituted C₂₋₆ alkynyl), —CN, —S(O)-alkyl (e.g., —S(O)—C₁₋₆ alkyl), —S(O)₂-alkyl (e.g., —S(O)₂—C₁₋₆ alkyl), or —OR³¹; or two adjacent R²² are joined to form an optionally substituted ring structure, such as an optionally substituted C₃₋₈ carbocyclic ring, optionally substituted 4-8 membered heterocyclic ring, optionally substituted phenyl, or optionally substituted 5 or 6 membered heteroaryl ring;

wherein:

each of R¹³ and R¹⁴ at each occurrence is independently hydrogen, a nitrogen protecting group, an optionally substituted alkyl (e.g., optionally substituted C₁₋₆ alkyl), an optionally substituted alkenyl (e.g., optionally substituted C₂₋₆ alkenyl), an optionally substituted alkynyl (e.g., optionally substituted C₂₋₆ alkynyl), an optionally substituted C₃₋₈ carbocyclic ring, an optionally substituted 3-8 membered heterocyclic ring, an optionally substituted phenyl, or an optionally substituted 5-10 membered heteroaryl; or R¹³ and R¹⁴ are joined to form a 3-8 membered optionally substituted heterocyclic or a 5-10 membered optionally substituted heteroaryl; and R³¹ at each occurrence is hydrogen, an oxygen protecting group, an optionally substituted alkyl (e.g., optionally substituted C₁₋₆ alkyl), an optionally substituted alkenyl (e.g., optionally substituted C₂₋₆ alkenyl), an optionally substituted alkynyl (e.g., optionally substituted C₂₋₆ alkynyl), an optionally substituted C₃₋₈ carbocyclic ring, an optionally substituted 3-8 membered heterocyclic ring, an optionally substituted phenyl, or an optionally substituted 5-10 membered heteroaryl.

47. The compound of embodiment 46, or a pharmaceutically acceptable salt thereof, characterized as having a Formula III-1 or III-2:

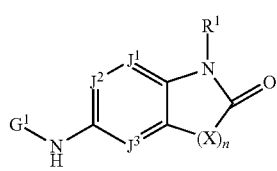

Formula III-1

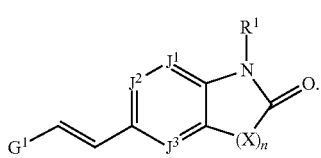

Formula III-2

48. The compound of embodiment 46 or 47, or a pharmaceutically acceptable salt thereof, wherein the

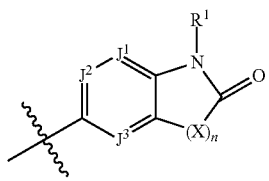

in Formula III is selected from the following:

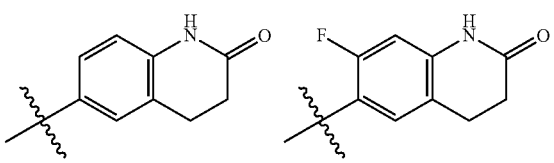

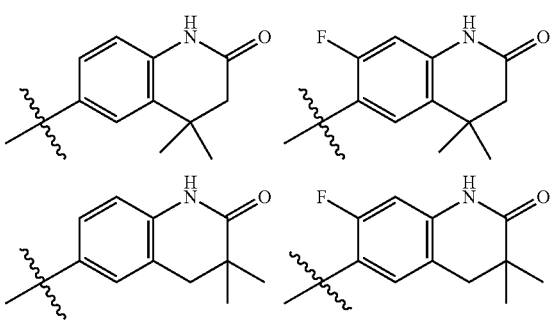

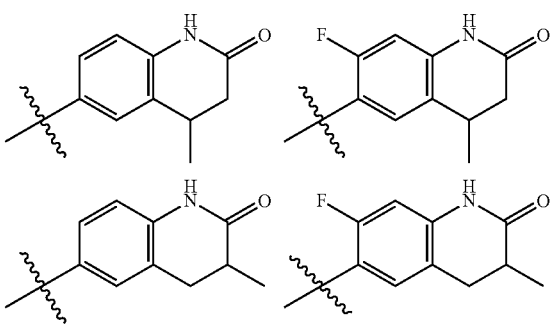

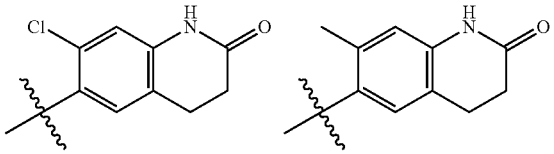

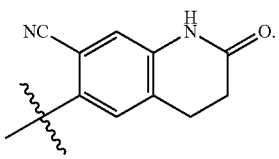

49. The compound of embodiment 46 or 47, or a pharmaceutically acceptable salt thereof, wherein the

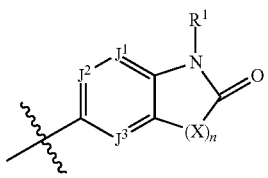

in Formula III is selected from the following:

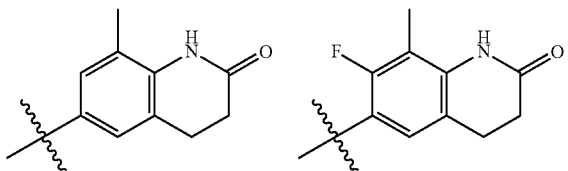

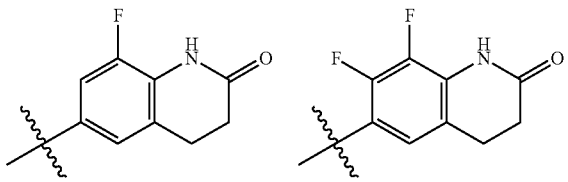

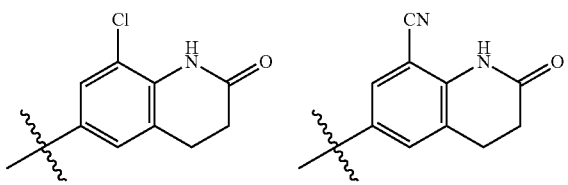

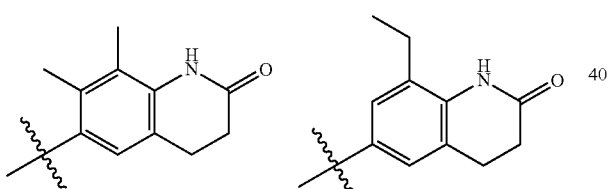

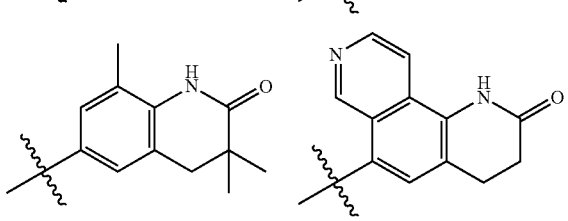

50. The compound of embodiment 46 or 47, or a pharmaceutically acceptable salt thereof, wherein the

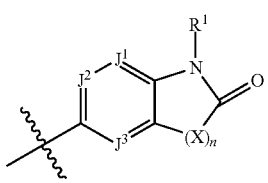

in Formula III is

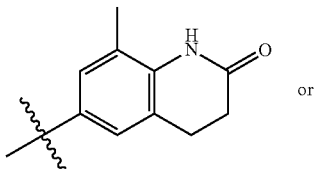

or

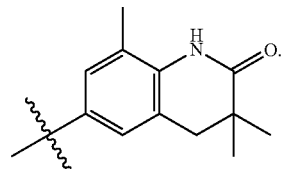

51. The compound of any one of embodiments 46-50, or a pharmaceutically acceptable salt thereof, wherein $G^1$ is selected from.

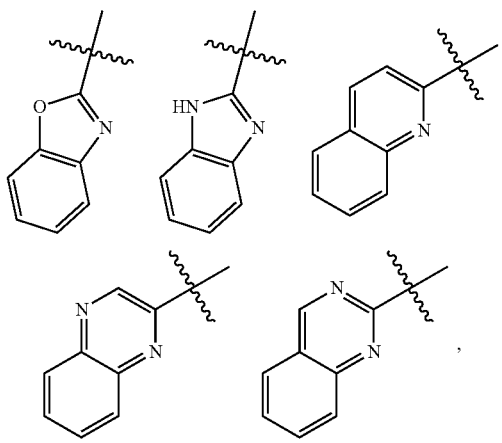

wherein each of which is optionally substituted, for example, with one or two substituents independently selected from Cl, methyl, and hydroxyl.

52. The compound of any one of embodiments 46-50, or a pharmaceutically acceptable salt thereof, wherein $G^1$ is selected from:

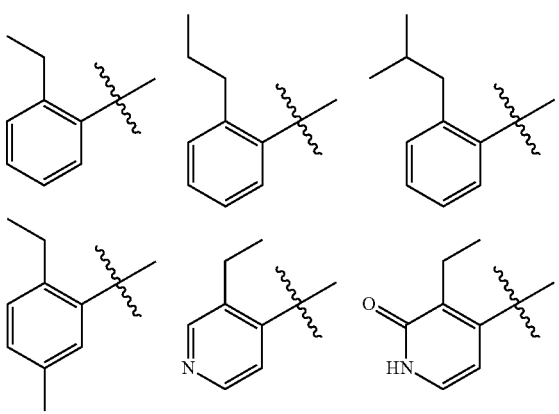

-continued

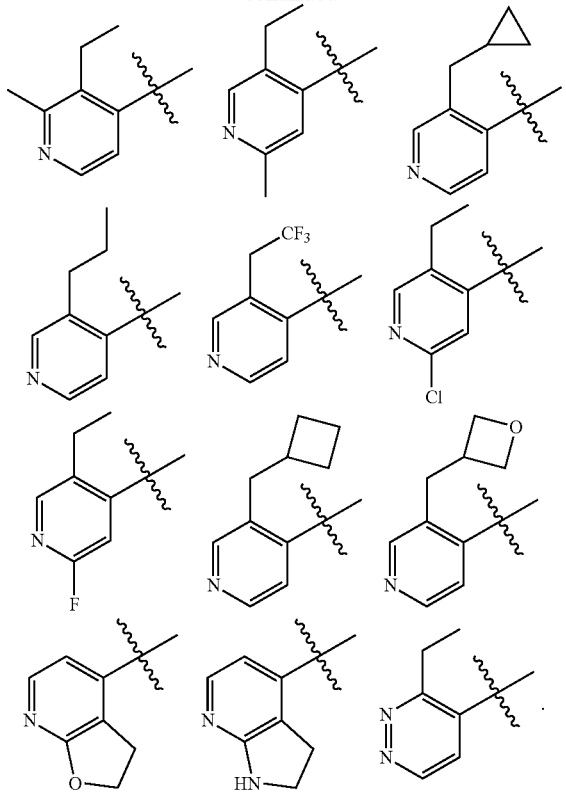

53. A compound selected from any of Compound Nos. 139-202, or a pharmaceutically acceptable salt thereof.
54. A pharmaceutical composition comprising the compound of any one of embodiments 1-53, or a pharmaceutically acceptable salt thereof, and optionally a pharmaceutically acceptable excipient or carrier.
55. A method of treating cancer in a subject in need thereof, the method comprising administering to the subject a therapeutically effective amount of the compound of any one of embodiments 1-53 or a pharmaceutical salt thereof, or the pharmaceutical composition of embodiment 54.
56. A method of treating metastatic cancer or chemoresistant cancer in a subject in need thereof, the method comprising administering to the subject a therapeutically effective amount of the compound of any one of embodiments 1-53 or a pharmaceutical salt thereof, or the pharmaceutical composition of embodiment 54.
57. A method of treating or preventing metastasis of a cancer in a subject in need thereof, the method comprising administering to the subject an effective amount of the compound of any one of embodiments 1-53 or a pharmaceutical salt thereof, or the pharmaceutical composition of embodiment 54.
58. A method of sensitizing cancer for chemotherapy in a subject in need thereof, the method comprising administering to the subject an effective amount of the compound of any one of embodiments 1-53 or a pharmaceutical salt thereof, or the pharmaceutical composition of embodiment 54.
59. The method of any one of embodiments 55-58, further comprising administering to the subject an effective amount of a second anti-cancer therapy, such as a chemotherapeutic agent, a receptor tyrosine kinase inhibitor, or a therapeutic antibody.
60. The method of any one of embodiments 55-59, wherein the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer.
61. A method of treating or preventing type 2 diabetes in a subject in need thereof, the method comprising administering to the subject an effective amount of the compound of any one of embodiments 1-53 or a pharmaceutical salt thereof, or the pharmaceutical composition of embodiment 54.
62. A method of treating or preventing a metabolic disease in a subject in need thereof, the method comprising administering to the subject an effective amount of the compound of any one of embodiments 1-53 or a pharmaceutical salt thereof, or the pharmaceutical composition of embodiment 54.
63. A method of inhibiting an aldehyde dehydrogenase in a subject in need thereof, comprising administering to the subject an effective amount of the compound of any one of embodiments 1-53 or a pharmaceutical salt thereof, or the pharmaceutical composition of embodiment 54.
64. A method of treating a disease or disorder associated with aldehyde dehydrogenase, preferably, a disease or disorder associated with aldehyde dehydrogenase isoform 1a3 (ALDH1a3) and/or 1a2 (ALDH1a2) in a subject in need thereof, comprising administering to the subject an effective amount of the compound of any one of embodiments 1-53 or a pharmaceutical salt thereof, or the pharmaceutical composition of embodiment 54.
65. The method of embodiment 64, wherein the disease or disorder is a proliferative disease or disorder or a metabolic disease or disorder.
66. A method of treating an endothelial cell or smooth muscle cell disease or disorder, such as pulmonary arterial hypertension or neointimal hyperplasia in a subject in need thereof, comprising administering to the subject an effective amount of the compound of any one of embodiments 1-53 or a pharmaceutical salt thereof, or the pharmaceutical composition of embodiment 54.
67. A method of antagonizing the retinoid pathway in a subject in need thereof, the method comprising administering to the subject an effective amount of the compound of any one of embodiments 1-53 or a pharmaceutical salt thereof, or the pharmaceutical composition of embodiment 54.
68. A method of treating a cancer in a subject in need thereof, the method comprising administering to the subject a therapeutically effective amount of the compound of any one of embodiments 1-53 or a pharmaceutical salt thereof, or the pharmaceutical composition of embodiment 54, in combination with an immunotherapy.
69. The method of embodiment 68, wherein the immunotherapy comprises administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.
70. The method of embodiment 68 or 69, wherein the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer.

71. A method of treating a cancer in a subject in need thereof, wherein the cancer is unresponsive to one or more immunotherapy or the subject has developed resistance to one or more immunotherapy, the method comprising administering to the subject a therapeutically effective amount of the compound of any one of embodiments 1-53 or a pharmaceutical salt thereof, or the pharmaceutical composition of embodiment 54, and optionally administering to the subject an immunotherapy.

72. The method of embodiment 71, wherein the cancer is unresponsive to treatment with anti-PD-1 or anti-PD-L1 antibodies.

73. The method of embodiment 71, wherein the subject has developed resistance to anti-PD-1 or anti-PD-L1 antibodies based treatment.

74. The method of any one of embodiments 71-73, comprising administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.

75. The method of any one of embodiments 71-74, wherein the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer.

76. A method of treating a disease or disorder associated with retinoid pathway activation in a subject in need thereof, the method comprising administering to the subject a therapeutically effective amount of the compound of any one of embodiments 1-53 or a pharmaceutical salt thereof, or the pharmaceutical composition of embodiment 54.

77. The method of embodiment 76, wherein the disease or disorder is associated with immune tolerance, induction of $T_{reg}$ cells and/or M2 macrophages, and/or effector T cell suppression.

78. The method of embodiment 77 or 78, wherein the disease or disorder is cancer.

79. The method of embodiment 78, wherein the cancer is a breast cancer, colorectal cancer, kidney cancer, ovarian cancer, gastric cancer, thyroid cancer, testicular cancer, cervical cancer, nasopharyngeal cancer, esophageal cancer, bile duct cancer, lung cancer, pancreatic cancer, prostate cancer, bone cancer, blood cancer, brain cancer, liver cancer, mesothelioma, melanoma, sarcoma, gastrointestinal stromal tumor, peripheral nerve sheath tumor, myeloma, and/or endometrial cancer.

80. The method of any one of embodiments 76-79, further comprising administering to the subject an immunotherapy (e.g., an immune checkpoint inhibitor).

81. The method of embodiment 80, wherein administering the immunotherapy comprises administering to the subject an anti-PD-1 antibody, anti-PD-L1 antibody, anti-CTLA4 antibody, IL-2, autologous T cell therapy, bispecific antibody therapy, anti-TGFβ antibody, a JAK/STAT inhibitor, or any combination thereof.

82. A method of male contraception in a subject in need thereof, the method comprising administering to the subject an effective amount of the compound of any one of embodiments 1-53 or a pharmaceutical salt thereof, or the pharmaceutical composition of embodiment 54.

83. A method of inhibiting $T_{reg}$ cell and/or M2 macrophage formation in a subject in need thereof, the method comprising administering to the subject an effective amount of the compound of any one of embodiments 1-53 or a pharmaceutical salt thereof, or the pharmaceutical composition of embodiment 54.

84. The method of embodiment 83, wherein the subject is characterized as having a cancer unresponsive to one or more immunotherapy or the subject has developed resistance to one or more immunotherapy.

REFERENCES

1 Hall, J. A., Grainger, J. R., Spencer, S. P. & Belkaid, Y. The role of retinoic acid in tolerance and immunity. *Immunity* 35, 13-22, doi: 10.1016/j.immuni.2011.07.002, S1074-7613 (11)00270-6 [pii] (2011).

2 Chen, Y. et al. Structure of the STRA6 receptor for retinol uptake. *Science* 353, doi:10.1126/science.aad8266 (2016).

3 Li, Y., Wongsiriroj, N. & Blaner, W. S. The multifaceted nature of retinoid transport and metabolism. Hepatobiliary Surg Nutr 3, 126-139, doi:10.3978/j.issn.2304-3881.2014.05.04 (2014).

4 Cheng, C., Michaels, J. & Scheinfeld, N. Alitretinoin: a comprehensive review. *Expert Opin Investig Drugs* 17, 437-443, doi:10.1517/13543784.17.3.437 (2008).

5 Meyskens, F. L., Jr., Goodman, G. E. & Alberts, D. S. 13-Cis-retinoic acid: pharmacology, toxicology, and clinical applications for the prevention and treatment of human cancer. *Crit Rev Oncol Hematol* 3, 75-101, doi:10.1016/s1040-8428 (85)80040-8 (1985).

6 Farjo, K. M., Moiseyev, G., Takahashi, Y., Crouch, R. K. & Ma, J. X. The 11-cis-retinol dehydrogenase activity of RDH10 and its interaction with visual cycle proteins. *Invest Ophthalmol Vis Sci* 50, 5089-5097, doi:10.1167/iovs.09-3797 (2009).

7 Sahu, B. & Maeda, A. Retinol Dehydrogenases Regulate Vitamin A Metabolism for Visual Function. *Nutrients* 8, doi:10.3390/nu8110746 (2016).

8 Kawaguchi, R., Zhong, M., Kassai, M., Ter-Stepanian, M. & Sun, H. Vitamin A Transport Mechanism of the Multitransmembrane Cell-Surface Receptor STRA6. *Membranes (Basel)* 5, 425-453, doi:10.3390/membranes5030425 (2015).

9 Kane, M. A., Bright, F. V. & Napoli, J. L. Binding affinities of CRBPI and CRBPII for 9-cis-retinoids. *Biochim Biophys Acta* 1810, 514-518, doi:10.1016/j.bbagen.2011.02.009 (2011).

10 Wang, X., Penzes, P. & Napoli, J. L. Cloning of a cDNA encoding an aldehyde dehydrogenase and its expression in *Escherichia coli*. Recognition of retinal as substrate. *J Biol Chem* 271, 16288-16293, doi: 10.1074/jbc.271.27.16288 (1996).

11 Duester, G. Retinoic acid synthesis and signaling during early organogenesis. *Cell* 134, 921-931, doi: 10.1016/j.cell.2008.09.002 (2008).

12 Liden, M. & Eriksson, U. Understanding retinol metabolism: structure and function of retinol dehydrogenases. *J Biol Chem* 281, 13001-13004, doi: 10.1074/jbc.R500027200 (2006).

13 Ziouzenkova, O. et al. Retinaldehyde represses adipogenesis and diet-induced obesity. *Nat Med* 13, 695-702, doi:10.1038/nm1587 (2007).

14 Belyaeva, O. V., Korkina, O. V., Stetsenko, A. V. & Kedishvili, N. Y. Human retinol dehydrogenase 13 (RDH13) is a mitochondrial short-chain dehydrogenase/reductase with a retinaldehyde reductase activity. *FEBS J* 275, 138-147, doi:10.1111/j.1742-4658.2007.06184.x (2008).

15 Napoli, J. L. A gene knockout corroborates the integral function of cellular retinol-binding protein in retinoid metabolism. *Nutr Rev* 58, 230-236, doi:10.1111/j.1753-4887.2000.tb01870.x (2000).

16 Pequerul, R. et al. Structural and kinetic features of aldehyde dehydrogenase 1A (ALDH1A) subfamily members, cancer stem cell markers active in retinoic acid biosynthesis. *Arch Biochem Biophys* 681, 108256, doi:10.1016/j.abb.2020.108256 (2020).

17 Heyman, R. A. et al. 9-cis retinoic acid is a high affinity ligand for the retinoid X receptor. *Cell* 68, 397-406, doi: 10.1016/0092-8674 (92)90479-v (1992).

18 Kane, M. A., Chen, N., Sparks, S. & Napoli, J. L. Quantification of endogenous retinoic acid in limited biological samples by LC/MS/MS. *Biochem J* 388, 363-369, doi: 10.1042/BJ20041867 (2005).

19 Isoherranen, N. & Zhong, G. Biochemical and physiological importance of the CYP26 retinoic acid hydroxylases. *Pharmacol Ther* 204, 107400, doi: 10.1016/j.pharmthera.2019.107400 (2019).

20 Allenby, G. et al. Binding of 9-cis-retinoic acid and all-trans-retinoic acid to retinoic acid receptors alpha, beta, and gamma. Retinoic acid receptor gamma binds all-trans-retinoic acid preferentially over 9-cis-retinoic acid. *J Biol Chem* 269, 16689-16695 (1994).

21 Kane, M. A. Analysis, occurrence, and function of 9-cis-retinoic acid. *Biochim Biophys Acta* 1821, 10-20, doi:10.1016/j.bbalip.2011.09.012 (2012).

22 You, C. S., Parker, R. S., Goodman, K. J., Swanson, J. E. & Corso, T. N. Evidence of cis-trans isomerization of 9-cis-beta-carotene during absorption in humans. *Am J Clin Nutr* 64, 177-183, doi:10.1093/ajcn/64.2.177 (1996).

23 Urbach, J. & Rando, R. R. Isomerization of all-trans-retinoic acid to 9-cis-retinoic acid. *Biochem J* 299 (Pt 2), 459-465, doi:10.1042/bj2990459 (1994).

24 Labrecque, J., Dumas, F., Lacroix, A. & Bhat, P. V. A novel isoenzyme of aldehyde dehydrogenase specifically involved in the biosynthesis of 9-cis and all-trans retinoic acid. BiochemJ305 (Pt 2), 681-684, doi: 10.1042/bj3050681 (1995).

25 Paterson, E. K., Ho, H., Kapadia, R. & Ganesan, A. K. 9-cis retinoic acid is the ALDH1A1 product that stimulates melanogenesis. *Exp Dermatol* 22, 202-209, doi: 10.1111/exd.12099 (2013).

26 Lin, M., Zhang, M., Abraham, M., Smith, S. M. & Napoli, J. L. Mouse retinal dehydrogenase 4 (RALDH4), molecular cloning, cellular expression, and activity in 9-cis-retinoic acid biosynthesis in intact cells. *J Biol Chem* 278, 9856-9861, doi:10.1074/jbc.M211417200 (2003).

27 Zhao, D. et al. NOTCH-induced aldehyde dehydrogenase 1A1 deacetylation promotes breast cancer stem cells. *J Clin Invest* 124, 5453-5465, doi: 10.1172/JC176611 (2014).

28 Feng, R. et al. Retinoic acid homeostasis through aldh1a2 and cyp26a1 mediates meiotic entry in Nile tilapia (*Oreochromis niloticus*). *Sci Rep* 5, 10131, doi: 10.1038/srep10131, [pii] (2015).

29 Yao, H. et al. CHD7 represses the retinoic acid synthesis enzyme ALDH1A3 during inner ear development. JCIInsight 3, doi:10.1172/jci.insight.97440 [pii] (2018).

30 Iwata, M. Retinoic acid production by intestinal dendritic cells and its role in T-cell trafficking. *Semin Immunol* 21, 8-13, doi:10.1016/j.smim.2008.09.002 (2009).

31 Yim, C. Y., Mao, P. & Spinella, M. J. Headway and hurdles in the clinical development of dietary phytochemicals for cancer therapy and prevention: lessons learned from vitamin A derivatives. AAPSJ16, 281-288, doi:10.1208/s12248-014-9562-2 (2014).

32 Yoshida, H. et al. Accelerated degradation of PML-retinoic acid receptor alpha (PML-RARA) oncoprotein by all-trans-retinoic acid in acute promyelocytic leukemia: possible role of the proteasome pathway. *Cancer Res* 56, 2945-2948 (1996).

33 Dupe, V. et al. A newborn lethal defect due to inactivation of retinaldehyde dehydrogenase type 3 is prevented by maternal retinoic acid treatment. *Proc Natl Acad Sci USA* 100, 14036-14041, doi:10.1073/pnas.2336223100 [pii] (2003).

34 Ghyselinck, N. B. et al. Role of the retinoic acid receptor beta (RARbeta) during mouse development. *IntJDev Biol* 41, 425-447 (1997).

35 Berenguer, M., Lancman, J. J., Cunningham, T. J., Dong, P. D. S. & Duester, G. Mouse but not zebrafish requires retinoic acid for control of neuromesodermal progenitors and body axis extension. *Dev Biol* 441, 127-131, doi:S0012-1606 (18)30290-2 [pii] 10.1016/j.ydbio.2018.06.019 (2018).

36 Hogarth, C. A., Amory, J. K. & Griswold, M. D. Inhibiting vitamin A metabolism as an approach to male contraception. Trends EndocrinolMetab 22, 136-144, doi:10.1016/j.tem.2011.01.001 (2011).

37 Duvic, M. et al. Topical treatment of cutaneous lesions of acquired immunodeficiency syndrome-related Kaposi sarcoma using alitretinoin gel: results of phase 1 and 2 trials. *Arch Dermatol* 136, 1461-1469, doi: 10.1001/archderm.136.12.1461 (2000).

38 Evans, T. Regulation of hematopoiesis by retinoid signaling. *Exp Hematol* 33, 1055-1061, doi:10.1016/j.exphem.2005.06.007 (2005).

39 Maldonado, R. A. & von Andrian, U. H. How tolerogenic dendritic cells induce regulatory T cells. Advances in immunology 108, 111-165, doi: 10.1016/B978-0-12-380995-7.00004-5 (2010).

40 Mucida, D., et al. Reciprocal TH17 ad regulatory T cell differnetiation mediated by retinoic acid. *Science* 317 (5835): p. 1958-68 (2007).

41 Galvin, K. C. et al. Blocking retinoic acid receptor-alpha enhances the efficacy of a dendritic cell vaccine against tumours by suppressing the induction of regulatory T cells. *Cancer Immunol Immunother* 62, 1273-1282, doi:10.1007/s00262-013-1432-8 (2013).

42 Pinzon-Charry, A. et al. Numerical and functional defects of blood dendritic cells in early- and late-stage 43. Scarlett, U. K. et al. Ovarian cancer progression is controlled by phenotypic changes in dendritic cells. *The Journal of experimental medicine* 209, 495-506, doi: 10.1084/jem.20111413 (2012).
44. Norian, L. A. et al. Tumor-infiltrating regulatory dendritic cells inhibit CD8+ T cell function via L-arginine metabolism. *Cancer research* 69, 3086-3094, doi: 10.1158/0008-5472.CAN-08-2826 (2009).
45. Tesone, A. J., Svoronos, N., Allegrezza, M. J. & Conejo-Garcia, J. R. Pathological mobilization and activities of dendritic cells in tumor-bearing hosts: challenges and opportunities for immunotherapy of cancer. Frontiers in immunology 4, 435, doi: 10.3389/fimmu.2013.00435 (2013).
46. Schindler, M., Drozdenko, G., Kuhl, A. A. & Worm, M. Immunomodulation in patients with chronic hand eczema treated with oral alitretinoin. *Int Arch Allergy Immunol* 165, 18-26, doi:10.1159/000365659 (2014).
47. Ruzicka, T. et al. Efficacy and safety of oral alitretinoin (9-cis retinoic acid) in patients with severe chronic hand eczema refractory to topical corticosteroids: results of a randomized, double-blind, placebo-controlled, multicentre trial. BrJDermatol 158, 808-817, doi: 10.1111/j.1365-2133.2008.08487.x (2008).
48. Alvarez, R. D. et al. The efficacy of 9-cis-retinoic acid (aliretinoin) as a chemopreventive agent for cervical dysplasia: results of a randomized double-blind clinical trial. *Cancer Epidemiol Biomarkers Prev* 12, 114-119 (2003).
49. Plaisancie, J. et al. Incomplete penetrance of biallelic ALDH1A3 mutations. *Eur J Med Genet* 59, 215-218, doi:10.1016/j.ejmg.2016.02.004, S1769-7212 (16) 30015-5 [pii] (2016).
50. Minkina, A. et al. Retinoic acid signaling is dispensable for somatic development and function in the mammalian ovary. *Dev Biol* 424, 208-220, doi:S0012-1606 (16)30849-1 [pii]10.1016/j.ydbio.2017.02.015 (2017).
51. Wang, S. et al. ALDH1A3 correlates with luminal phenotype in prostate cancer. *Tumour Biol* 39, 1010428317703652, doi:10.1177/1010428317703652 (2017).
52. Eirew, P. et al. Aldehyde dehydrogenase activity is a biomarker of primitive normal human mammary luminal cells. *Stem Cells* 30, 344-348, doi:10.1002/stem.1001 (2012).
53. Bowles, J. et al. ALDH1A1 provides a source of meiosis-inducing retinoic acid in mouse fetal ovaries. *Nat Commun* 7, 10845, doi: 10.1038/ncomms10845 [pii] (2016).
54. Blanco-Gandia, M. C. & Rodriguez-Arias, M. Pharmacological treatments for opiate and alcohol addiction: a historical perspective of the last 50 years. *Eur J Pharmacol*, doi:S0014-2999 (18)30451-5 [pii] 10.1016/j.ejphar.2018.08.007 (2018).
55. Nechushtan, H. et al. A phase IIb trial assessing the addition of disulfiram to chemotherapy for the treatment of metastatic non-small cell lung cancer. *Oncologist* 20, 366-367, doi:10.1634/theoncologist.2014-0424 [pii] (2015).
56. Heller, C. G., Moore, D. J. & Paulsen, C. A. Suppression of spermatogenesis and chronic toxicity in men by a new series of bis(dichloroacetyl) diamines. *Toxicol Appl Pharmacol* 3, 1-11, doi:10.1016/0041-008x(61)90002-3 (1961).
57. Niederreither, K., Subbarayan, V., Dolle, P. & Chambon, P. Embryonic retinoic acid synthesis is essential for early mouse post-implantation development. *Nat Genet* 21, 444-448, doi:10.1038/7788 (1999).
58. <Ryckebusch2008-LACZ stain of Aldh1a2 and deficiency in heart development.pdf>.
59. Mucida, D. et al. Reciprocal TH17 and regulatory T cell differentiation mediated by retinoic acid. *Science* 317, 256-260, doi: 10.1126/science.1145697 (2007).
60. Lee, S. W. et al. Cutting edge: 4-1BB controls regulatory activity in dendritic cells through promoting optimal expression of retinal dehydrogenase. *J Immunol* 189, 2697-2701, doi:10.4049/jimmunol.1201248 [pii] (2012).
61. Zhu, B. et al. IL-4 and retinoic acid synergistically induce regulatory dendritic cells expressing Aldh1a2. *J Immunol* 191, 3139-3151, doi:10.4049/jimmunol.1300329 [pii] (2013).
62. Yokota-Nakatsuma, A., Ohoka, Y., Takeuchi, H., Song, S. Y. & Iwata, M. Beta 1-integrin ligation and TLR ligation enhance GM-CSF-induced ALDH1A2 expression in dendritic cells, but differentially regulate their anti-inflammatory properties. *Sci Rep* 6, 37914, doi: 10.1038/srep37914 (2016).
63. Zaman, T. S. et al. Notch Balances Th17 and Induced Regulatory T Cell Functions in Dendritic Cells by Regulating Aldh1a2 Expression. *J Immunol* 199, 1989-1997, doi:10.4049/jimmunol.1700645 (2017).
64. Strainic, M. G. et al. CD55 Is Essential for CD103(+) Dendritic Cell Tolerogenic Responses that Protect against Autoimmunity. *Am J Pathol* 189, 1386-1401, doi:10.1016/j.ajpath.2019.04.008 (2019).
65. Guilliams, M. et al. Skin-draining lymph nodes contain dermis-derived CD103(-) dendritic cells that constitutively produce retinoic acid and induce Foxp3(+) regulatory T cells. *Blood* 115, 1958-1968, doi: 10.1182/blood-2009-09-245274 [pii] (2010).
66. Manicassamy, S. et al. Toll-like receptor 2-dependent induction of vitamin A-metabolizing enzymes in dendritic cells promotes T regulatory responses and inhibits autoimmunity. *NatMed* 15, 401-409, doi:10.1038/nm.1925 (2009).
67. <Maniccasammy2010-Beta-cat induces Raldh to promote Treg.pdf>.
68. Lombardi, V., Speak, A. O., Kerzerho, J., Szely, N. & Akbari, O. CD8alpha(+)beta(-) and CD8alpha(+)beta (+) plasmacytoid dendritic cells induce Foxp3(+) regulatory T cells and prevent the induction of airway hyper-reactivity. *Mucosal Immunol* 5, 432-443, doi: 10.1038/mi.2012.20 [pii] (2012).
69. Xu, Y. et al. In Vivo Generation of Gut-Homing Regulatory T Cells for the Suppression of Colitis. *J Immunol* 202, 3447-3457, doi: 10.4049/jimmunol.1800018 (2019).
70. Yang, Y. et al. Tolerogenic properties of CD206+ macrophages appeared in the sublingual mucosa after repeated antigen-painting. *Int Immunol*, doi:10.1093/intimm/dxaa014 (2020).
71. Soroosh, P. et al. Lung-resident tissue macrophages generate Foxp3+ regulatory T cells and promote airway tolerance. *J Exp Med* 210, 775-788, doi: 10.1084/jem.20121849 (2013).
72. Gundra, U. M. et al. Alternatively activated macrophages derived from monocytes and tissue macrophages are phenotypically and functionally distinct. *Blood* 123, e110-122, doi: 10.1182/blood-2013-08-520619 (2014).

73 Denning, T. L., Wang, Y. C., Patel, S. R., Williams, I. R. & Pulendran, B. Lamina propria macrophages and dendritic cells differentially induce regulatory and interleukin 17-producing T cell responses. *Nat Immunol* 8, 1086-1094, doi:10.1038/ni1511 (2007).
74 Chang, Y. C. et al. Epigenetic control of MHC class II expression in tumor-associated macrophages by decoy receptor 3. *Blood* 111, 5054-5063, doi: 10.1182/blood-2007-12-130609 (2008).
75 Spiegl, N., Didichenko, S., McCaffery, P., Langen, H. & Dahinden, C. A. Human basophils activated by mast cell-derived IL-3 express retinaldehyde dehydrogenase-II and produce the immunoregulatory mediator retinoic acid. Blood 112, 3762-3771, doi: 10.1182/blood-2008-01-135251 [pii] (2008).
76 Broadhurst, M. J. et al. Upregulation of retinal dehydrogenase 2 in alternatively activated macrophages during retinoid-dependent type-2 immunity to helminth infection in mice. *PLoS Pathog* 8, e1002883, doi: 10.1371/journal.ppat.1002883 (2012).
77 Kannan, Y. et al. TPL-2 Regulates Macrophage Lipid Metabolism and M2 Differentiation to Control TH2-Mediated Immunopathology. *PLoSPathog* 12, e1005783, doi:10.1371/journal.ppat.1005783 (2016).
78 Kim, E. W. et al. Vitamin A Metabolism by Dendritic Cells Triggers an Antimicrobial Response against *Mycobacterium tuberculosis.* mSphere 4, doi:10.1128/mSphere.00327-19 (2019).
79 Zheng, J. et al. Radiation and host retinoic acid signaling promote the induction of gut-homing donor T cells after allogeneic hematopoietic stem cell transplantation. *Am J Transplant* 20, 64-74, doi:10.1111/ajt.15501 (2020).
80 Thangavelu, G. et al. Dendritic Cell Expression of Retinal Aldehyde Dehydrogenase-2 Controls Graft-versus-Host Disease Lethality. *JImmunol* 202, 2795-2805, doi: 10.4049/jimmunol.1800899 (2019).
81 Styrkarsdottir, U. et al. Severe osteoarthritis of the hand associates with common variants within the ALDH1A2 gene and with rare variants at 1p31. *Nat Genet* 46, 498-502, doi: 10.1038/ng.2957 (2014).
82 Sun, J. et al. Histone demethylase LSD1 is critical for endochondral ossification during bone fracture healing. *Sci Adv* 6, doi: 10.1126/sciadv.aaz1410 (2020).
83 Hughes, N. E. et al. Identification of potent and selective retinoic acid receptor gamma (RARgamma) antagonists for the treatment of osteoarthritis pain using structure based drug design. *BioorgMed Chem Lett* 26, 3274-3277, doi:10.1016/j.bmcl.2016.05.056 (2016).
84 Chen, Y. et al. Structural Basis of ALDH1A2 Inhibition by Irreversible and Reversible Small Molecule Inhibitors. *ACS Chem Biol* 13, 582-590, doi:10.1021/acschembio.7b00685 (2018).
85 Amory, J. K. et al. Suppression of spermatogenesis by bisdichloroacetyldiamines is mediated by inhibition of testicular retinoic acid biosynthesis. *JAndrol* 32, 111-119, doi:10.2164/jandrol.110.010751 (2011).
86 Ginestier, C. et al. ALDH1 is a marker of normal and malignant human mammary stem cells and a predictor of poor clinical outcome. *Cell Stem Cell* 1, 555-567, doi:10.1016/j.stem.2007.08.014, S1934-5909 (07) 00133-6 [pii] (2007).
87 Marcato, P. et al. Aldehyde dehydrogenase activity of breast cancer stem cells is primarily due to isoform ALDH1A3 and its expression is predictive of metastasis. *Stem Cells* 29, 32-45, doi:10.1002/stem.563 (2011).
88 Devalaraja, S. et al. Tumor-Derived Retinoic Acid Regulates Intratumoral Monocyte Differentiation to Promote Immune Suppression. *Cell*, doi:10.1016/j.cell.2020.02.042 (2020).
89 Luo, Y. et al. ALDH1A isozymes are markers of human melanoma stem cells and potential therapeutic targets. *Stem Cells* 30, 2100-2113, doi: 10.1002/stem.1193 (2012).
90 Perez-Alea, M. et al. ALDH1A3 is epigenetically regulated during melanocyte transformation and is a target for melanoma treatment. *Oncogene* 36, 5695-5708, doi: 10.1038/onc.2017.160 [pii](2017).
91 Sullivan, K. E., Rojas, K., Cerione, R. A., Nakano, I. & Wilson, K. F. The stem cell/cancer stem cell marker ALDH1A3 regulates the expression of the survival factor tissue transglutaminase, in mesenchymal glioma stem cells. Oncotarget 8, 22325-22343, doi:10.18632/oncotarget.16479 [pii] (2017).
92 Flahaut, M. et al. Aldehyde dehydrogenase activity plays a Key role in the aggressive phenotype ofneuroblastoma. *BMC Cancer* 16, 781, doi:10.1186/s12885-016-2820-1, 10.1186/s12885-016-2820-1 [pii] (2016).
93 Mao, P. et al. Mesenchymal glioma stem cells are maintained by activated glycolytic metabolism involving aldehyde dehydrogenase 1A3. *Proc Natl Acad Sci USA* 110, 8644-8649, doi:10.1073/pnas.1221478110 [pii] (2013).
94 Wu, W. et al. Aldehyde dehydrogenase 1A3 (ALDH1A3) is regulated by autophagy in human glioblastoma cells. *Cancer Lett* 417, 112-123, doi:S0304-3835 (18)30009-0 [pii]10.1016/j.canlet.2017.12.036 (2018).
95 Zhang, W. et al. ALDH1A3: A Marker of Mesenchymal Phenotype in Gliomas Associated with Cell Invasion. *PLoS One* 10, e0142856, doi:10.1371/journal.pone.0142856, PONE-D-15-27556 [pii] (2015).
96 Cheng, P. et al. FOXD1-ALDH1A3 Signaling Is a Determinant forthe Self-Renewal and Tumorigenicity of Mesenchymal Glioma Stem Cells. *Cancer Res* 76, 7219-7230, doi:0008-5472.CAN-15-2860 [pii] 10.1158/0008-5472.CAN-15-2860 (2016).
97 Ni, W. et al. High expression of ALDH1A3 might independently influence poor progression-free and overall survival in patients with glioma via maintaining glucose uptake and lactate production. *Cell BiolInt*, doi: 10.1002/cbin.11257 (2019).
98 Shao, C. et al. Essential role of aldehyde dehydrogenase 1A3 for the maintenance of non-small cell lung cancer stem cells is associated with the STAT3 pathway. *Clin Cancer Res* 20, 4154-4166, doi: 10.1158/1078-0432.CCR-13-3292 [pii] (2014).
99 Yun, X. et al. Targeting USP22 Suppresses Tumorigenicity and Enhances Cisplatin Sensitivity Through ALDH1A3 Downregulation in Cancer-Initiating Cells from Lung Adenocarcinoma. *Mol Cancer Res* 16, 1161-1171, doi:10.1158/1541-7786.MCR-18-0042 [pii] (2018).
100 Rebollido-Rios, R. et al. Dual disruption of aldehyde dehydrogenases 1 and 3 promotes functional changes in the glutathione redox system and enhances chemosensitivity in nonsmall cell lung cancer. *Oncogene*, doi: 10.1038/s41388-020-1184-9 (2020).
101 Jia, J. et al. An integrated transcriptome and epigenome analysis identifies a novel candidate gene for pancreatic cancer. BMCMed Genomics 6, 33, doi: 10.1186/1755-8794-6-33 [pii] (2013).

102 Kim, I. G., Lee, J. H., Kim, S. Y., Kim, J. Y. & Cho, E. W. Fibulin-3 negatively regulates ALDH1 via c-MET suppression and increases gamma-radiation-induced sensitivity in some pancreatic cancer cell lines. *Biochem Biophys Res Commun* 454, 369-375, doi: 10.1016/j.bbrc.2014.10.084, S0006-291X(14)01893-2 [pii] (2014).

103 Golubovskaya, V. et al. Down-regulation of ALDH1A3, CD44 or MDR1 sensitizes resistant cancer cells to FAK autophosphorylation inhibitor Y15. *JCancer Res Clin Oncol* 141, 1613-1631, doi:10.1007/s00432-015-1924-3 (2015).

104 Lee, S., Bae, J. S., Jung, C. K. & Chung, W. Y. Extensive lymphatic spread of papillary thyroid microcarcinoma is associated with an increase in expression of genes involved in epithelial-mesenchymal transition and cancer stem cell-like properties. CancerMed 8, 6528-6537, doi:10.1002/cam4.2544 (2019).

105 Canino, C. et al. A STAT3-NFkB/DDIT3/CEBPbeta axis modulates ALDH1A3 expression in chemoresistant cell subpopulations. *Oncotarget* 6, 12637-12653, doi:3703 [pii]10.18632/oncotarget.3703 (2015).

106 Cortes-Dericks, L., Froment, L., Boesch, R., Schmid, R. A. & Karoubi, G. Cisplatin-resistant cells in malignant pleural mesothelioma cell lines show ALDH(high) CD44(+) phenotype and sphere-forming capacity. *BMC Cancer* 14, 304, doi:10.1186/1471-2407-14-304 [pii] (2014).

107 di Martino, S. et al. HSP90 inhibition alters the chemotherapy-driven rearrangement of the oncogenic secretome. *Oncogene* 37, 1369-1385, doi:10.1038/s41388-017-0044-8, 10.1038/s41388-017-0044-8 [pii] (2018).

108 Casanova-Salas, I. et al. MiR-187 Targets the Androgen-Regulated Gene ALDH1A3 in Prostate Cancer. *PLoS One* 10, e0125576, doi:10.1371/journal.pone.0125576, PONE-D-14-46743 [pii](2015).

109 Kashii-Magaribuchi, K. et al. Induced Expression of Cancer Stem Cell Markers ALDH1A3 and Sox-2 in Hierarchical Reconstitution of Apoptosis-resistant Human Breast Cancer Cells. *Acta Histochem Cytochem* 49, 149-158, doi: 10.1267/ahc.16031, JST.JSTAGE/ahc/16031 [pii] (2016).

110 Marcato, P. et al. Aldehyde dehydrogenase 1A3 influences breast cancer progression via differential retinoic acid signaling. *Mol Oncol* 9, 17-31, doi: 10.1016/j.molonc.2014.07.010, S1574-7891 (14) 00165-3 [pii] (2015).

111 Thomas, M. L. et al. Citral reduces breast tumor growth by inhibiting the cancer stem cell marker ALDH1A3. *Mol Oncol* 10, 1485-1496, doi:S1574-7891 (16)30085-0 [pii]10.1016/j.molonc.2016.08.004 (2016).

112 Yamashita, D. et al. Identification of ALDH1A3 as a viable therapeutic target in breast cancer metastasis-initiating cells. *Mol Cancer Ther*, doi: 10.1158/1535-7163.MCT-19-0461 (2020).

113 Gui, S. et al. p53 functional states are associated with distinct aldehyde dehydrogenase transcriptomic signatures. *Sci Rep* 10, 1097, doi:10.1038/s41598-020-57758-5 (2020).

114 Chen, M. H. et al. ALDH1A3, the Major Aldehyde Dehydrogenase Isoform in Human Cholangiocarcinoma Cells, Affects Prognosis and Gemcitabine Resistance in Cholangiocarcinoma Patients. *Clin Cancer Res* 22, 4225-4235, doi: 10.1158/1078-0432.CCR-15-1800 [pii] (2016).

115 Zhang, W. et al. Genome-wide DNA methylation profiling identifies ALDH1A3 promoter methylation as a prognostic predictor in G-CIMP-primary glioblastoma. *Cancer Lett* 328, 120-125, doi:10.1016/j.canlet.2012.08.033, S0304-3835 (12)00534-4 [pii] (2013).

116 Yang, Z. L. et al. Positive ALDH1A3 and negative GPX3 expressions are biomarkers for poor prognosis of gallbladder cancer. *Dis Markers* 35, 163-172, doi: 10.1155/2013/187043 (2013).

117 Trasino, S. E., Harrison, E. H. & Wang, T. T. Androgen regulation of aldehyde dehydrogenase 1A3 (ALDH1A3) in the androgen-responsive human prostate cancer cell line LNCaP. *Exp Biol Med* (Maywood) 232, 762-771, doi:232/6/762 [pii] (2007).

118 Kim-Muller, J. Y. et al. Aldehyde dehydrogenase 1a3 defines a subset of failing pancreatic beta cells in diabetic mice. *Nat Commun* 7, 12631, doi: 10.1038/ncomms12631 [pii] (2016).

119 Wang, Y. et al. Paraneoplastic beta Cell Dedifferentiation in non-diabetic Patients with Pancreatic Cancer. *J Clin Endocrinol Metab*, doi:10.1210/clinem/dgz224 (2019).

120 Davey, J. R. et al. Intravascular Follistatin gene delivery improves glycemic control in a mouse model of type 2 diabetes. *FASEB J*, doi: 10.1096/fj.201802059RRR (2020).

121 Wang, Y. et al. Paraneoplastic beta Cell Dedifferentiation in Nondiabetic Patients with Pancreatic Cancer. *J Clin Endocrinol Metab* 105, doi: 10.1210/clinem/dgz224 (2020).

122 Shimamura, M., Karasawa, H., Sakakibara, S. & Shinagawa, A. Raldh3 expression in diabetic islets reciprocally regulates secretion of insulin and glucagon from pancreatic islets. *Biochem Biophys Res Commun* 401, 79-84, doi:10.1016/j.bbrc.2010.09.013, S0006-291X(10)01688-8 [pii](2010).

123 Nagai, N., Murao, T., Okamoto, N. & Ito, Y. Disulfiram reduces elevated blood glucose levels in Otsuka Long-Evans Tokushima Fatty (OLETF) rats, a model of type 2 diabetes. *J Oleo Sci* 58, 485-490, doi: 10.5650/jos.58.485 (2009).

124 Xie, X. et al. *ALDH1A3 Regulations of Matricellular Proteins Promote Vascular Smooth Muscle Cell Proliferation*. *iScience* 19, 872-882, doi:10.1016/j.isci.2019.08.044 (2019).

125 Moretti, A. et al. Crystal structure of human aldehyde dehydrogenase 1A3 complexed with NAD+ and retinoic acid. *Sci Rep* 6, 35710, doi: 10.1038/srep35710 [pii] (2016).

126 Gibb, Z., Lambourne, S. R., Curry, B. J., Hall, S. E. & Aitken, R. J. Aldehyde Dehydrogenase Plays a Pivotal Role in the Maintenance of Stallion Sperm Motility. *Biol Reprod* 94, 133, doi:10.1095/biolreprod.116.140509 [pii] (2016).

127 Schilderink, R. et al. The SCFA butyrate stimulates the epithelial production of retinoic acid via inhibition of epithelial HDAC. Am JPhysiol Gastrointest Liver Physiol 310, G1138-1146, doi:10.1152/ajpgi.00411.2015 (2016).

128 Jang, J. H. et al. Aldehyde dehydrogenase 3A1 protects airway epithelial cells from cigarette smoke-induced DNA damage and cytotoxicity. *Free Radic Biol Med* 68, 80-86, doi:10.1016/j.freeradbiomed.2013.11.028, S0891-5849 (13)01533-5 [pii] (2014).

129 Kurth, I. et al. Cancer stem cell related markers of radioresistance in head and neck squamous cell carcinoma. *Oncotarget* 6, 34494-34509, doi:10.18632/oncotarget.5417 [pii] (2015).

130 Wu, W. et al. Lipid Peroxidation Plays an Important Role in Chemotherapeutic Effects of Temozolomide and the Development of Therapy Resistance in Human Glioblastoma. Transl Oncol 13, 100748, doi: 10.1016/j.tranon.2020.100748 (2020).

131 <Tamori2018-methyglyoxal detox and Aldh1a3 strongly correlated in grade 3 basal breast cancers.pdf>.

132 Coyle, K. M. et al. Breast cancer subtype dictates DNA methylation and ALDH1A3-mediated expression of tumor suppressor RARRES1. *Oncotarget* 7, 44096-44112, doi:10.18632/oncotarget.9858 [pii] (2016).

133 Shiokawa, A., Kotaki, R., Takano, T., Nakajima-Adachi, H. & Hachimura, S. Mesenteric lymph node CD11b(-) CD103(+) PD-L1 (High) dendritic cells highly induce regulatory T cells. Immunology 152, 52-64, doi:10.1111/imm.12747 (2017).

134 Hong, Y. et al. beta-catenin promotes regulatory T-cell responses in tumors by inducing vitamin A metabolism in dendritic cells. *Cancer Res* 75, 656-665, doi:10.1158/0008-5472.CAN-14-2377 (2015).

135 Swoboda, A. & Nanda, R. Immune Checkpoint Blockade for Breast Cancer. Cancer treatment and research 173, 155-165, doi:10.1007/978-3-319-70197-4_10 (2018).

136 Plitas, G. et al. Regulatory T Cells Exhibit Distinct Features in Human Breast Cancer. *Immunity* 45, 1122-1134, doi:10.1016/j.immuni.2016.10.032 (2016).

137 Chen, L. et al. Rejection of metastatic 4T1 breast cancer by attenuation of Treg cells in combination with immune stimulation. *Mol Ther* 15, 2194-2202, doi: S1525-0016 (16)32736-8 [pii]10.1038/sj.mt.6300310 (2007).

138 Jang, J. E. et al. Crosstalk between Regulatory T Cells and Tumor-Associated Dendritic Cells Negates Antitumor Immunity in Pancreatic Cancer. *Cell reports* 20, 558-571, doi:10.1016/j.celrep.2017.06.062 (2017).

139 Marabelle, A. et al. Depleting tumor-specific Tregs at a single site eradicates disseminated tumors. *J Clin Invest* 123, 2447-2463, doi:64859 [pii]10.1172/JC164859 (2013).

140 Peggs, K. S., Quezada, S. A., Chambers, C. A., Korman, A. J. & Allison, J. P. Blockade of CTLA-4 on both effector and regulatory T cell compartments contributes to the antitumor activity of anti-CTLA-4 antibodies. *J Exp Med* 206, 1717-1725, doi: 10.1084/jem.20082492 [pii] (2009).

141 Koppaka, V. et al. Aldehyde dehydrogenase inhibitors: a comprehensive review of the pharmacology, mechanism of action, substrate specificity, and clinical application. *Pharmacol Rev* 64, 520-539, doi:10.1124/pr.111.005538 [pii] (2012).

142 Moreb, J. S. et al. The enzymatic activity of human aldehyde dehydrogenases 1A2 and 2 (ALDH1A2 and ALDH2) is detected by Aldefluor, inhibited by diethylaminobenzaldehyde and has significant effects on cell proliferation and drug resistance. *Chem Biol Interact* 195, 52-60, doi:10.1016/j.cbi.2011.10.007, S0009-2797 (11)00311-5 [pii] (2012).

143 Khanna, M. et al. Discovery of a novel class of covalent inhibitor for aldehyde dehydrogenases. *J Biol Chem* 286, 43486-43494, doi:10.1074/jbc.M111.293597 [pii] (2011).

144 Yasgar, A. et al. A High-Content Assay Enables the Automated Screening and Identification of Small Molecules with Specific ALDH1A1-Inhibitory Activity. *PLoS One* 12, e0170937, doi:10.1371/journal.pone.0170937, PONE-D-16-39942 [pii] (2017).

145 Kim, J. Y. et al. Disulfiram targets cancer stem-like properties and the HER2/Akt signaling pathway in HER2-positive breast cancer. *Cancer Lett* 379, 39-48, doi:10.1016/j.canlet.2016.05.026, S0304-3835 (16) 30339-1 [pii] (2016).

146 Buchman, C. D., Mahalingan, K. K. & Hurley, T. D. Discovery of a series of aromatic lactones as ALDH1/2-directed inhibitors. *Chem Biol Interact* 234, 38-44, doi:10.1016/j.cbi.2014.12.038 (2015).

147 Chefetz, I. et al. A Pan-ALDH1A Inhibitor Induces Necroptosis in Ovarian Cancer Stem-like Cells. *Cell Rep* 26, 3061-3075 e3066, doi:10.1016/j.celrep.2019.02.032 (2019).

148 Condello, S. et al. beta-Catenin-regulated ALDH1A1 is a target in ovarian cancer spheroids. Oncogene 34, 2297-2308, doi:10.1038/onc.2014.178 (2015).

149 Jimenez, R. et al. Inhibitors of aldehyde dehydrogenases of the 1A subfamily as putative anticancer agents: Kinetic characterization and effect on human cancer cells. *Chem Biol Interact* 306, 123-130, doi:10.1016/j.cbi.2019.04.004 (2019).

150 Morgan, C. A. & Hurley, T. D. Characterization of two distinct structural classes of selective aldehyde dehydrogenase 1A1 inhibitors. *J Med Chem* 58, 1964-1975, doi:10.1021/jm501900s (2015).

151 Liang, D. et al. Discovery of coumarin-based selective aldehyde dehydrogenase 1A1 inhibitors with glucose metabolism improving activity. *Eur J Med Chem* 187, 111923, doi:10.1016/j.ejmech.2019.111923 (2020).

152 Huddle, B. C. et al. Structure-Based Optimization of a Novel Class of Aldehyde Dehydrogenase 1A (ALDH1A) Subfamily-Selective Inhibitors as Potential Adjuncts to Ovarian Cancer Chemotherapy. *J Med Chem* 61, 8754-8773, doi:10.1021/acs.jmedchem.8b00930 (2018).

153 Yang, S. M. et al. Discovery of Orally Bioavailable, Quinoline-Based Aldehyde Dehydrogenase 1A1 (ALDH1A1) Inhibitors with Potent Cellular Activity. *J Med Chem* 61, 4883-4903, doi:10.1021/acs.jmedchem.8b00270 (2018).

154 Kimble-Hill, A. C., Parajuli, B., Chen, C. H., Mochly-Rosen, D. & Hurley, T. D. Development of selective inhibitors for aldehyde dehydrogenases based on substituted indole-2,3-diones. *J Med Chem* 57, 714-722, doi:10.1021/jm401377v (2014).

155 Fan, X. et al. Targeted disruption of Aldh1a1 (Raldh1) provides evidence for a complex mechanism of retinoic acid synthesis in the developing retina. *Mol Cell Biol* 23, 4637-4648 (2003).

156 Bowles, J. et al. Male-specific expression of Aldh1a1 in mouse and chicken fetal testes: implications for retinoid balance in gonad development. Dev Dyn 238, 2073-2080, doi:10.1002/dvdy.22024 (2009).

157 Levi, B. P., Yilmaz, O. H., Duester, G. & Morrison, S. J. Aldehyde dehydrogenase la1 is dispensable for stem cell function in the mouse hematopoietic and nervous systems. *Blood* 113, 1670-1680, doi: 10.1182/blood-2008-05-156752 [pii] (2009).

158 Chute, J. P. et al. Inhibition of aldehyde dehydrogenase and retinoid signaling induces the expansion of human hematopoietic stem cells. *Proc Natl Acad Sci USA* 103, 11707-11712, doi:0603806103 [pii]10.1073/pnas.0603806103 (2006).

159 Cooper, T. T. et al. Inhibition of Aldehyde Dehydrogenase-Activity Expands Multipotent Myeloid Progenitor Cells with Vascular Regenerative Function. *Stem Cells* 36, 723-736, doi:10.1002/stem.2790 (2018).

160 Arnold, S. L. et al. Importance of ALDH1A enzymes in determining human testicular retinoic acid concentrations. *JLipid Res* 56, 342-357, doi:10.1194/jlr.M054718 [pii] (2015).

161 Kiefer, F. W. et al. Retinaldehyde dehydrogenase 1 regulates a thermogenic program in white adipose tissue. *NatMed* 18, 918-925, doi:10.1038/nm.2757 [pii] (2012).

162 Kim, J. I. et al. Aldehyde dehydrogenase la1 mediates a GABA synthesis pathway in midbrain dopaminergic neurons. *Science* 350, 102-106, doi: 10.1126/science.aac4690, 350/6256/102 [pii](2015).

163 Lassen, N. et al. Multiple and additive functions of ALDH3A1 and ALDH1A1: cataract phenotype and ocular oxidative damage in Aldh3a1(-/-)/Aldh1a1 (-/-) knock-out mice. *J Biol Chem* 282, 25668-25676, doi: 10.1074/jbc.M702076200 (2007).

164 Liu, Y. et al. ALDH1A1 mRNA expression in association with prognosis of triple-negative breast cancer. *Oncotarget* 6, 41360-41369, doi: 10.18632/oncotarget.6023 [pii] (2015).

165 Anthony, T. E. & Heintz, N. The folate metabolic enzyme ALDH1L1 is restricted to the midline of the early CNS, suggesting a role in human neural tube defects. *JComp Neurol* 500, 368-383, doi:10.1002/cne.21179 (2007).

166 Ducker, G. S. et al. Reversal of Cytosolic One-Carbon Flux Compensates for Loss of the Mitochondrial Folate Pathway. *CellMetab* 24, 640-641, doi: S1550-4131 (16)30491-0 [pii]10.1016/j.cmet.2016.09.011 (2016).

167 Pappa, A. et al. Human aldehyde dehydrogenase 3A1 inhibits proliferation and promotes survival of human corneal epithelial cells. *J Biol Chem* 280, 27998-28006, doi:M503698200 [pii]10.1074/jbc.M503698200 (2005).

168 Black, W. et al. Molecular mechanisms of ALDH3A1-mediated cellular protection against 4-hydroxy-2-nonenal. *Free Radic Biol Med* 52, 1937-1944, doi: 10.1016/j.freeradbiomed.2012.02.050, S0891-5849 (12)00156-6 [pii] (2012).

169 Rizzo, W. B., Lin, Z. & Carney, G. Fatty aldehyde dehydrogenase: genomic structure, expression and mutation analysis in Sjogren-Larsson syndrome. *Chem Biol Interact* 130-132, 297-307, doi:10.1016/s0009-2797 (00)00273-8 (2001).

170 Majera, D. et al. Targeting genotoxic and proteotoxic stress-response pathways in human prostate cancer by clinically available PARP inhibitors, vorinostat and disulfiram. *Prostate* 79, 352-362, doi:10.1002/pros.23741 (2019).

What is claimed is:

1. A compound of Formula (IV-C):

(IV-C)

or a pharmaceutically acceptable salt, stereoisomer, or tautomer thereof,
wherein:
$R^{20}$ is H, halo, or $C_{1-4}$ alkyl;
$R^{20'}$ is H, halo, or $C_{1-4}$ alkyl;
$R^{21}$ is H, halo, or $C_{1-4}$ alkyl;
$R^{21'}$ is H, halo, or $C_{1-4}$ alkyl; or
$R^{20}$ and $R^{20'}$, taken together with the carbon atoms to which they are attached, form a $C_{3-8}$ carbocyclyl or 3- to 8-membered heterocyclyl;
$R^{22}$ is halo, CN, $C_{1-6}$ alkyl, $C_{1-6}$ haloalkyl, $C_{1-6}$ cyanoalkyl, or carbocyclyl;
$R^{22'}$ is H, halo, $C_{1-6}$ alkyl, or $C_{1-6}$ haloalkyl; or
$R^{22}$ and $R^{22'}$, taken together with the carbon atoms to which they are attached, form a carbocyclyl, heterocyclyl, or heteroaryl, wherein the carbocyclyl, heterocyclyl, or heteroaryl is optionally substituted with one or more independently selected halo substituents;
each $R^{100}$ is independently halo, $C_{1-6}$ alkyl, $C_{1-6}$ haloalkyl, $C_{1-6}$ alkylene-carbocyclyl, or $C_{1-6}$ alkylene-heterocyclyl; or
two vicinal $R^{100}$, taken together with the carbon atoms to which they are attached, form a carbocyclyl or heterocyclyl, wherein the carbocyclyl or heterocyclyl is optionally substituted with one or more independently selected halo substituents; and
p is 0, 1, or 2.

2. The compound of claim 1, or a pharmaceutically acceptable salt, stereoisomer, or tautomer thereof, wherein:
(i) $R^{20}$ is H, halo, or $C_{1-4}$ alkyl;
$R^{20'}$ is H;
$R^{21}$ is H, halo, or $C_{1-4}$ alkyl; and
$R^{21'}$ is H; or
(ii) $R^{20}$ and $R^{20'}$, taken together with the carbon atoms to which they are attached, form a cyclopropyl or 5- or 6-membered heterocyclyl;
$R^{21}$ is H; and
$R^{21'}$ is H.

3. The compound of claim 1, or a pharmaceutically acceptable salt, stereoisomer, or tautomer thereof, wherein:
$R^{20}$ is H, F, or $CH_3$;
$R^{20'}$ is H;
$R^{21}$ is H, F, or $CH_3$; and
$R^{21'}$ is H.

4. The compound of claim 1, or a pharmaceutically acceptable salt, stereoisomer, or tautomer thereof, wherein:
$R^{20}$ is H;
$R^{20'}$ is H;
$R^{21}$ is H;
$R^{21'}$ is H;
$R^{22}$ is $C_{1-6}$ alkyl; and
$R^{22'}$ is $C_{1-6}$ alkyl.

5. The compound of claim 1, or a pharmaceutically acceptable salt, stereoisomer, or tautomer thereof, wherein:

R²⁰ is H;
R²⁰' is H;
R²¹ is H;
R²¹' is H;
R¹⁰⁰ is CH₂CF₃; and
p is 1.

6. The compound of claim 1, or a pharmaceutically acceptable salt, stereoisomer, or tautomer thereof, wherein:
R²² is C₁₋₆ alkyl;
R¹⁰⁰ is CH₂CF₃; and
p is 1.

7. The compound of claim 1, wherein the compound is of Formula (IV-D):

(IV-D)

or a pharmaceutically acceptable salt, stereoisomer, or tautomer thereof,
wherein:
R²² is halo, CN, C₁₋₆ alkyl, C₁₋₆ haloalkyl, C₁₋₆ cyanoalkyl, or carbocyclyl;
R²²' is H, halo, C₁₋₆ alkyl, or C₁₋₆ haloalkyl; and
each R¹⁰⁰ is independently halo, C₁₋₆ alkyl, C₁₋₆ haloalkyl, C₁₋₆ alkylene-carbocyclyl, or C₁₋₆ alkylene-heterocyclyl.

8. The compound of claim 7, or a pharmaceutically acceptable salt, stereoisomer, or tautomer thereof, wherein R²² is halo or C₁₋₄ alkyl.

9. The compound of claim 7, or a pharmaceutically acceptable salt, stereoisomer, or tautomer thereof, wherein R²² is F.

10. The compound of claim 7, or a pharmaceutically acceptable salt, stereoisomer, or tautomer thereof, wherein R²² is C₁₋₄ alkyl.

11. The compound of claim 10, or a pharmaceutically acceptable salt, stereoisomer, or tautomer thereof, wherein R²²' is H.

12. The compound of claim 10, or a pharmaceutically acceptable salt, stereoisomer, or tautomer thereof, wherein each R¹⁰⁰ is an independently selected C₁₋₆ haloalkyl.

13. The compound of claim 11, or a pharmaceutically acceptable salt, stereoisomer, or tautomer thereof, wherein each R¹⁰⁰ is an independently selected C₁₋₆ haloalkyl.

14. The compound of claim 7, or a pharmaceutically acceptable salt, stereoisomer, or tautomer thereof, wherein R²² is CH₃.

15. The compound of claim 7, or a pharmaceutically acceptable salt, stereoisomer, or tautomer thereof, wherein R²² is H, halo or C₁₋₆ alkyl.

16. The compound of claim 7, or a pharmaceutically acceptable salt, stereoisomer, or tautomer thereof, wherein R²² is H.

17. The compound of claim 7, or a pharmaceutically acceptable salt, stereoisomer, or tautomer thereof, wherein R²² is F.

18. The compound of claim 7, or a pharmaceutically acceptable salt, stereoisomer, or tautomer thereof, wherein R²² is CH₃.

19. The compound of claim 7, or a pharmaceutically acceptable salt, stereoisomer, or tautomer thereof, wherein each R¹⁰⁰ is independently halo, C₁₋₆ alkyl, or C₁₋₆ haloalkyl.

20. The compound of claim 7, or a pharmaceutically acceptable salt, stereoisomer, or tautomer thereof, wherein each R¹⁰⁰ is independently Cl, CH₂CH₃, or CH₂CF₃.

21. The compound of claim 7, or a pharmaceutically acceptable salt, stereoisomer, or tautomer thereof, wherein p is 1.

22. The compound of claim 7, or a pharmaceutically acceptable salt, stereoisomer, or tautomer thereof, wherein p is 2.

23. The compound of claim 7, or a pharmaceutically acceptable salt, stereoisomer, or tautomer thereof, wherein:
R¹⁰⁰ is CH₂CH₃; and
p is 1.

24. The compound of claim 7, or a pharmaceutically acceptable salt, stereoisomer, or tautomer thereof, wherein:
R¹⁰⁰ is CH₂CF₃; and
p is 1.

25. The compound of claim 7, or a pharmaceutically acceptable salt, stereoisomer, or tautomer thereof, wherein:
each R¹⁰' is independently Cl or CH₂CF₃; and
p is 2.

26. The compound of claim 7, wherein the compound is:

or a pharmaceutically acceptable salt or tautomer thereof.

27. The compound of claim 7, wherein the compound is:

or a pharmaceutically acceptable salt or tautomer thereof.

28. The compound of claim 1, wherein the compound is:

or a pharmaceutically acceptable salt, stereoisomer, or tautomer thereof.

29. The compound of claim 1, wherein the compound is selected from the group consisting of:

251
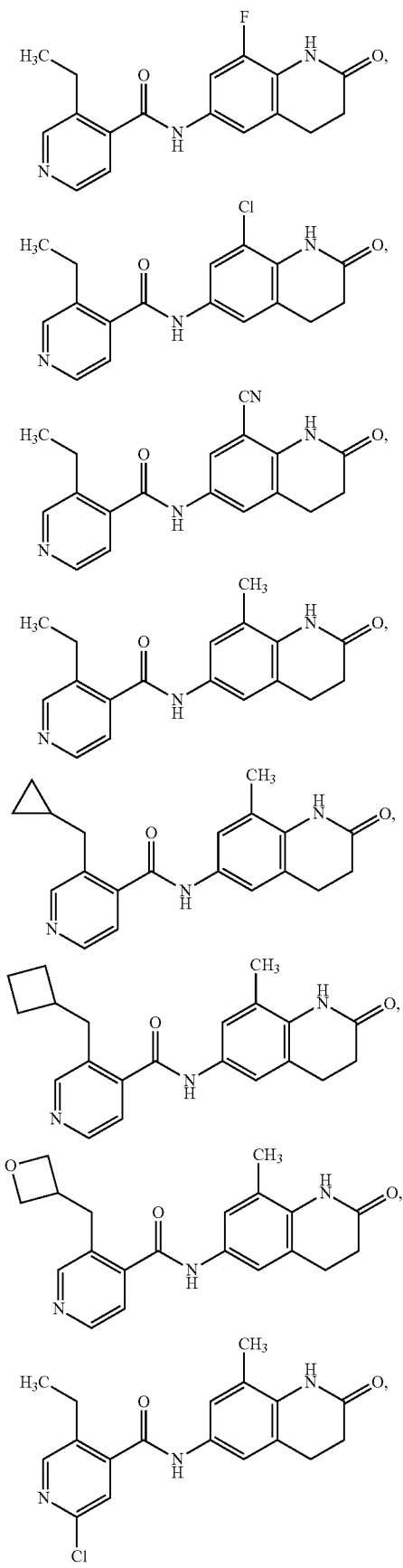
252
-continued
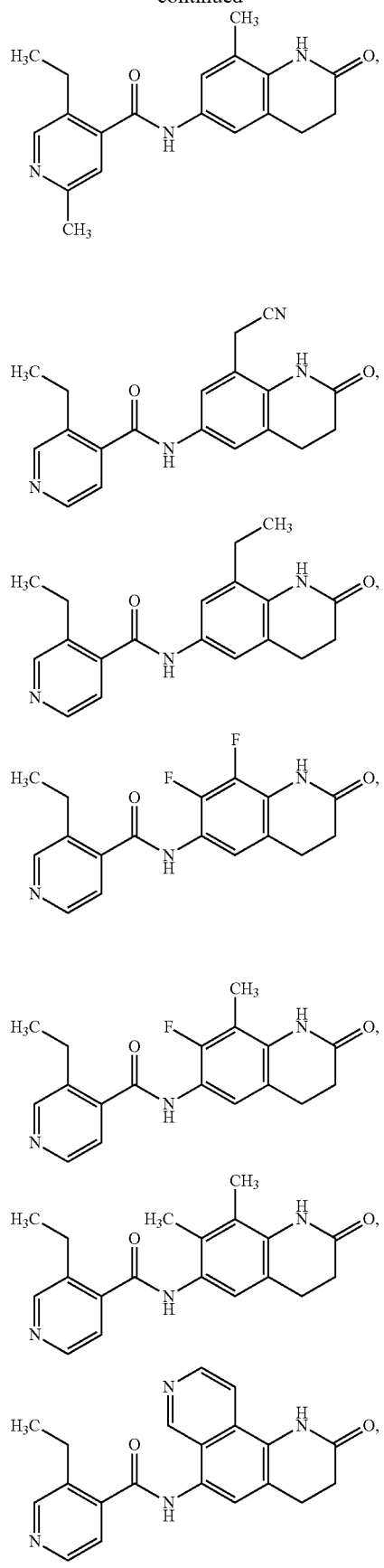

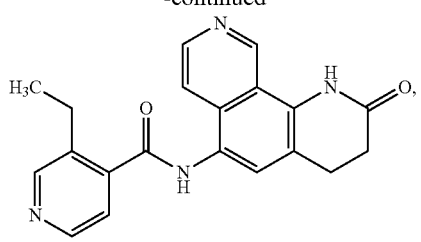
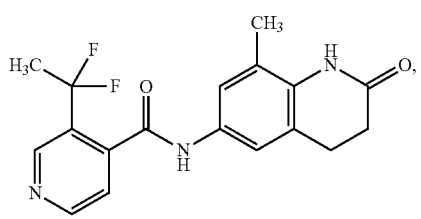
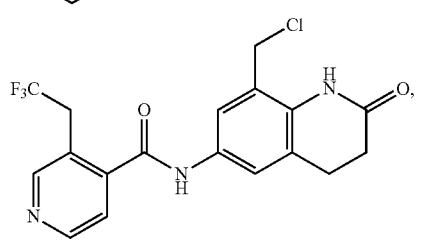
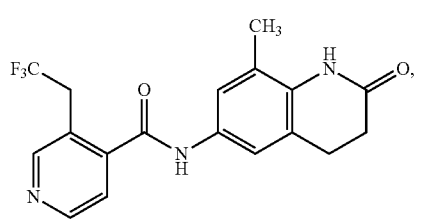 [SMILES: Cc1cc(NC(=O)c2ccncc2CC(F)(F)F)cc2c1NC(=O)CC2]
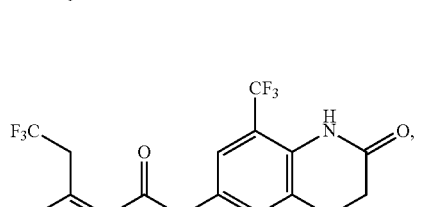
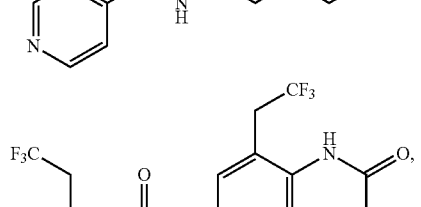
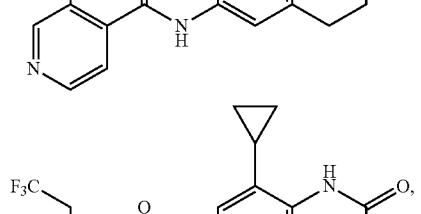
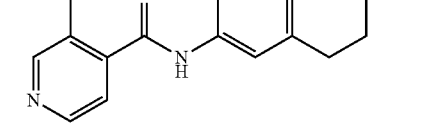
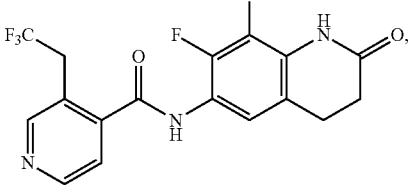
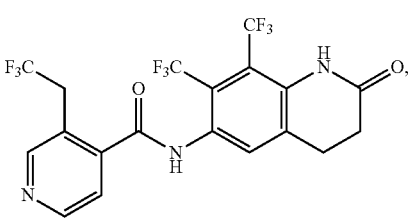
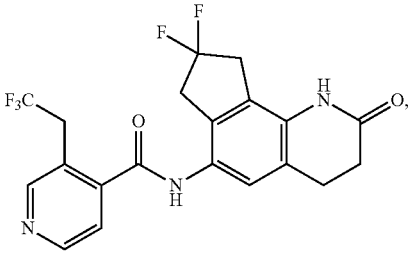
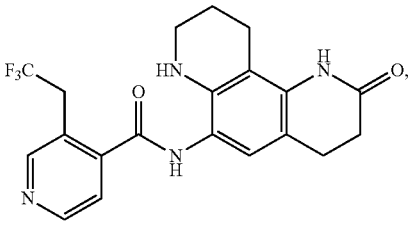
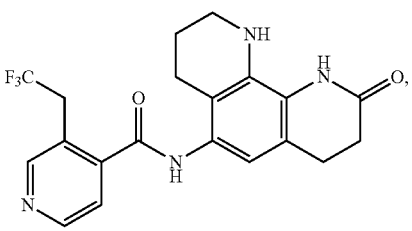
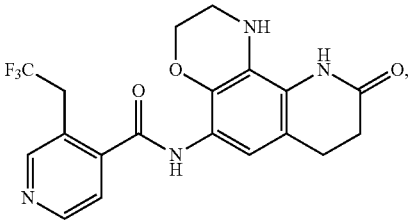
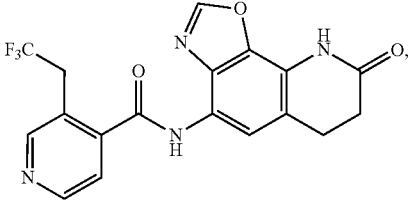

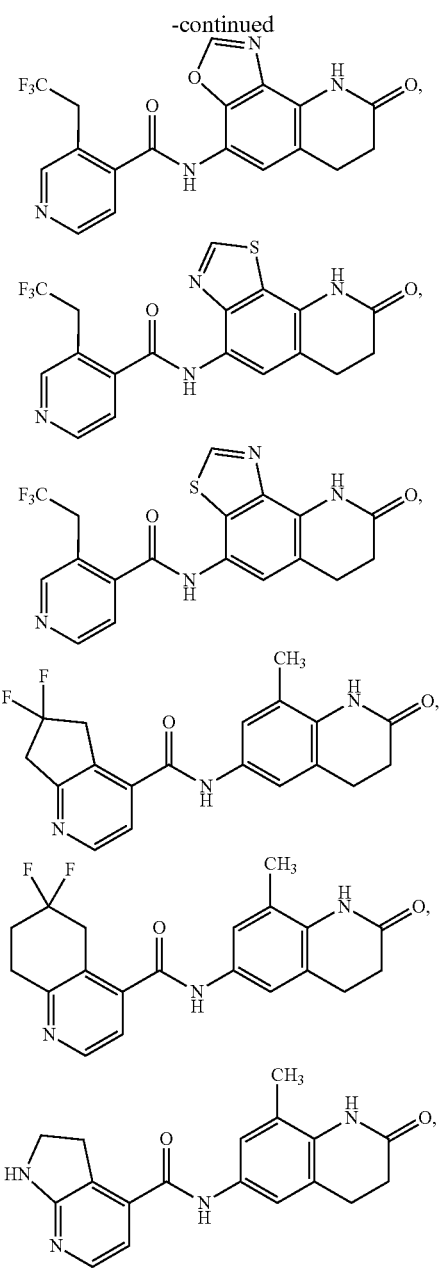
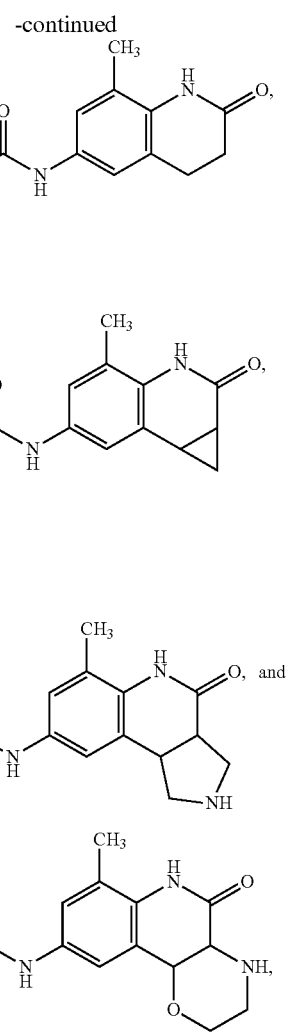
or a pharmaceutically acceptable salt, stereoisomer, or tautomer thereof.
30. A pharmaceutical composition comprising a pharmaceutically acceptable excipient or carrier and the compound of claim 1, or a pharmaceutically acceptable salt, stereoisomer, or tautomer thereof.
* * * * *

UNITED STATES PATENT AND TRADEMARK OFFICE
CERTIFICATE OF CORRECTION

PATENT NO. : 12,054,475 B2
APPLICATION NO. : 18/488924
DATED : August 6, 2024
INVENTOR(S) : Mark Esposito et al.

Page 1 of 1

It is certified that error appears in the above-identified patent and that said Letters Patent is hereby corrected as shown below:

In the Claims

In Claim 2, Column 248, Line 46, please replace "$R^{21}$ is H; or" with --$R^{21'}$ is H; or--.

In Claim 15, Column 249, Line 58, please replace "$R^{22}$ is H, halo or $C_{1-6}$alkyl" with --$R^{22'}$ is H, halo or $C_{1-6}$alkyl--.

In Claim 16, Column 249, Line 61, please replace "$R^{22}$ is H" with --$R^{22'}$ is H--.

In Claim 17, Column 249, Line 64, please replace "R22 is F" with --$R^{22'}$ is F--.

In Claim 18, Column 249, Line 67, please replace "$R^{22}$ is $CH_3$" with --$R^{22'}$ is $CH_3$--.

In Claim 25, Column 250, Line 24, please replace "each $R^{10'}$ is independently C1 or $CH_2CF_3$" with --each $R^{100}$ is independently Cl or $CH_2CF_3$; and--.

In Claim 29, Column 253, Line 25, please replace

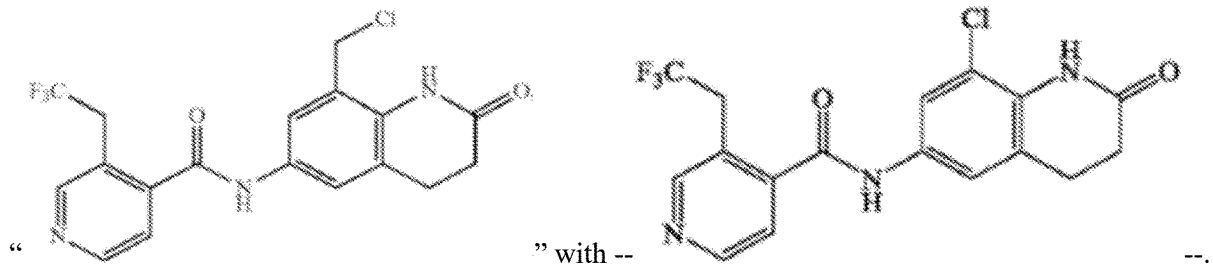

Signed and Sealed this
Seventh Day of January, 2025

Derrick Brent
*Acting Director of the United States Patent and Trademark Office*